US012281106B2

(12) United States Patent
Jung et al.

(10) Patent No.: US 12,281,106 B2
(45) Date of Patent: Apr. 22, 2025

(54) CONDENSED CYCLIC COMPOUND, ORGANIC LIGHT-EMITTING DEVICE INCLUDING SAME, AND ELECTRONIC DEVICE INCLUDING ORGANIC LIGHT-EMITTING DEVICE

(71) Applicants: Samsung Electronics Co., Ltd., Suwon-si (KR); SAMSUNG SDI CO., LTD., Yongin-si (KR)

(72) Inventors: Yongsik Jung, Seoul (KR); Youngchun Kwon, Yongin-si (KR); Younsuk Choi, Seongnam-si (KR); Hosuk Kang, Suwon-si (KR); Eunsuk Kwon, Suwon-si (KR); Jhunmo Son, Yongin-si (KR); Soonok Jeon, Suwon-si (KR); Yeonsook Chung, Seoul (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 523 days.

(21) Appl. No.: 16/885,595

(22) Filed: May 28, 2020

(65) Prior Publication Data
US 2020/0377490 A1    Dec. 3, 2020

(30) Foreign Application Priority Data

May 30, 2019    (KR) .................. 10-2019-0064069

(51) Int. Cl.
| | | |
|---|---|---|
| C07D 409/04 | (2006.01) | |
| C07D 209/82 | (2006.01) | |
| C07D 401/04 | (2006.01) | |
| C07D 403/04 | (2006.01) | |
| C07D 407/04 | (2006.01) | |
| C07F 7/08 | (2006.01) | |
| H10K 50/12 | (2023.01) | |
| H10K 85/40 | (2023.01) | |
| H10K 85/60 | (2023.01) | |

(52) U.S. Cl.
CPC ......... *C07D 409/04* (2013.01); *C07D 209/82* (2013.01); *C07D 401/04* (2013.01); *C07D 403/04* (2013.01); *C07D 407/04* (2013.01); *C07F 7/0816* (2013.01); *H10K 50/12* (2023.02); *H10K 85/40* (2023.02); *H10K 85/654* (2023.02); *H10K 85/6572* (2023.02); *H10K 85/6574* (2023.02); *H10K 85/6576* (2023.02)

(58) Field of Classification Search
CPC .................................................. C07D 209/82
See application file for complete search history.

(56) References Cited

U.S. PATENT DOCUMENTS

| | | |
|---|---|---|
| 6,670,054 B1 | 12/2003 | Hu et al. |
| 9,966,537 B2 | 5/2018 | Gray et al. |
| 10,103,334 B2 | 10/2018 | Wright et al. |
| 10,421,746 B2 | 9/2019 | Bergmann |
| 10,669,473 B2 | 6/2020 | Ambrosek et al. |
| 2015/0162553 A1 | 6/2015 | Kim et al. |
| 2017/0369439 A1 | 12/2017 | Jung et al. |

(Continued)

FOREIGN PATENT DOCUMENTS

| | | |
|---|---|---|
| DE | 102016115851 B3 | 7/2017 |
| DE | 102016115853 A1 | 3/2018 |

(Continued)

OTHER PUBLICATIONS

English Abstract of DE 10-2016-115853.

(Continued)

*Primary Examiner* — Noble E Jarrell
(74) *Attorney, Agent, or Firm* — CANTOR COLBURN LLP

(57) ABSTRACT

Provided are a condensed cyclic compound, an organic light-emitting device including the condensed cyclic compound, and an electronic device including the organic light-emitting device. The condensed cyclic compound is represented by Formula 1, wherein $R_{12}$ is a group represented by Formula 2-1 and $R_{13}$ is a group represented by Formula 2-2.

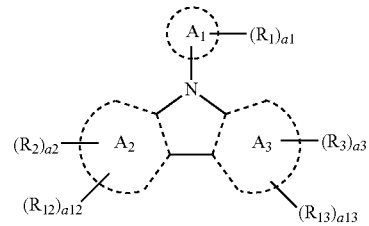

Formula 1

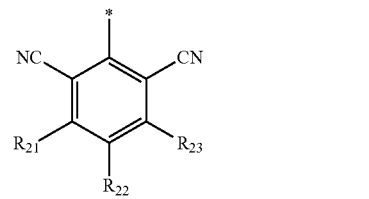

Formula 2-1

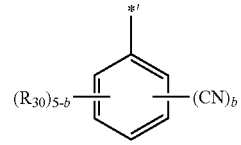

Formula 2-2

7 Claims, 1 Drawing Sheet

(56) References Cited

U.S. PATENT DOCUMENTS

| | | | |
|---|---|---|---|
| 2018/0166634 A1* | 6/2018 | Numata | C07D 487/04 |
| 2019/0062312 A1* | 2/2019 | Zink | H10K 85/6572 |
| 2019/0194130 A1 | 6/2019 | Bergmann et al. | |
| 2019/0198778 A1 | 6/2019 | Bergmann et al. | |
| 2019/0292151 A1* | 9/2019 | Esteban | C07D 519/00 |
| 2022/0059773 A1* | 2/2022 | Han | C07D 491/048 |

FOREIGN PATENT DOCUMENTS

| | | | | |
|---|---|---|---|---|
| EP | 3034506 | A1 | 6/2016 | |
| EP | 3315581 | A1 | 5/2018 | |
| EP | 3421461 | * | 2/2019 | |
| JP | 2006306783 | A | 11/2006 | |
| JP | 2017084859 | A | 5/2017 | |
| KR | 1020110056728 | A | 5/2011 | |
| KR | 1020170100552 | A | 9/2017 | |
| KR | 20180068882 | A | 6/2018 | |
| KR | 1020180076551 | A | 7/2018 | |
| KR | 10-2018-0109193 | | * 10/2018 | |
| KR | 20200068396 | A | 6/2020 | |
| WO | 2015060635 | A1 | 4/2015 | |
| WO | 2016043394 | A1 | 3/2016 | |
| WO | 2016109386 | A1 | 7/2016 | |
| WO | 2016116528 | A1 | 7/2016 | |
| WO | WO2016107459 | A1 | 7/2016 | |
| WO | 2018001820 | A1 | 1/2018 | |
| WO | 2018001821 | A | 1/2018 | |
| WO | 2019002355 | A1 | 1/2019 | |
| WO | WO 2019038448 | | * 2/2019 | |
| WO | WO-2020043482 | A1 * | 3/2020 | C07D 403/14 |
| WO | WO 2020048863 | | * 3/2020 | |
| WO | WO-2020060286 | A1 * | 3/2020 | C07D 405/14 |

OTHER PUBLICATIONS

English Abstract of DE10-2016-115851.
English Abstract of JP 2017-084859.
English abstract of JP2006-306783.
English Abstract of KR 10-2011-0056728.
English Abstract of KR 10-2018-0076551.
English Abstract of WO 2015-060635.
English Abstract of WO 2016-043394.
English Abstract of KR 2020-0068396.
English Translation of Office Action dated Jan. 4, 2024, issued in corresponding KR Patent Application No. 10-2019-0064069, 14 pp.
Office Action dated Jan. 4, 2024, issued in corresponding KR Patent Application No. 10-2019-0064069, 13 pp.

* cited by examiner

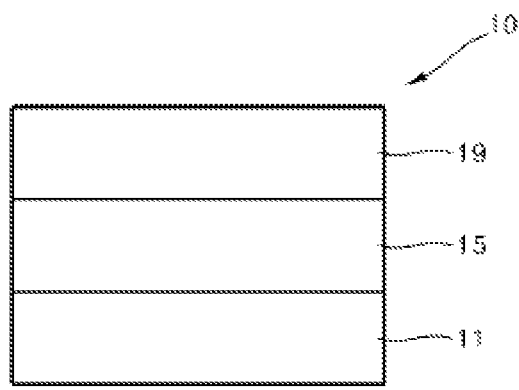

CONDENSED CYCLIC COMPOUND, ORGANIC LIGHT-EMITTING DEVICE INCLUDING SAME, AND ELECTRONIC DEVICE INCLUDING ORGANIC LIGHT-EMITTING DEVICE

CROSS-REFERENCE TO RELATED APPLICATION

This application claims priority to and the benefit of Korean Patent Application No. 10-2019-0064069, filed on May 30, 2019, in the Korean Intellectual Property Office, the content of which is incorporated herein in its entirety by reference.

BACKGROUND

1. Field

The present disclosure relates to a condensed cyclic compound, an organic light-emitting device including the condensed cyclic compound, and an electronic device including the organic light-emitting device.

2. Description of the Related Art

Organic light-emitting devices (OLEDs) are self-emission devices which produce full-color images. In addition, OLEDs have wide viewing angles and exhibit excellent driving voltage and response speed characteristics.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state to thereby generate light.

SUMMARY

Provided are a condensed cyclic compound, an organic light-emitting device including the condensed cyclic compound, and an electronic device including the organic light-emitting device.

Additional aspects will be set forth in part in the description which follows and, in part, will be apparent from the description, or may be learned by practice of the presented embodiments.

According to an aspect of an embodiment, a condensed cyclic compound is represented by Formula 1:

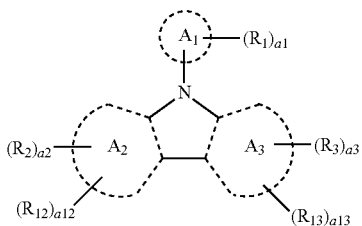

Formula 1

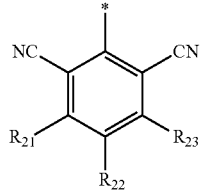

Formula 2-1

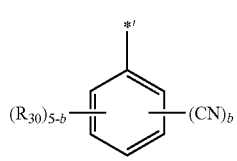

Formula 2-2 wherein, in Formulae 1, 2-1, and 2-2, rings $A_1$ to $A_3$ are each independently a $C_5$-$C_{30}$ carbocyclic group or a $C_1$-$C_{30}$ heterocyclic group, $R_1$ to $R_3$, $R_{21}$ to $R_{23}$, and $R_{30}$ are each independently hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{10}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), —S($Q_1$), or —C(=O)($Q_1$), a1 to a3 are each independently an integer from 0 to 10; when a1 is 2 or greater, at least two $R_1$(s) are identical to or different from each other; when a2 is 2 or greater, at least two $R_2$(s) are identical to or different from each other; and when a3 is 2 or greater, at least two $R_3$(s) are identical to or different from each other, $R_{12}$ is a group represented by Formula 2-1,
$R_{13}$ is a group represented by Formula 2-2,
$R_2$ and $R_{21}$ to $R_{23}$ do not include a carbazole group,
a12 is an integer from 1 to 4,
a13 is an integer from 0 to 4,
b is an integer from 0 to 5,
* indicates a binding site to ring $A_2$, *' indicates a binding site to ring $A_3$, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, —$B(Q_{16})(Q_{17})$, or a combination thereof;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —$CD_3$, —$CD_2H$, —$CDH_2$, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, —$B(Q_{26})(Q_{27})$, or a combination thereof; or —$Si(Q_{31})(Q_{32})(Q_{33})$, —$N(Q_{34})(Q_{35})$—$B(Q_{36})(Q_{37})$, or a combination thereof, wherein $Q_1$ to $Q_7$, $Q_{11}$ to $Q_{17}$, $Q_{21}$ to $Q_{27}$, and $Q_{31}$ to $Q_{37}$ are each independently hydrogen, deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

According to an aspect of another embodiment, an organic light-emitting device may include: a first electrode; a second electrode; and an organic layer between the first electrode and the second electrode, the organic layer including an emission layer and at least one condensed cyclic compound described above.

According to an aspect of another embodiment, an electronic device may include the organic light-emitting device.

BRIEF DESCRIPTION OF THE DRAWING

These and/or other aspects will become apparent and more readily appreciated from the following description of the embodiments, taken in conjunction with the accompanying drawings in which:

The FIGURE is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES It will be understood that relative terms are intended to encompass different orientations of the device in addition to the orientation depicted in the FIGURES For example, if the device in one of the FIGURES is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the FIGURES is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

According to an aspect, a condensed cyclic compound may be represented by Formula 1:

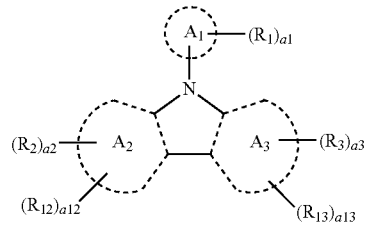

Formula 1

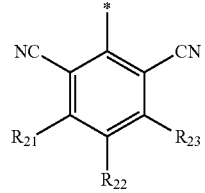

Formula 2-1

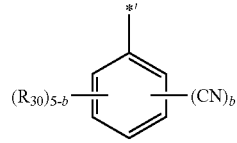

Formula 2-2 wherein, in Formula 1, rings $A_1$ to $A_3$ may each independently be a $C_5$-$C_{30}$ carbocyclic group or a $C_1$-$C_{30}$ heterocyclic group.

In some embodiments, rings $A_1$ to $A_3$ may each independently be:

a benzene group, a naphthalene group, an anthracene group, a phenanthrene group, a triphenylene group, a pyrene group, a chrysene group, an indole group, a furan group, a silole group, a germole group, a borole group, a phosphole group, a thiophene group, a cyclopentadiene group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group, but embodiments are not limited thereto.

In some embodiments, rings $A_2$ and $A_3$ may each independently be a benzene group, a naphthalene group, an anthracene group, a phenanthrene group, a triphenylene group, a pyrene group, or a chrysene group.

In Formulae 1, 2-1, and 2-2, $R_1$ to $R_3$, $R_{21}$ to $R_{23}$, and $R_{30}$ may each independently be hydrogen, deuterium, —F, —C, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), —S($Q_1$), or —C(=O)($Q_1$), In some embodiments, $R_2$ and $R_{21}$ to $R_{23}$ may each independently be:
  hydrogen, deuterium, —F, —C, —Br, —I, a hydroxyl group, a cyano group (CN), a nitro group, an amino group, a $C_1$-$C_{60}$ alkyl group, or a $C_1$-$C_{60}$ alkoxy group;
  a $C_1$-$C_{60}$ alkyl group or a $C_1$-$C_{60}$ alkoxy group, each substituted with at least one deuterium, —F, —C, —Br, —I, a hydroxyl group, a cyano group (CN), a nitro group, an amino group, or a combination thereof;
  a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;
  a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one a deuterium, —F, —Cl, —Br, —I, a hydroxyl group, a cyano group (CN), a nitro group, an amino group, a $C_1$-$C_{60}$ alkyl group, a $C_1$-$C_{60}$ alkoxy group, a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof, or
  —Si($Q_1$)($Q_2$)($Q_3$), —N($Q_4$)($Q_5$), —B($Q_6$)($Q_7$), —S($Q_1$), or —C(=O)($Q_1$),
  wherein $Q_1$ to $Q_7$ may each independently be hydrogen, deuterium, a $C_1$-$C_{10}$ alkyl group, a phenyl group, a biphenyl group, a naphthyl group, a fluorenyl group, a carbazolyl group, a dibenzofuranyl group, a dibenzothiophenyl group, a pyridinyl group, a pyrimidinyl group, a pyrazinyl group, or a triazinyl group, but embodiments are not limited thereto.

In some embodiments, $R_1$, $R_3$, and $R_{30}$ may each independently be:
  hydrogen, deuterium, —F, —Cl, —Br, —I, a hydroxyl group, a cyano group (CN), a nitro group, an amino group, a $C_1$-$C_{60}$ alkyl group, or a $C_1$-$C_{60}$ alkoxy group;
  a $C_1$-$C_{60}$ alkyl group and a $C_1$-$C_{60}$ alkoxy group, each substituted with at least one deuterium, —F, —Cl, —Br, —I, a hydroxyl group, a cyano group (CN), a nitro group, or an amino group;
  a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, OR an imidazopyrimidinyl group; a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, each substituted with at least one a deuterium, —F, —Cl, —Br, —I, a hydroxyl group, a cyano group (CN), a nitro group, an amino group, a $C_1$-$C_{60}$ alkyl group, a $C_1$-$C_{60}$ alkoxy group, a cyclopentyl group, a cyclohexyl group, a cycloheptyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof; or —Si($Q_1$)($Q_2$)($Q_3$), —N($Q_4$)($Q_5$), —B($Q_6$)($Q_7$), —S($Q_1$), or —C(=O)($Q_1$), wherein $Q_1$ to $Q_7$ may each independently be hydrogen, deuterium, a $C_1$-$C_{10}$ alkyl group, a phenyl group, a biphenyl group, a naphthyl group, a fluorenyl group, a carbazolyl group, a dibenzofuranyl group, a dibenzothiophenyl group, a pyridinyl group, a pyrimidinyl group, a pyrazinyl group, or a triazinyl group.

In some embodiments, $R_{21}$ to $R_{23}$ and $R_{30}$ may each independently be:

hydrogen, deuterium, —F, —C, —Br, —I, a hydroxyl group, a nitro group, an amino group, a $C_1$-$C_{20}$ alkyl group, or a $C_1$-$C_{20}$ alkoxy group; or a $C_1$-$C_{20}$ alkyl group or a $C_1$-$C_{20}$ alkoxy group, each substituted with at least one deuterium, —F, —C, —Br, —I, a hydroxyl group, a nitro group, an amino group, or a combination thereof, but embodiments are not limited thereto.

In Formula 1, a1 to a3 may each independently be an integer from 0 to 10; when a1 is 2 or greater, at least two $R_1$(s) may be identical to or different from each other; when a2 is 2 or greater, at least two $R_2$(s) may be identical to or different from each other; and when a3 is 2 or greater, at least two $R_3$(s) may be identical to or different from each other.

In Formula 1, $R_{12}$ may be a group represented by Formula 2-1.

In Formula 1, $R_{13}$ may be a group represented by Formula 2-2.

In Formula 1, a12 may be an integer from 1 to 4, and a13 may be an integer from 0 to 4.

In some embodiments, a12+a13≥2, but embodiments are not limited thereto.

In some embodiments, a12 may be 2, and a13 may be 0. In some embodiments, a12 may be 1, and a13 may be 1. In some embodiments, a12 may be 1, and a13 may be 2.

In Formula 2-2, b may be an integer from 0 to 5.

In some embodiments, a13 may be 1, and b may be 1 to 5.

In some embodiments, a13 may be 1, and b may be an integer from 1 to 4. In some embodiments, a13 may be 1, and b may be an integer from 1 to 3. In some embodiments, a13 may be 1, and b may be 1 or 2.

* indicates a binding site to ring $A_2$, and *' indicates a binding site to ring $A_3$.

In some embodiments, the group represented by Formula 2-2 may be a group represented by any one of Formulae 2-2(1) to 2-2(15):

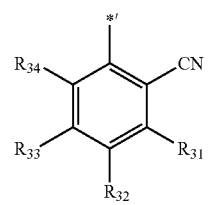

2-2(1)

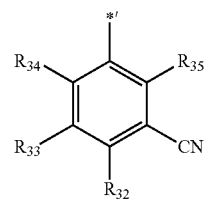

2-2(2)

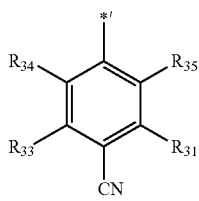 2-2(3)
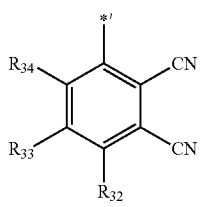 2-2(4)
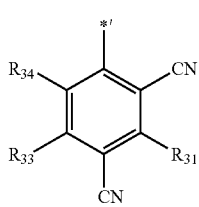 2-2(5)
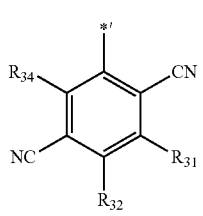 2-2(6)
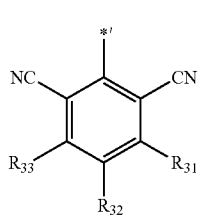 2-2(7)
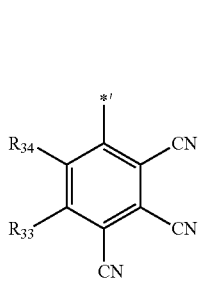 2-2(8)
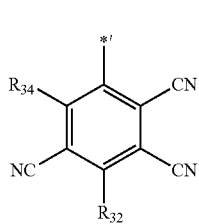 2-2(9)
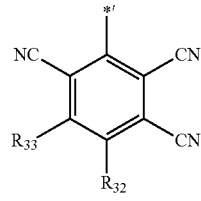 2-2(10)
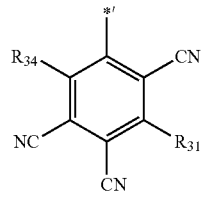 2-2(11)
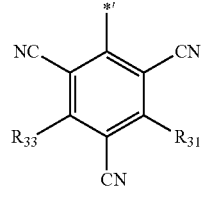 2-2(12)
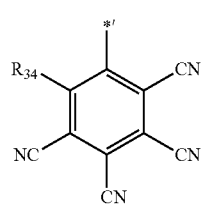 2-2(13)
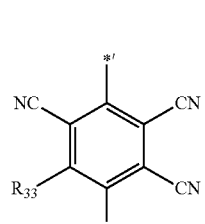 2-2(14)
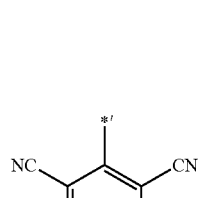 2-2(15)
wherein, in Formulae 2-2(1) to 2-2(15),
$R_{31}$, $R_{32}$, $R_{33}$, $R_{34}$, and $R_{35}$ may each be understood by referring to the descriptions of $R_{30}$ provided herein.
In some embodiments, the group represented by Formula 1 may be a group represented by Formulae 3-1 to 3-4:

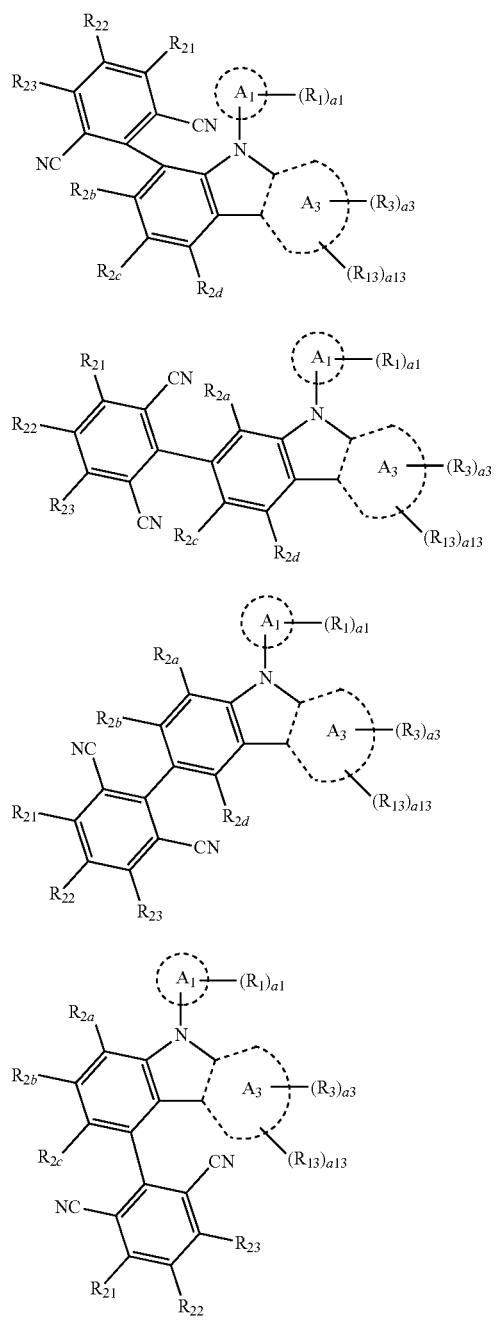

wherein, in Formulae 3-1 to 3-4, $A_1$, $A_3$, $R_1$, $R_3$, $R_{13}$, $R_{21}$, $R_{22}$, $R_{23}$, a1, a3, and a13 may respectively be understood by referring to the descriptions of $A_1$, $A_3$, $R_1$, $R_3$, $R_{13}$, $R_{21}$, $R_{22}$, $R_{23}$, a1, a3, and a13 provided herein, and $R_{2a}$, $R_{2b}$, $R_{2c}$, and $R_{2d}$ may each be understood by referring to the description of $R_2$ provided herein.

In some embodiments, in Formulae 3-1 to 3-4, a13 may be 0 or 1, and $R_{21}$ to $R_{23}$ may each be hydrogen.

In some embodiments, the group represented by Formula 1 may be a group represented by Formulae 4-1 to 4-16:

-continued
4-5

4-6
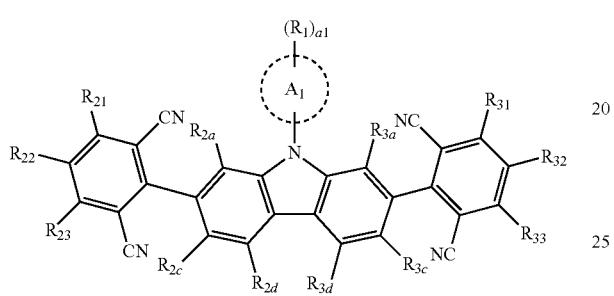
4-7
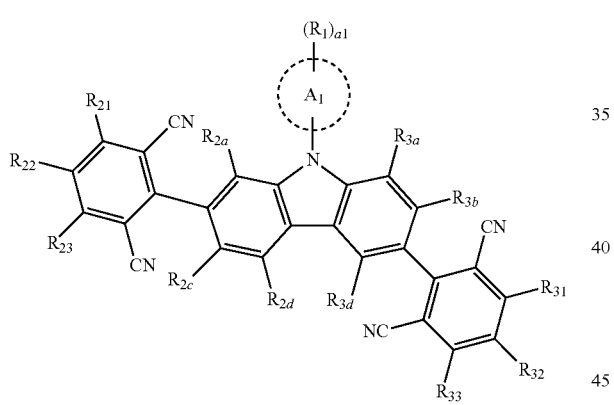
4-8
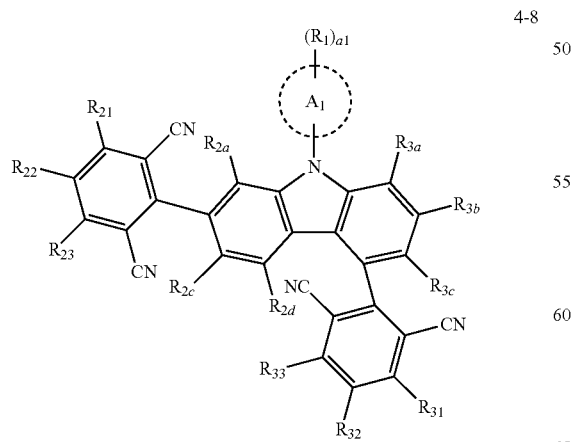
-continued
4-9
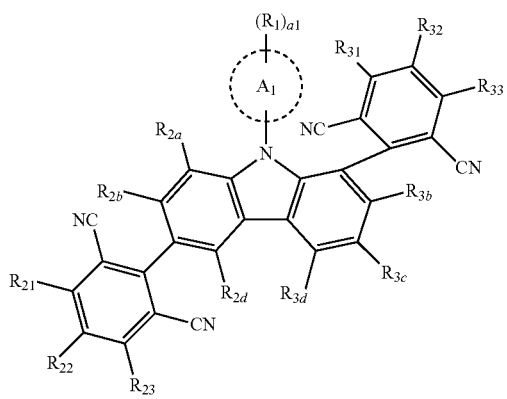
4-10
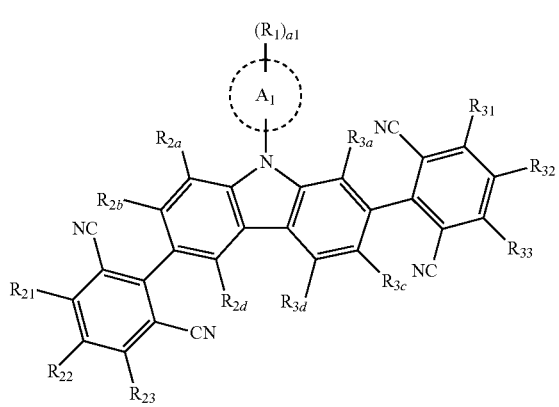
4-11
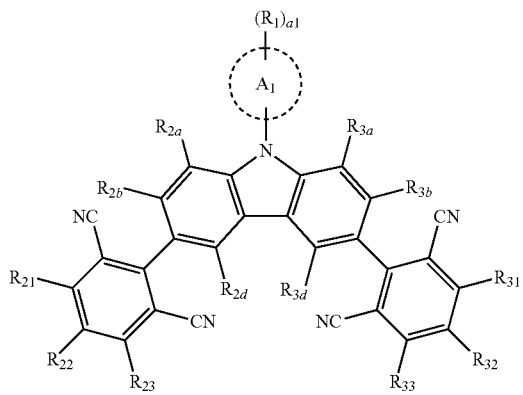

4-12

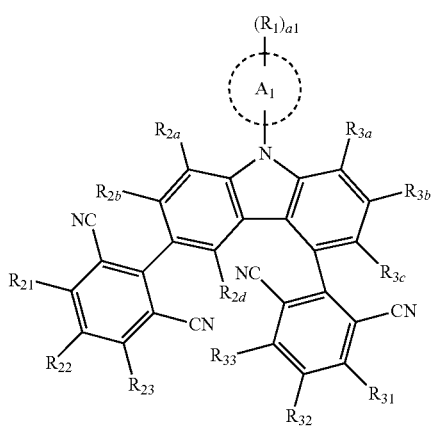

4-13

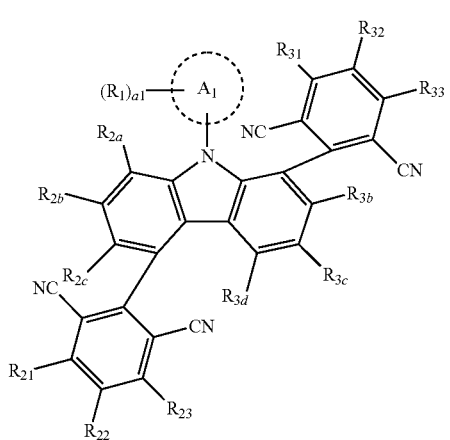

4-14

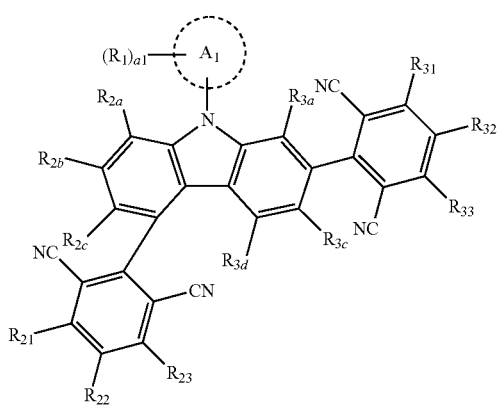

4-15

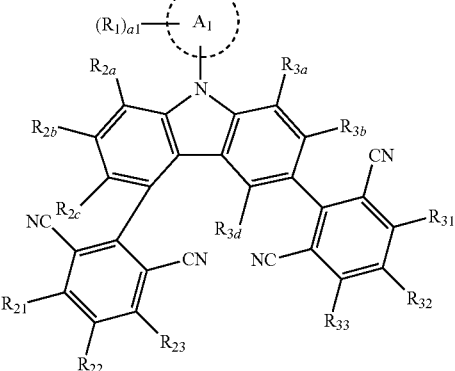

4-16

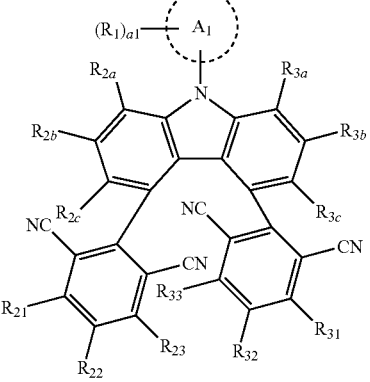

wherein, in Formulae 4-1 to 4-16, $A_1$, $R_1$, a1, $R_{21}$, $R_{22}$, and $R_{23}$ may respectively be understood by referring to the descriptions of $A_1$, $R_1$, a1, $R_{21}$, $R_{22}$, and $R_{23}$ provided herein, $R_{2a}$, $R_{2b}$, and $R_{2c}$ may each be understood by referring to the description of $R_2$ provided herein, $R_{3a}$, $R_{3b}$, and $R_{3c}$ may each be understood by referring to the description of $R_3$ provided herein, and $R_{31}$, $R_{32}$, and $R_{33}$ may each be understood by referring to the description of $R_{30}$ provided herein.

In some embodiments, in Formulae 4-1 to 4-16, $R_{21}$ to $R_{23}$ and $R_{31}$ to $R_{33}$ may each independently be:

hydrogen, deuterium, —F, —Cl, —Br, —I, a hydroxyl group, a nitro group, an amino group, a methyl group, an ethyl group, an n-propyl group, an iso-propyl group, an n-butyl group, an iso-butyl group, a sec-butyl group, a tert-butyl group, an n-pentyl group, a tert-pentyl group, a neo-pentyl group, an iso-pentyl group, a sec-pentyl group, a 3-pentyl group, or a sec-isopentyl group; or a methyl group, an ethyl group, an n-propyl group, an iso-propyl group, an n-butyl group, an iso-butyl group, a sec-butyl group, a tert-butyl group, an n-pentyl group, a tert-pentyl group, a neo-pentyl group, an iso-pentyl group, a sec-pentyl group, a 3-pentyl group, or a sec-isopentyl group, each substituted with at least one deuterium, —F, —Cl, —Br, —I, a hydroxyl group, a nitro group, an amino group, or a combination thereof.

In some embodiments, the condensed cyclic compound may be of Compounds 1 to 280, but embodiments are not limited thereto:

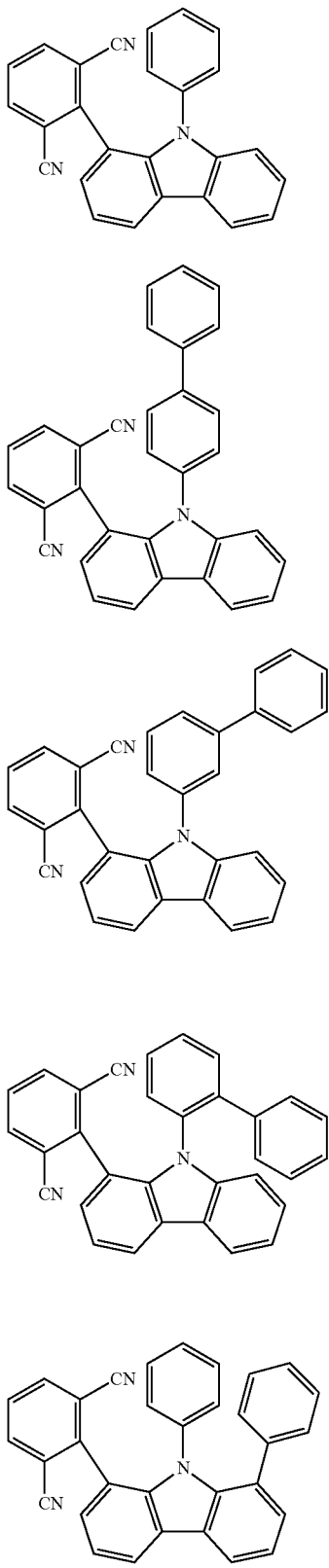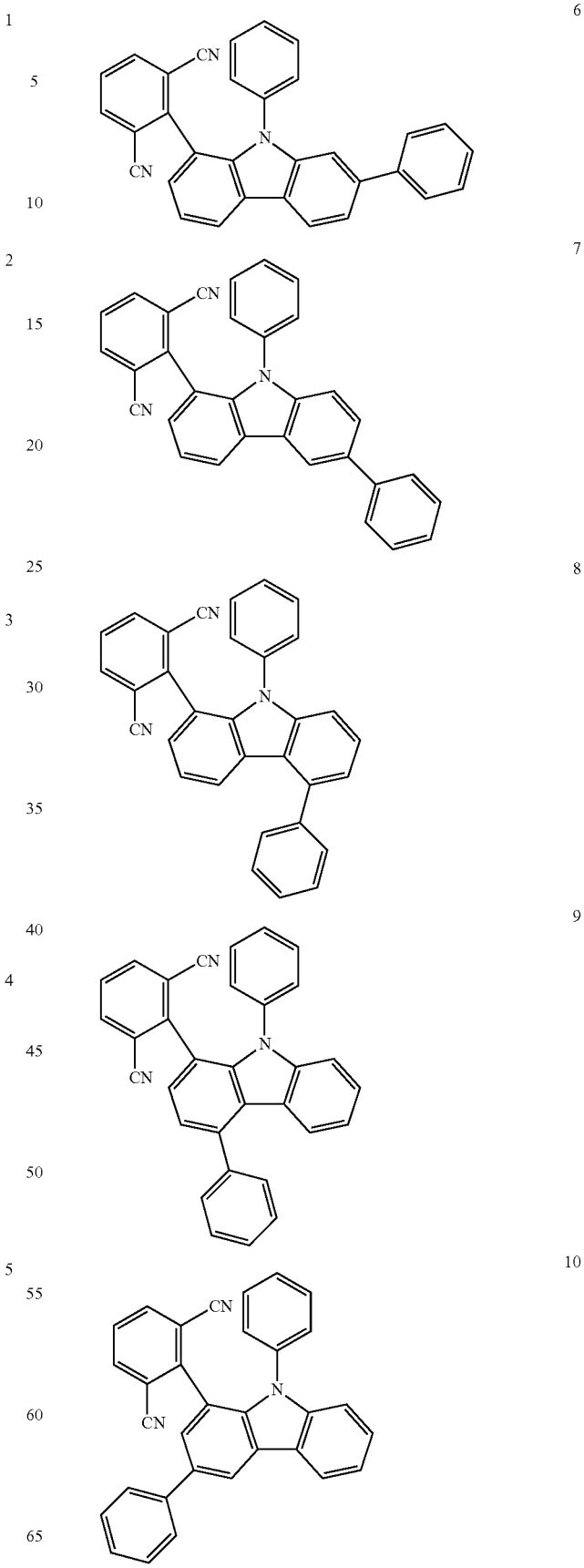

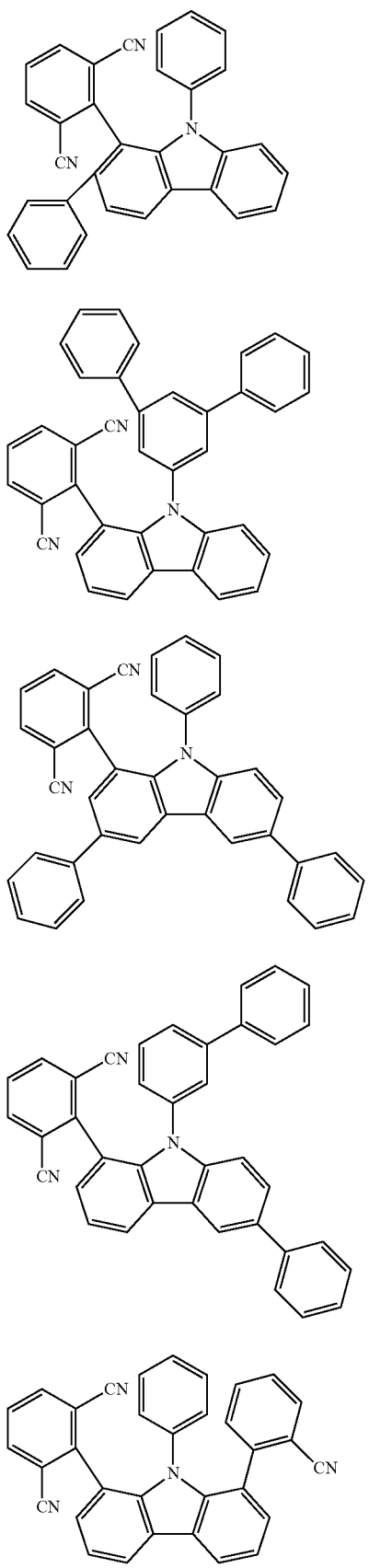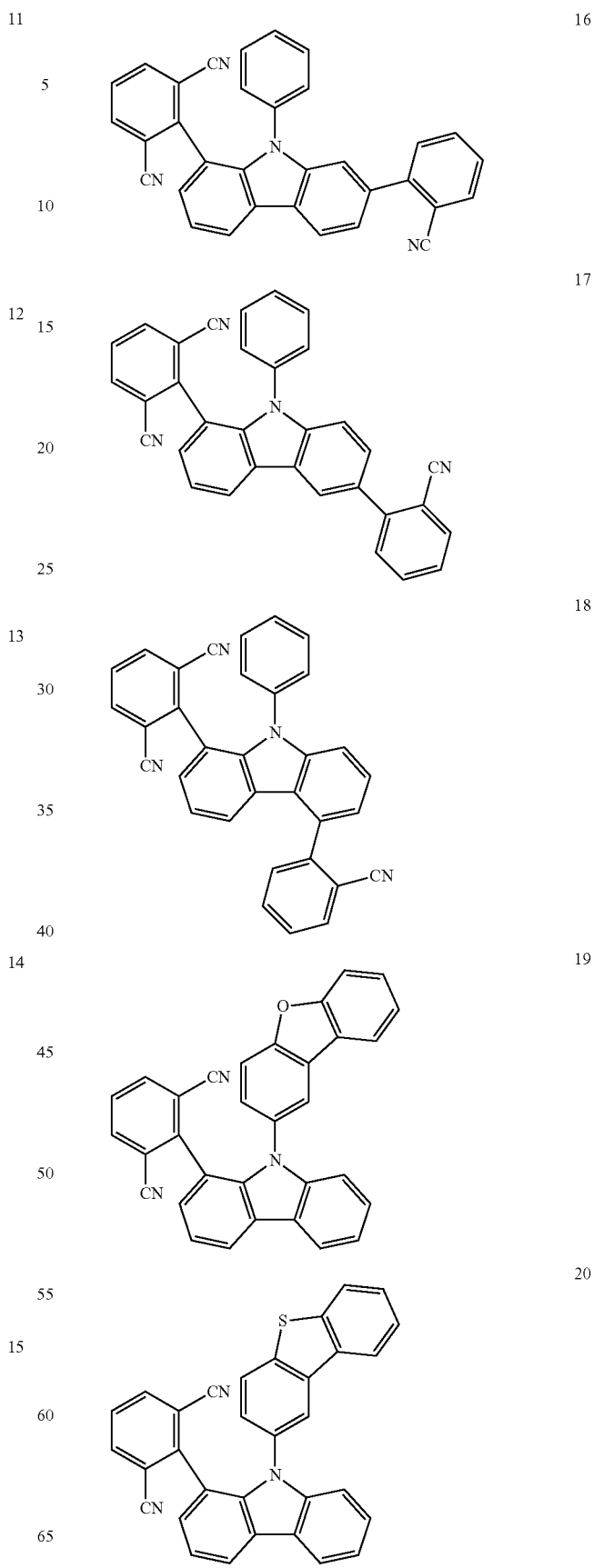

21
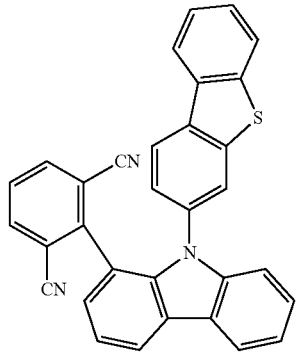
22
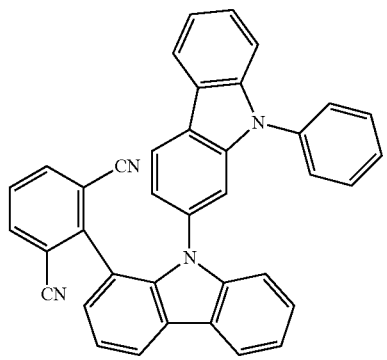
23
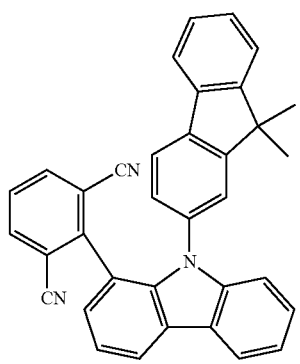
24
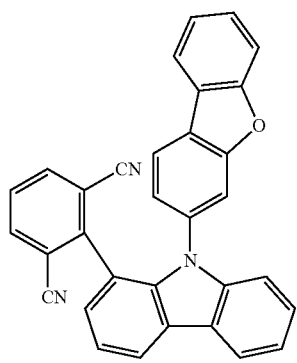
25
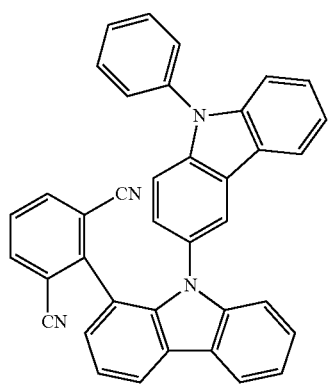
26
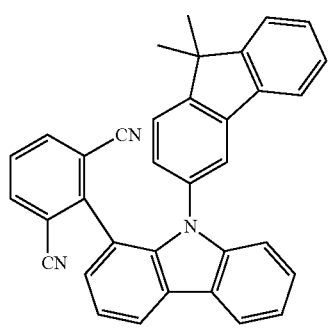
27
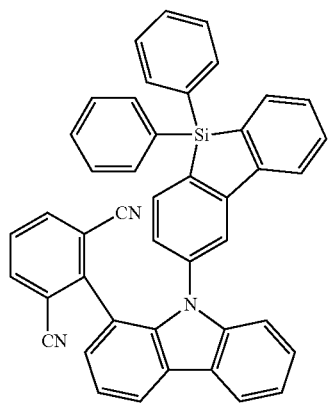
28
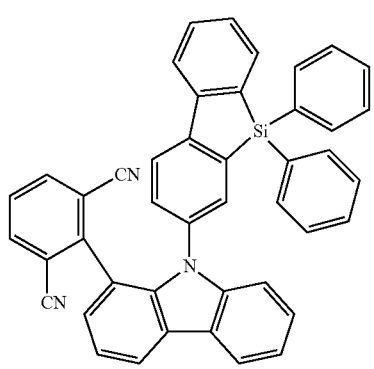

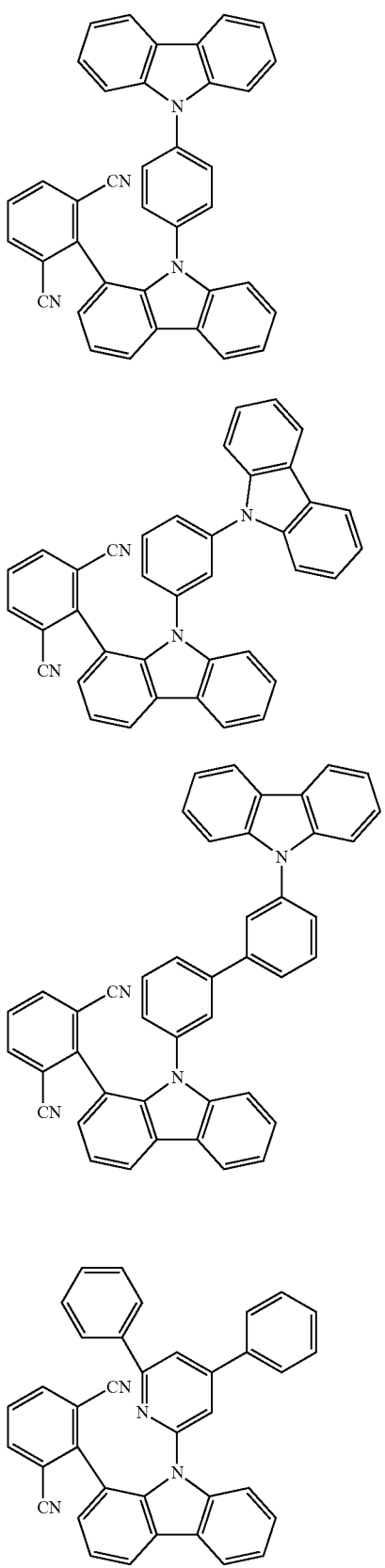
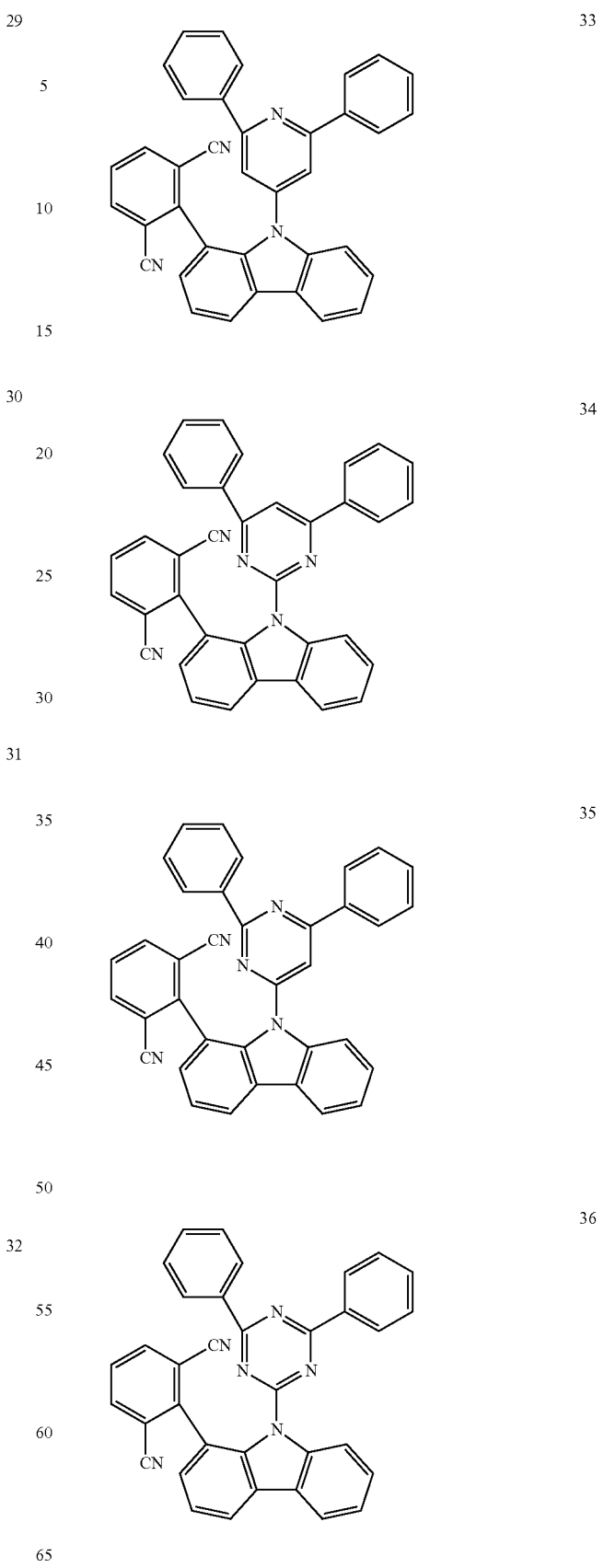

37
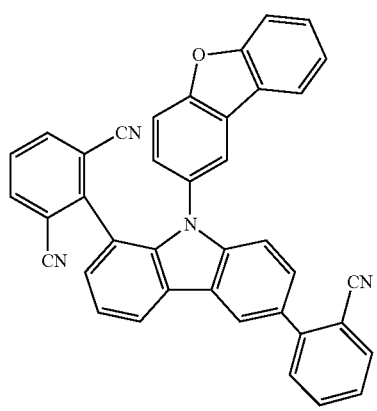
38
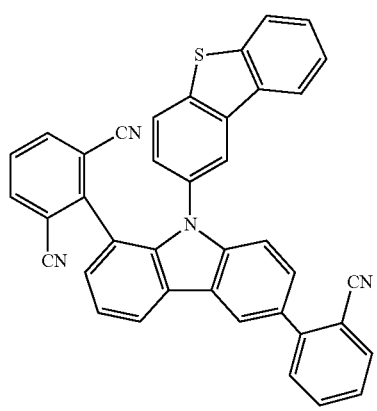
39
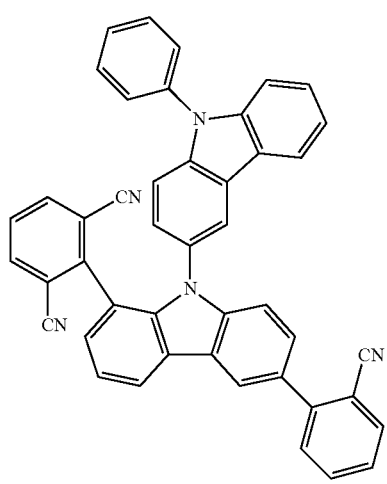
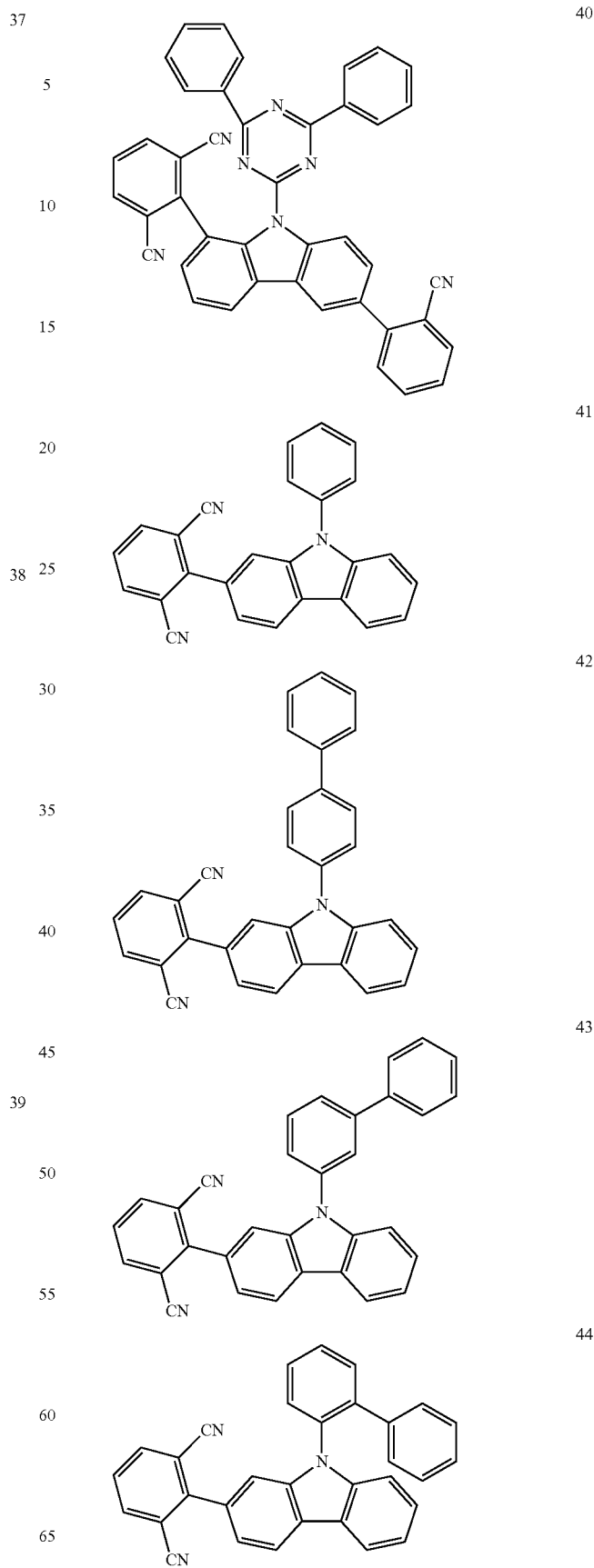

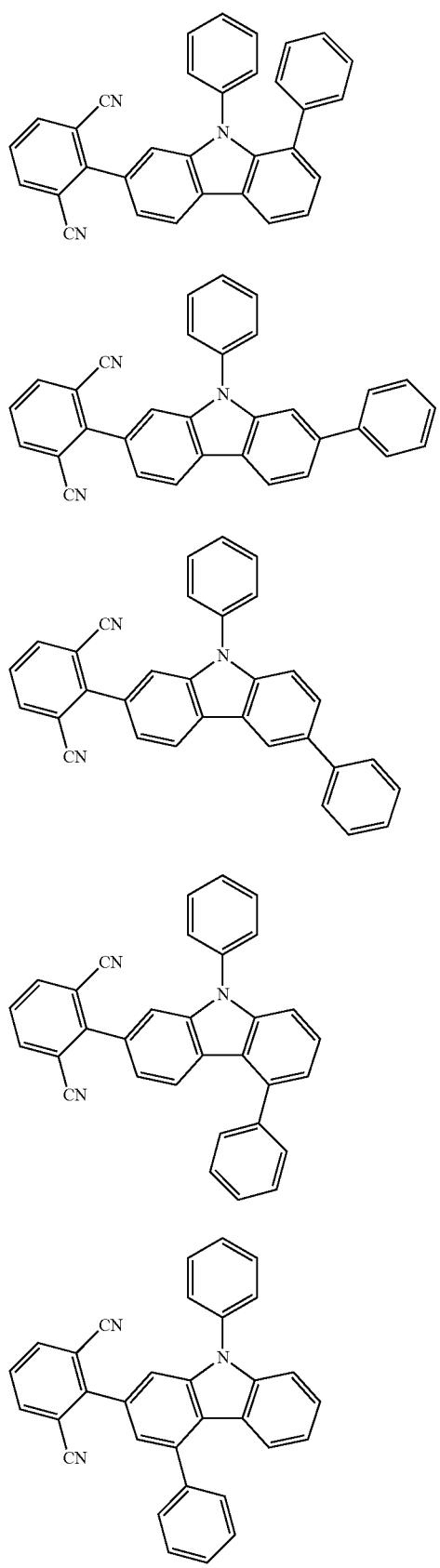
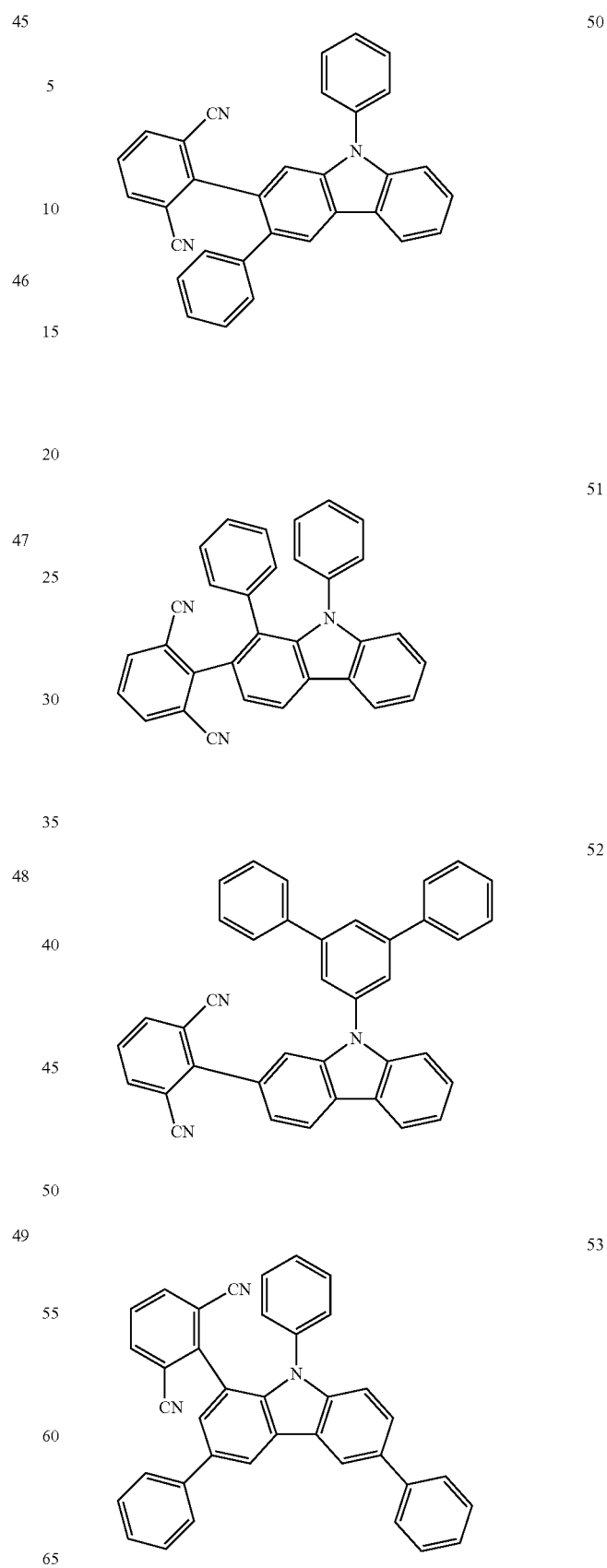

54
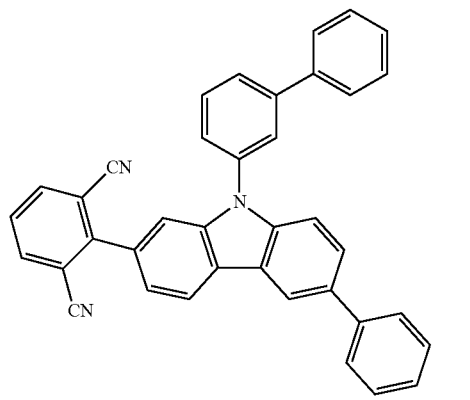
55
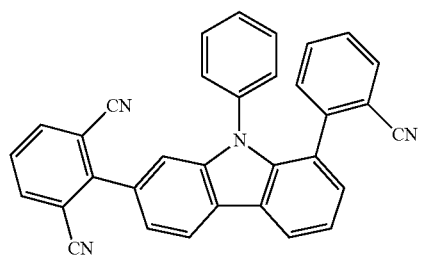
56
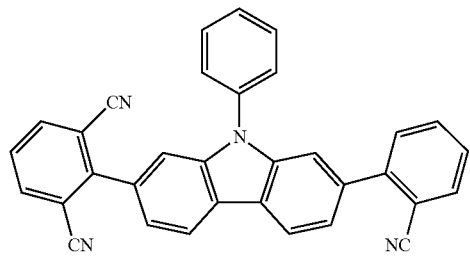
57
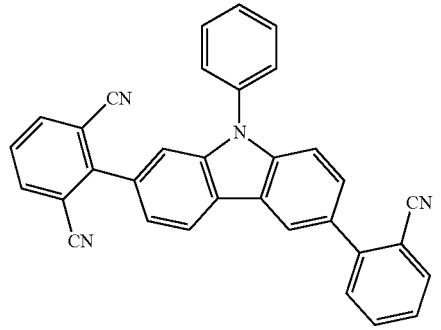
58
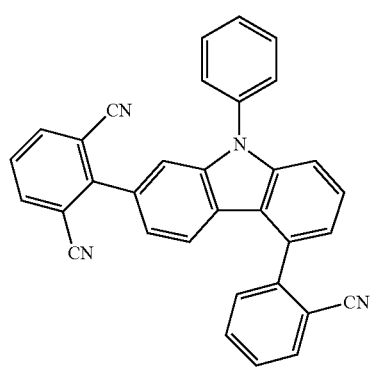
59
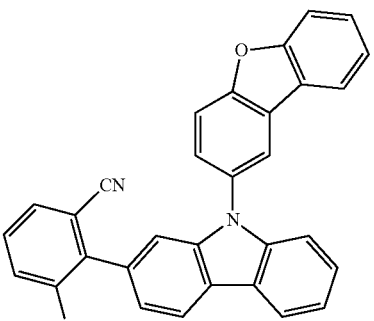
60
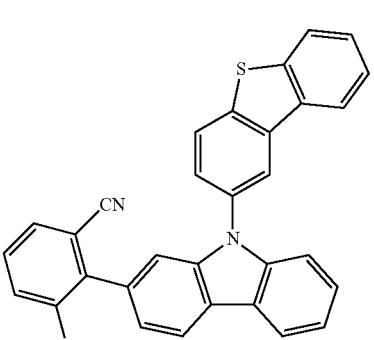
61
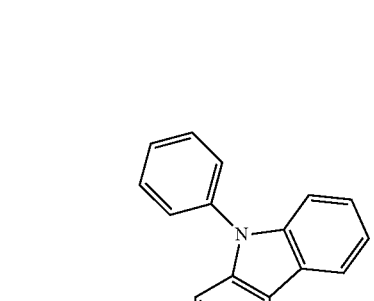
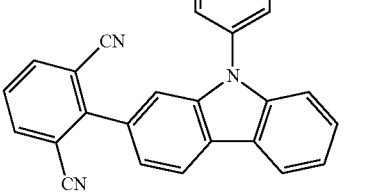
62
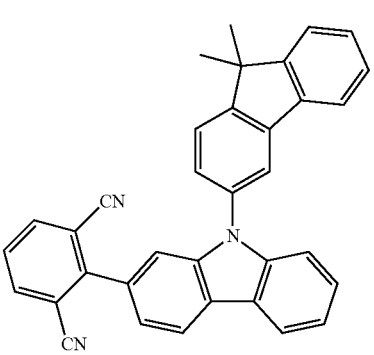

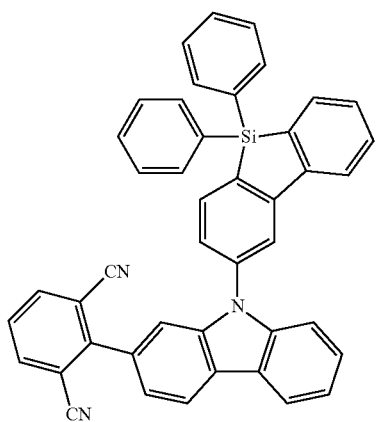
63
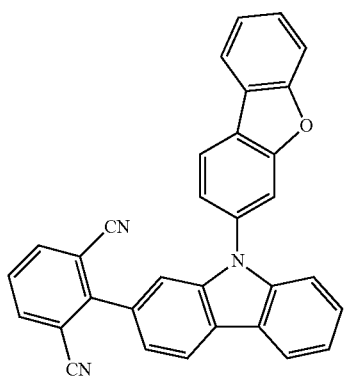
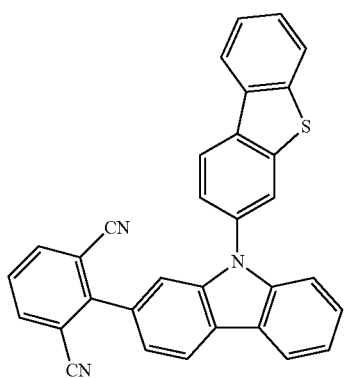
65
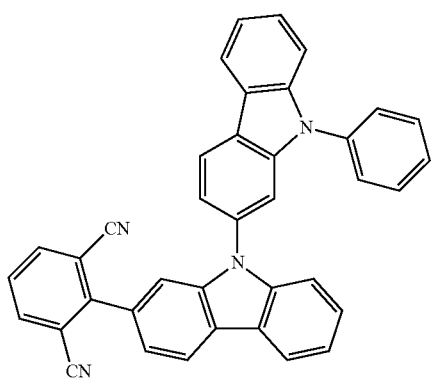
66
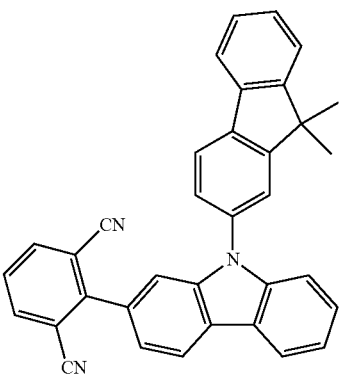
67
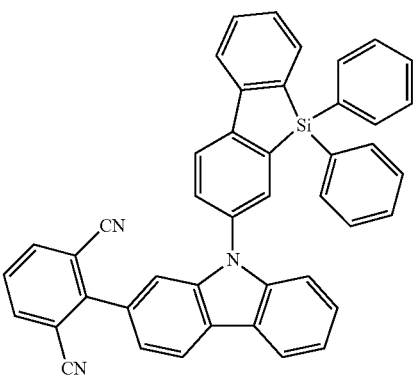
68
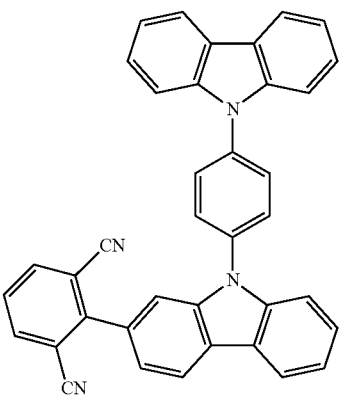
69
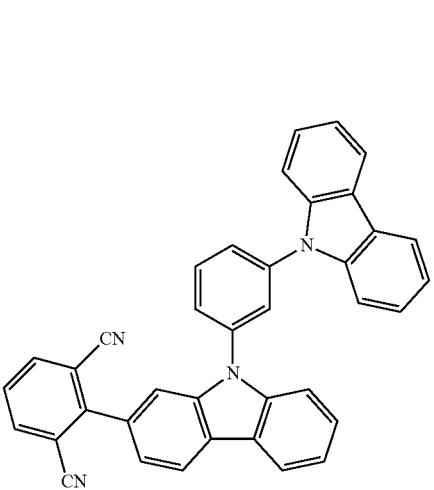
70

-continued
71
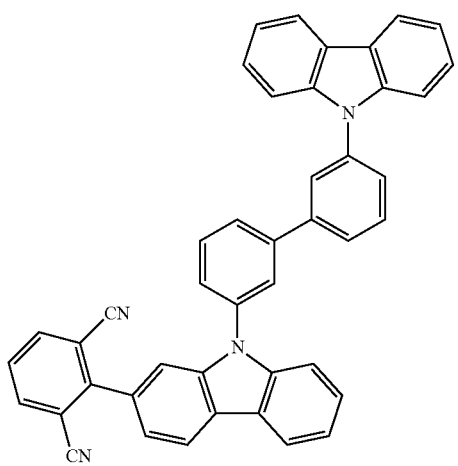
72
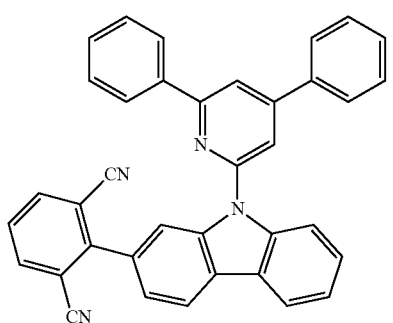
73
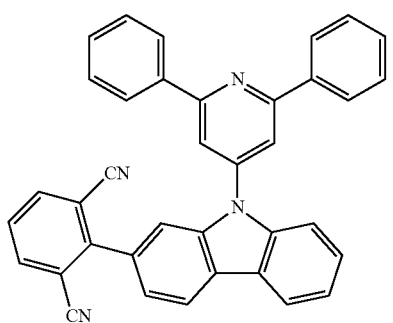
74
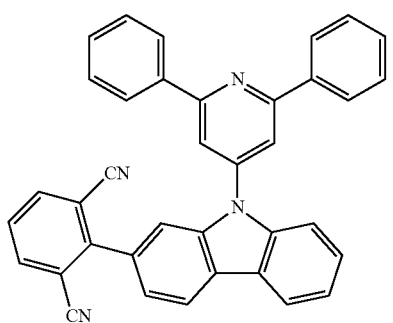
-continued
75
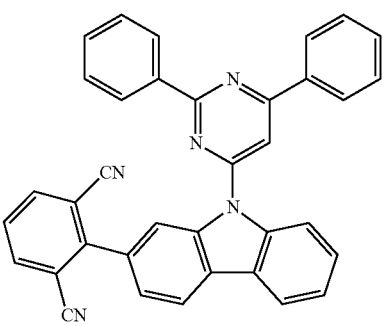
76
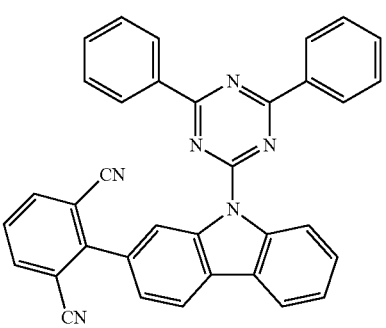
77
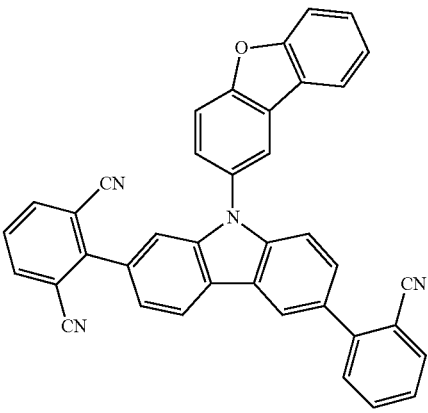
78
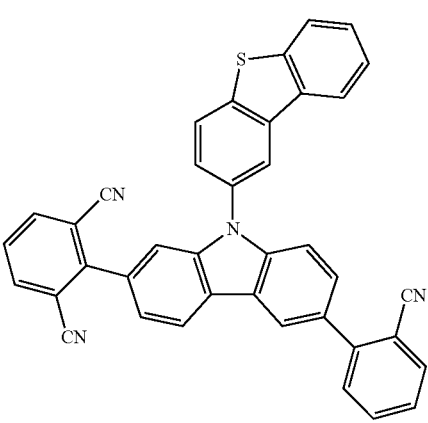

79
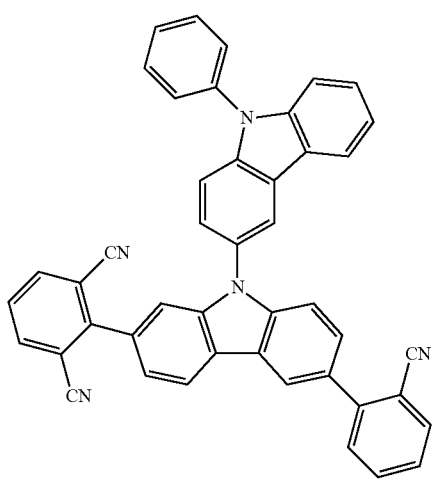
80
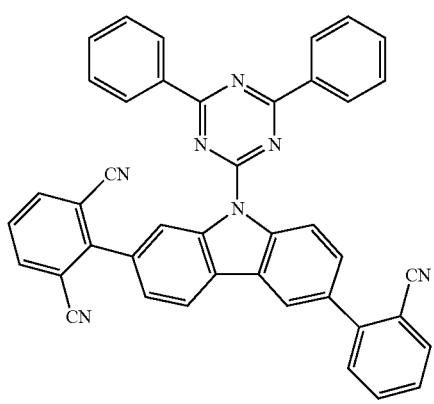
81
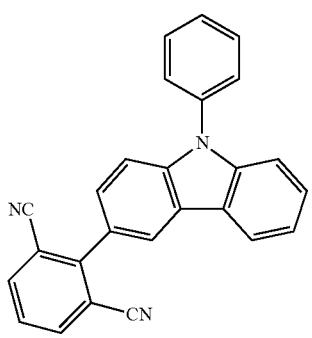
82
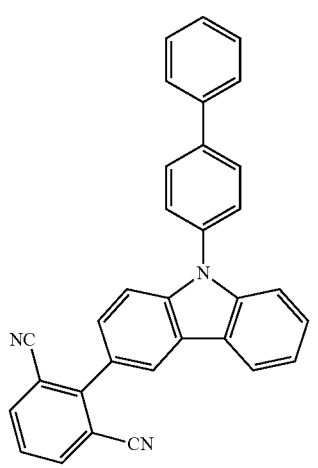
83
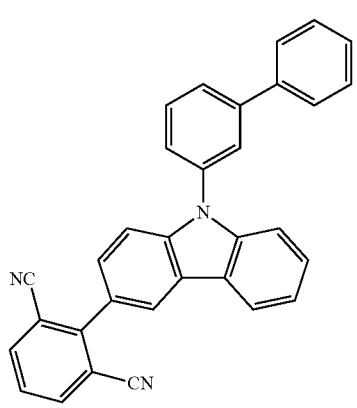
84
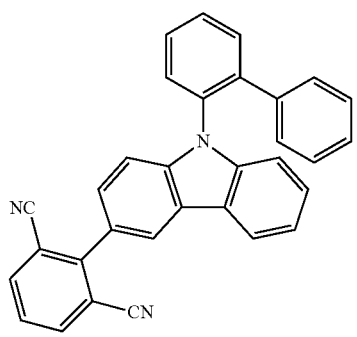
85
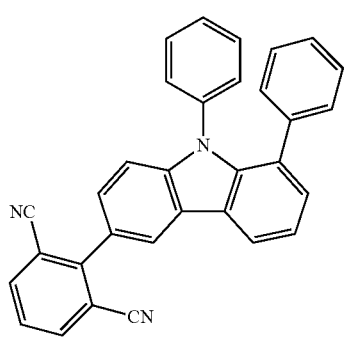

86
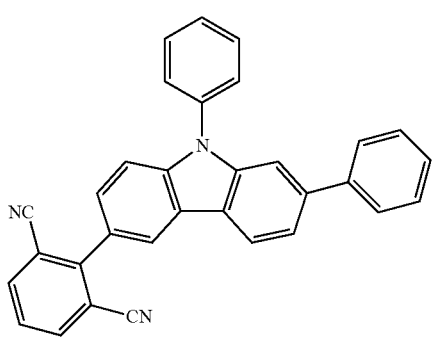
87
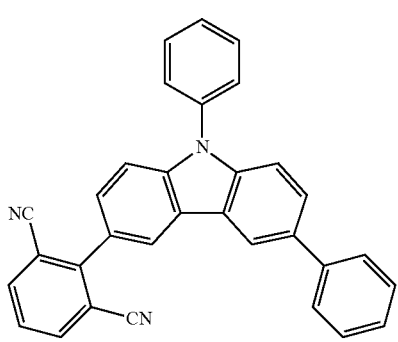
88
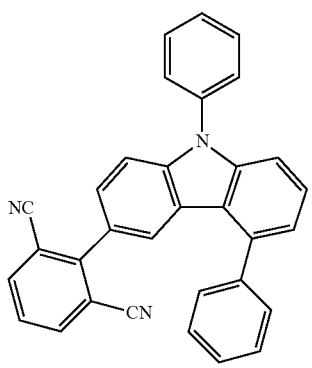
89
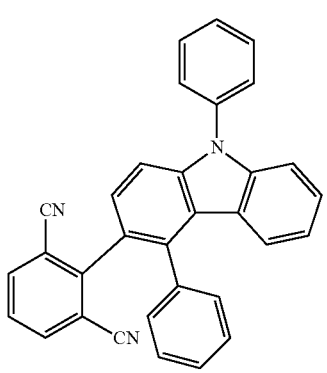
90
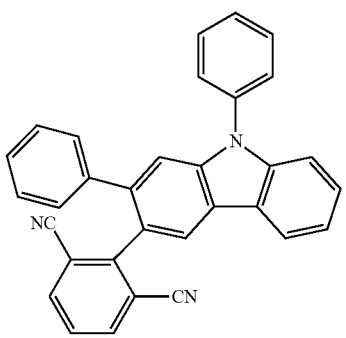
91
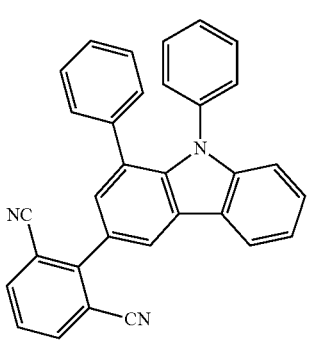
92
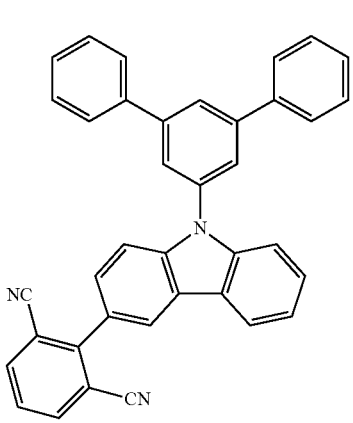
93
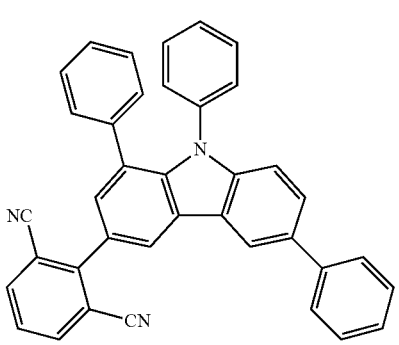

-continued
94
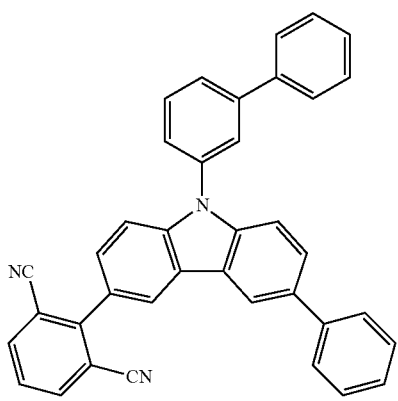
95
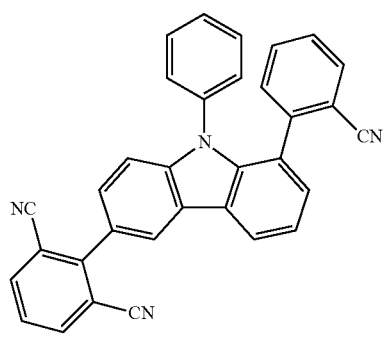
96
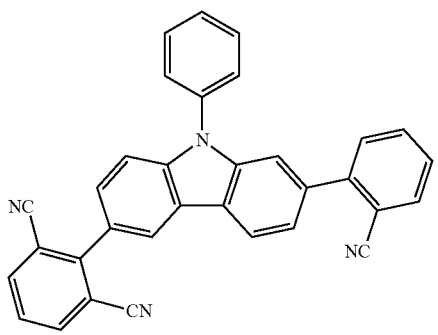
97
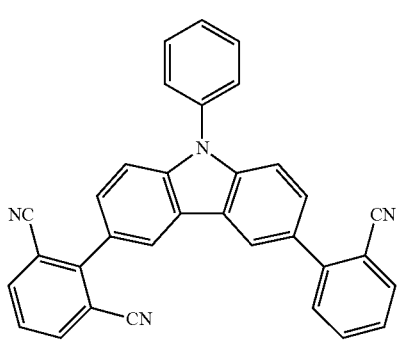
-continued
98
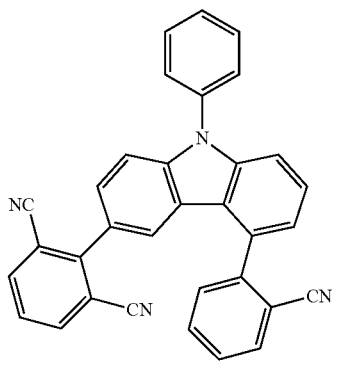
99
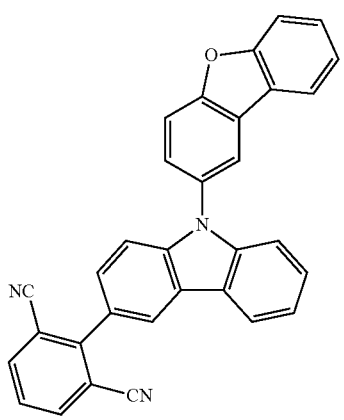
100
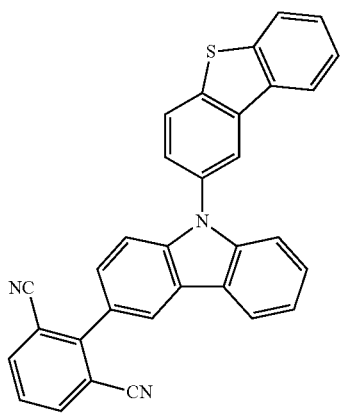
101
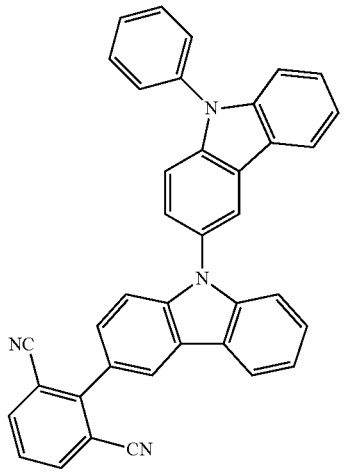

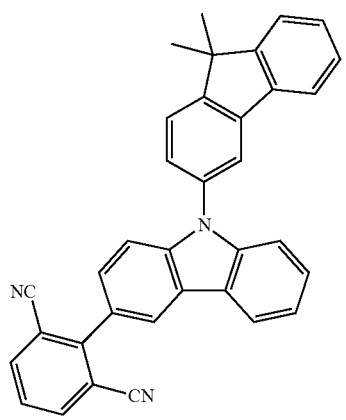
101
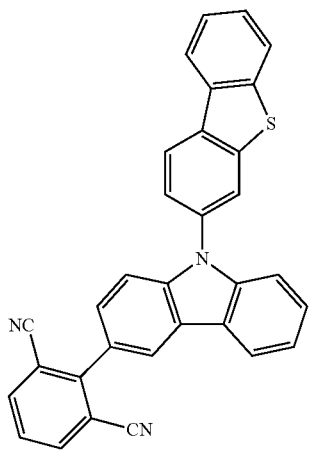
102
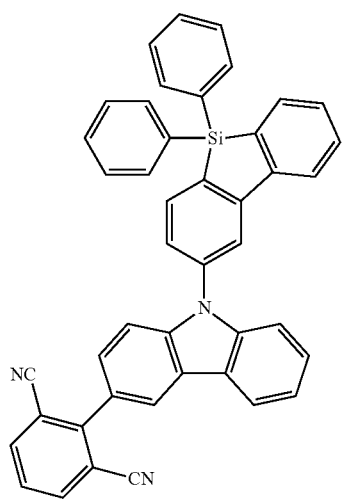
103
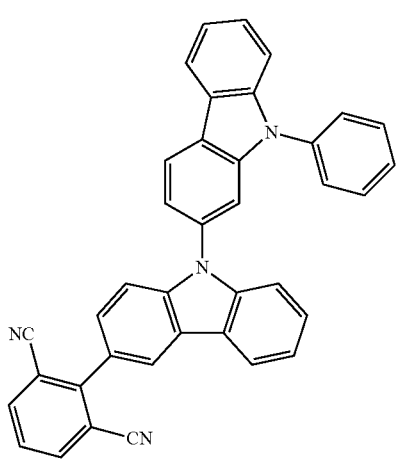
105
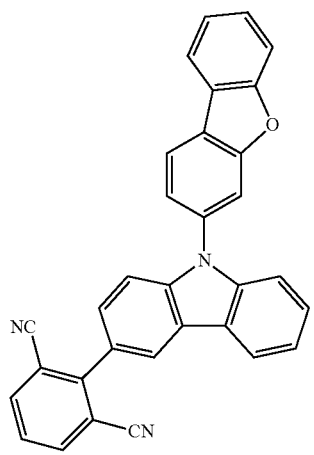
104
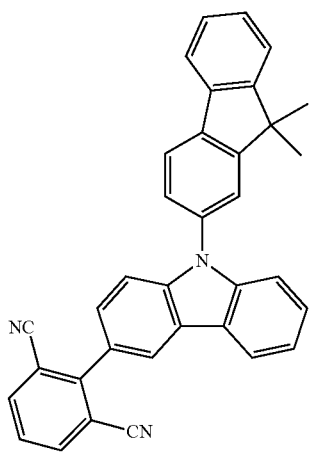
106
107

108
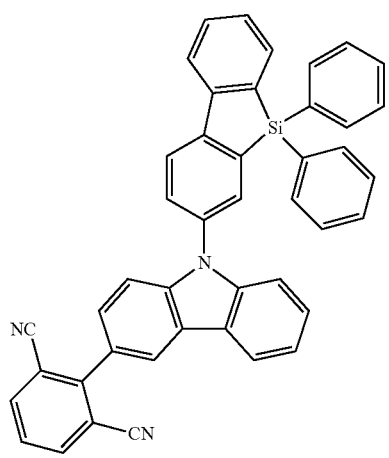
109
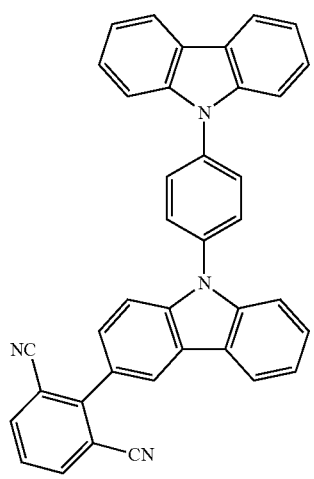
110
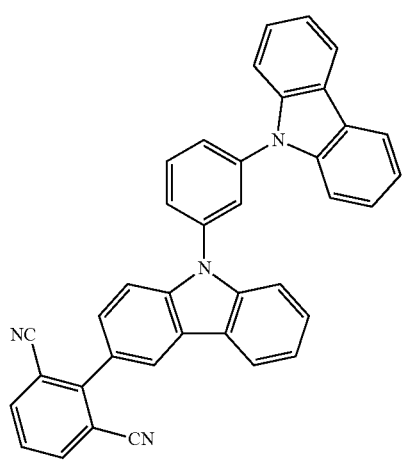
111
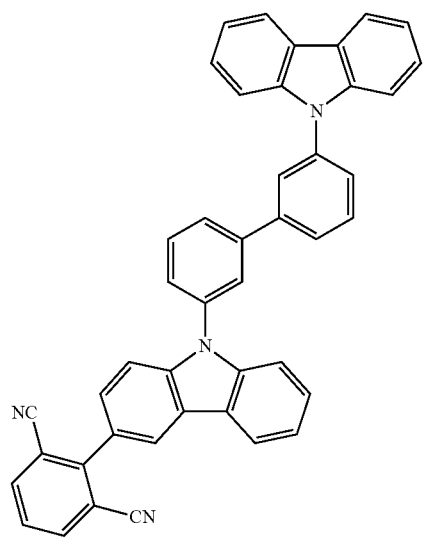
112
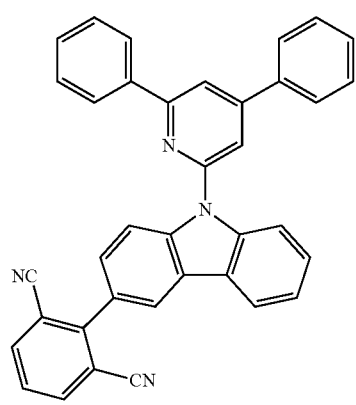
113
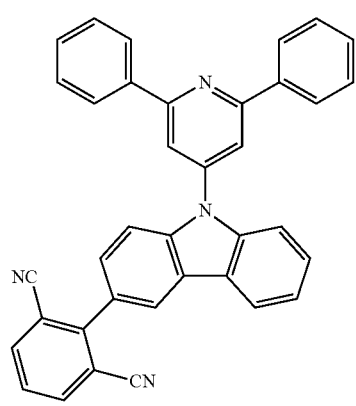

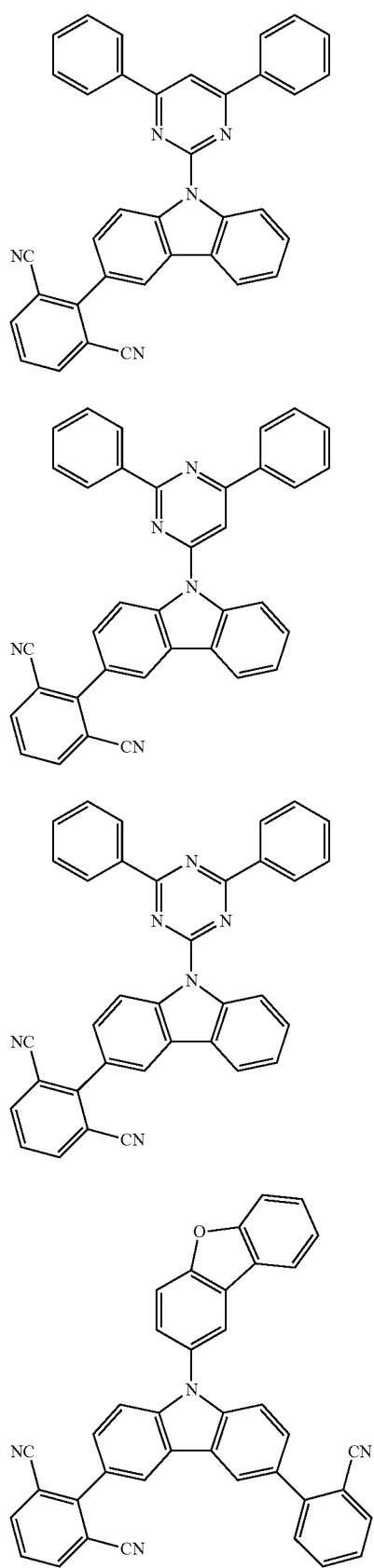
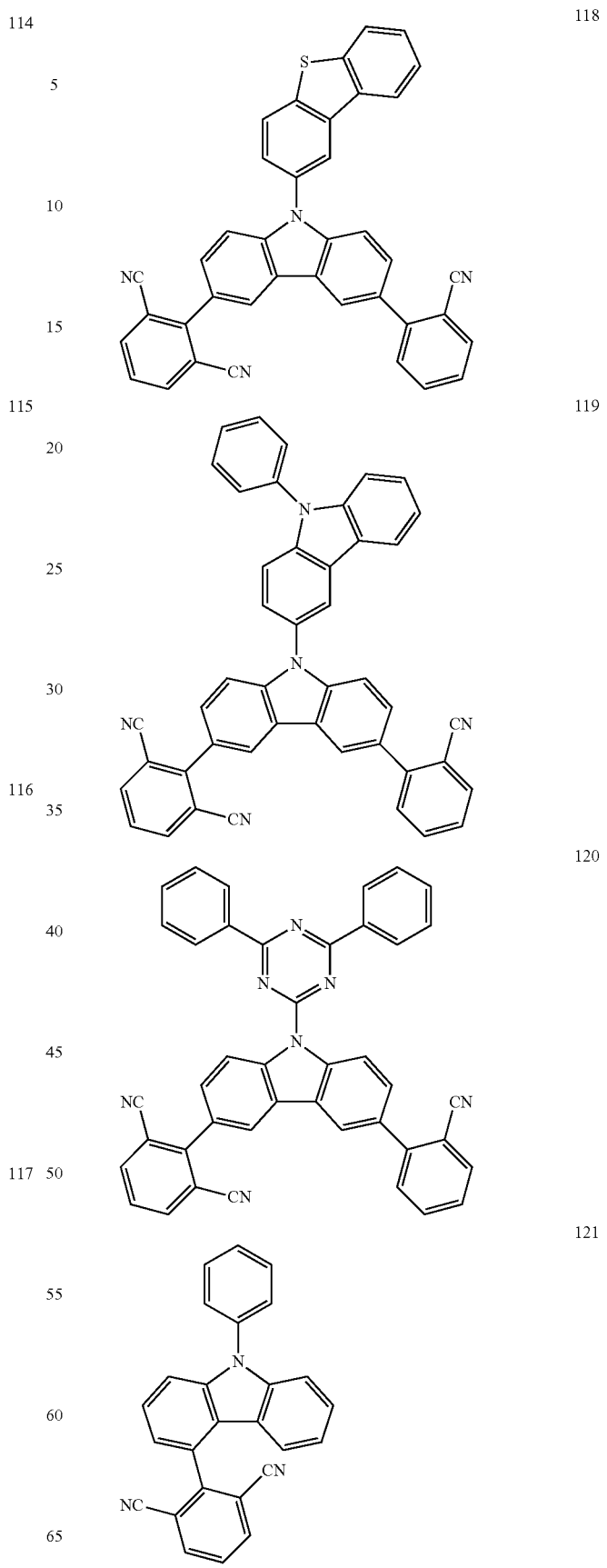

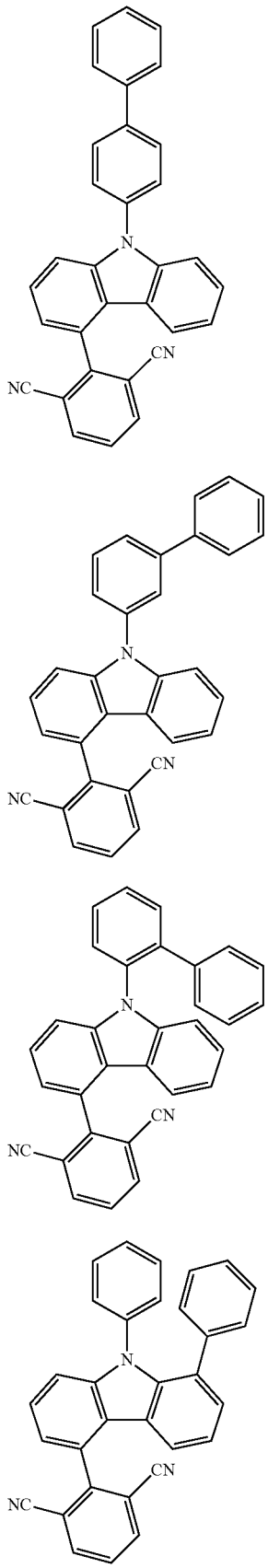
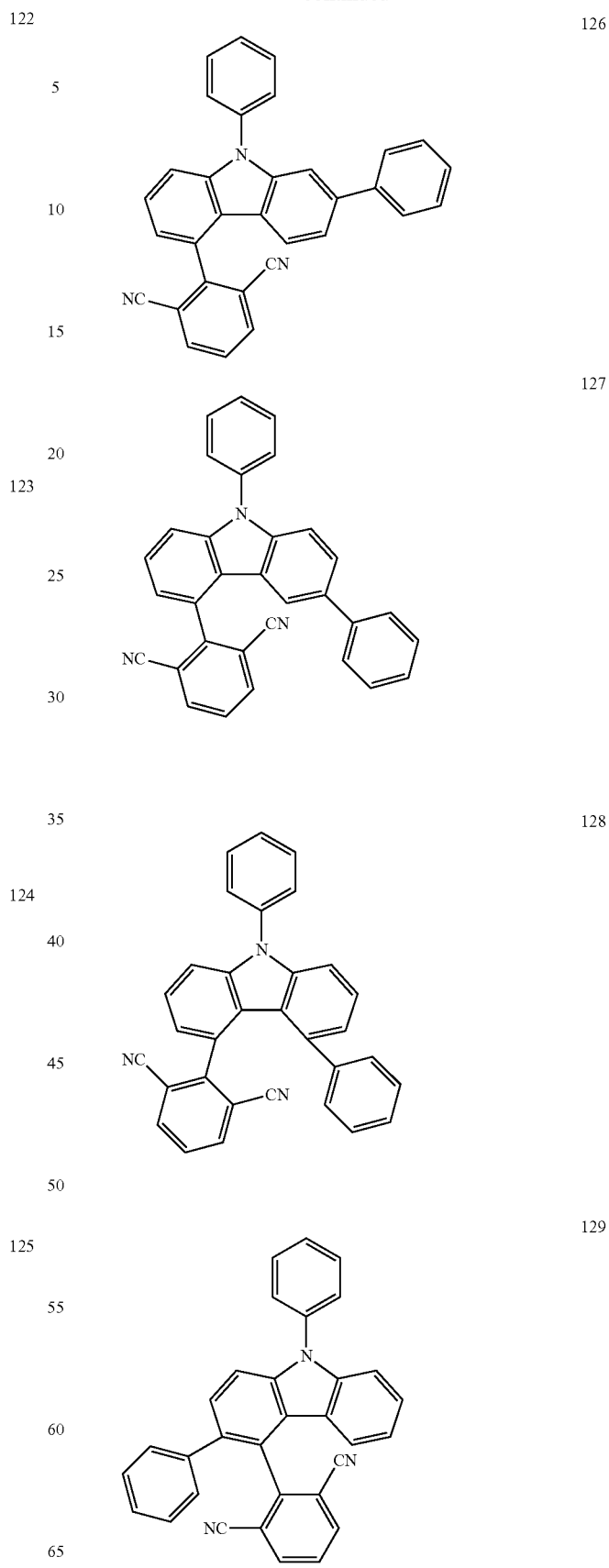

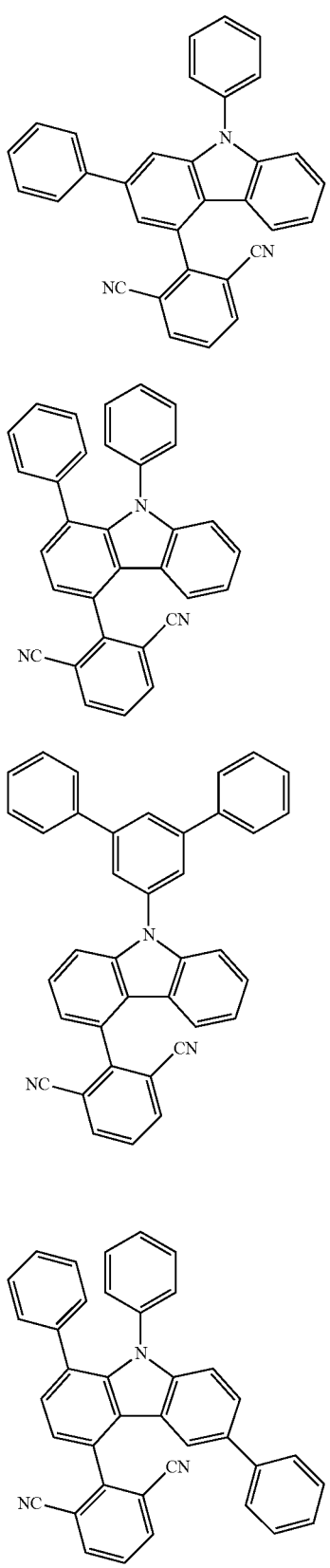
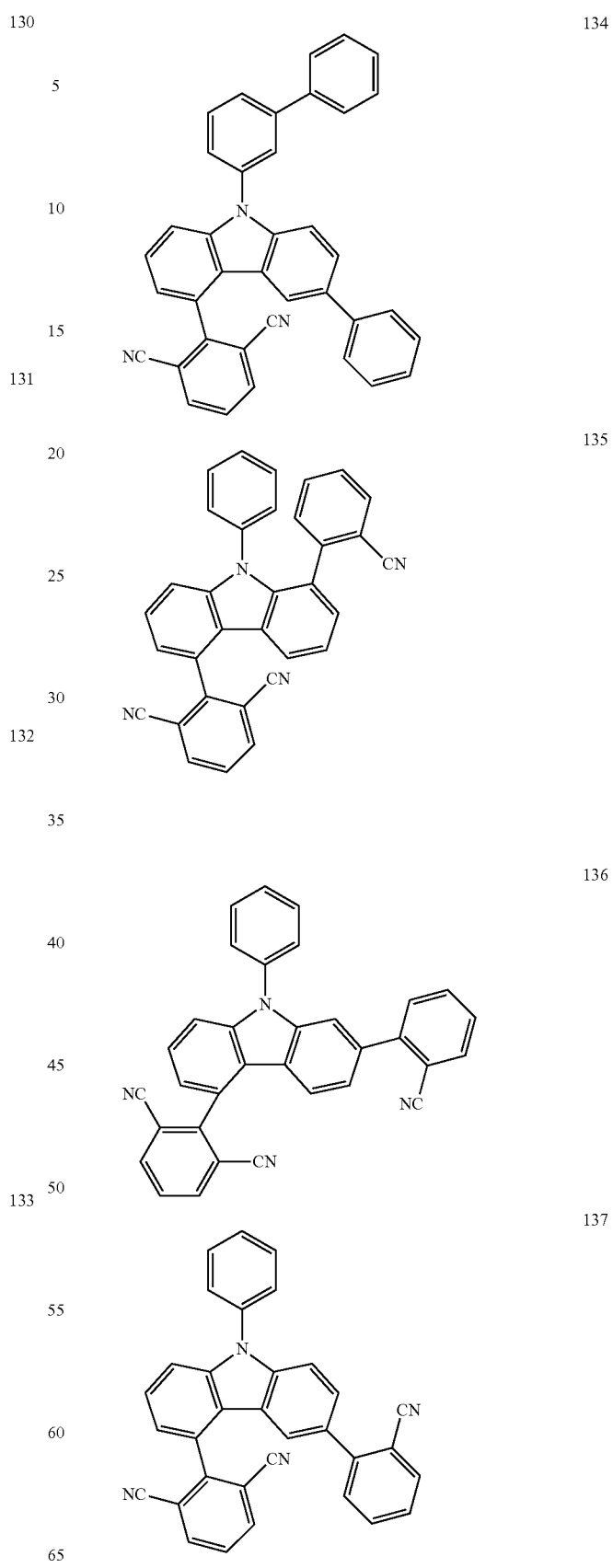

138
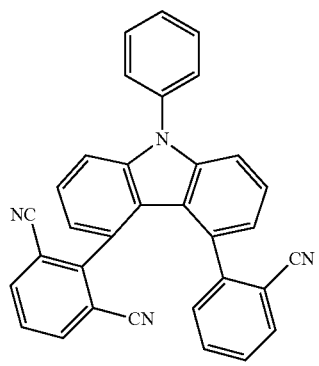
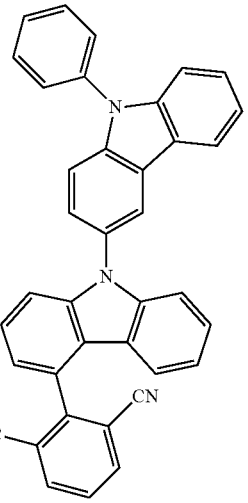
141
139
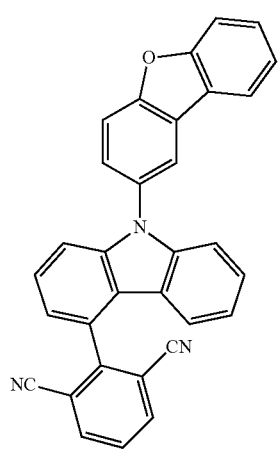
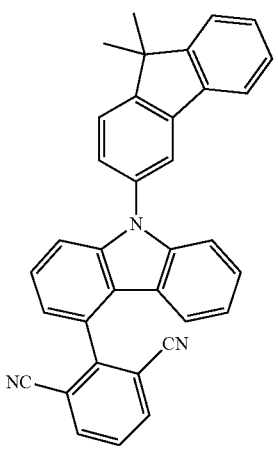
142
140
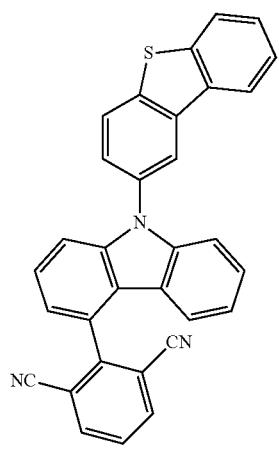
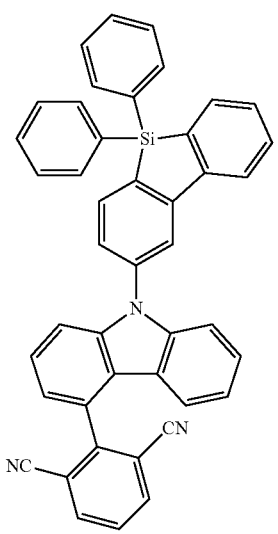
143

144
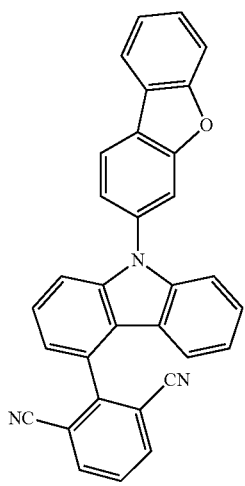
145
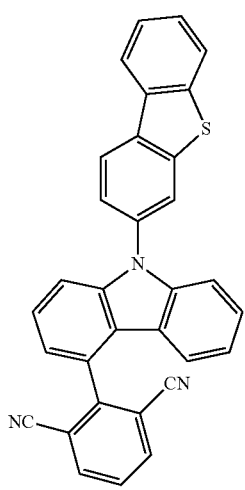
146
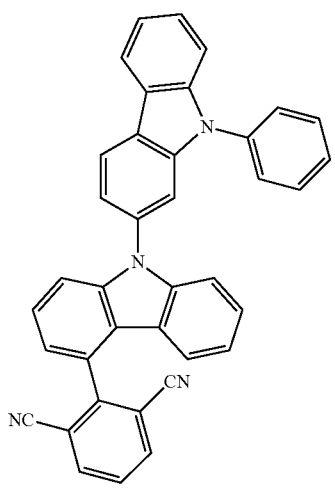
147
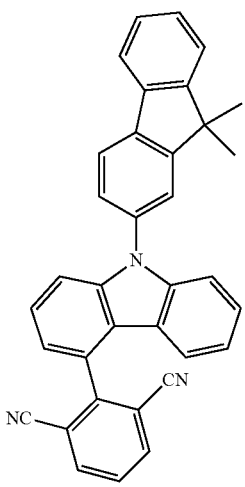
148
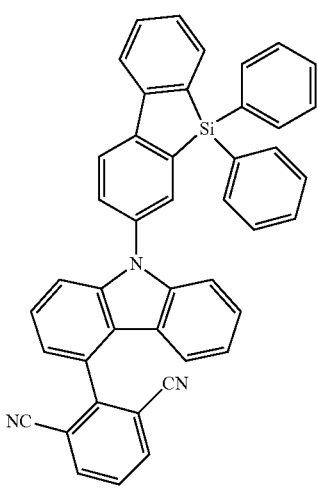
149
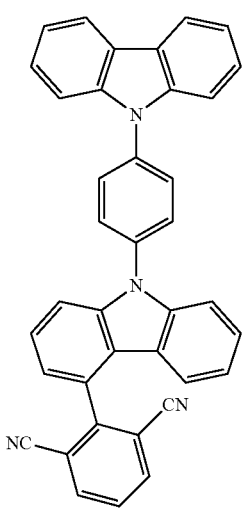

150
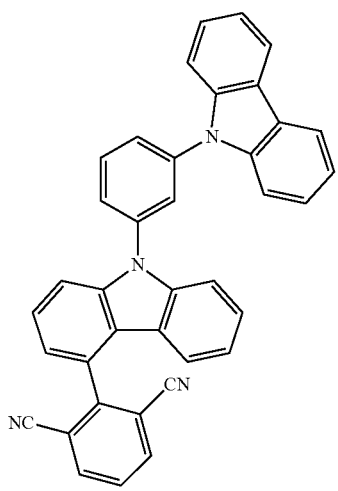
151
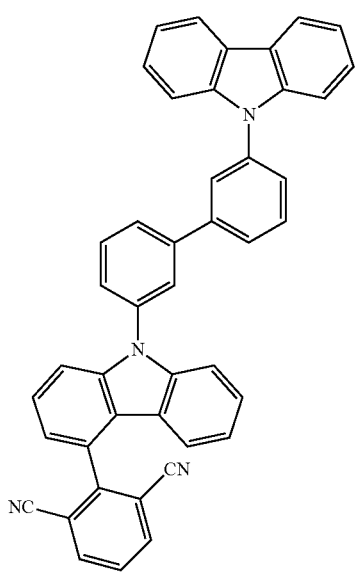
152
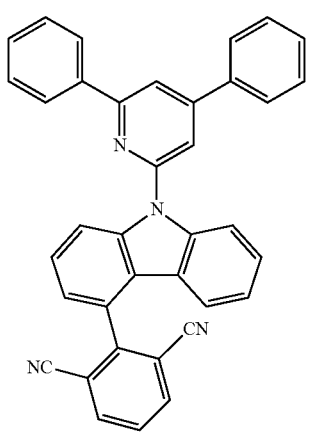
153
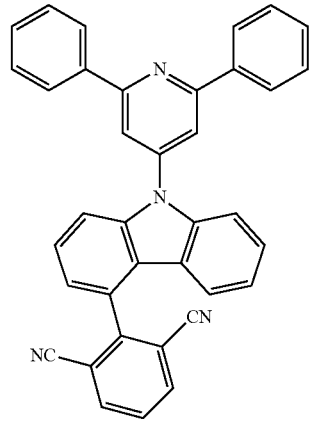
154
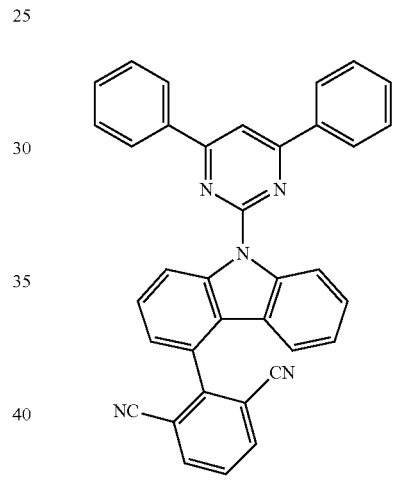
155
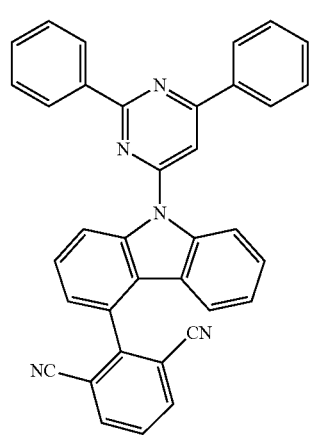

-continued
156
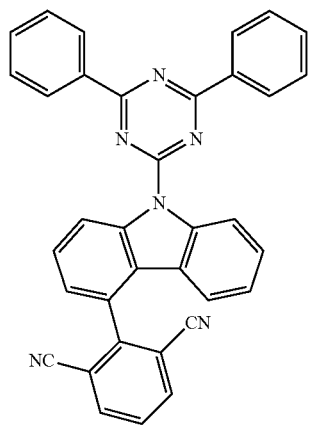
157
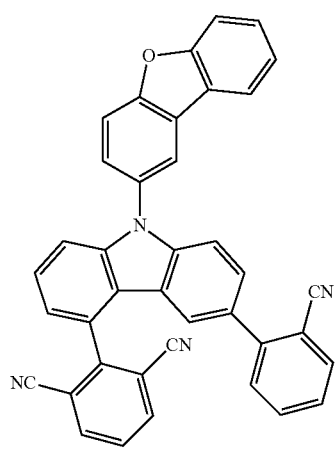
158
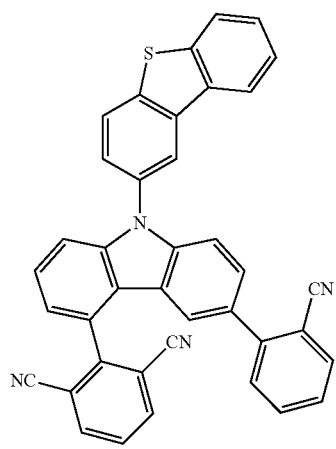
-continued
159
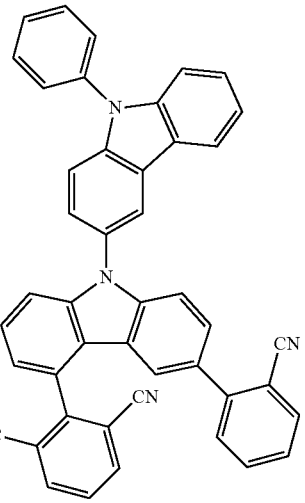
160
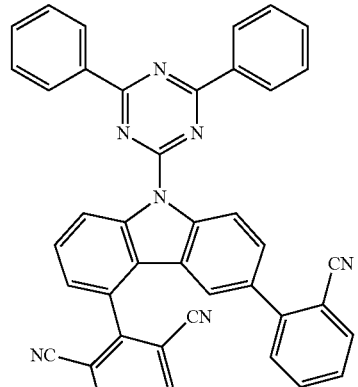
161
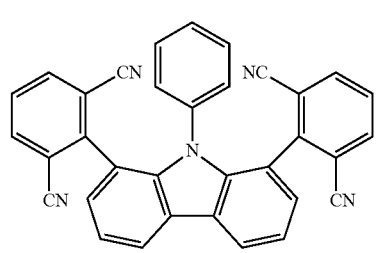
162
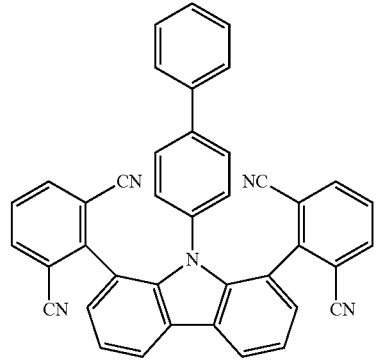

163
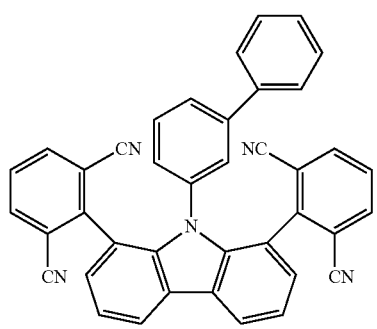
164
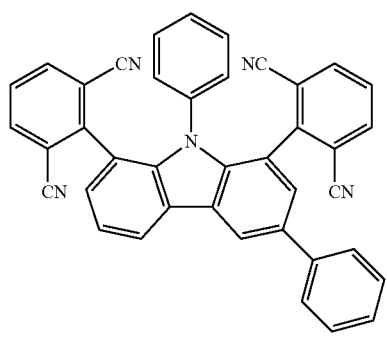
165
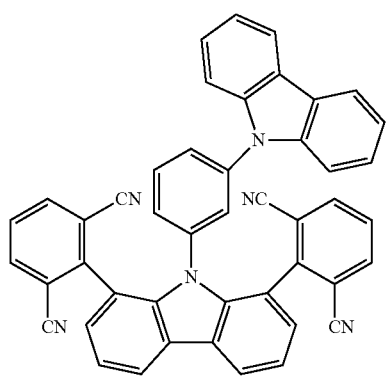
166
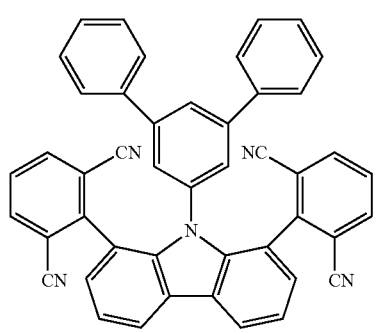
167
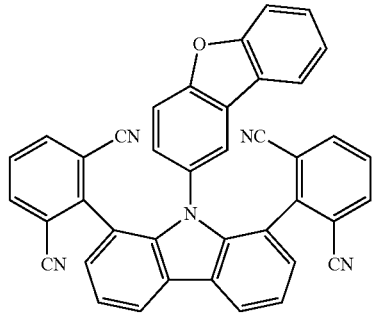
168
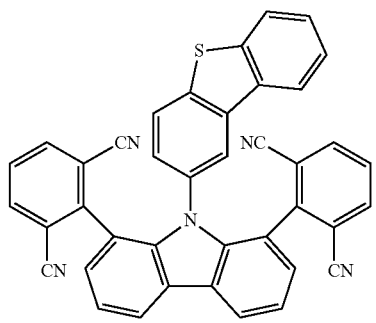
169
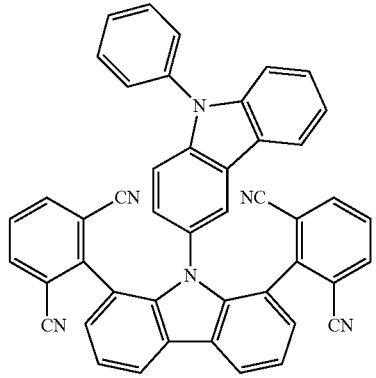
170
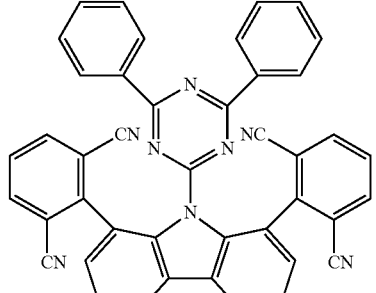
171
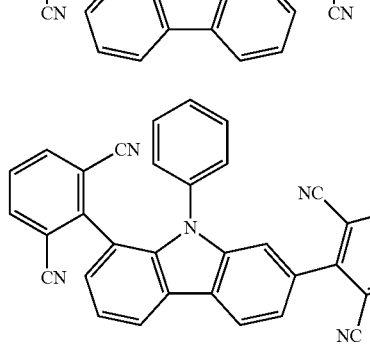

-continued
172
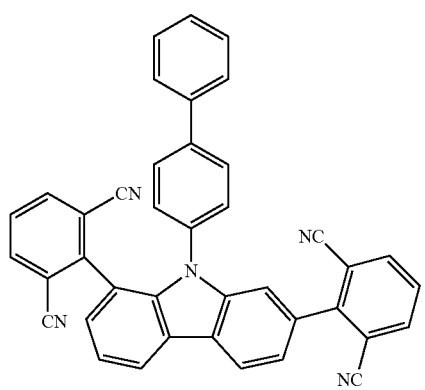
173
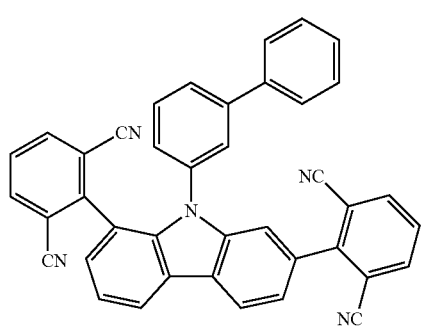
174
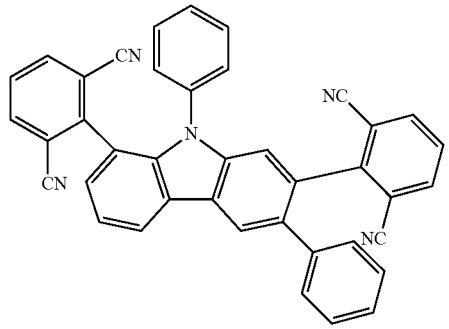
175
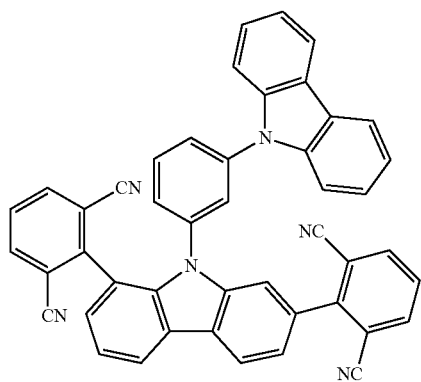
-continued
176
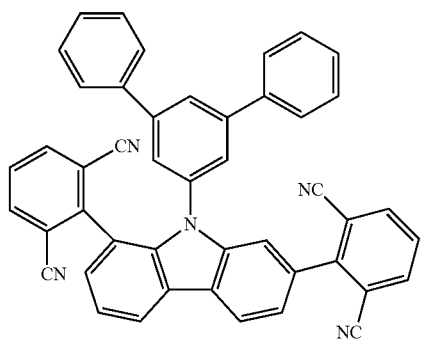
177
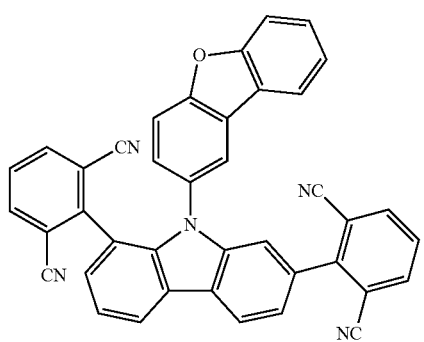
178
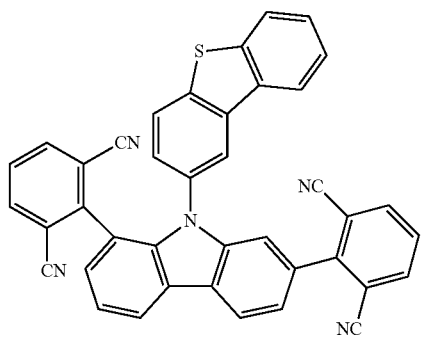
179
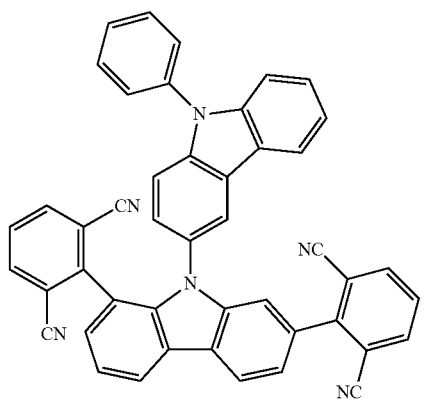

180
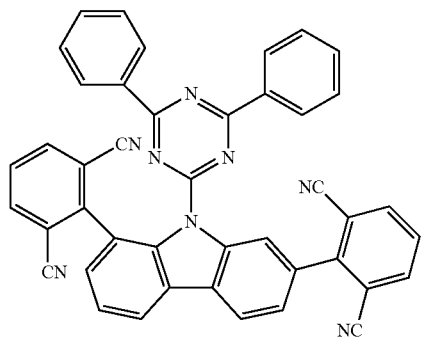
181
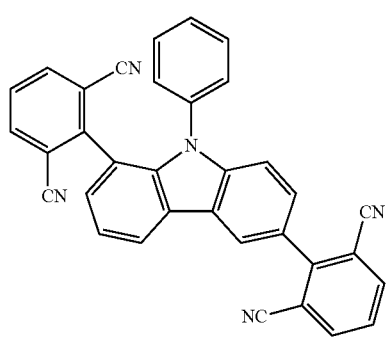
182
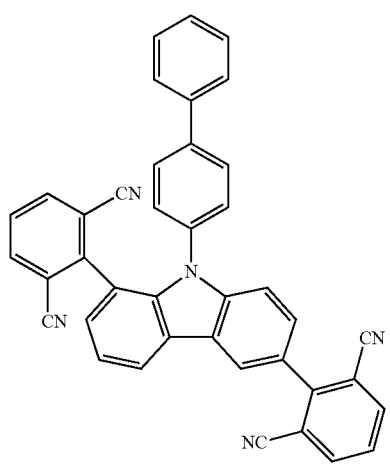
183
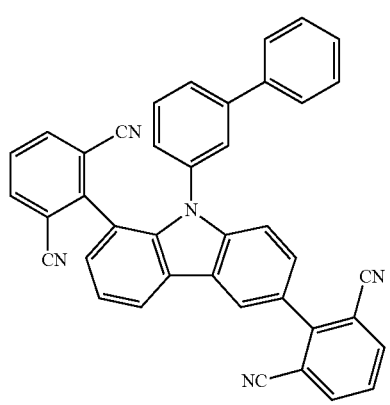
184
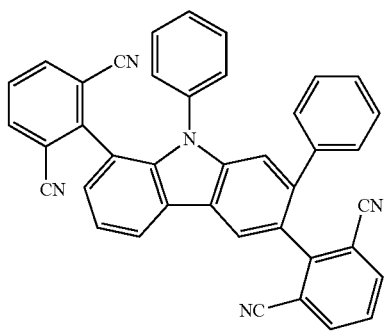
185
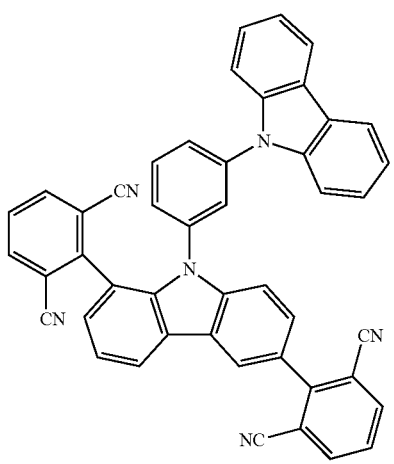
186
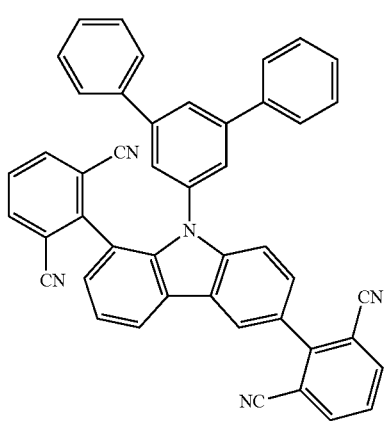
187
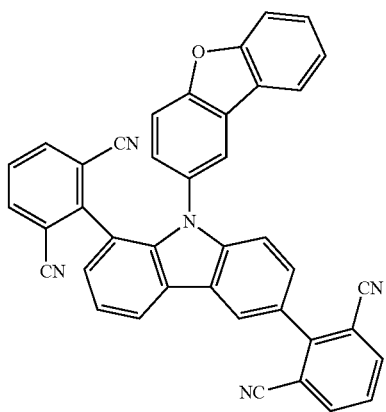

188
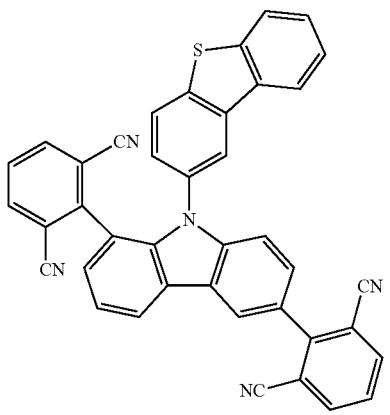
189
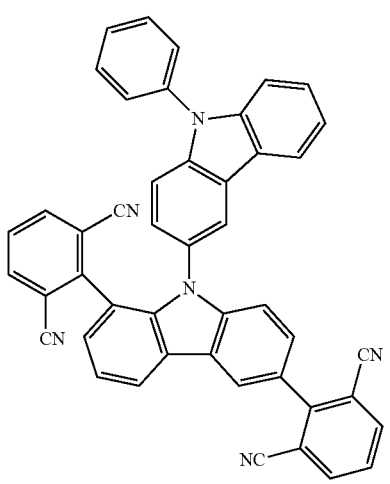
190
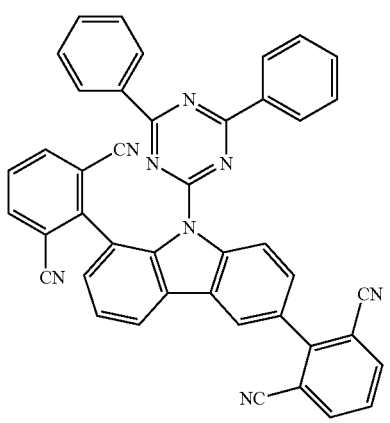
191
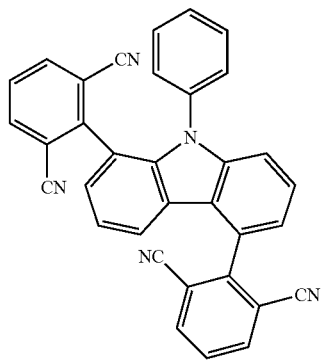
192
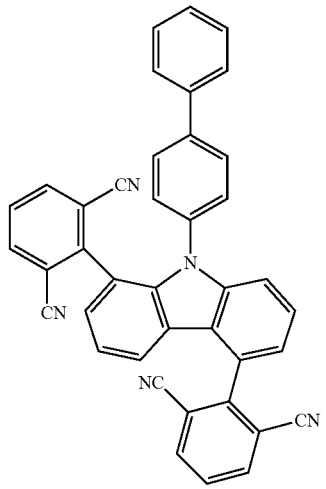
193
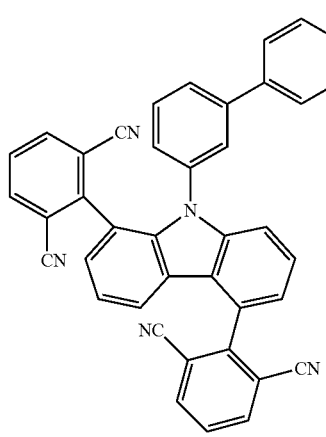
194
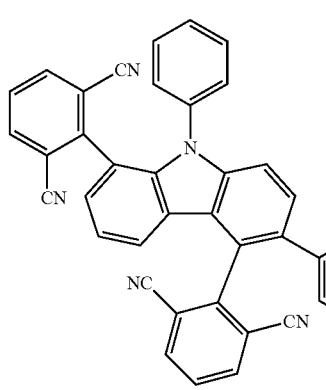

195
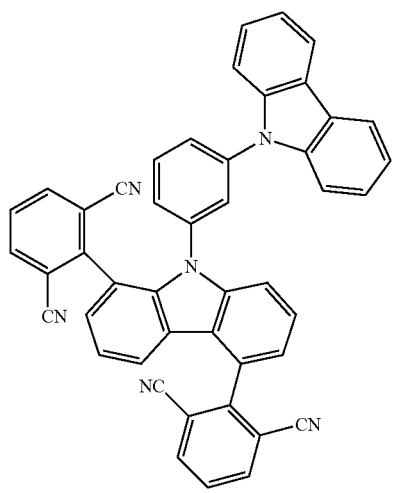
196
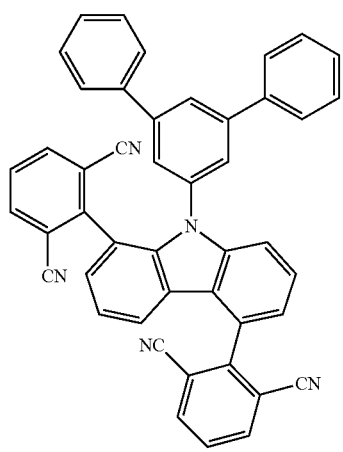
197
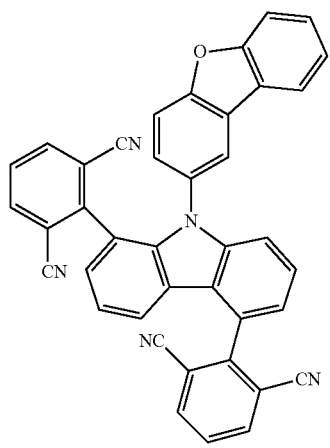
198
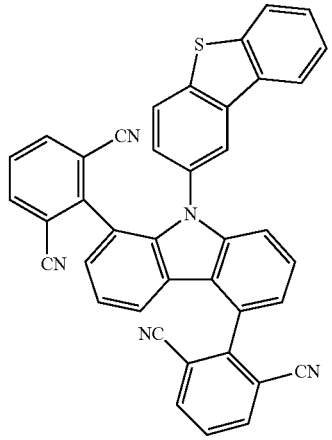
199
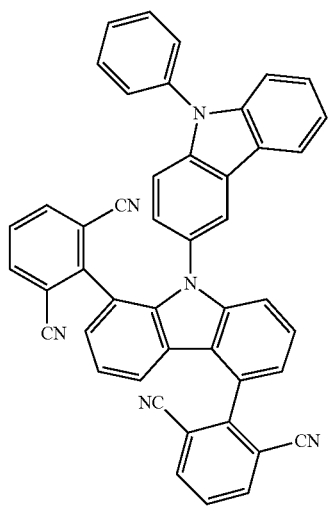
200
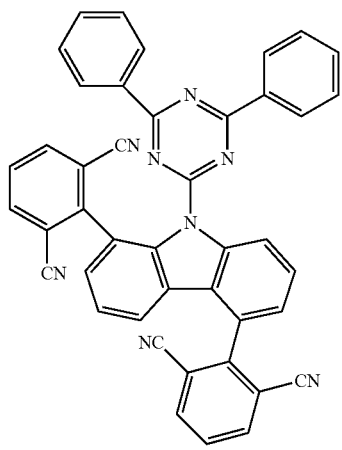
201
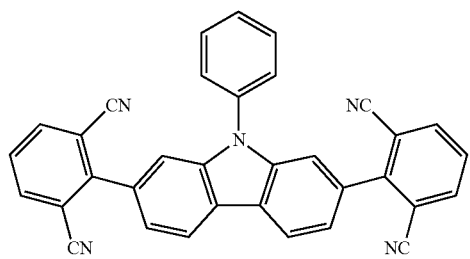

202
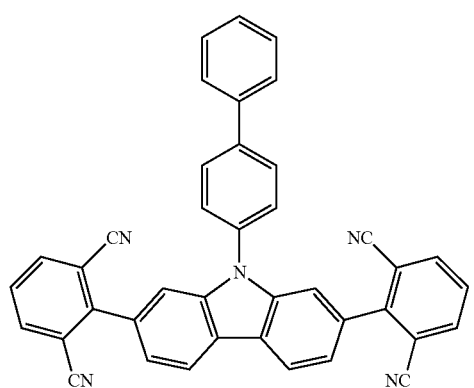
203
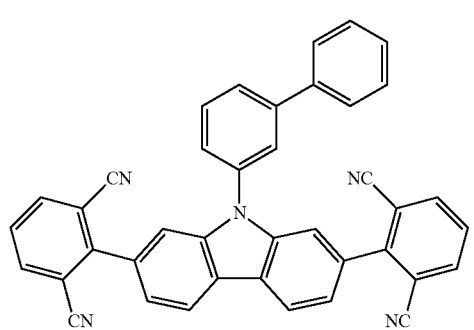
204
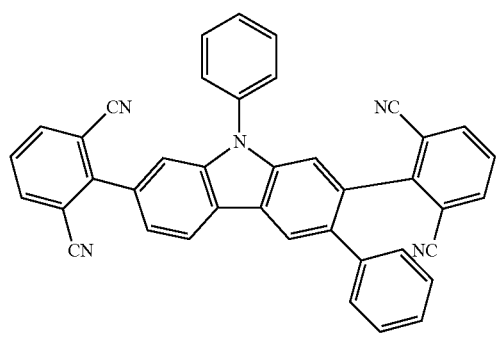
205
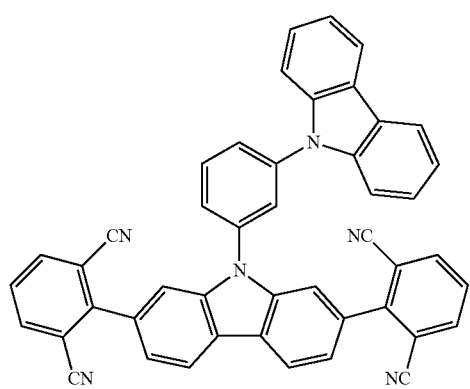
206
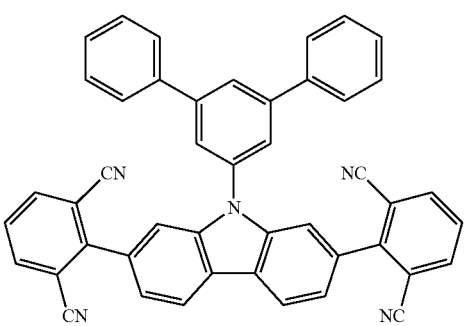
207
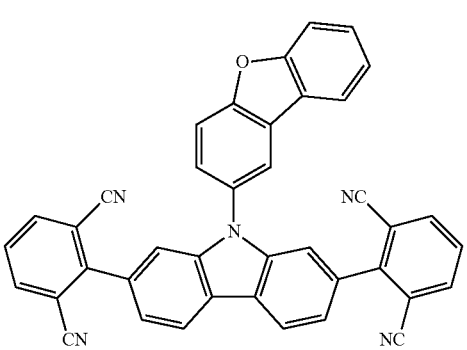
208
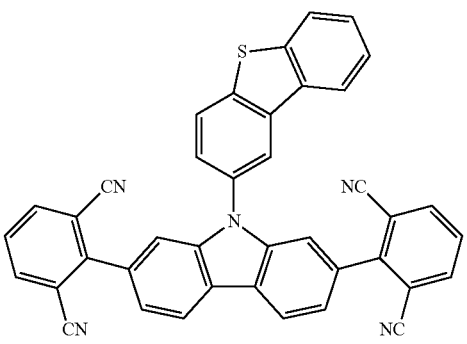
209
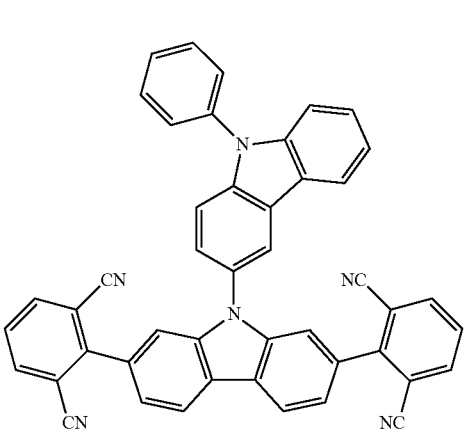

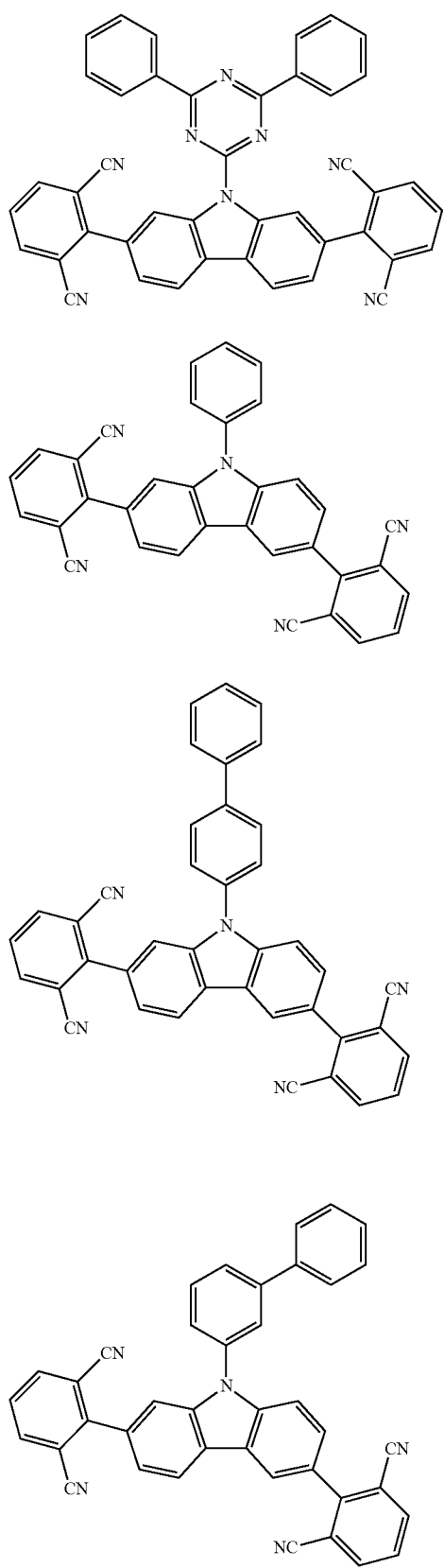
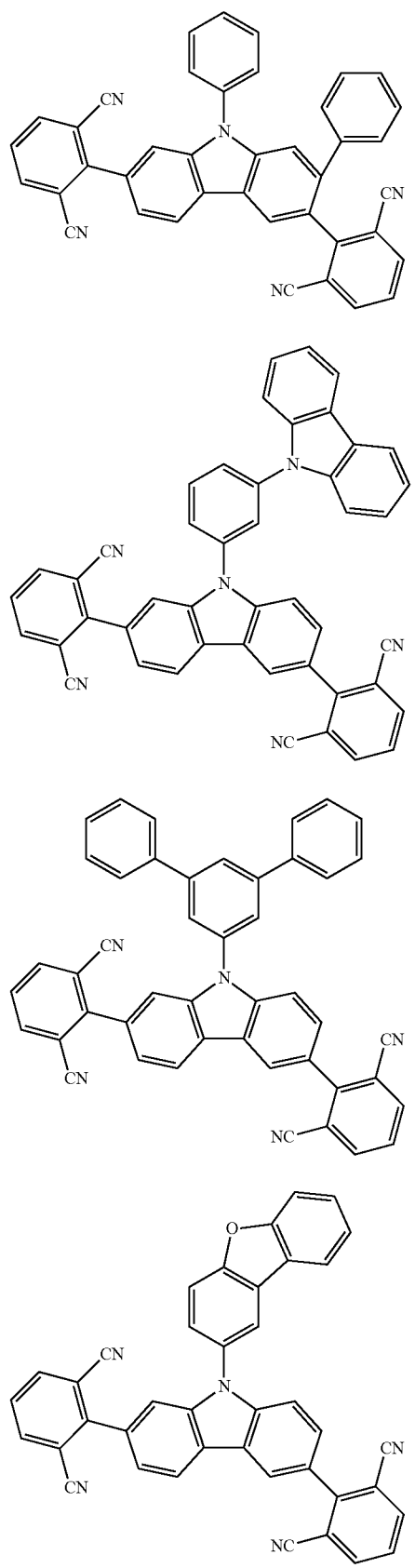

-continued
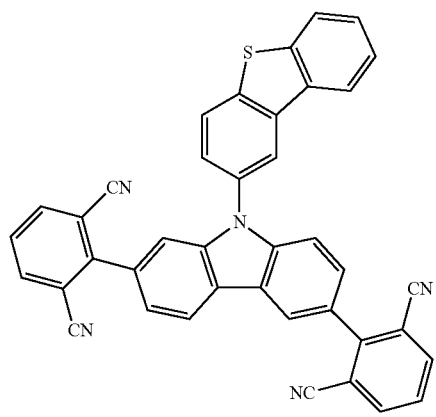
218
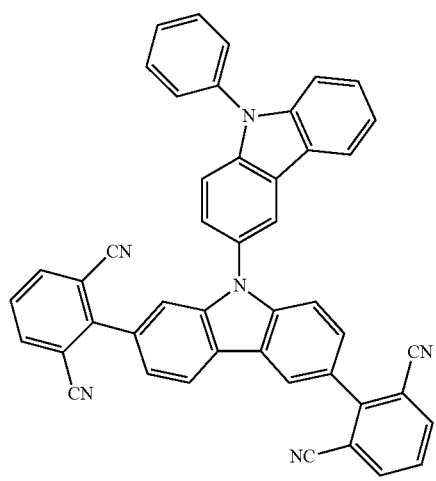
219
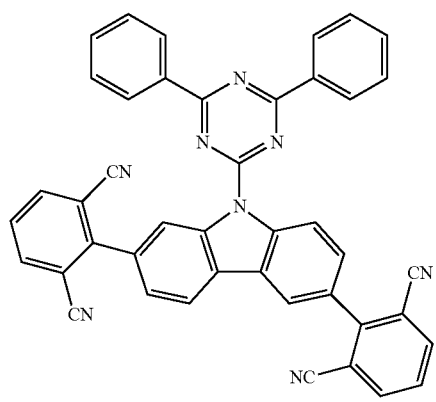
220
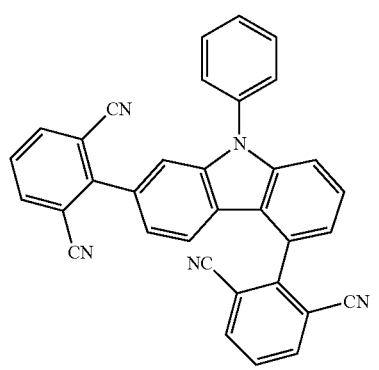
221
-continued
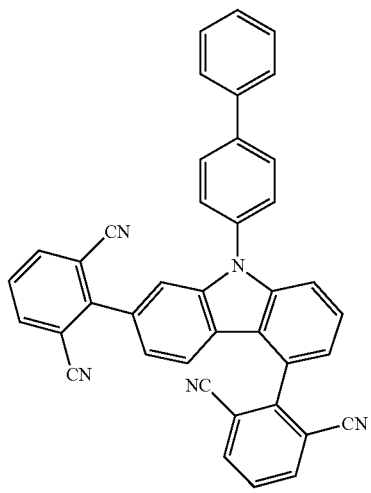
222
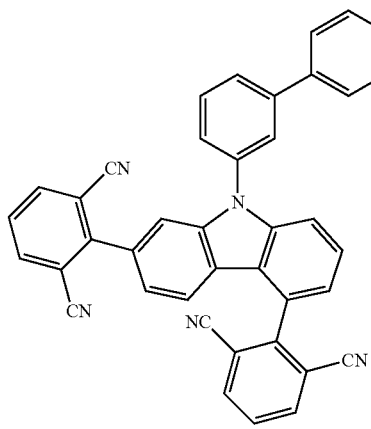
223
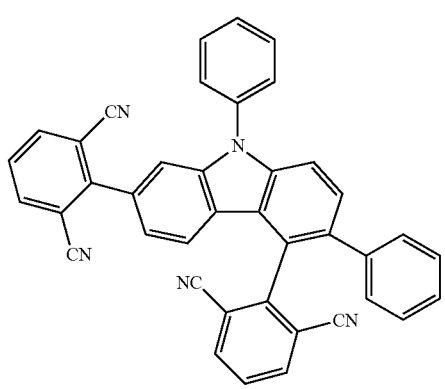
224

225
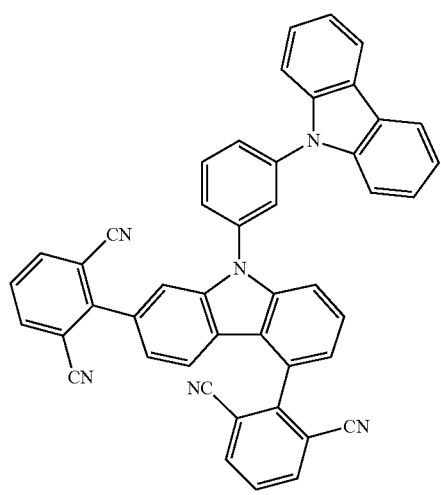
226
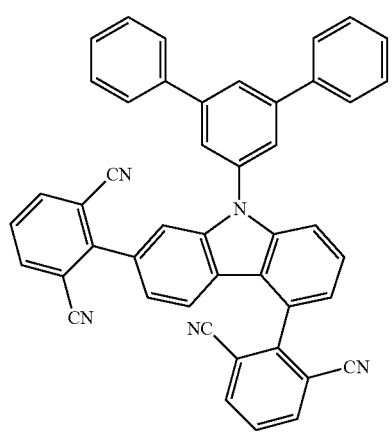
227
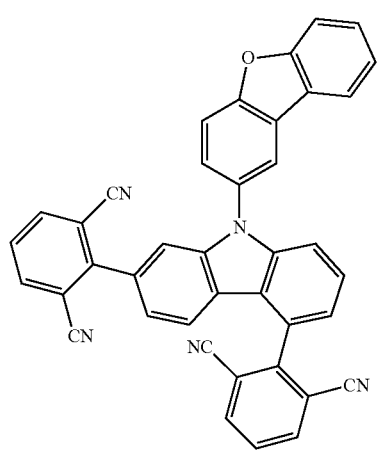
228
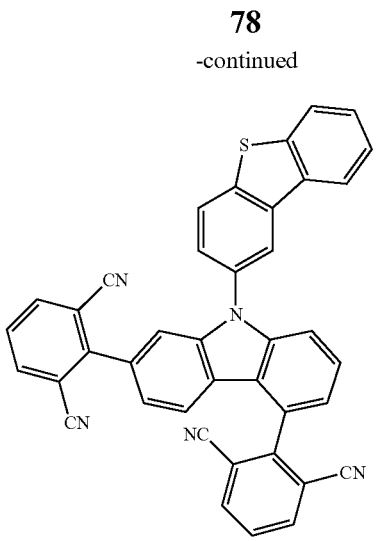
229
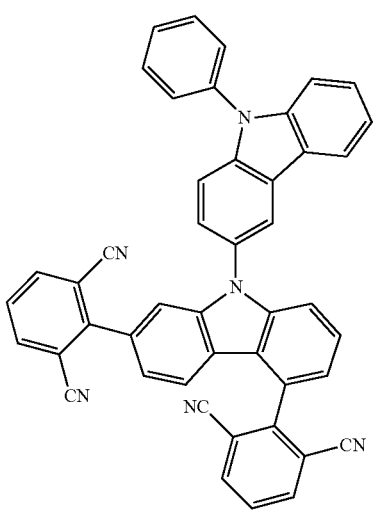
230
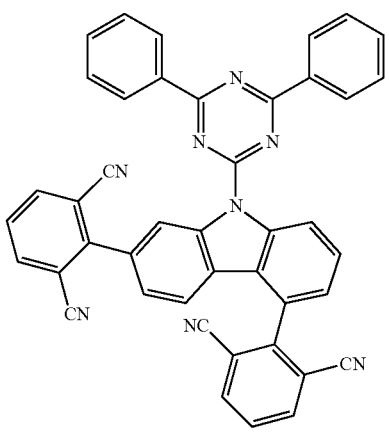

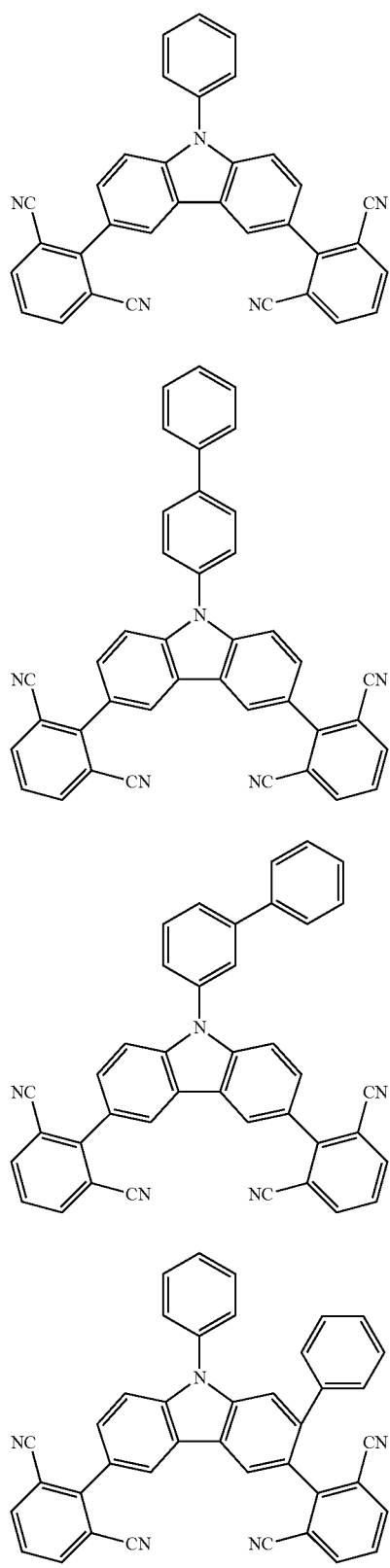
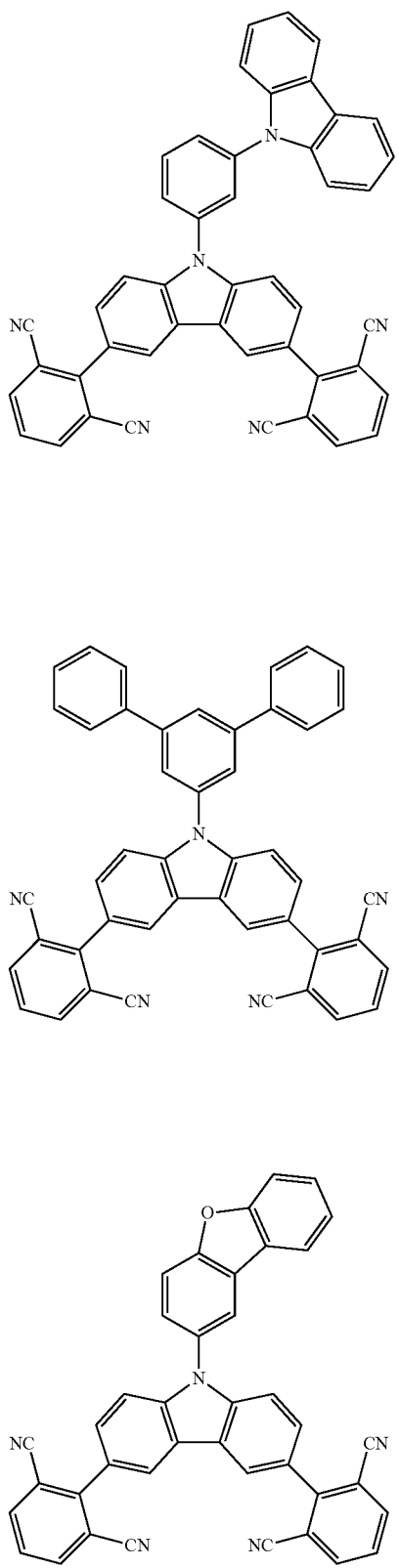

238
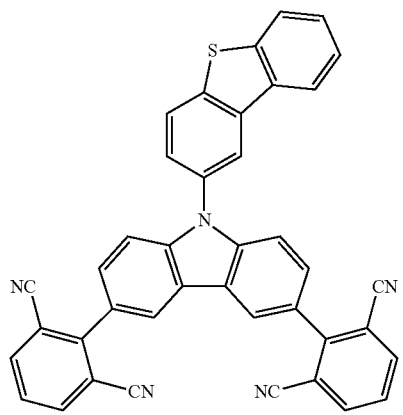
239
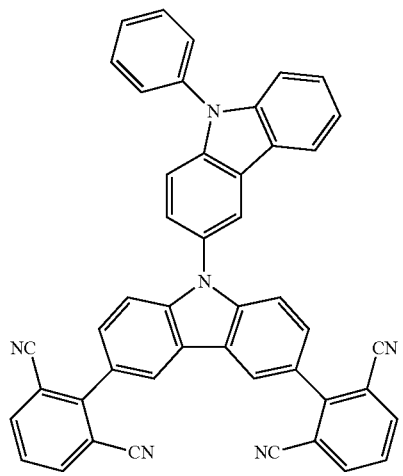
240
241
242
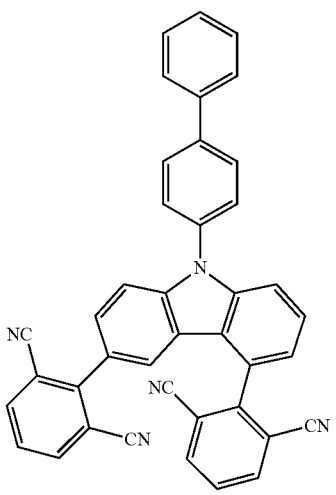
243
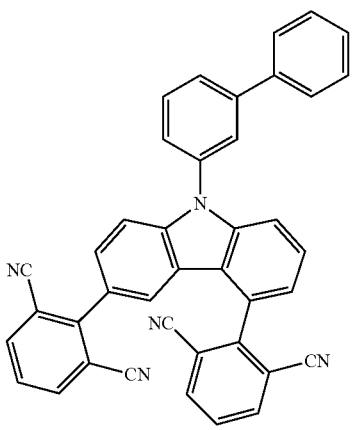
244
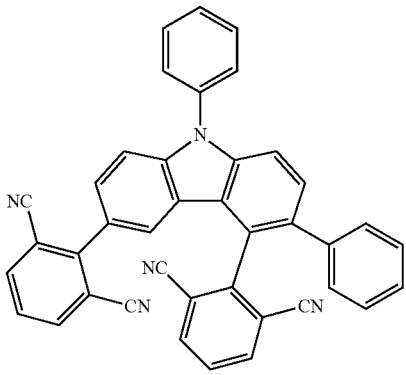

245
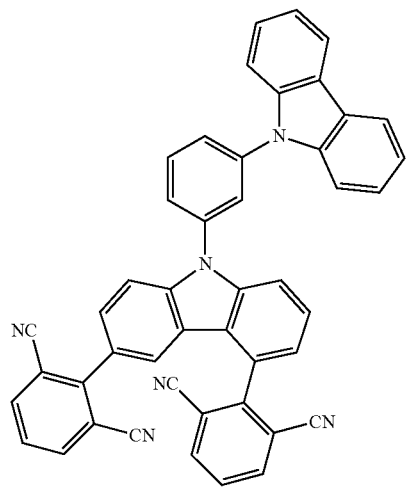
246
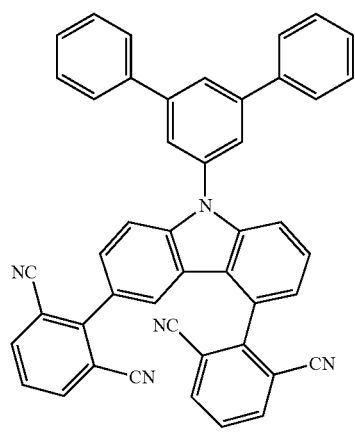
247
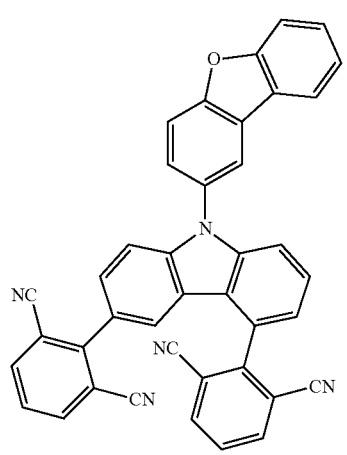
248
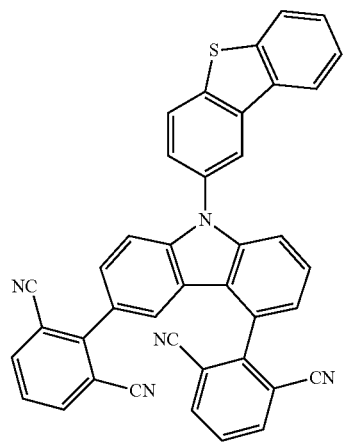
249
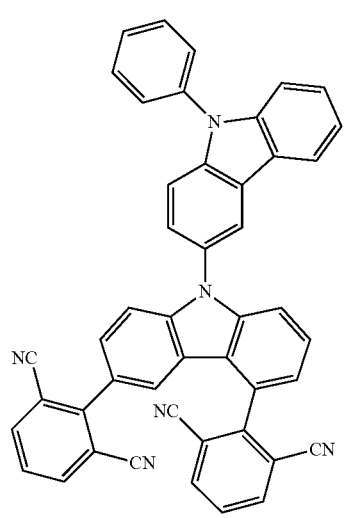
250
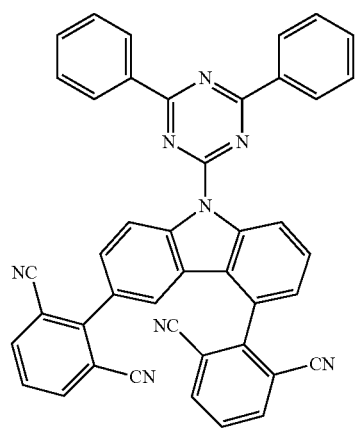

251
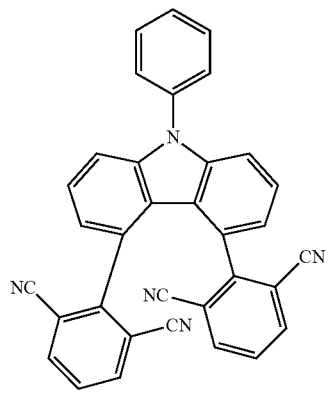
252
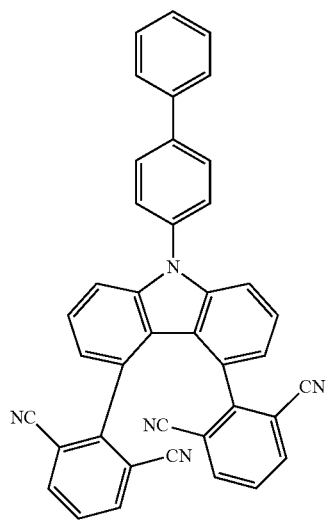
253
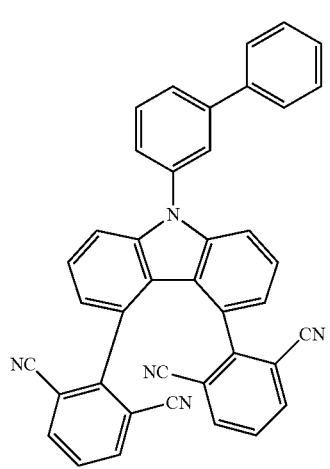
254
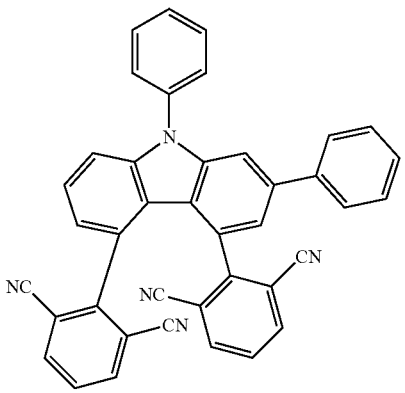
255
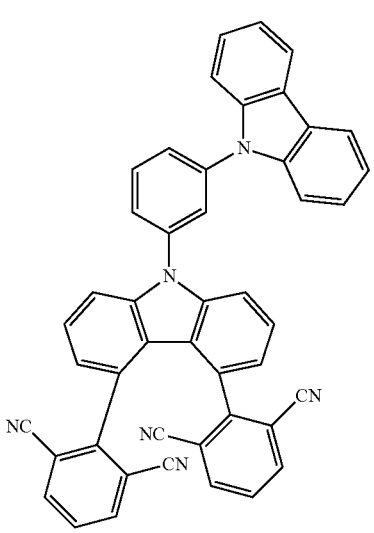
256
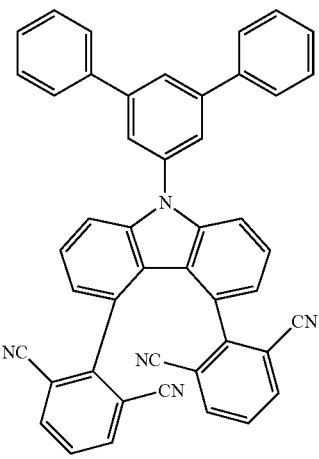

257
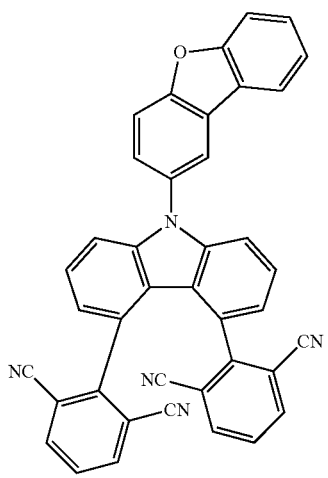
258
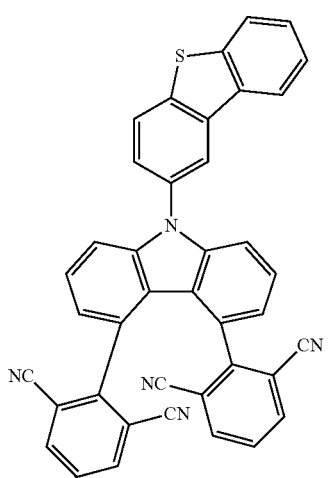
259
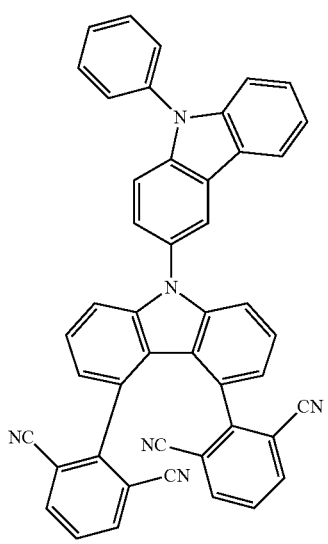
260
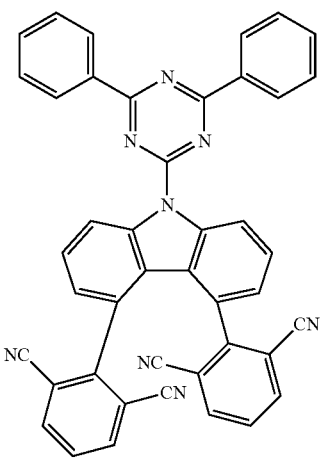
261
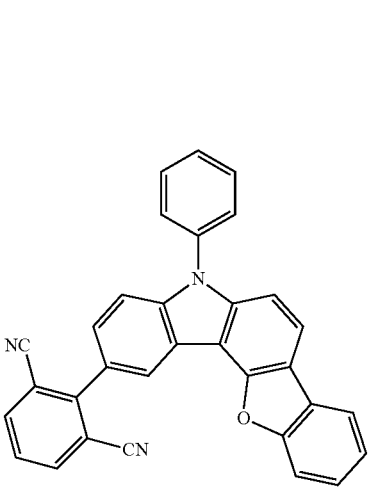
262
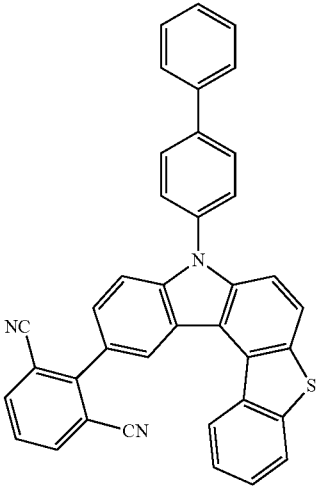

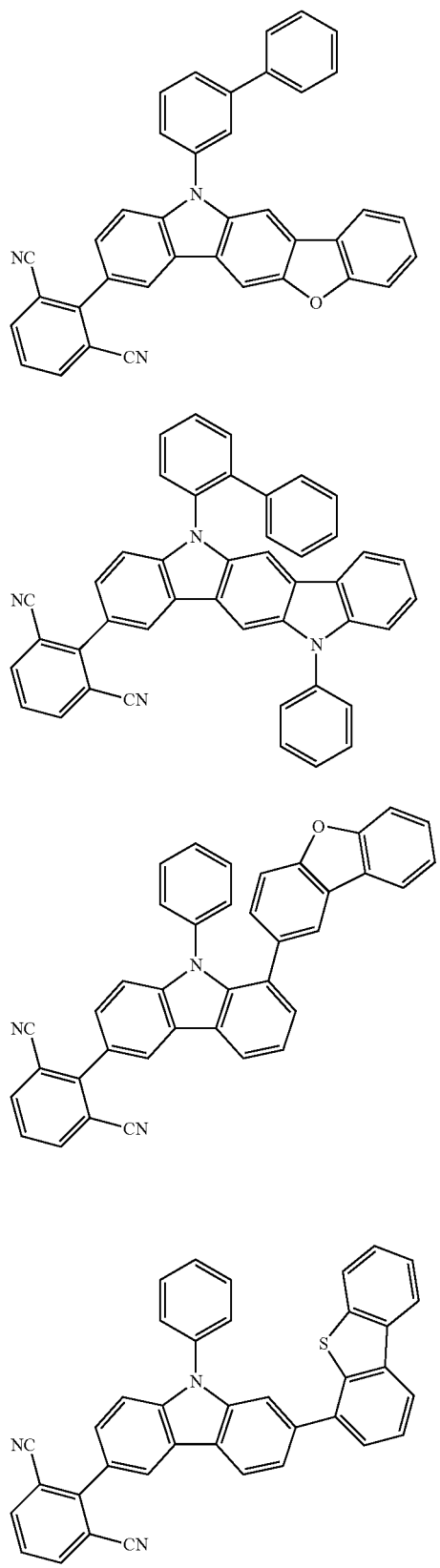
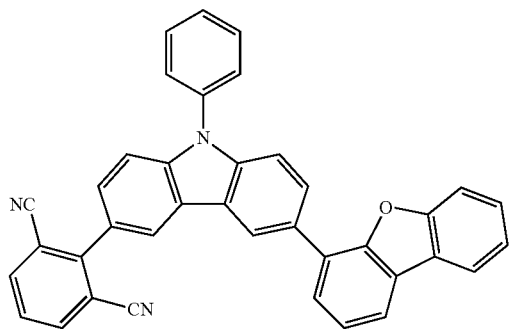
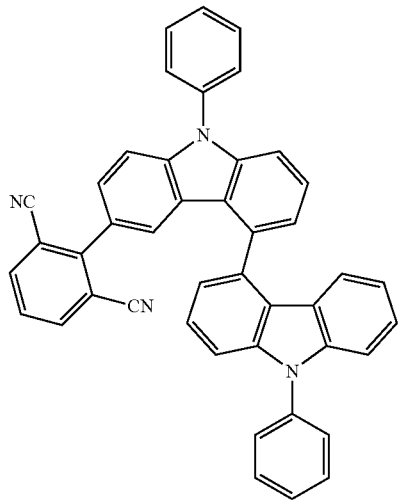
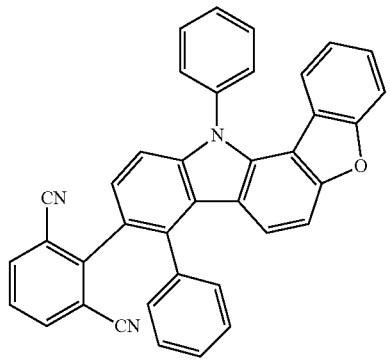
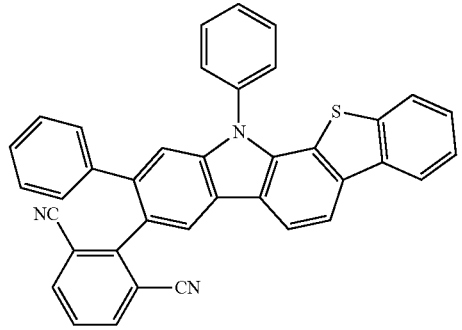

-continued
271
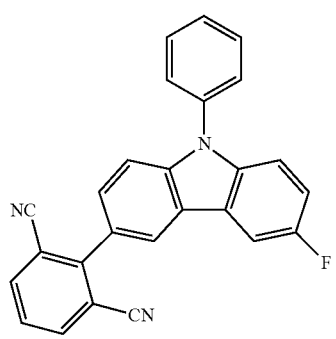
272
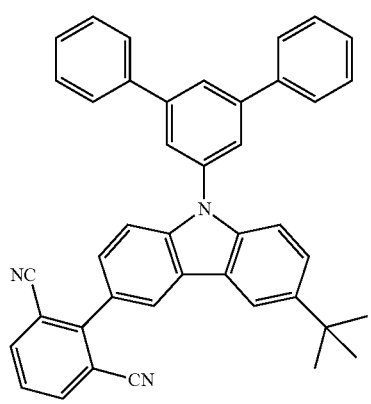
273
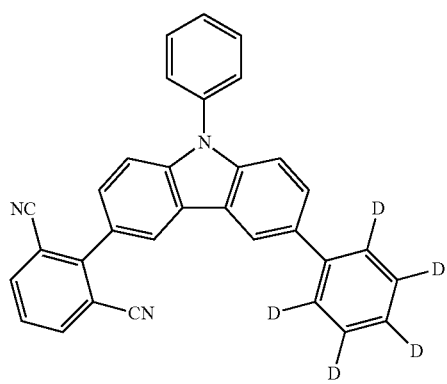
274
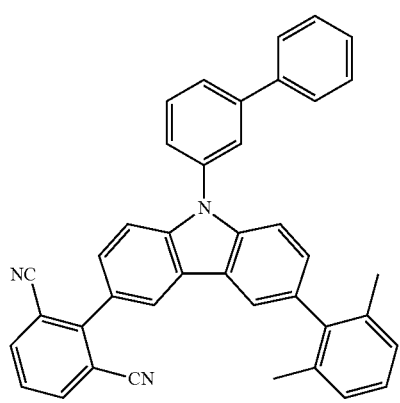
-continued
275
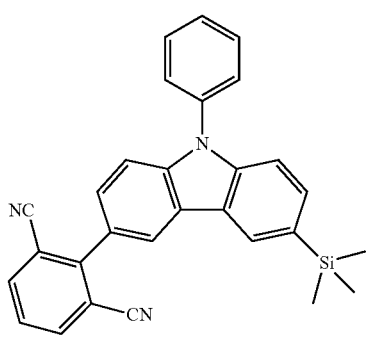
276
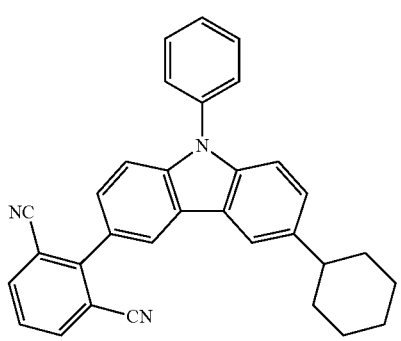
277
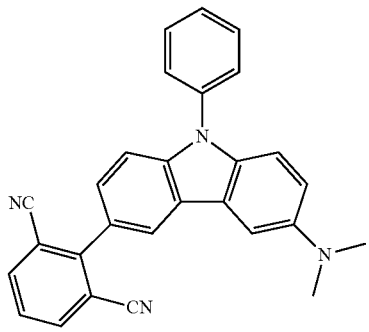
278
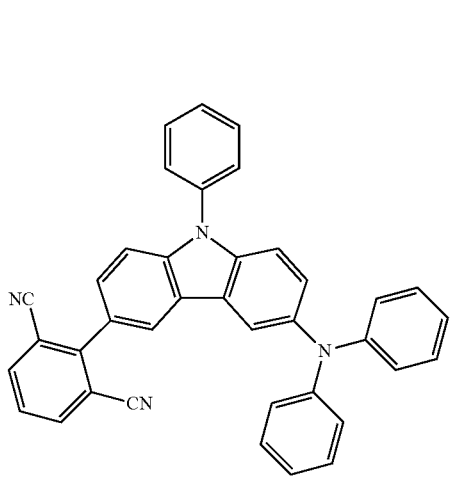

-continued

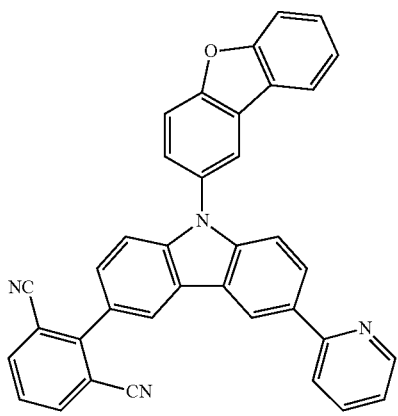

279

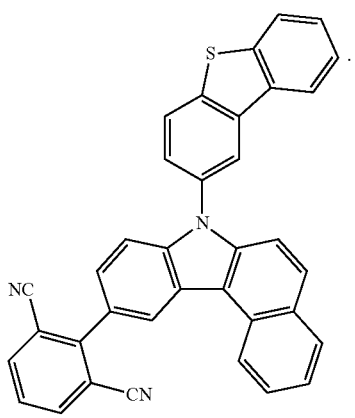

280

Formula 1 may have a structure in which a benzene ring substituted with a cyano group at an ortho position is bound to a condensed ring containing nitrogen. Accordingly, due to the steric effect between the cyano group substituted at the ortho position in the benzene ring and the condensed ring, a length of a conjugation bond may be short, thus securing a relatively high triplet energy ($T_1$) level.

In addition, since Formula 1 may include "a benzene ring substituted with a cyano group at an ortho position" represented by Formula 2-1 having excellent electron mobility, an electronic device, e.g., an organic light-emitting device, including the condensed cyclic compound may have improved luminescence efficiency. Furthermore, since the condensed cyclic compound may include a condensed ring containing nitrogen (e.g., a carbazole group), the condensed cyclic compound may have a high glass transition temperature (Tg) and a high decomposition temperature (Td), thus having excellent thermal stability. Accordingly, an electronic device, e.g., an organic light-emitting device, including the condensed cyclic compound may have a long lifespan.

When an additional carbazole group is bound to a benzene ring in a condensed ring containing nitrogen, e.g., a carbazole group, the two adjacent carbazole groups may have a large steric hindrance and have a wide bond angle, deteriorating molecular stability. Accordingly, thermal stability and lifespan of an electronic device may be deteriorated. In addition, a triplet energy ($T_1$) level may be low, and thus, an application to a blue light-emitting device may be difficult.

Further, when an additional substituent is introduced to a benzene ring substituted with a cyano group at an ortho position, a length of a conjugation bond may be long, and a triplet energy ($T_1$) level may also be low, and thus, an application to a blue light-emitting device may be difficult.

Furthermore, when a cyano group is not substituted, when one cyano group is introduced only, or when a methyl group, an amine group, or a carbazole group is substituted instead of a cyano group, a length of a conjugation bond between the carbazole group and the phenyl group may be long. Thus, a triplet energy ($T_1$) level may be low, and the lowest unoccupied molecular orbital (LUMO) energy level may also be high, and sufficient electron mobility may not be easily secured.

When a cyano group is not substituted at an ortho position, due to the steric effect between the cyano group substituted at the ortho position in the benzene ring and the condensed ring, a length of a conjugation bond may not be short, thus lowering a triplet energy ($T_1$) level.

As described above, the condensed cyclic compound represented by Formula 1 may have suitable electrical characteristics for a material for organic light-emitting devices, e.g., a host material in an emission layer, in particular, blue light-emitting devices. Accordingly, an organic light-emitting device including the condensed cyclic compound may have high efficiency and/or a long lifespan.

For example, the highest occupied molecular orbital (HOMO), LUMO, $T_1$, and singlet ($S_1$) energy levels of the compounds described above were evaluated by using Gaussian according to a density functional theory (DFT) method (structure optimization is performed at a degree of B3LYP, and 6-31G(d,p)). The results thereof are shown in Table 1.

TABLE 1

| Compound No. | HOMO (eV) | LUMO (eV) | $T_1$ energy level (eV) | $S_1$ energy level (eV) |
|---|---|---|---|---|
| 81 | −5.577 | −1.905 | 2.923 | 3.187 |
| 83 | −5.570 | −1.905 | 2.918 | 3.181 |
| 93 | −5.905 | −2.071 | 2.939 | 3.349 |
| 231 | −5.769 | −1.950 | 2.924 | 3.333 |
| A | −5.273 | −1.982 | 2.691 | 2.735 |
| B | −5.614 | −2.180 | 2.870 | 2.945 |
| C | −5.631 | −2.552 | 2.460 | 2.555 |
| D | −5.863 | −2.698 | 2.530 | 2.640 |
| E | −5.139 | −1.117 | 2.893 | 3.527 |
| F | −5.255 | −0.783 | 3.111 | 3.858 |

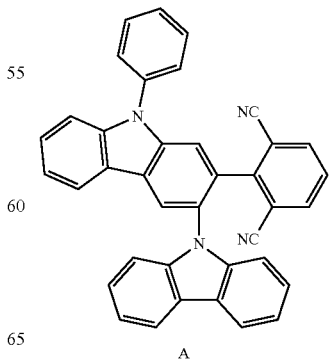

A

TABLE 1-continued

| Compound No. | HOMO (eV) | LUMO (eV) | $T_1$ energy level (eV) | $S_1$ energy level (eV) |
|---|---|---|---|---|

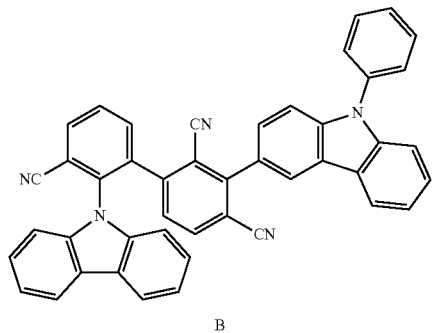

B

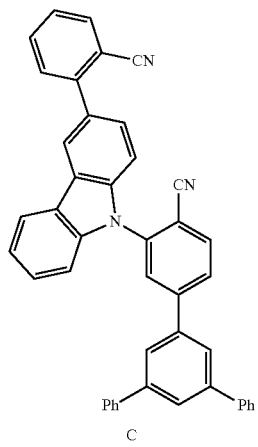

C

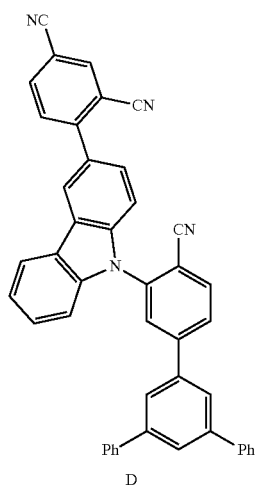

D

TABLE 1-continued

| Compound No. | HOMO (eV) | LUMO (eV) | $T_1$ energy level (eV) | $S_1$ energy level (eV) |
|---|---|---|---|---|

E

F

Referring to the results of Table 1, the condensed cyclic compound represented by Formula 1 was found to have suitable electrical characteristics for use as a host in an electronic device, e.g., an organic light-emitting device.

A method of synthesizing the condensed cyclic compound represented by Formula 1 may be apparent to one of ordinary skill in the art by referring to Synthesis Examples provided herein.

The condensed cyclic compound represented by Formula 1 may be suitable for use in an organic layer of an organic light-emitting device, for example, as a host in an emission layer of the organic layer. Thus, according to another aspect, there is provided an organic light-emitting device that may include a first electrode; a second electrode; and an organic layer between the first electrode and the second electrode, the organic layer including an emission layer and at least one condensed cyclic compound represented by Formula 1.

As the organic light-emitting device has an organic layer including the condensed cyclic compound represented by Formula 1, the organic light-emitting device may have a low driving voltage, high efficiency, high luminance, high quantum efficiency, and long lifespan.

In some embodiments, in the organic light-emitting device,
the first electrode may be an anode, the second electrode may be a cathode,
the organic layer may include a hole transport region between the first electrode and the emission layer and an electron transport region between the emission layer and the second electrode,
the hole transport region may include a hole injection layer, a hole transport layer, an electron blocking layer, a buffer layer, or a combination thereof, and the electron transport region may include a hole blocking layer, an electron transport layer, an electron injection layer, or a combination thereof, but embodiments are not limited thereto.

In some embodiments, an emission layer in the organic light-emitting device may include at least one condensed cyclic compound represented by Formula 1.

In some embodiments, the emission layer in the organic light-emitting device may include a host and a dopant, wherein the host may include at least one condensed cyclic compound represented by Formula 1, and the dopant may include a phosphorescent dopant or a fluorescent dopant. In some embodiments, the dopant may include a phosphorescent dopant (e.g., a transition metal-containing organometallic compound or an organometallic compound represented by Formula 81 provided herein). A content of the host in the emission layer may be greater than that of the dopant in the emission layer. The host may further include any suitable host, in addition to the condensed cyclic compound represented by Formula 1.

The emission layer may emit red light, green light, or blue light. In some embodiments, the emission layer may emit blue light.

In some embodiments, the emission layer may be a blue emission layer including a phosphorescent dopant, but embodiments are not limited thereto.

In some embodiments, the organic layer may include an electron transport region between the emission layer and the second electrode, wherein the at least one condensed cyclic compound represented by Formula 1 may be included in the electron transport region of the organic light-emitting device.

In some embodiments, an electron transport region of the organic light-emitting device may include at least one a hole blocking layer and an electron transport layer, wherein at least one the hole blocking layer and the electron transport layer may include the at least one condensed cyclic compound represented by Formula 1.

In some embodiments, an electron transport region of the organic light-emitting device may include a hole blocking layer, wherein the hole blocking layer may include the at least one condensed cyclic compound represented by Formula 1. The hole blocking layer may be in a direct contact with the emission layer.

In one or more embodiments, the electron transport region may include a hole blocking layer and an electron transport layer, wherein the hole blocking layer may be between the emission layer and the electron transport layer and include at least one condensed cyclic compound represented by Formula 1.

In one or more embodiments, the organic layer of the organic light-emitting device may further include a transition metal-containing organometallic compound (e.g., an organometallic compound represented by Formula 81), in addition to the condensed cyclic compound represented by Formula 1:

$$M(L_{81})_{n81}(L_{82})_{n82}$$ Formula 81

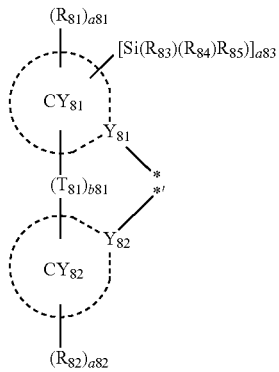

Formula 81A wherein, in Formulae 81 and 81A,

M may be a transition metal (e.g., iridium (Ir), platinum (Pt), palladium (Pd), gold (Au), osmium (Os), titanium (Ti), zirconium (Zr), hafnium (Hf), europium (Eu), terbium (Tb), thulium (Tm), or rhodium (Rh)), $L_{81}$ may be a ligand represented by Formula 81A, n81 may be an integer from 1 to 3; and when n81 is 2 or greater, at least two $L_{81}$(s) may be identical to or different from each other, $L_{82}$ may be an organic ligand, n82 may be an integer from 0 to 4; and when n82 is 2 or greater, at least two $L_{82}$(s) may be identical to or different from each other, $Y_{81}$ and $Y_{82}$ may each independently be carbon (C) or nitrogen (N), rings $CY_{81}$ and $CY_{82}$ may each independently be a $C_5$-$C_{30}$ carbocyclic group and a $C_1$-$C_{30}$ heterocarbocyclic group, rings $CY_{81}$ and $CY_{82}$ may optionally be bound via an organic linking group, $T_{81}$ may be a single bond, a double bond, *—N($R_{86}$)—*', *—B($R_{86}$)—*', *—P($R_{86}$)—*, *—C($R_{86}$)($R_{87}$)—*', *—Si($R_6$)($R_7$)—*', —Ge($R_{86}$)($R_{87}$)—*', *—S—*', *—Se—*', *—O—*', *—C(=O)—*', *—S(=O)—*', *—S(=O)$_2$—*', *—C($R_{86}$)=*', *=C($R_6$)—*', *—C($R_{86}$)=C($R_{87}$)—*', *—C(=S)—*, or *—C≡C—*', wherein * and *' each indicate a binding site to an adjacent atom, b81 may be 1, 2, or 3, $R_{81}$ to $R_{87}$ may each independently be hydrogen, deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{81}$)($Q_{82}$)($Q_{83}$), —N($Q_{84}$)($Q_{85}$), —B($Q_{86}$)($Q_{87}$), or —P(=O)($Q_{88}$)($Q_{89}$), a81 to a83 may each independently be an integer from 0 to 5, when a81 is 2 or greater, at least two $R_{81}$(s) may be identical to or different from each other, when a82 is 2 or greater, at least two $R_{82}$(s) may be identical to or different from each other, when a81 is 2 or greater, at least two adjacent $R_{81}$(s) may optionally be bound to form a $C_5$-$C_{30}$ carbocyclic group or a $C_1$-$C_{30}$ heterocyclic group, each substituted with at least one $R_{88}$ (e.g., a benzene group, a cyclopentane group, a cyclohexane group, a cyclopentene group, a cyclohexene group, a norbonane group, a a naphthalene group, a benzoindene group, a benzoindole group, a benzofuran group, a benzothiophene group, a pyridine group, a pyrimidine group, or a pyrazine group, each unsubstituted or substituted with at least one $R_{88}$), when a82 is 2 or greater, at least two adjacent $R_{82}$(s) may optionally be bound to form a $C_5$-$C_{30}$ carbocyclic group or a $C_1$-$C_{30}$ heterocyclic group, each substituted with at least one $R_{88}$ (e.g., a benzene group, a cyclopentane group, a cyclohexane group, a cyclopentene group, a cyclohexene group, a norbonane group, a naphthalene group, a benzoindene group, a benzoindole group, a benzofuran group, a benzothiophene group, a pyridine group, a pyrimidine group, or a pyrazine group, each unsubstituted or substituted with at least one $R_{88}$), $R_{88}$ may be understood by referring to the description of $R_{81}$ provided herein, $R_{89}$ may be understood by referring to the description of $R_{82}$ provided herein, in Formula 81A, * and *' each indicate a binding site to M in Formula 81, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be: deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{91}$)($Q_{92}$)($Q_{93}$), or a combination thereof, wherein $Q_{81}$ to $Q_{89}$ and $Q_{91}$ to $Q_{93}$ may each independently be hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In some embodiments, in Formula 81A,
a83 may be 1 or 2, and
$R_{83}$ to $R_{85}$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group, each substituted with at least one deuterium, a $C_1$-$C_{10}$ alkyl group, a phenyl group, or a combination thereof, but embodiments are not limited thereto.

In one or more embodiments, in Formula 81A,
$Y_{81}$ may be N, $Y_{84}$ may be N or C, and
rings $CY_{81}$ and $CY_{82}$ may each independently be a cyclopentadiene group, a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an iso-benzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilole group, or a 2,3-dihydro-1H-imidazole group.

In one or more embodiments, in Formula 81A, $Y_{81}$ may be N, $Y_{84}$ may be C, ring $CY_{81}$ may be 5-membered rings including two N atoms as ring-forming atoms, and ring $CY_{82}$ may be a benzene group, a naphthalene group a fluorene group, a dibenzofuran group, and a dibenzothiophene group, but embodiments are not limited thereto.

In one or more embodiments, in Formula 81A, $Y_{81}$ may be N, $Y_{84}$ may be C, ring $CY_{81}$ may be an imidazole group or a 2,3-dihydro-1H-imidazole group, and ring $CY_{82}$ may be a benzene group, a naphthalene group a fluorene group, a dibenzofuran group, or a dibenzothiophene group, but embodiments are not limited thereto.

In one or more embodiments, in Formula 81A, $Y_{81}$ may be nitrogen, $Y_{84}$ may be carbon, ring $CY_{81}$ may be a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an iso-benzothiazole group, a benzoxazole group, or an isobenzoxazole group, or ring $CY_{82}$ may be a cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, or a dibenzosilole group.

In one or more embodiments, in Formula 81A, $R_{81}$ and $R_{82}$ may each independently be:

hydrogen, deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, or a combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof; or —B($Q_{86}$)($Q_{87}$) and —P(=O)(Q)($Q_{89}$), wherein $Q_{86}$ to $Q_{89}$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —CHDCD$_2$H, —CHDCDH$_2$, —CHDCD$_3$, —CD$_2$CD$_3$, —CD$_2$CD$_2$H, or —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one deuterium, a C$_1$-C$_{10}$ alkyl group, or a phenyl group.

In one or more embodiments, in Formula 81A, at least one R$_{81}$(s) in the number of a81 and R$_{82}$(s) in the number of a82 may be a cyano group.

In one or more embodiments, in Formula 81A, at least one R$_{82}$(s) in the number of a82 may be a cyano group.

In one or more embodiments, in Formula 81A, at least one of R$_{81}$(s) in the number of a81 and R$_{82}$(s) in the number of a82 may be deuterium.

In one or more embodiments, in Formula 81, L$_{82}$ may be a ligand represented by Formulae 3-1(1) to 3-1(60), 3-1(61) to 3-1(69), 3-1(71) to 3-1(79), 3-1(81) to 3-1(88), 3-1(91) to 3-1(98), or 3-1(101) to 3-1(114):

3-1(1)

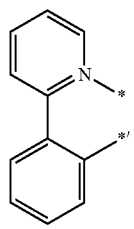

3-1(2)

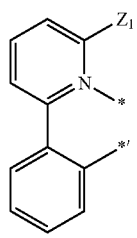

3-1(3)

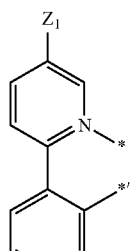

3-1(4)

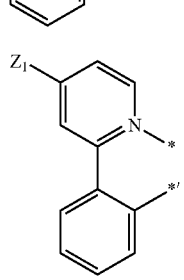

-continued 3-1(5)

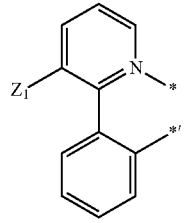

3-1(6)

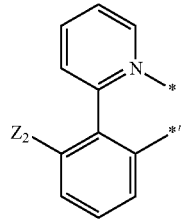

3-1(7)

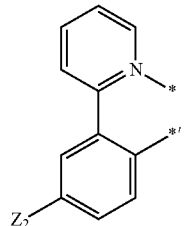

3-1(8)

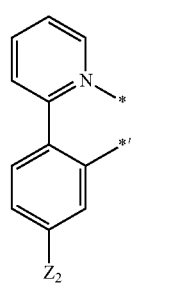

3-1(9)

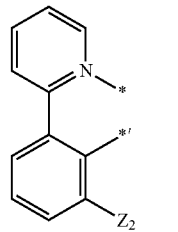

3-1(10)

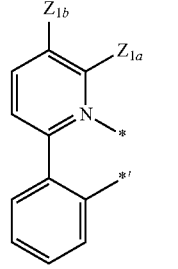

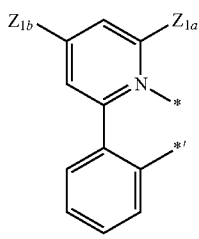 3-1(11)
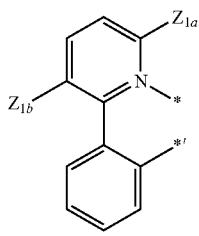 3-1(12)
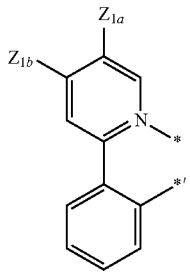 3-1(13)
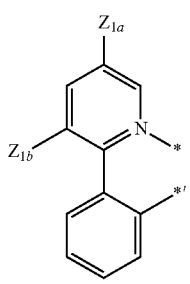 3-1(14)
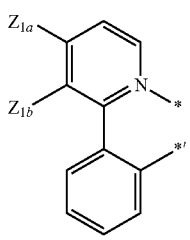 3-1(15)
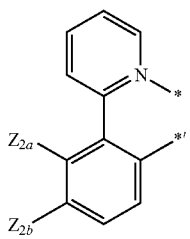 3-1(16)
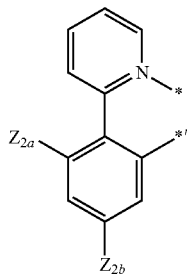 3-1(17)
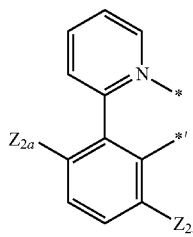 3-1(18)
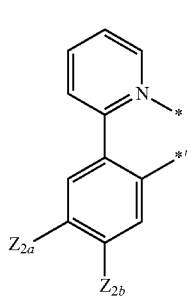 3-1(19)
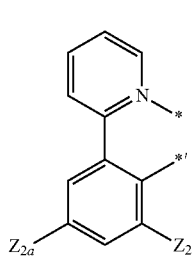 3-1(20)
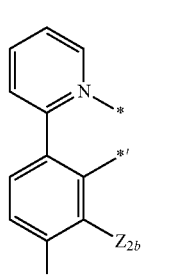 3-1(21)
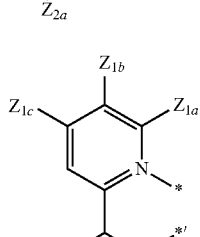 3-1(22)

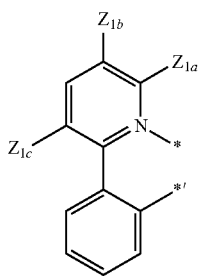
3-1(23)
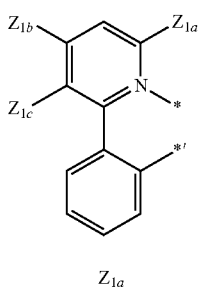
3-1(24)
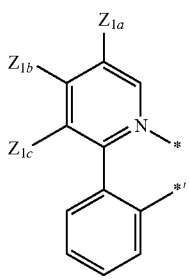
3-1(25)
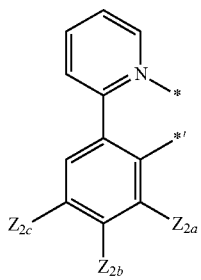
3-1(26)
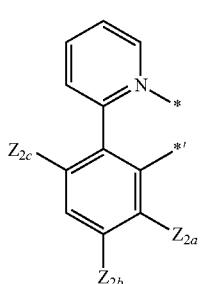
3-1(27)
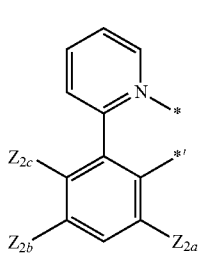
3-1(28)
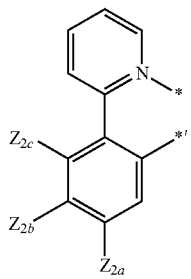
3-1(29)
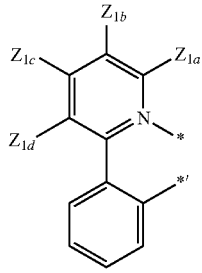
3-1(30)
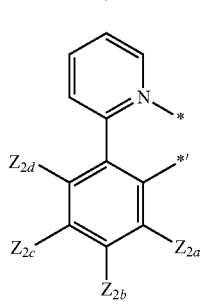
3-1(31)
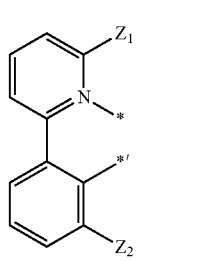
3-1(32)
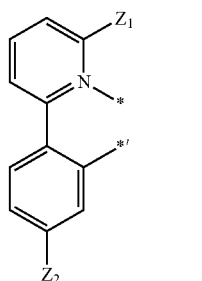
3-1(33)
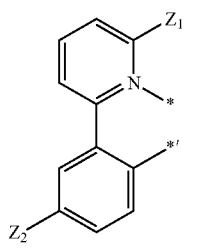
3-1(34)

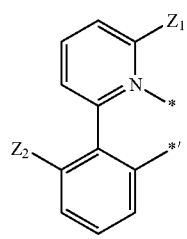 3-1(35)
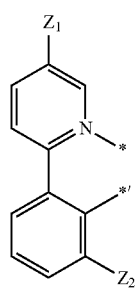 3-1(36)
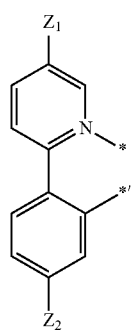 3-1(37)
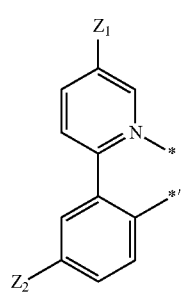 3-1(38)
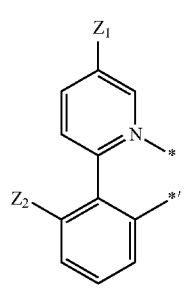 3-1(39)
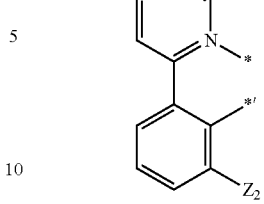 3-1(40)
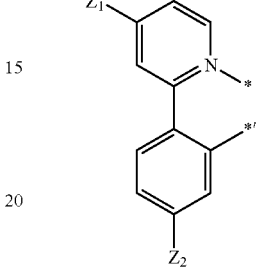 3-1(41)
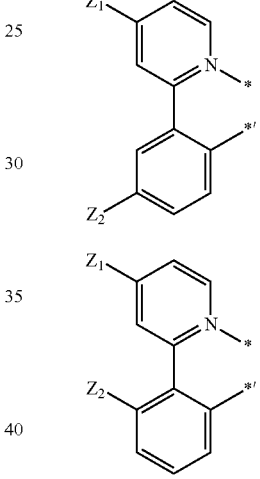 3-1(42)
3-1(43)
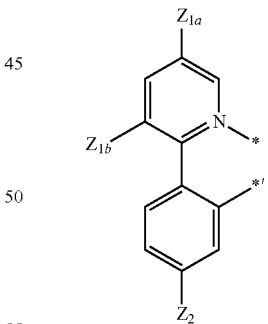 3-1(44)
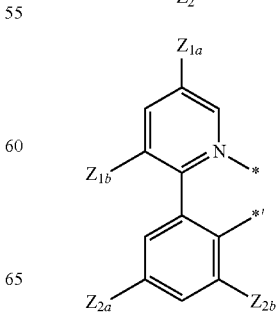 3-1(45)

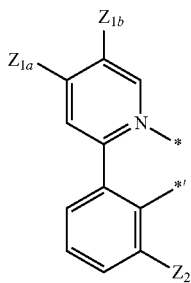
3-1(46)
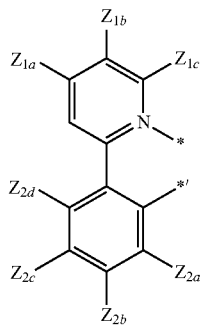
3-1(51)
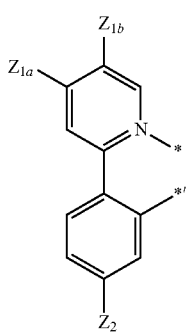
3-1(47)
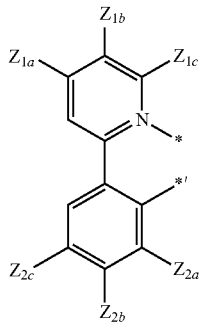
3-1(52)
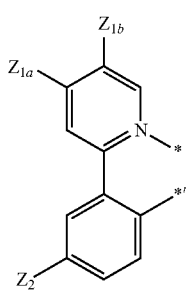
3-1(48)
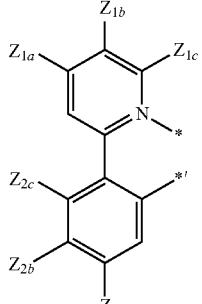
3-1(53)
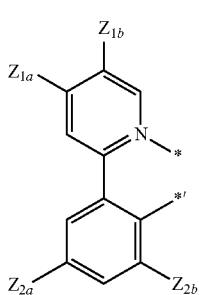
3-1(49)
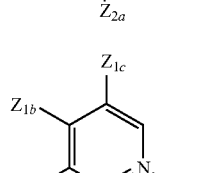
3-1(54)
3-1(50)
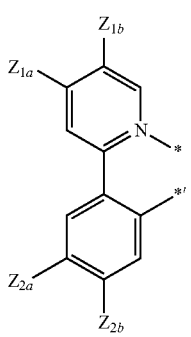
3-1(55)

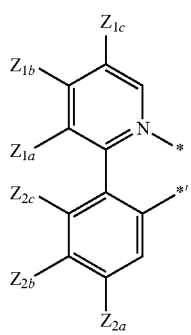
3-1(56)
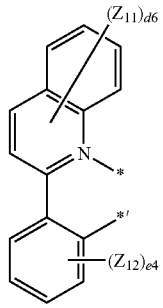
3-1(61)
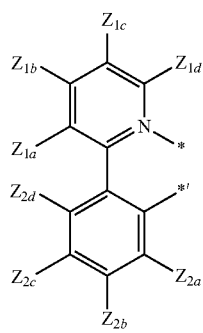
3-1(57)
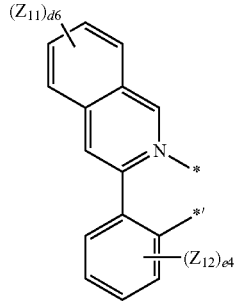
3-1(62)
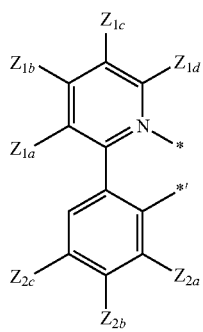
3-1(58)
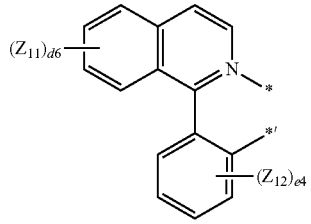
3-1(63)
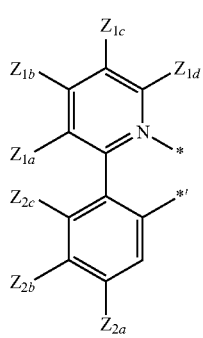
3-1(59)
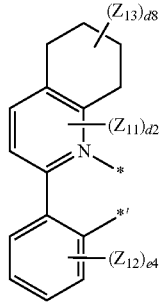
3-1(64)
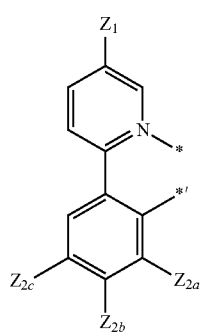
3-1(60)
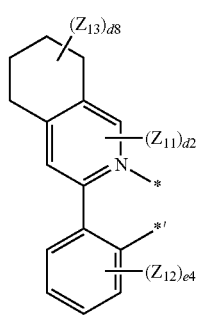
3-1(65)

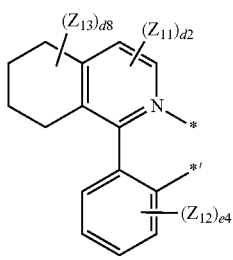 3-1(66)
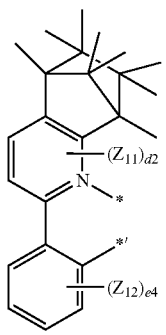 3-1(67)
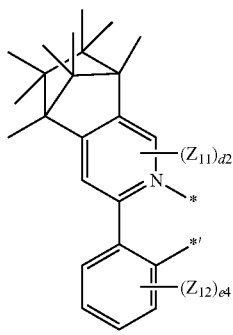 3-1(68)
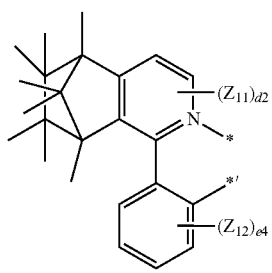 3-1(69)
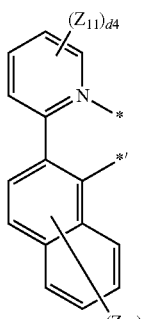 3-1(71)
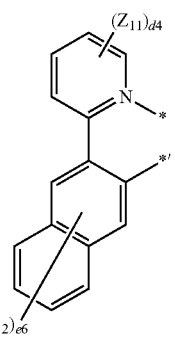 3-1(72)
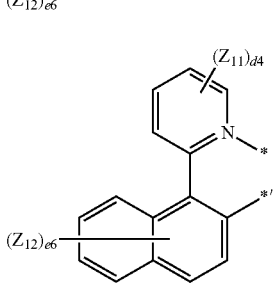 3-1(73)
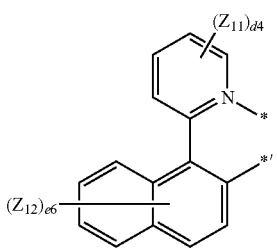 3-1(74)
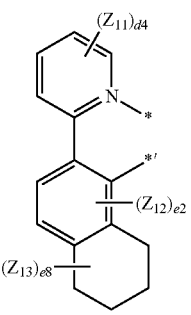 3-1(75)
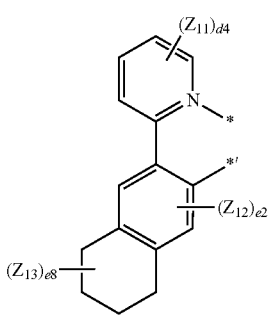 3-1(75)
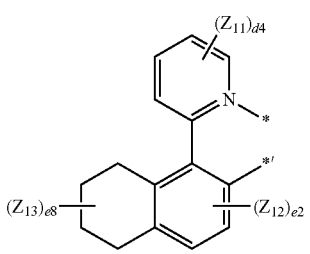 3-1(76)

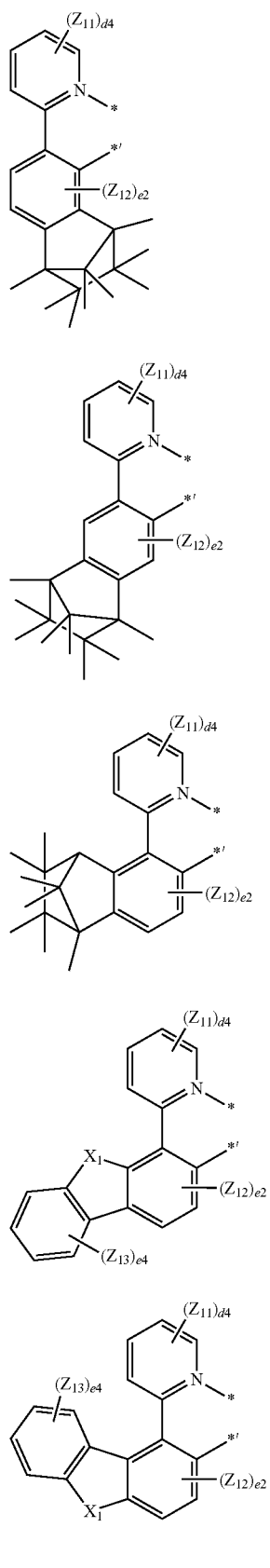
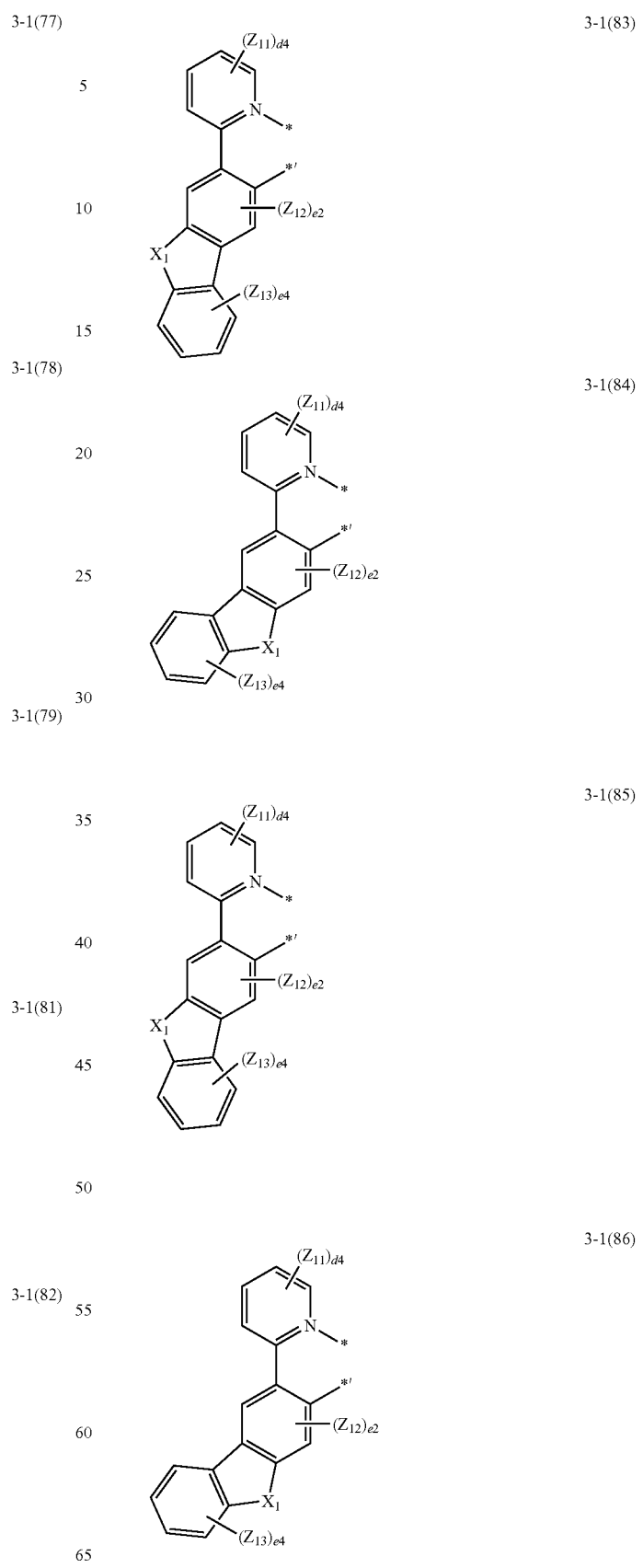

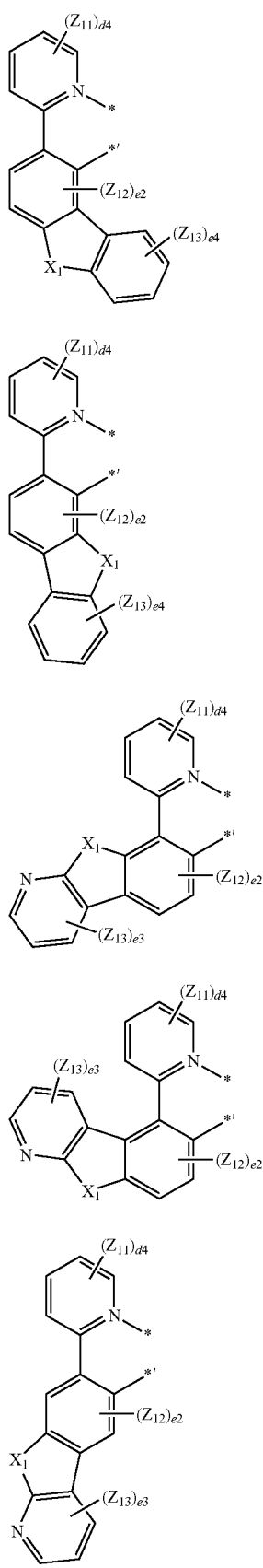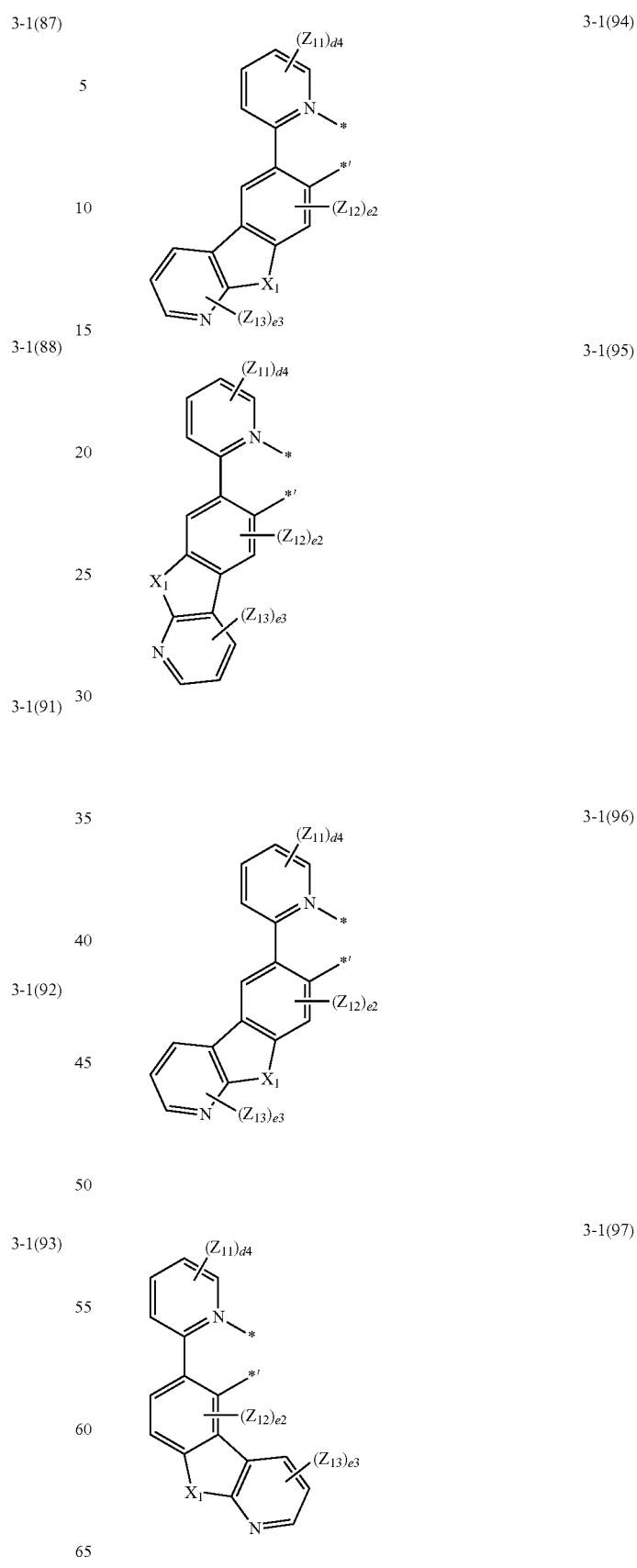

-continued
3-1(98)
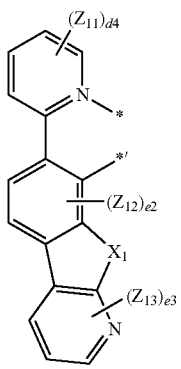
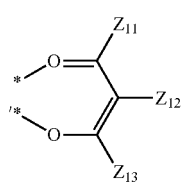
3-1(101)
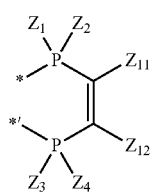
3-1(102)
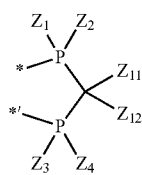
3-1(103)
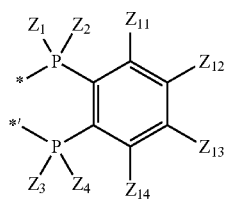
3-1(104)
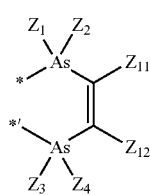
3-1(105)
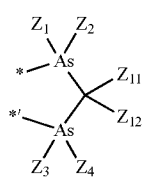
3-1(106)
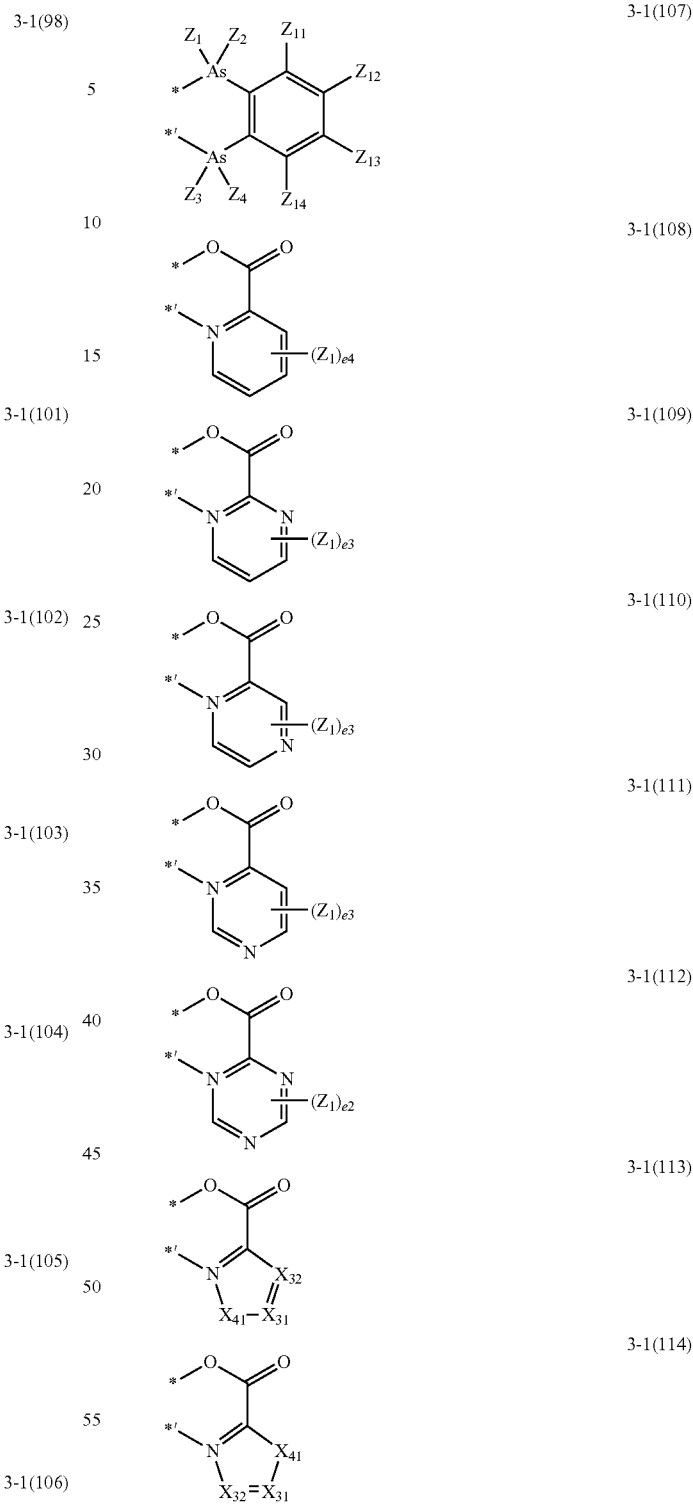
wherein, in Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114),
$X_1$ may be O, S, $C(Z_{21})(Z_{22})$, or $N(Z_{23})$,
$X_{31}$ may be N or $C(Z_{1a})$, $X_{32}$ may be N or $C(Z_{1b})$,
$X_{41}$ may be O, S, $N(Z_{1a})$, or $C(Z_{1a})(Z_{1b})$,
$Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with at least one deuterium, —F, —C, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, or a combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof; or —B(Q$_{86}$)(Q$_{87}$) or —P(=O)(Q)(Q$_{89}$), wherein Q$_{86}$ to Q$_{89}$ may each independently be:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, or —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one deuterium, a C$_1$-C$_{10}$ alkyl group, or a phenyl group.

d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and

* and *' each indicate a binding site to M in Formula 1.

In one or more embodiments, in Formula 81, M may be Ir, and a sum of n81 and n82 may be 3. In one or more embodiments, in Formula 81, M may be Pt, and a sum of n81 and n82 may be 2.

In one or more embodiments, the organometallic compound represented by Formula 81 may be neutral and may not include ion pairs of cations and anions.
In one or more embodiments, the organometallic compound represented by Formula 81 may include at least one of Compounds PD1 to PD78 and FIr$_6$, but embodiments are not limited thereto:
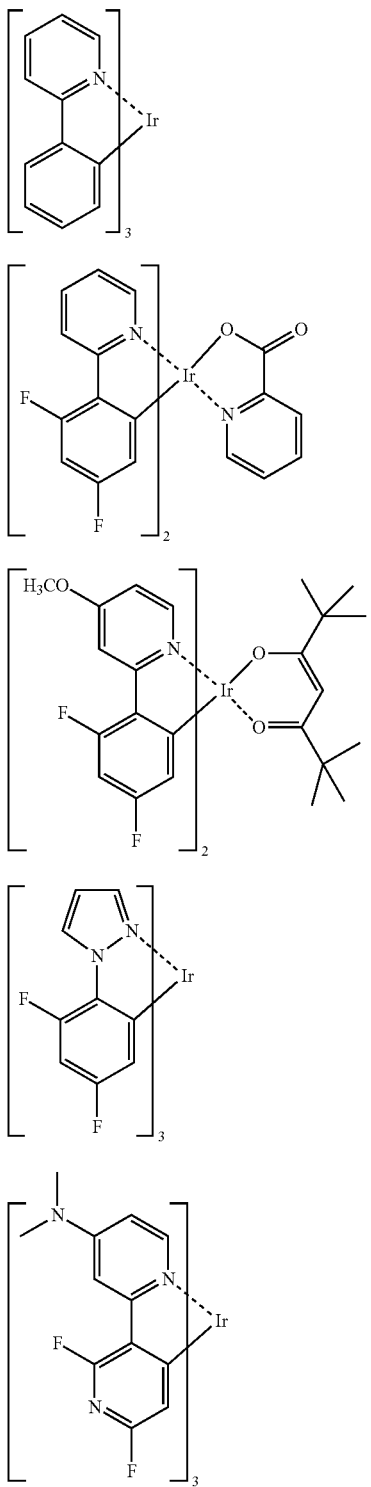
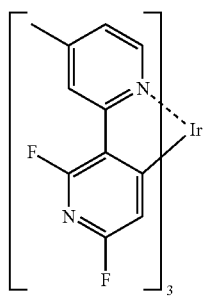
PD6
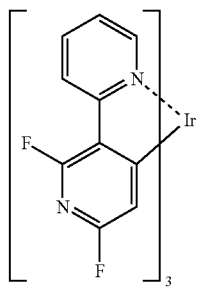
PD7
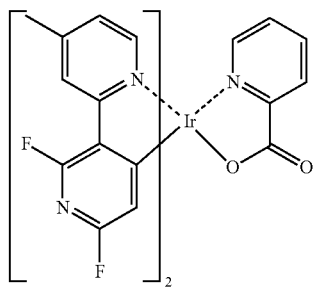
PD8
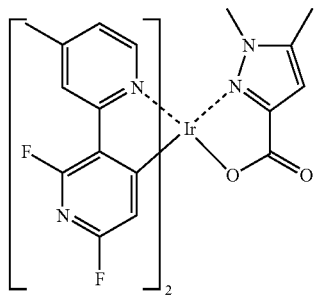
PD9
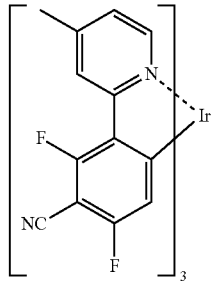
PD10

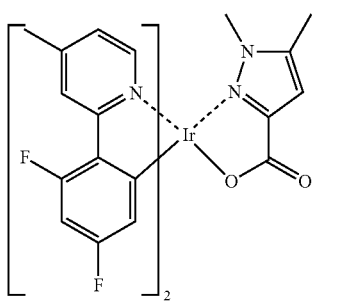
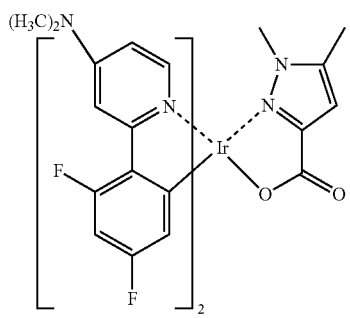
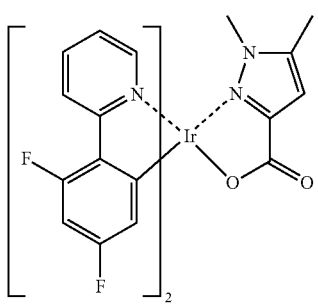
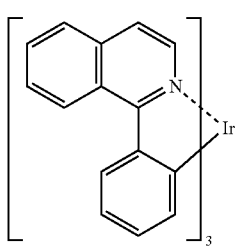
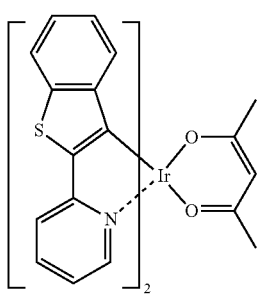
PD11
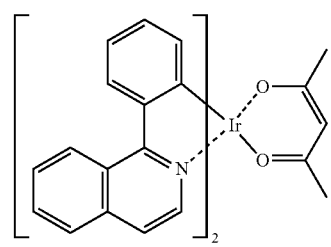 PD16
PD12
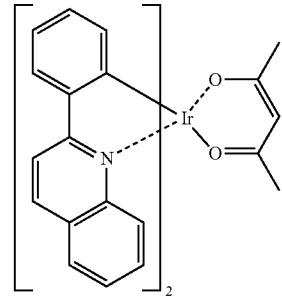 PD17
PD13
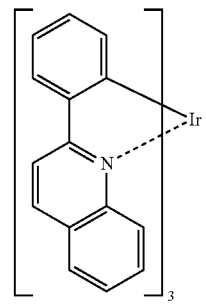 PD18
PD14
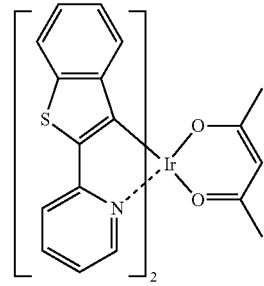 PD19
PD15
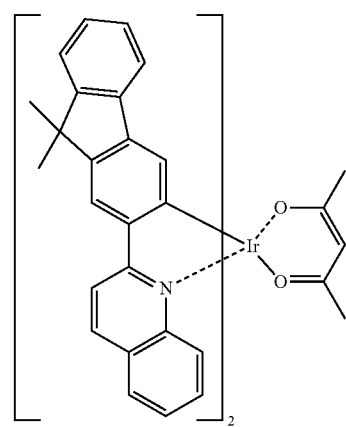 PD20

-continued
PD21 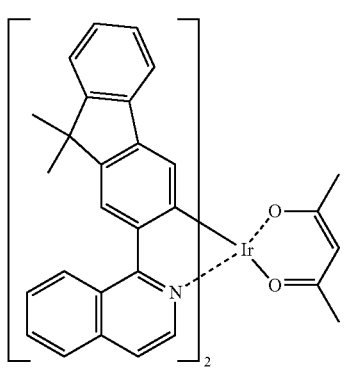
PD22 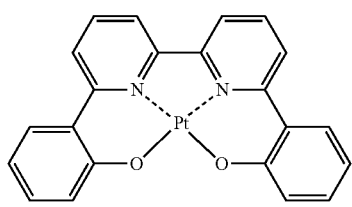
PD23 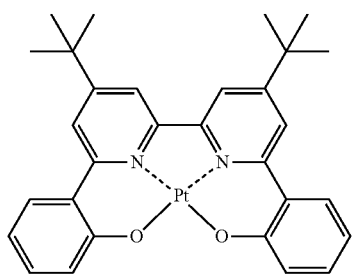
PD24 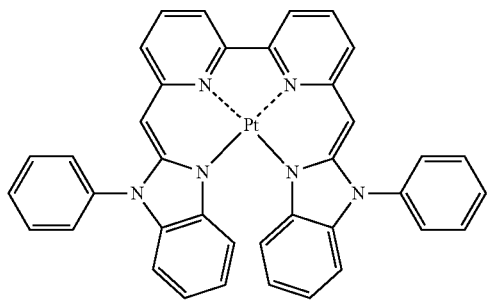
PD25 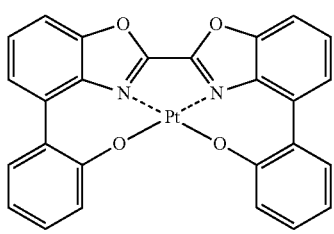
PD26 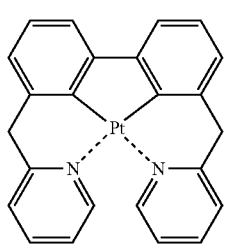
-continued
PD27 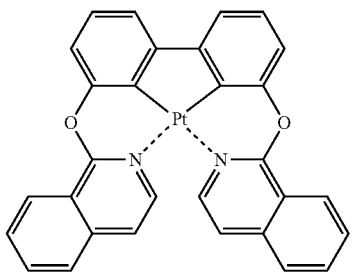
PD28 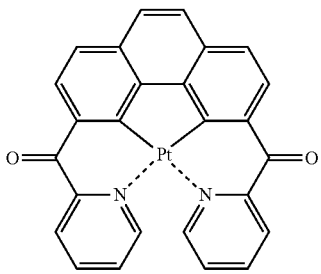
PD29 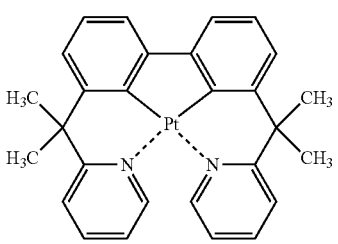
PD30 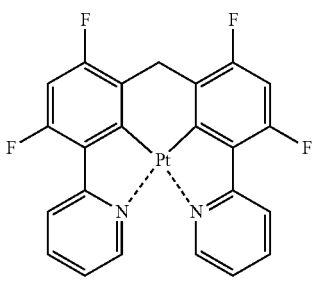
PD31 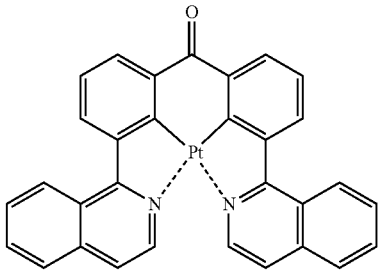
PD32 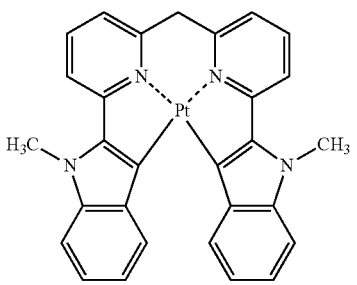

-continued
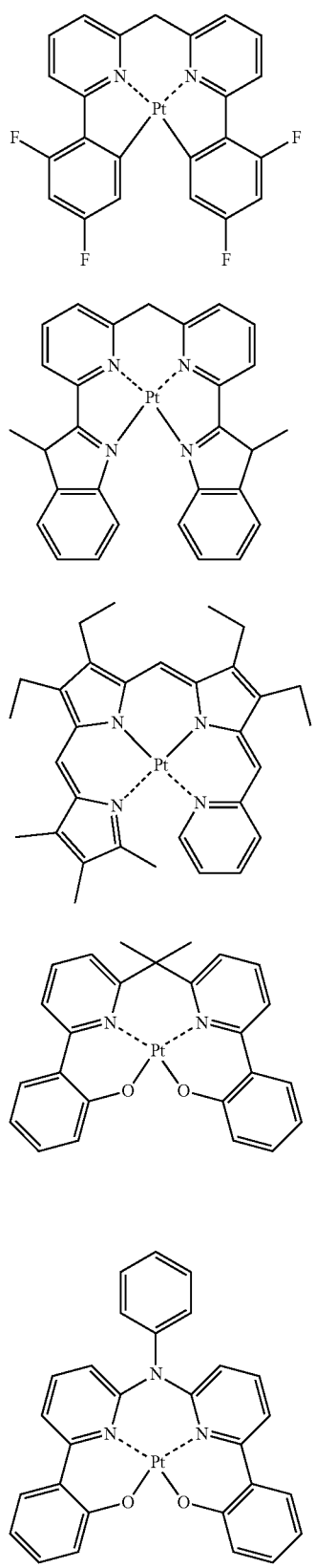
PD33
PD34
PD35
PD36
PD37
-continued
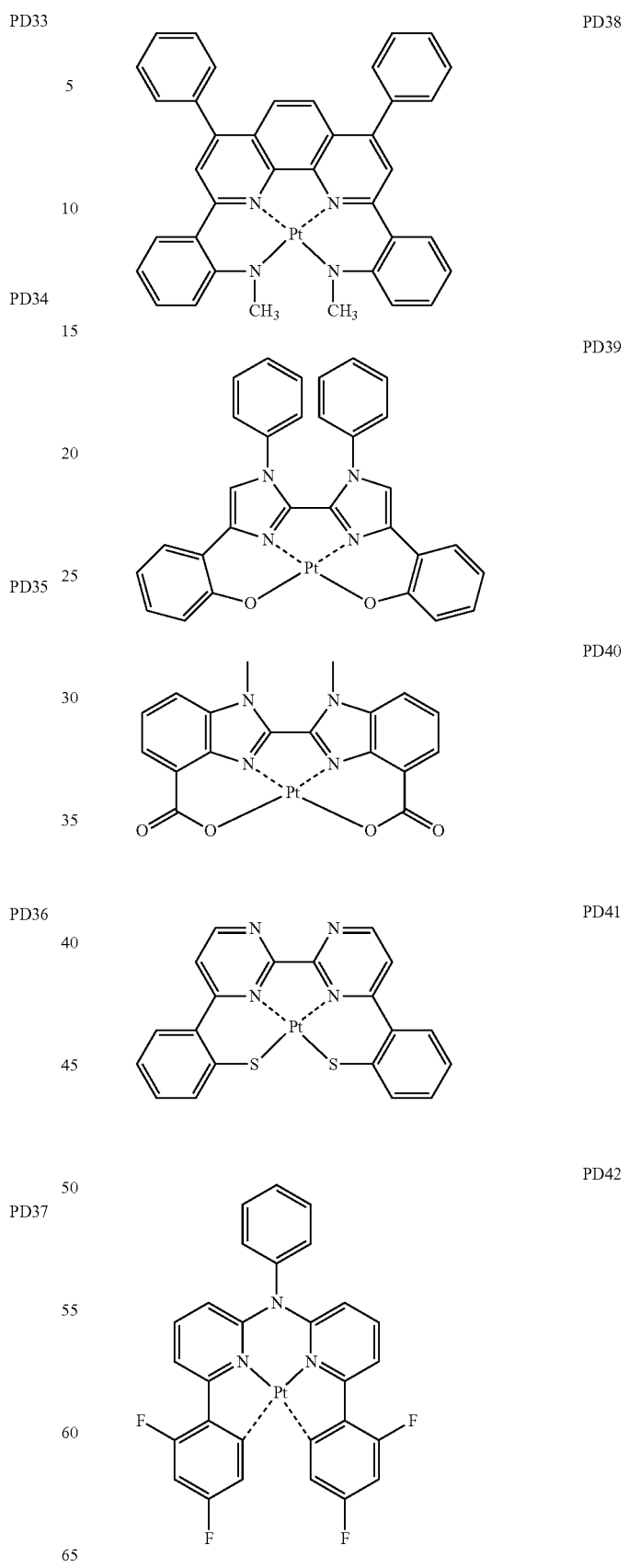
PD38
PD39
PD40
PD41
PD42

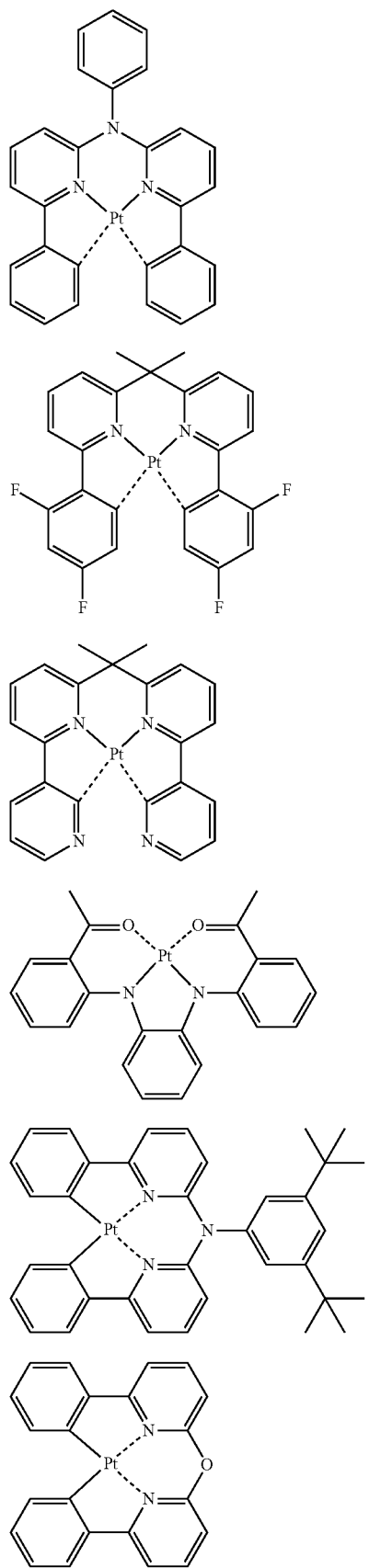
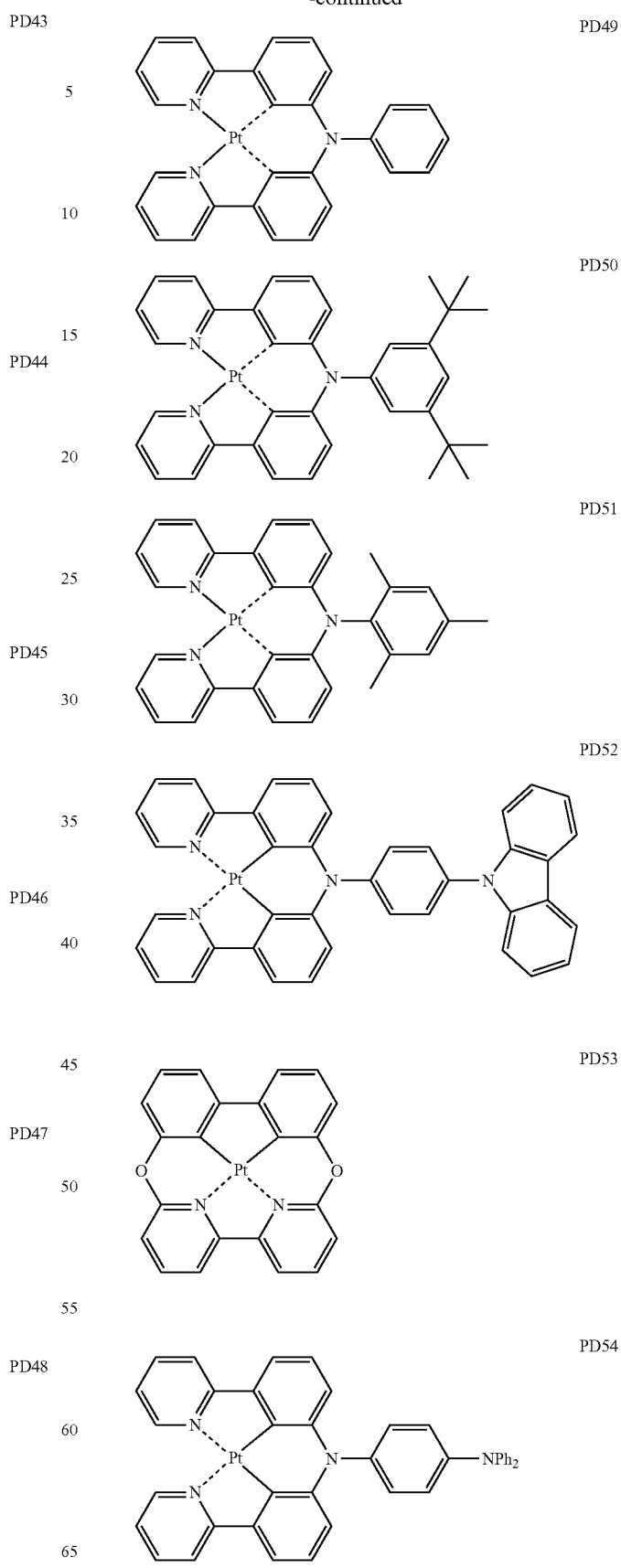

-continued
PD55
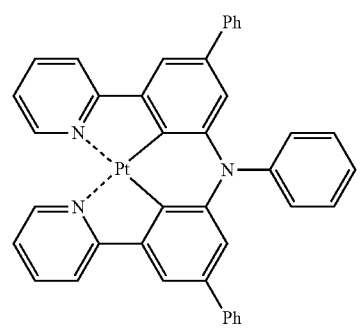
PD56
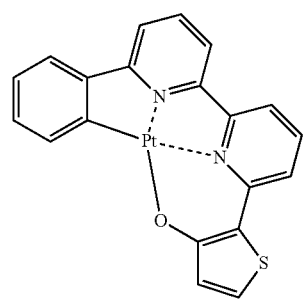
PD57
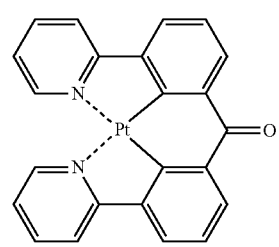
PD58
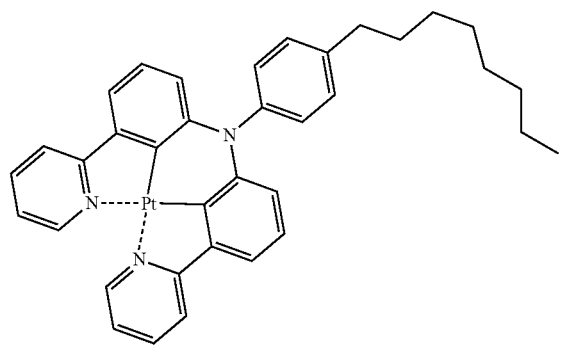
PD59
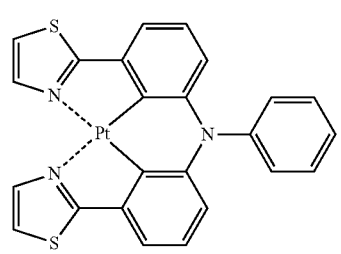
-continued
PD60
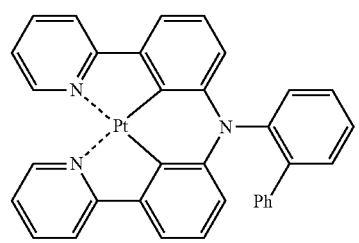
PD61
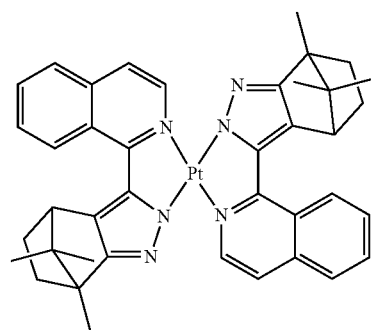
PD62
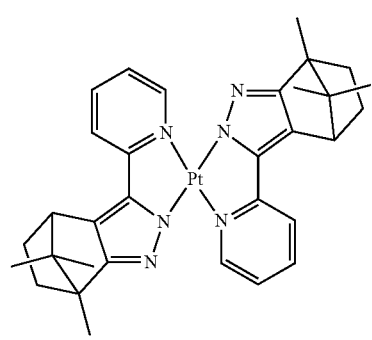
PD63
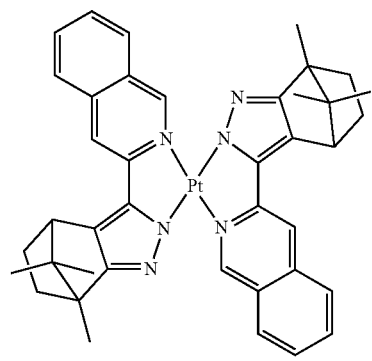
PD64
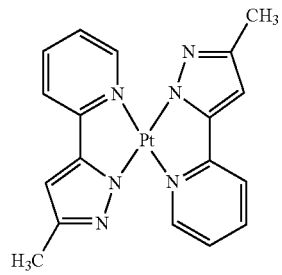

-continued
PD65
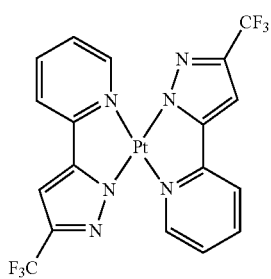
PD66
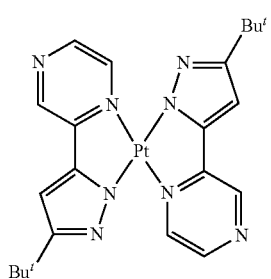
PD67
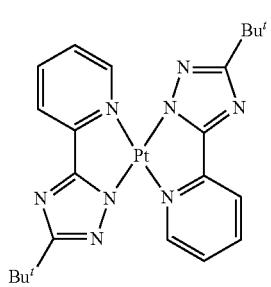
PD68
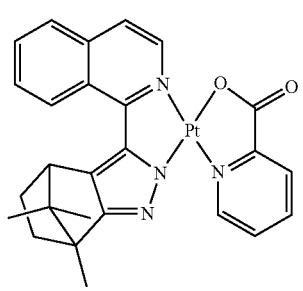
PD69
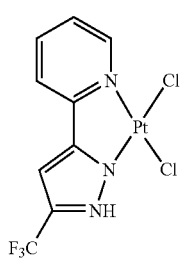
-continued
PD70
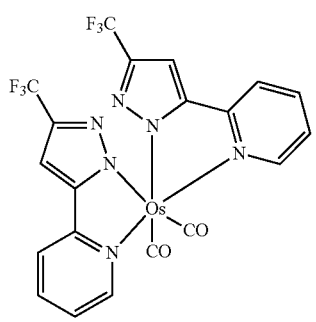
PD71
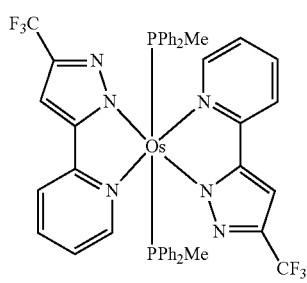
PD72
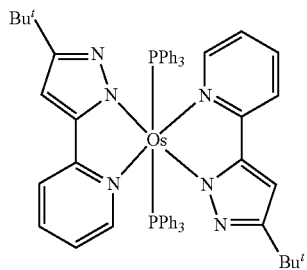
PD73
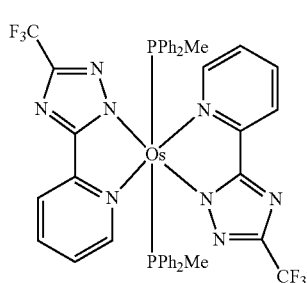
PD74
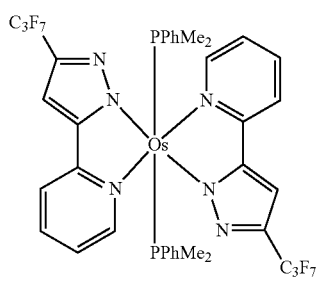

-continued

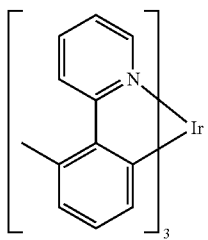

PD75

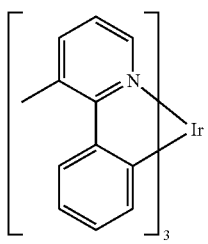

PD76

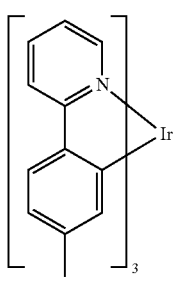

PD77

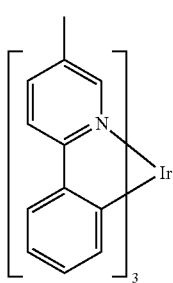

PD78

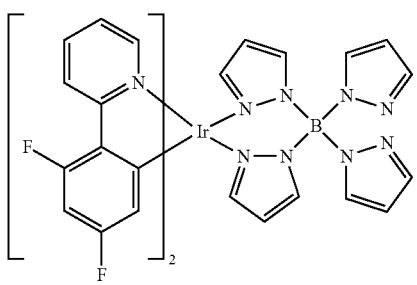

FIr6

The expression the "(organic layer) including at least one condensed cyclic compound", as used herein, may be construed as meaning the "(organic layer) may include a condensed cyclic compound represented by Formula 1 or at least two different condensed cyclic compounds represented by Formula 1".

For example, the organic layer may include Compound 1 only as the condensed cyclic compound. In this embodiment, Compound 1 may be included in the emission layer of the organic light-emitting device. In some embodiments, Compounds 1 and 2 may be included in the organic layer as the condensed cyclic compounds. In this embodiment, Compounds 1 and 2 may be present in the same layer (for example, Compounds 1 and 2 may be both present in an emission layer), or in different layers (for example, Compound 1 may be present in an emission layer, and Compound 2 may be present in a hole blocking layer).

The first electrode may be an anode, which is a hole injection electrode, and the second electrode may be a cathode, which is an electron injection electrode. In some embodiments, the first electrode may be a cathode, which is an electron injection electrode, and the second electrode may be an anode, which is a hole injection electrode.

The term "organic layer" as used herein refers to a single and/or a plurality of layers disposed between the first electrode and the second electrode in an organic light-emitting device. The "organic layer" may include not only organic compounds but also organometallic complexes including metals.

The FIGURE illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to the FIGURE. The organic light-emitting device 10 may include a first electrode 11, an organic layer 15, and a second electrode 19, which may be sequentially layered in this stated order.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

The first electrode 11 may be formed by depositing or sputtering, onto the substrate, a material for forming the first electrode 11. The first electrode 11 may be an anode. The material for forming the first electrode 11 may be materials with a high work function for easy hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), and zinc oxide (ZnO). In some embodiments, the material for forming the first electrode 11 may be a metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including a plurality of layers. In some embodiments, the first electrode 11 may have a triple-layered structure of ITO/Ag/ITO, but embodiments are not limited thereto.

The organic layer 15 may be on the first electrode 11.

The organic layer 15 may include a hole transport region, an emission layer, and an electron transport region.

The hole transport region may be between the first electrode 11 and the emission layer.

The hole transport region may include at least one a hole injection layer, a hole transport layer, an electron blocking layer, and a buffer layer.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using one or more suitable methods, such as vacuum deposition, spin coating, casting, and Langmuir-Blodgett (LB) deposition.

When a hole injection layer is formed by vacuum-deposition, for example, the vacuum deposition may be performed at a temperature in a range of about 100° C. to about 500° C., at a vacuum pressure in a range of about 10-8 torr to about 10-3 torr, and at a rate in a range of about 0.01 Angstroms per second (A/sec) to about 100 Å/sec, though the conditions may vary depending on a compound used as a hole injection material and a structure and thermal properties of a desired hole injection layer, but embodiments are not limited thereto.

When a hole injection layer is formed by spin coating, the spin coating may be performed at a rate in a range of about 2,000 revolutions per minute (rpm) to about 5,000 rpm and at a temperature in a range of about 80° C. to 200° C. to facilitate removal of a solvent after the spin coating, though the conditions may vary depending on a compound used as a hole injection material and a structure and thermal properties of a desired hole injection layer, but embodiments are not limited thereto.

The conditions for forming a hole transport layer and an electron blocking layer may be inferred from the conditions for forming the hole injection layer.

The hole transport region may include at least one m-MTDATA, TDATA, 2-TNATA, NPB, β-NPB, TPD, spiro-TPD, spiro-NPB, methylated-NPB, TAPC, HMTPD, 4,4',4"-tris (N-carbazolyl)triphenylamine(TCTA), polyaniline/dodecylbenzenesulfonicacid (PANI/DBSA), poly(3,4-ethylenedioxythiophene)/poly(4-styrenesulfonate) (PEDOT/PSS), polyaniline/camphor-sulfonic acid (PANI/CSA), polyaniline)/poly(4-styrenesulfonate (PANI/PSS), a compound represented by Formula 201, a compound represented by Formula 202, or a combination thereof:

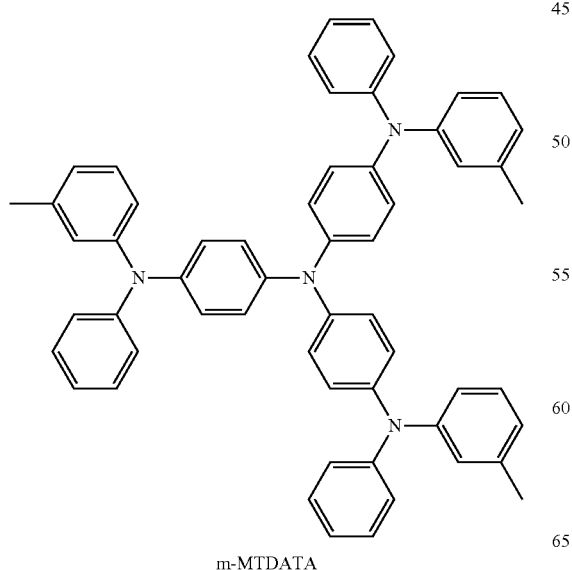

m-MTDATA

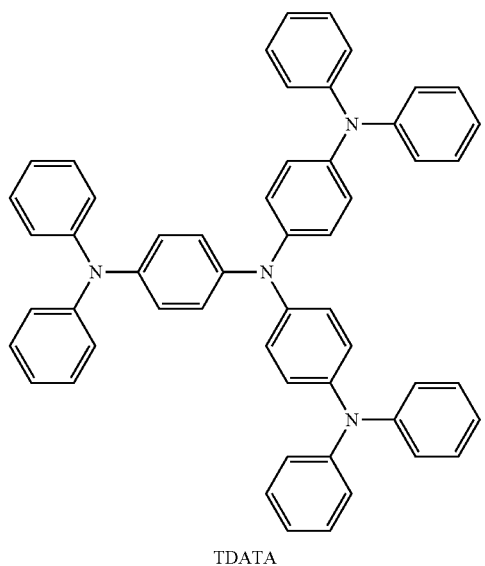

TDATA

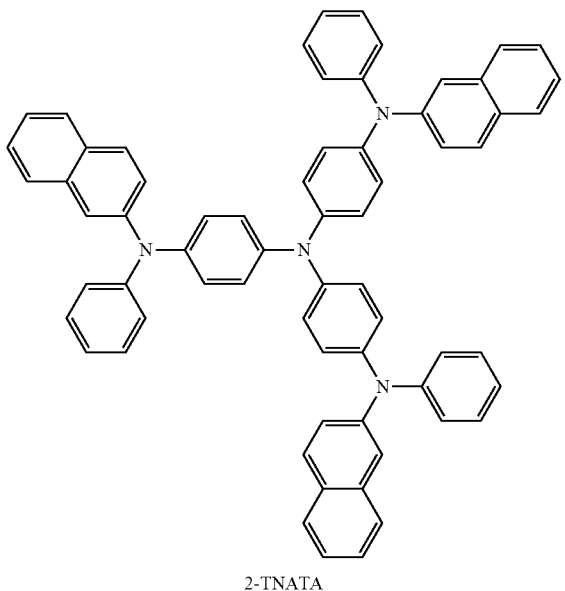

2-TNATA

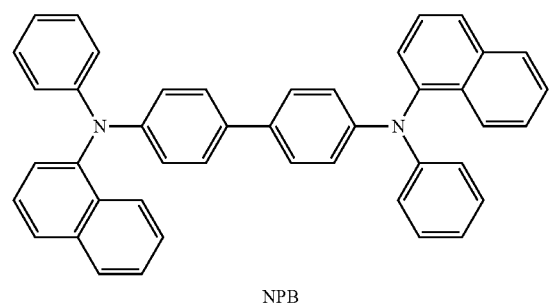

NPB

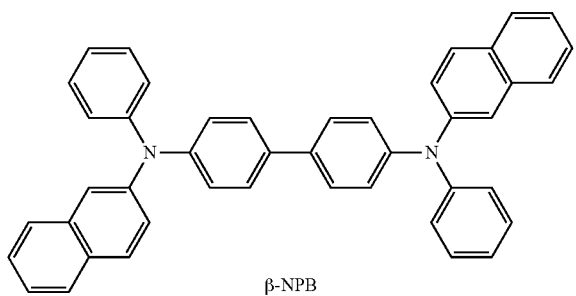

β-NPB

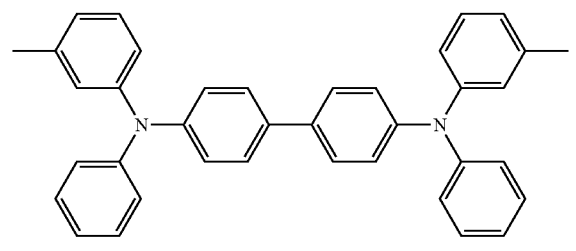

TPD

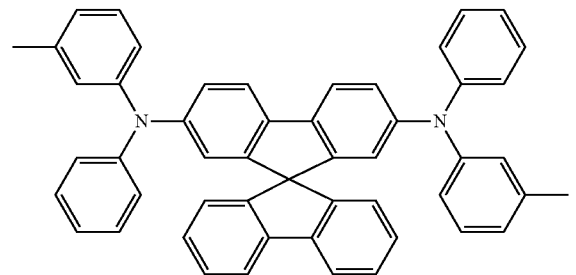

Spiro-TPD

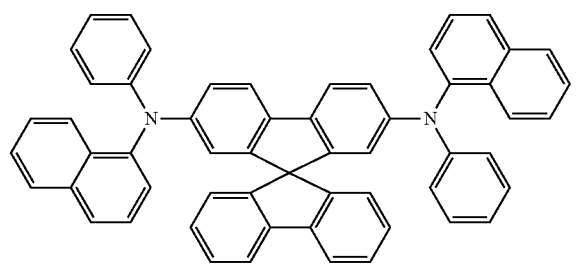

Spiro-NPB

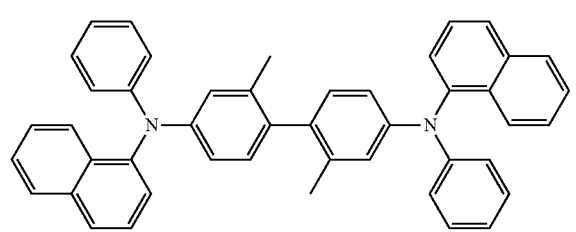

methylated NPB

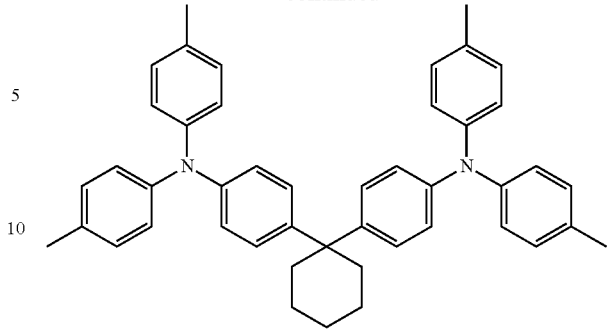

TAPC

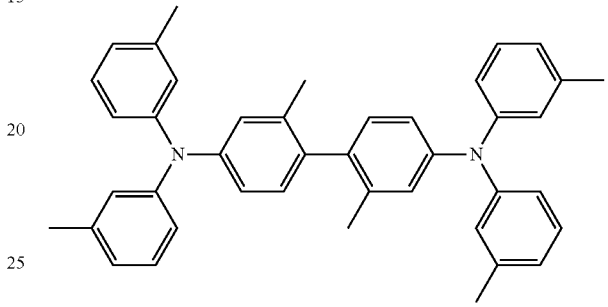

HMTPD

Formula 201

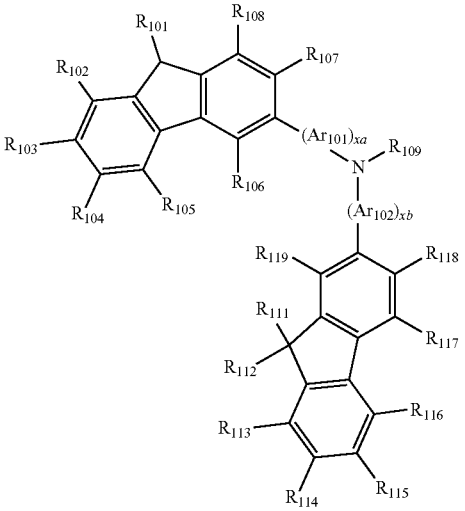

Formula 202

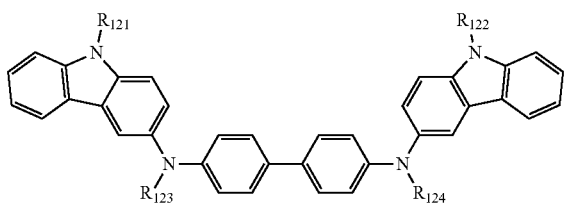

wherein, in Formula 201, $Ar_{101}$ and $Ar_{102}$ may each independently be
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof.

In Formula 201, xa and xb may each independently be an integer from 0 to 5. In some embodiments, xa and xb may each independently be an integer from 0 to 2. In some embodiments, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), or a $C_1$-$C_{10}$ alkoxy group (e.g., a methoxy group, an ethoxy group, a propoxy group, a butoxy group, or a pentoxy group);

a $C_1$-$C_{10}$ alkyl group or a $C_1$-$C_{10}$ alkoxy group, each substituted with at least one deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or a combination thereof;

a phenyl group, a naphthyl group, an anthracenyl group, a fluorenyl group, or a pyrenyl group; and a phenyl group, a naphthyl group, an anthracenyl group, a fluorenyl group, or a pyrenyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or a combination thereof, but embodiments are not limited thereto.

In Formula 201, $R_{109}$ may be:

a phenyl group, a naphthyl group, an anthracenyl group, or a pyridinyl group; or a phenyl group, a naphthyl group, an anthracenyl group, and a pyridinyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, or a pyridinyl group.

In some embodiments, the compound represented by Formula 201 may be represented by Formula 201A, but embodiments are not limited thereto:

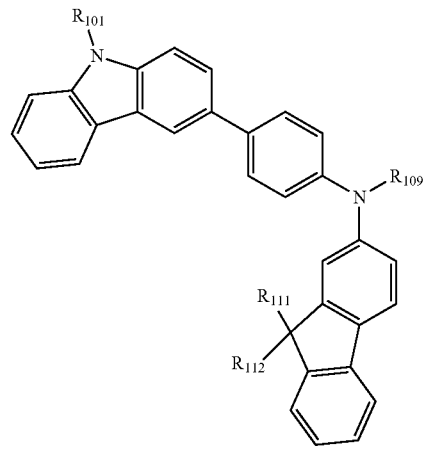

Formula 201A wherein, in Formula 201A, $R_{101}$, $R_{111}$, $R_{112}$, and $R_{109}$ may respectively be understood by referring to the description of $R_{11}$, $R_{111}$, $R_{112}$, and $R_{109}$ provided herein.

In some embodiments, the compounds represented by Formulae 201 and 202 may include Compounds HT1 to HT20, but embodiments are not limited thereto:

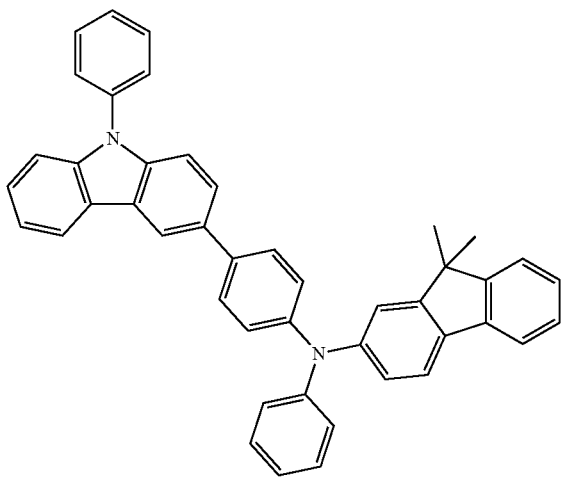

HT1

HT2
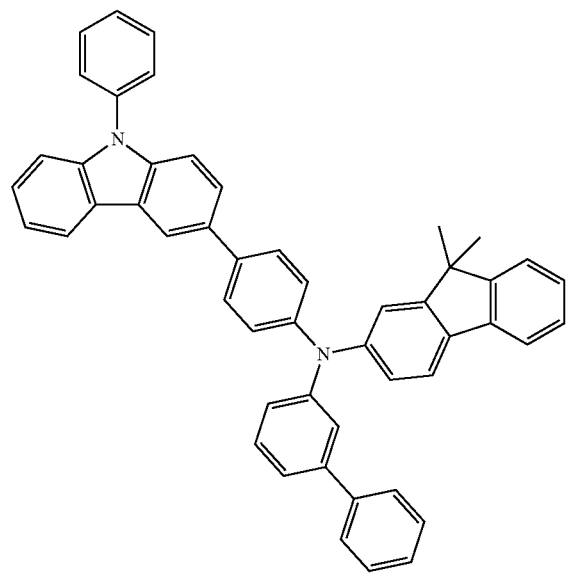
HT3
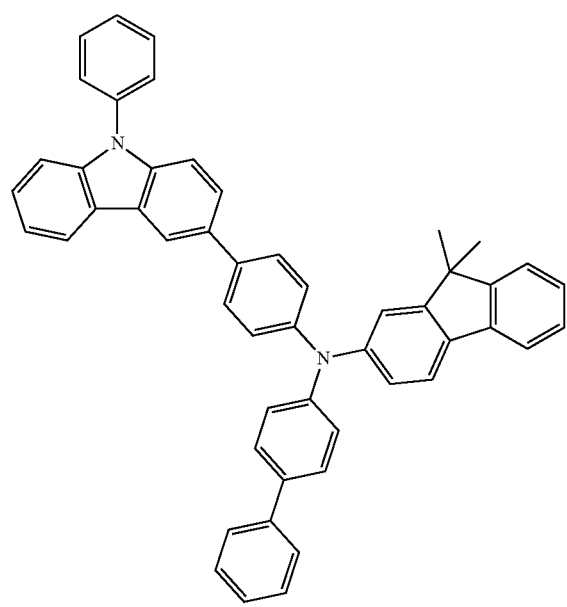
HT4
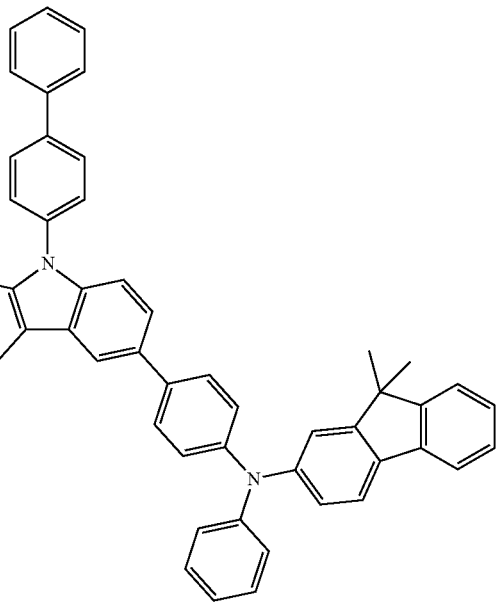
HT5
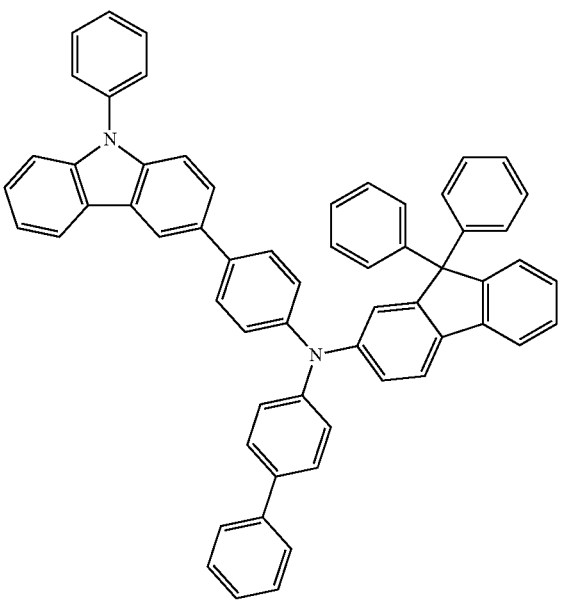

HT6
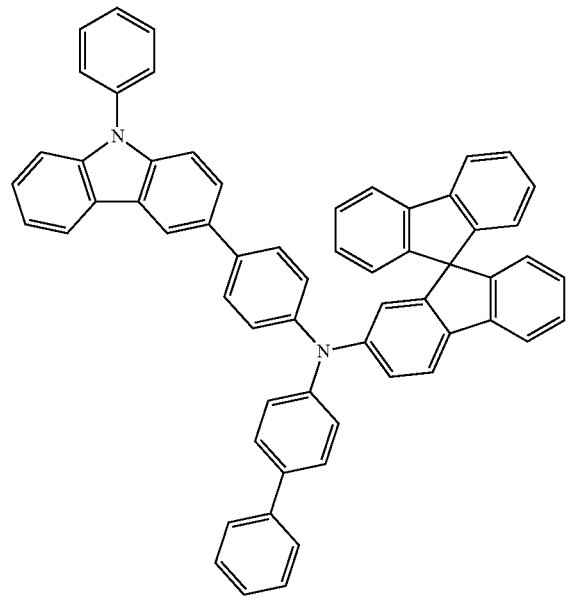
HT8
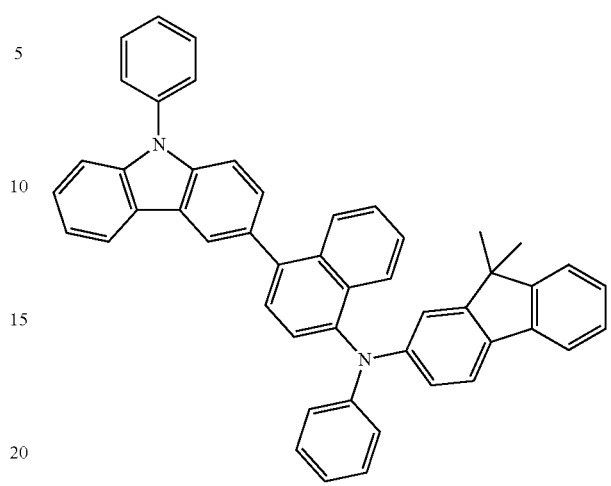
HT9
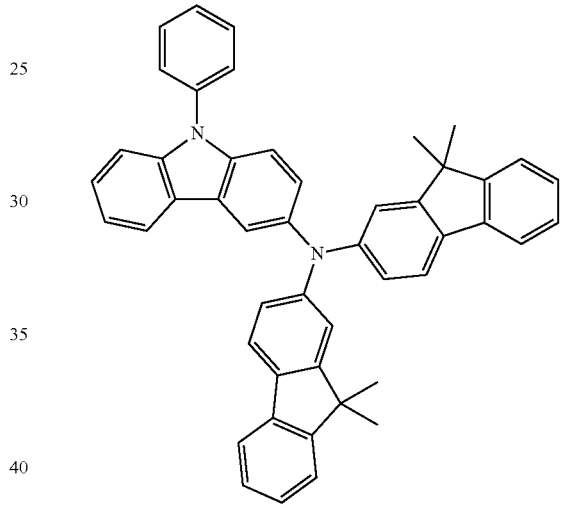
HT7
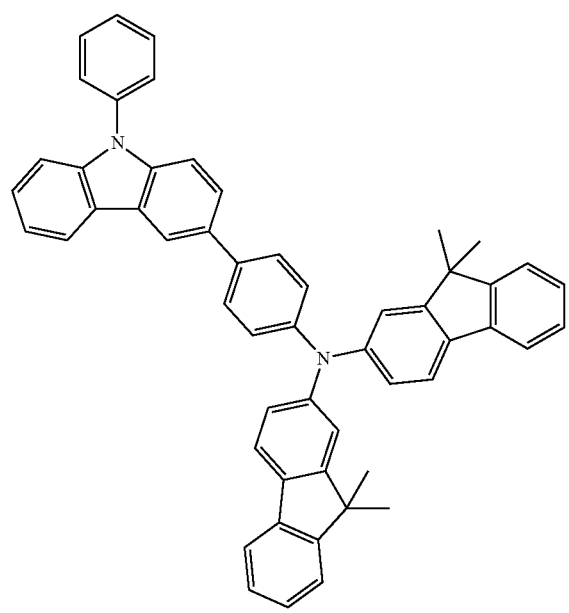
HT10
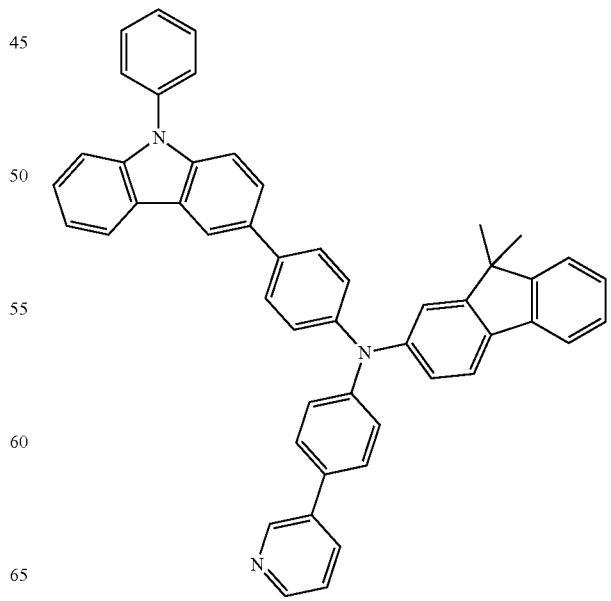

HT11
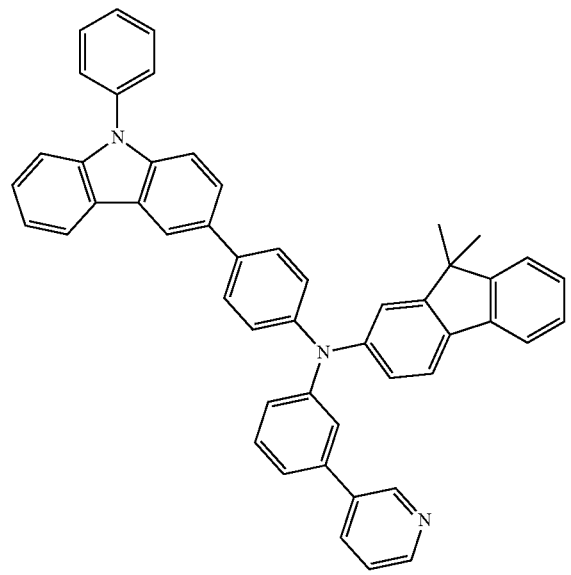
HT12
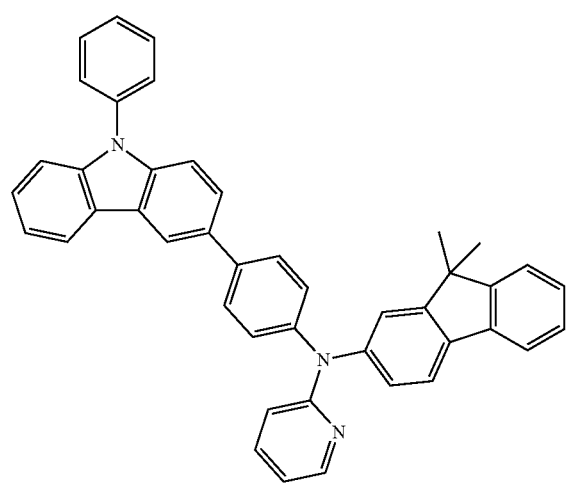
HT13
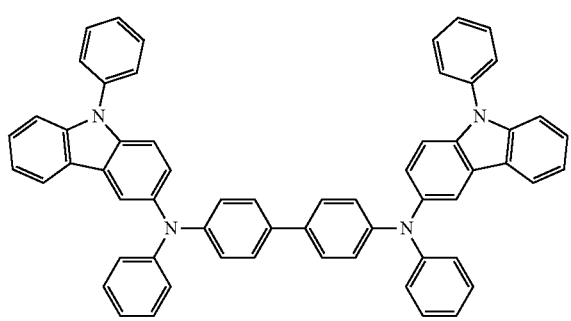
HT14
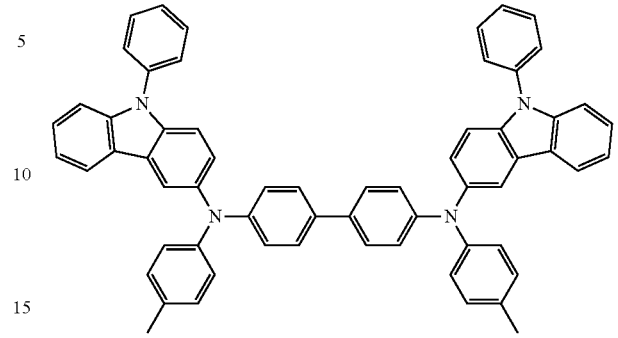
HT15
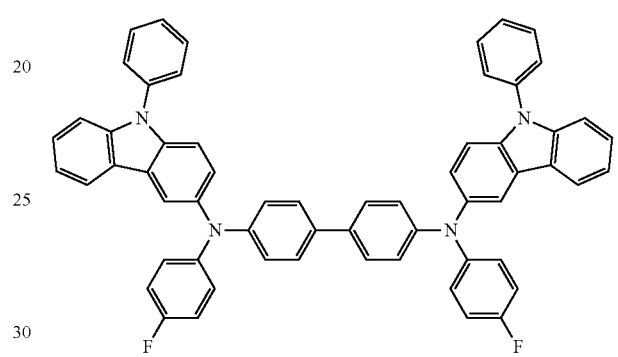
HT16
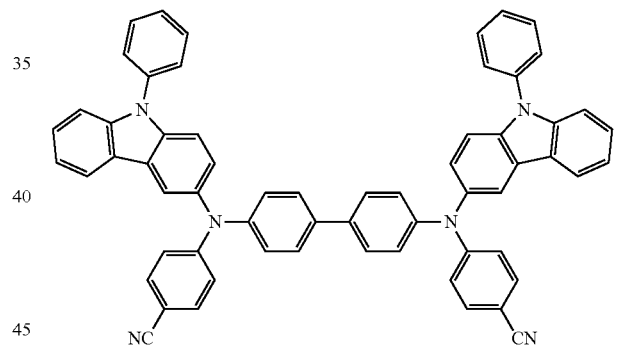
HT17
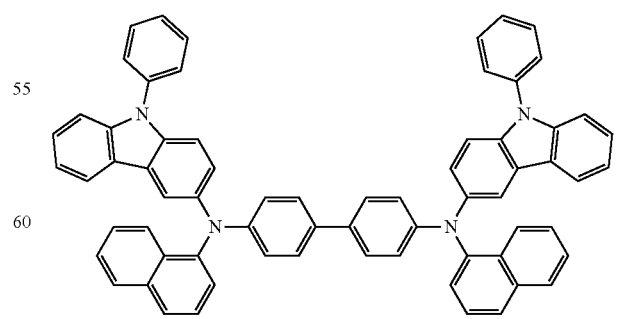

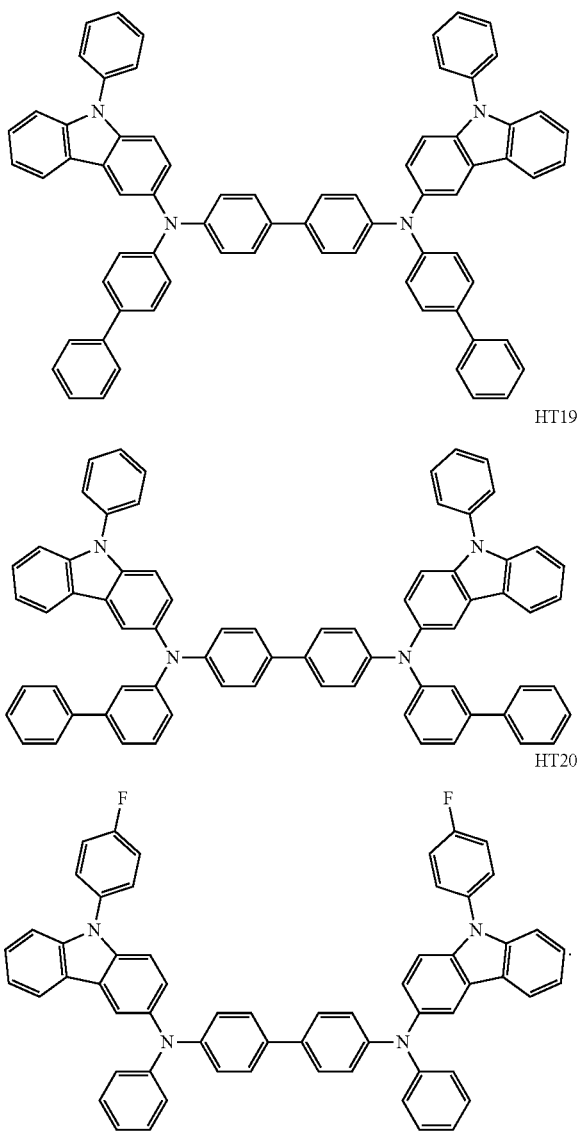

derivative, a metal oxide, and a compound containing a cyano group, but embodiments are not limited thereto. For example, non-limiting examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or Compound HT-D2, but embodiments are not limited thereto:

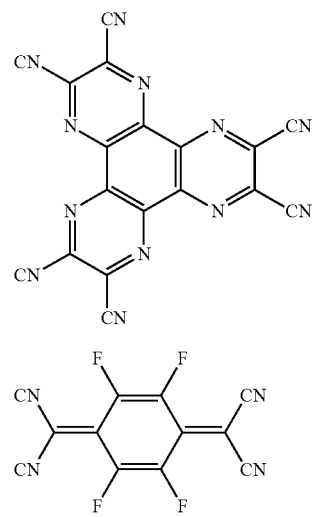

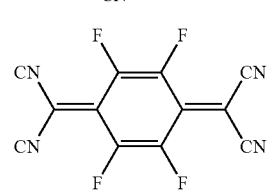

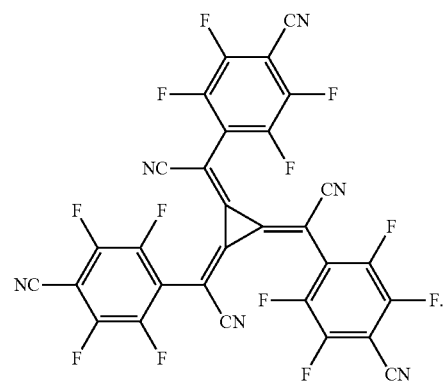

The thickness of the hole transport region may be in a range of about 100 Angstroms (Å) to about 10,000 Å, for example, about 100 Å to about 1,000 Å. When the hole transport region includes at least one a hole injection layer and a hole transport layer, the thickness of the hole injection layer may be in a range of about 100 Å to about 10,000 Å, for example, about 100 Å to about 1,000 Å, the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, excellent hole transport characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant. The p-dopant may include one of a quinone derivative, a metal oxide, and a compound containing a cyano group, but embodiments are not limited thereto.

The hole transport region may further include a buffer layer.

The buffer layer may compensate for an optical resonance distance depending on a wavelength of light emitted from the emission layer to improve the efficiency of an organic light-emitting device.

An emission layer may be formed on the hole transport region by using one or more suitable methods, such as vacuum deposition, spin coating, casting, or LB deposition. When the emission layer is formed by vacuum deposition or spin coating, vacuum deposition and coating conditions for forming the emission layer may be generally similar to those conditions for forming a hole injection layer, though the conditions may vary depending on a compound that is used.

The hole transport region may further include an electron blocking layer. The electron blocking layer may include any suitable known material, e.g., mCP, but embodiments are not limited thereto:

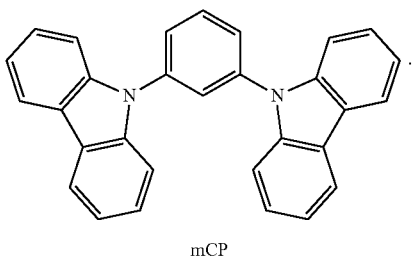 [SMILES: c1cc(-n2c3ccccc3c3ccccc32)cc(-n2c3ccccc3c3ccccc32)c1]

mCP

The thickness of the electron blocking layer may be in a range of about 50 Å to about 1,000 Å, and in some embodiments, about 70 Å to about 500 Å. When the thickness of the electron blocking layer is within any of these ranges, excellent electron blocking characteristics may be obtained without a substantial increase in driving voltage.

When the organic light-emitting device 10 is a full-color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light. In some embodiments, the structure of the emission layer may vary.

The emission layer may include the condensed cyclic compound represented by Formula 1.

In some embodiments, the emission layer may include the condensed cyclic compound represented by Formula 1 only.

In some embodiments, the emission layer may further include
the condensed cyclic compound represented by Formula 1 and
the organometallic compound represented by Formula 81.

The condensed cyclic compound represented by Formula 1 and the organometallic compound represented by Formula 81 may be understood by referring to the descriptions for those provided herein.

When the emission layer includes the host and the dopant, an amount of the dopant may be a range of about 0.01 parts to about 20 parts by weight based on about 100 parts by weight of the emission layer, but embodiments are not limited thereto. When the amount of the dopant is within this range, light emission without quenching may be realized.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Next, an electron transport region may be formed on the emission layer.

The electron transport region may include at least one a hole blocking layer, an electron transport layer, and an electron injection layer.

In some embodiments, the electron transport region may have a hole blocking layer/an electron transport layer/an electron injection layer structure or an electron transport layer/an electron injection layer structure, but embodiments are not limited thereto. The electron transport layer may have a single-layered structure or a multi-layered structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer, for example, may include at least one of BCP and Bphen, but embodiments are not limited thereto:

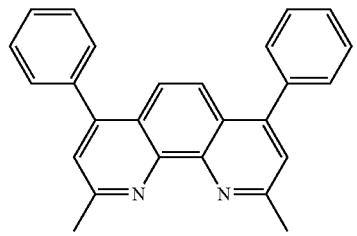

BCP

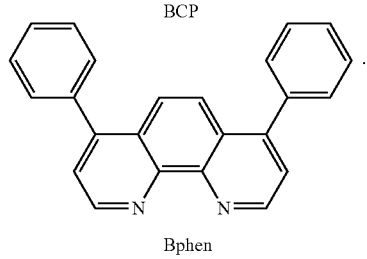

Bphen

The hole blocking layer may include the condensed cyclic compound represented by Formula 1.

The thickness of the hole blocking layer may be in a range of about 20 Å to about 1,000 Å, for example, about 30 Å to about 300 Å. When the thickness of the hole blocking layer is within any of these ranges, excellent hole blocking characteristics may be obtained without a substantial increase in driving voltage.

The electron transport layer may further include at least one of BCP, Bphen, Alq$_3$, BAlq, TAZ, and NTAZ:

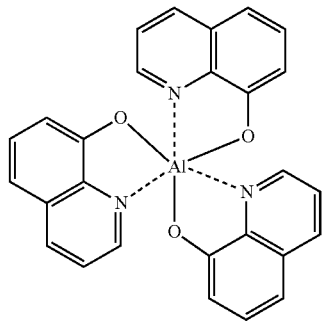

Alq$_3$

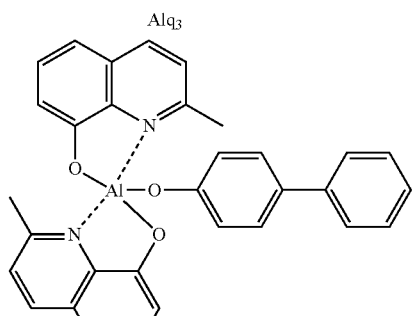

BAlq

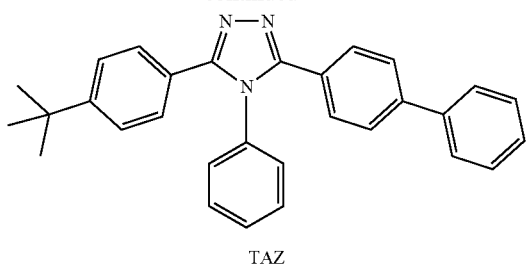

TAZ

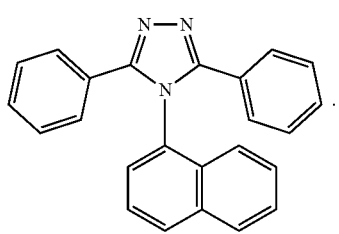

NTAZ

In some embodiments, the electron transport layer may include at least one Compounds ET1, ET2, and ET3, but embodiments are not limited thereto:

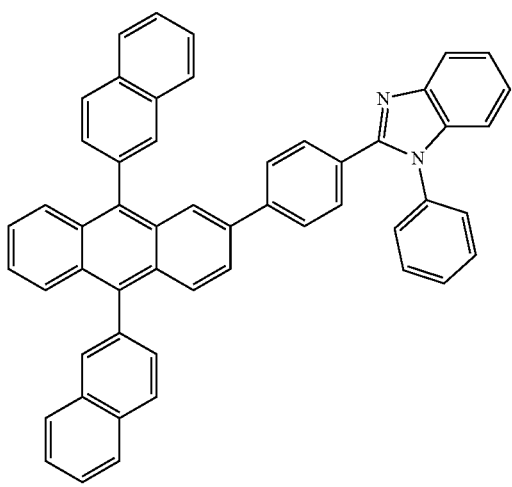

ET1

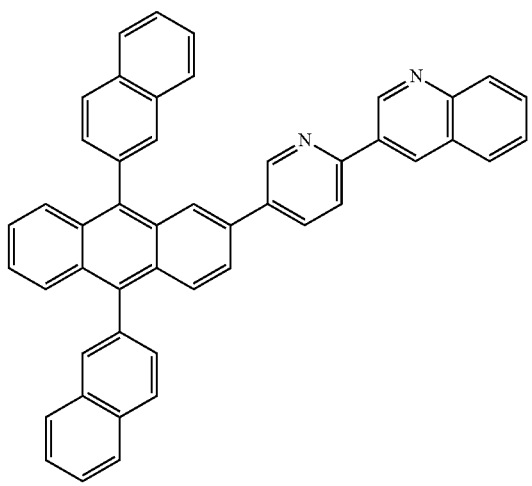

ET2

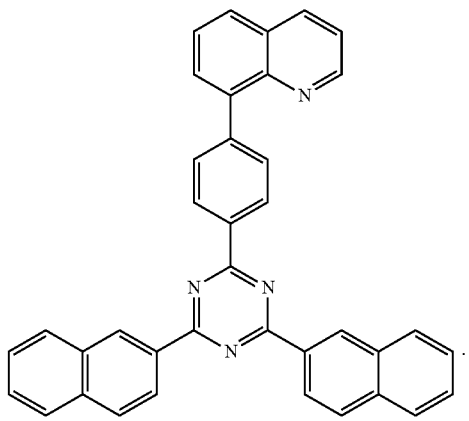

ET3

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport layer may further include a material containing metal, in addition to the materials described above.

The material containing metal may include a Li complex. The Li complex may include, e.g., Compound ET-D1 (lithium 8-hydroxyquinolate, LiQ) or Compound ET-D2:

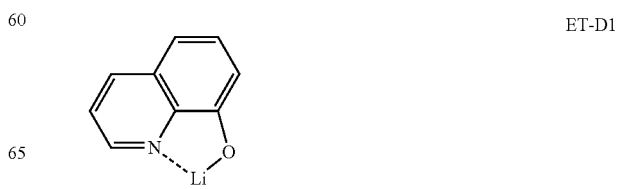

ET-D1

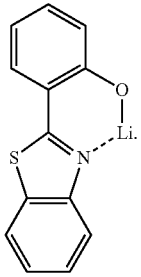

ET-D2

The electron transport region may include an electron injection layer that facilitates electron injection from the second electrode 19.

The electron injection layer may include at least one of LiQ, LiF, NaCl, CsF, $Li_2$, and BaO.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

The second electrode 19 may be on the organic layer 15. The second electrode 19 may be a cathode. A material for forming the second electrode 19 may be a material with a relatively low work function, such as a metal, an alloy, an electrically conductive compound, and a mixture thereof. Examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device. In some embodiments, the material for forming the second electrode 19 may vary.

Hereinbefore the organic light-emitting device 10 has been described with reference to the FIGURE, but embodiments are not limited thereto.

According to an aspect of another embodiment, an electronic apparatus may include an organic light-emitting device including the condensed-cyclic compound represented by Formula 1. In some embodiments, the electronic device may include a display apparatus, but embodiments are not limited thereto.

The term "$C_1$-$C_{60}$ alkyl group" as used herein refers to a linear or branched aliphatic saturated hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_1$ alkyl group). Examples thereof include a methoxy group, an ethoxy group, and an isopropyloxy group.

The term "$C_2$-$C_{60}$ alkenyl group" as used herein refers to a group formed by placing at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group including at least one N, O, P, Si, B, Se, Ge, Te, S, or a combination thereof as a ring-forming atom and 1 to 10 carbon atoms. Examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group including at least one N, O, P, Si, B, Se, Ge, Te, S, or a combination thereof as a ring-forming atom, 2 to 10 carbon atoms, and at least one double bond in its ring. Examples of the $C_2$-$C_{10}$ heterocycloalkenyl group include a 2,3-dihydrofuranyl group and a 2,3-dihydrothiophenyl group. The term "$C_1$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having an aromatic system having at least one N, O, P, Si, B, Se, Ge, Te, S, or a combination thereof, as a ring-forming atom and 1 to 60 carbon atoms. The term "$C_1$-$C_{60}$ heteroarylene group" as used herein refers to a divalent group having an aromatic system having at least one N, O, P, Si, B, Se, Ge, Te, S, or a combination thereof, as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein is represented by —$OA_{102}$ (wherein $A_{102}$ is the $C_6$-$C_{60}$ aryl group). The term "$C_6$-$C_{60}$ arylthio group" as used herein is represented by —$SA_{103}$ (wherein $A_{103}$ is the $C_6$-$C_{60}$ aryl group).

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom N, O, P, Si, and S as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

In Formula 1 of the present specification, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, —$B(Q_{16})(Q_{17})$, or a combination thereof;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —$CD_3$, —$CD_2H$, —$CDH_2$, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, —$B(Q_{26})(Q_{27})$, or a combination thereof; or —$Si(Q_{31})(Q_{32})(Q_{33})$, —$N(Q_{34})(Q_{35})$ or —$B(Q_{36})(Q_{37})$.

In the present specification, $Q_1$ to $Q_7$, $Q_{11}$ to $Q_{17}$, $Q_{21}$ to $Q_{27}$, and $Q_{31}$ to $Q_{37}$ may each independently be hydrogen, deuterium, —F, —C, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a monovalent non-aromatic condensed polycyclic group, or a monovalent non-aromatic condensed heteropolycyclic group.

The symbols * and *' as used herein, unless defined otherwise, refer to a binding site to an adjacent atom in the formula.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an amount of B used was identical to an amount of A used based on molar equivalence.

EXAMPLES

Synthesis Example 1: Synthesis of Compound 81

Compound 81 was synthesized based on the following Reaction Scheme:

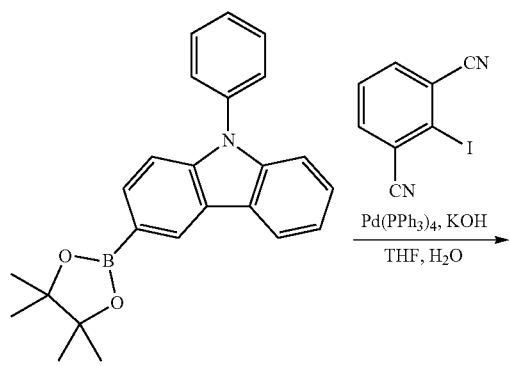

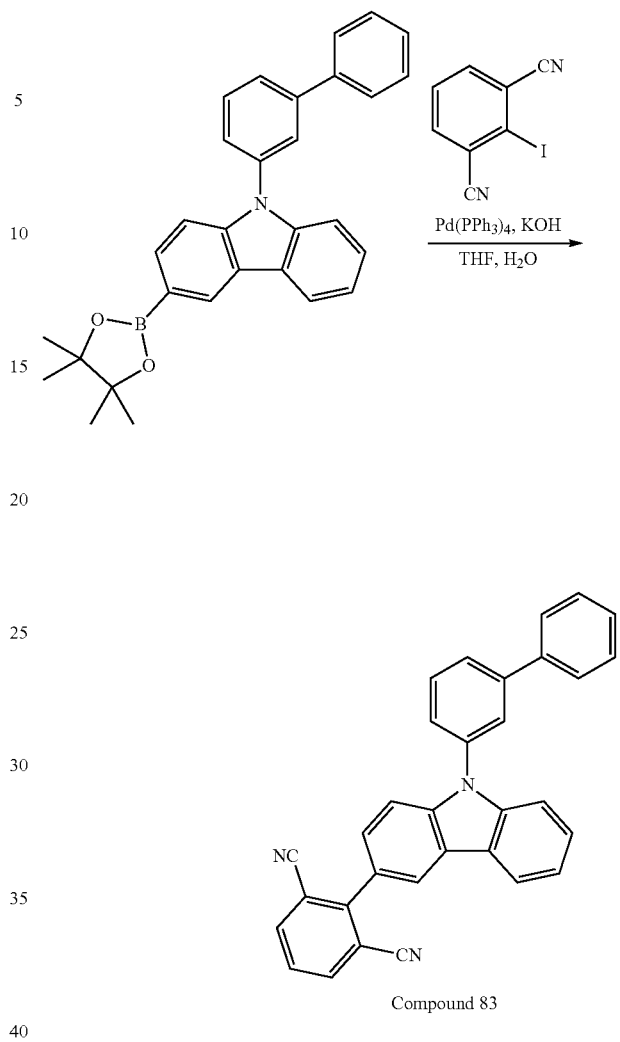

Compound 81

Compound 83

Synthesis of Compound 81

10.0 grams (g) (27.1 millimole (mmol)) of 9-phenyl-3-(4,4,5,5-tetramethyl-1,3,2-dioxaborolan-2-yl)-9H-carbazole, 8.26 g (32.5 mmol) of 2-iodoisophthalonitrile, 6.23 g (5.42 mmol) of tetrakistriphenylphosphine palladium (0) (Pd(PPh$_3$)$_4$), and 12.2 g (217 mmol) of potassium hydroxide were mixed with a mixture solution of 150 mL of tetrahydrofuran (THF) and 100 mL of water, followed by stirring under reflux for 2 hours. Once the reaction was complete, the reaction mixture was cooled to room temperature, and an aqueous solution layer was removed therefrom by ethyl acetate (EA)/water extraction, followed by concentration of an organic solvent under reduced pressure. The solid product was heated and dissolved in dichloromethane (DCM), followed by filtration under reduced pressure through silica gel chromatography. The product was recrystallized using dichloromethane (DCM)/n-hexane, thereby obtaining a desired compound, 5.20 g of Compound 81 (yield: 52%).

LC-Mass (calculated value: 369.13 g/mol, measured value: M+1=370 g/mol)

Synthesis Example 2: Synthesis of Compound 83

Compound 83 was synthesized based on the following Reaction Scheme:

Synthesis of Compound 83

A desired compound, 5.50 g of Compound 83 (yield: 55%), was obtained in substantially the same manner as in Synthesis of Compound 81, except that 10.0 g (14.9 mmol) of 9-([1,1'-biphenyl]-3-yl)-3-(4,4,5,5-tetramethyl-1,3,2-dioxaborolan-2-yl)-9H-carbazole was used instead of 9-phenyl-3-(4,4,5,5-tetramethyl-1,3,2-dioxaborolan-2-yl)-9H-carbazole.

LC-Mass (calculated value: 455.16 g/mol, measured value: M+1=456 g/mol)

Synthesis Example 3: Synthesis of Compound 93

Compound 93 was synthesized based on the following Reaction Scheme:

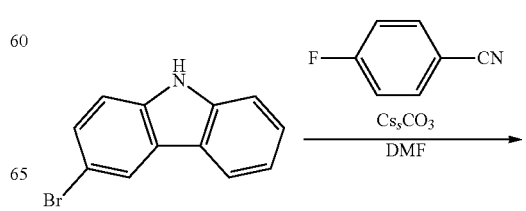

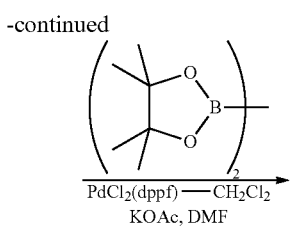

(A)

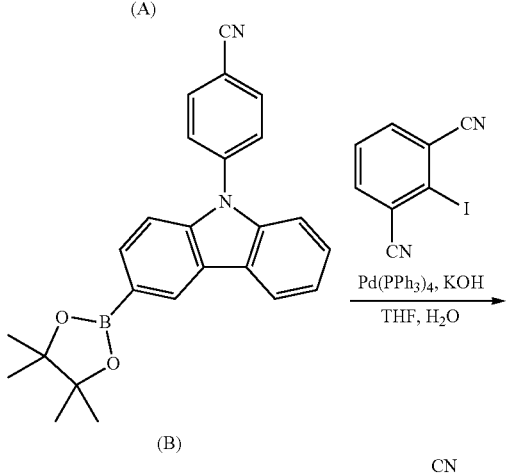

(B)

Compound 93

Synthesis of Intermediate (A)

10.0 g (40.6 mmol) of 3-bromo-9H-carbazole, 5.91 g (48.8 mmol) of 4-fluorobenzonitrile, and 26.5 g (81.3 mmol) of cesium carbonate were dissolved in 100 mL of dimethyl formamide (DMF), followed by stirring under reflux for 1 hour. Once the reaction was complete, the reaction mixture was cooled to room temperature, and the reaction mixture was diluted with water, extracted with ethyl acetate (EA), followed by concentration of the organic layer under reduced pressure. The product was separated through silica gel column chromatography to obtain a desired compound, 13.4 g of Intermediate (A) (yield: 95%).

LC-Mass (calculated value: 346.01 g/mol, measured value: M+1=347 g/mol)

Synthesis of Intermediate (B)

13.4 g (38.6 mmol) of Intermediate (A), 11.8 g (46.3 mmol) of bis(pinacolato)diboron, 1.41 g (1.93 mmol) of PdCl$_2$(dppf).CH$_2$Cl$_2$, and 11.4 g (116 mmol) of potassium acetate were mixed with 130 mL of DMF, followed by stirring under reflux at a temperature of 100° C. for 18 hours. Once the reaction was complete, the reaction mixture was cooled to room temperature and underwent filtration through silica gel chromatography, followed by concentration under reduced pressure of the filtrate. The product was purified using silica gel column chromatography. The product was recrystallized using dichloromethane (DCM)/n-hexane, thereby obtaining a desired compound, 10.0 g of Intermediate (B) (yield: 66%).

LC-Mass (calculated value: 394.19 g/mol, measured value: M+1=395 g/mol)

Synthesis of Compound 93

A desired compound, 4.30 g of Compound 93 (yield: 44%), was obtained in substantially the same manner as in Synthesis of Compound 81, except that 9.80 g (24.9 mmol) of Intermediate (B) was used instead of 9-phenyl-3-(4,4,5,5-tetramethyl-1,3,2-dioxaborolan-2-yl)-9H-carbazole.

LC-Mass (calculated value: 394.12 g/mol, measured value: M+1=395 g/mol)

Synthesis Example 4: Synthesis of Compound 231

Compound 231 was synthesized based on the following Reaction Scheme:

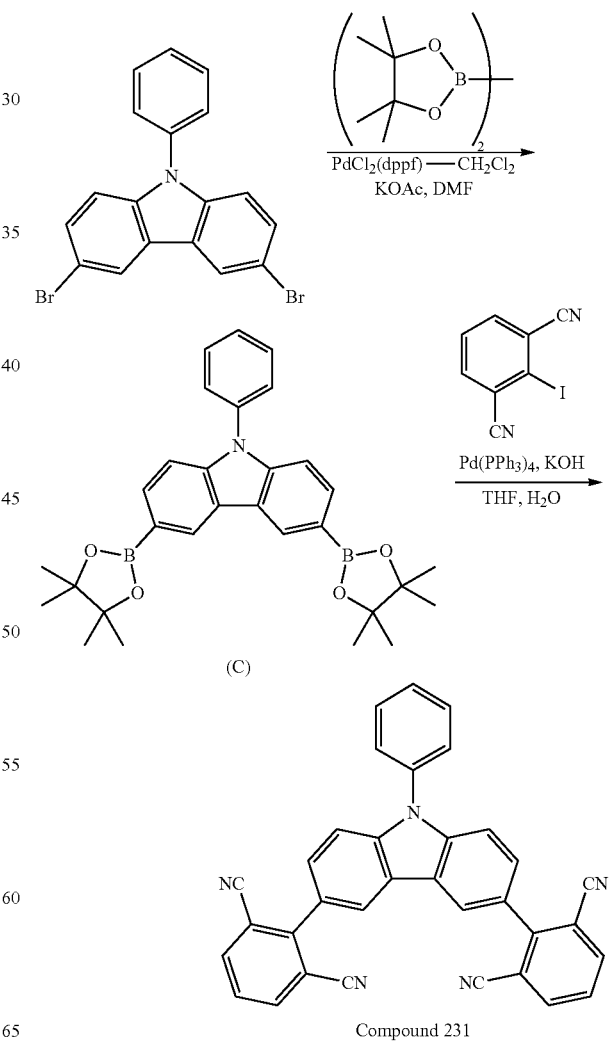

(C)

Compound 231

Synthesis of Intermediate (C)

16.2 g (40.4 mmol) of 3,6-dibromo-9-phenyl-9H-carbazole, 30.8 g (121 mmol) of bis(pinacolato)diboron, 2.96 g (4.04 mmol) of $PdC_2(dppf).CH_2Cl_2$, and 11.9 g (121 mmol) of potassium acetate were mixed with 100 mL of DMF, followed by stirring under reflux at a temperature of 150° C. for 18 hours. Once the reaction was complete, the reaction mixture was cooled to room temperature and underwent filtration through silica gel chromatography, followed by concentration of the organic layer under reduced pressure of the filtrate. The product was purified using silica gel column chromatography. The product was recrystallized using dichloromethane (DCM)/n-hexane, thereby obtaining a desired compound, 10.5 g of Intermediate (C) (yield: 53%).

LC-Mass (calculated value: 495.28 g/mol, measured value: M+1=496 g/mol)

Synthesis of Compound 231

4.80 g (9.69 mmol) of Intermediate(C), 5.02 g (24.2 mmol) of 2-bromoisophthalonitrile, 4.48 g (3.88 mmol) of tetrakistriphenylphosphine palladium (0) $(Pd(PPh_3)_4)$, and 8.16 g (145 mmol) of potassium hydroxide were mixed with a mixture solution of 80 mL of THF and 70 mL of water, followed by stirring under reflux for 1 hour. Once the reaction was complete, the reaction mixture was cooled to room temperature, and the reaction mixture was extracted therefrom by ethyl acetate (EA)/water extraction, followed by concentration of the organic layer under reduced pressure. The product was purified using silica gel column chromatography. The product was recrystallized using dichloromethane (DCM)/n-hexane, thereby obtaining a desired compound, 1.54 g of Compound 231 (yield: 32%).

LC-Mass (calculated value: 495.15 g/mol, measured value: M+1=496 g/mol)

Example 1

As a first electrode (an anode), a glass substrate having an indium tin oxide (ITO) electrode deposited thereon at a thickness of 1,500 Å was washed with distilled water in the presence of ultrasound waves. Once the washing with distilled water was complete, ultrasound wave washing was performed on the substrate using solvents, such as isopropyl alcohol, acetone, and methanol. Subsequently, the substrate was dried, transferred to a plasma washer, washed for 5 minutes using oxygen plasma, and mounted in a vacuum depositor.

Compound HT3 and Compound HT-D2 were co-deposited on the ITO electrode of the glass substrate to form a hole injection layer having a thickness of 100 Å. Subsequently, Compound HT3 was deposited on the hole injection layer to form a hole transport layer having a thickness of 1,300 Å. mCP was next deposited on the hole transport layer to form an electron blocking layer having a thickness of 100 Å, thereby forming a hole transport region.

Subsequently, Compound 81 (host) and FIr6 (dopant, 10 percent by weight (wt %)) were co-deposited on the hole transport region to form an emission layer having a thickness of about 400 Å.

BCP was vacuum-deposited on the emission layer to form a hole blocking layer having a thickness of 100 Å. Compound ET3 and Liq were then co-deposited on the hole blocking layer to form an electron transport layer having a thickness of 300 Å. Next, Liq was vacuum-deposited on the electron transport layer to form an electron injection layer having a thickness of 10 Å, and then, Al second electrode (a cathode) having a thickness of 1,200 Å was formed on the electron injection layer, thereby completing the manufacture of an organic light-emitting device.

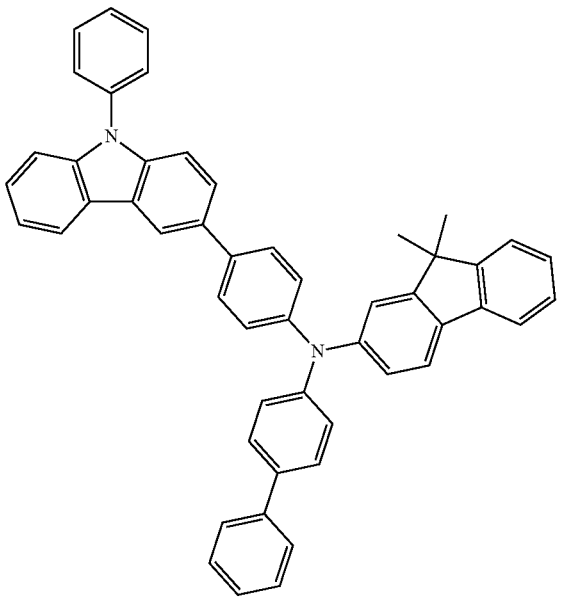

HT3

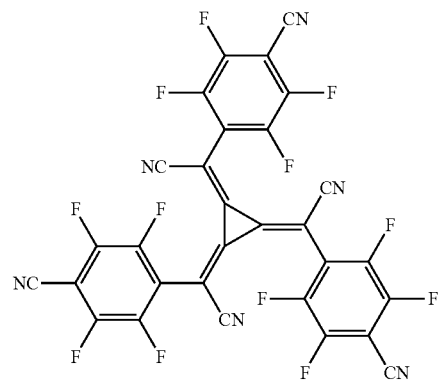

HT-D2

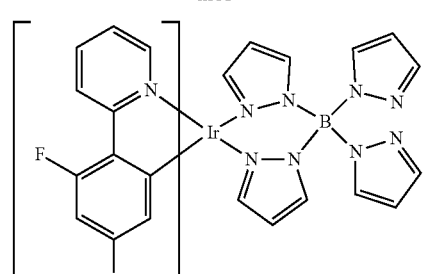

mCP

FIr6

-continued

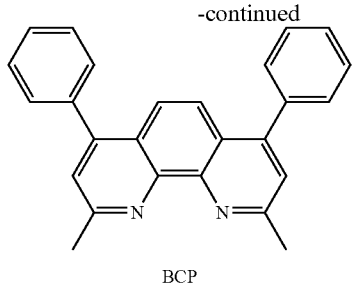
BCP

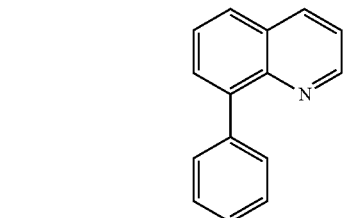
ET3

Examples 2 to 4 and Comparative Examples A to F

Organic light-emitting devices were manufactured in substantially the same manner as in Example 1, except that the compounds shown in Table 2 were used instead of Compound 1 as a host in the formation of an emission layer.

Evaluation Example 1: Evaluation of Characteristics of Organic Light-Emitting Device The driving voltage (V), current efficiency (cd/A), and durability ($T_{95}$ at 1,000 nit, hour) of the organic light-emitting devices manufactured in Examples 1 to 4 and Comparative Examples A to H were measured by using Keithley source-measure unit (SMU) 2400 and aluminance meter (Minolta Cs-1000A). The results thereof are shown in Table 2. The durability ($T_{95}$) indicates a time (hour) for the luminance of each light-emitting device to decline to 95% of its initial luminance of 100%. In Table 2, the driving voltage, current efficiency, and durability of Examples 1 to 4 and Comparative Examples B to F are each represented relative to those of Comparative Example A.

TABLE 2

| Host Compound | Driving voltage (relative value, %) | Current efficiency (relative value, %) | Durability (relative value, %) | Color |
|---|---|---|---|---|
| Example 1 | 81 | 87 | 168 | 204 | Blue |
| Example 2 | 83 | 84 | 183 | 198 | Blue |
| Example 3 | 93 | 74 | 186 | 253 | Blue |
| Example 4 | 231 | 95 | 142 | 168 | Blue |
| Comparative Example A | 100 | 100 | 100 | 100 | Blue |

TABLE 2-continued

| Host Compound | Driving voltage (relative value, %) | Current efficiency (relative value, %) | Durability (relative value, %) | Color |
|---|---|---|---|---|
| Comparative Example B | 105 | 98 | 105 | Blue |
| Comparative Example C | 132 | 105 | 97 | Blue |
| Comparative Example D | 137 | 109 | 93 | Blue |
| Comparative Example E | 190 | 58 | 29 | Blue |
| Comparative Example F | 194 | 65 | 33 | Blue |

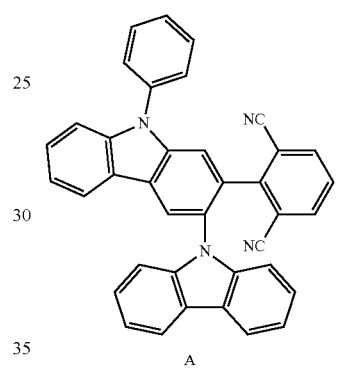
A

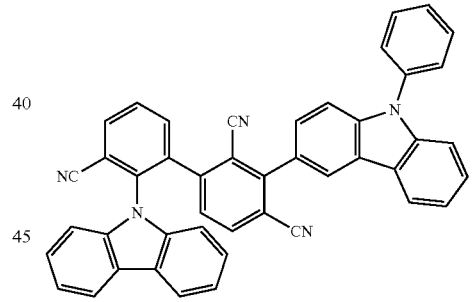
B

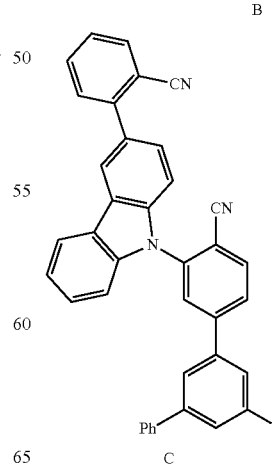
C

TABLE 2-continued

| Host Compound | Driving voltage (relative value, %) | Current efficiency (relative value, %) | Durability (relative value, %) | Color |
|---|---|---|---|---|

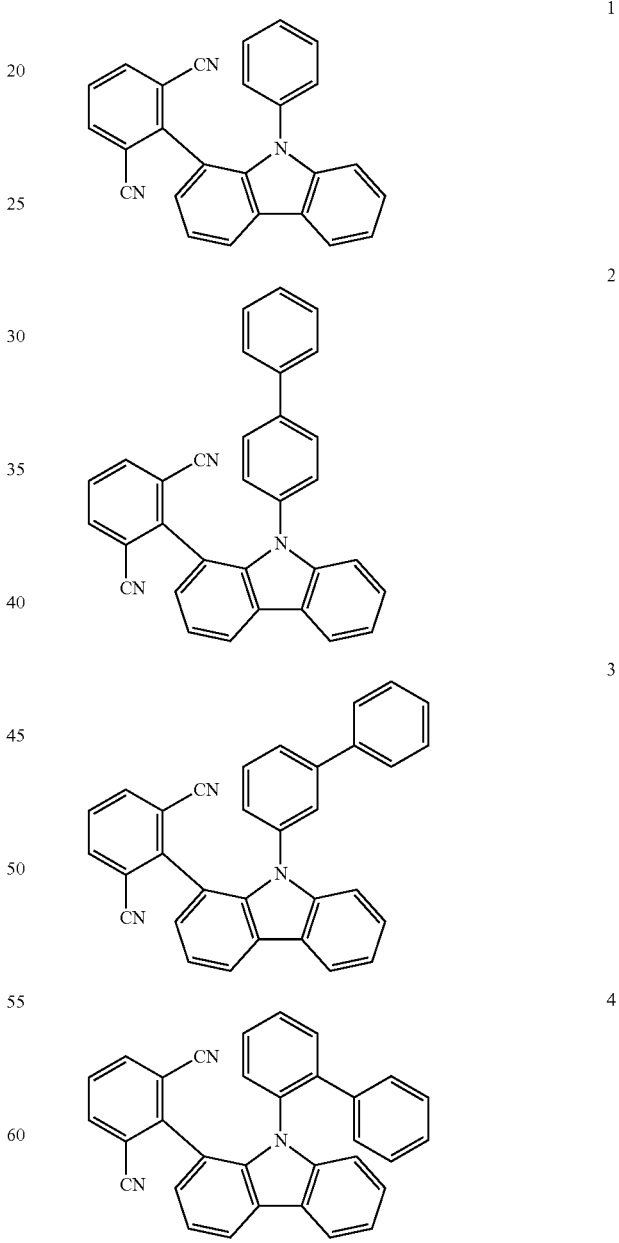

Referring to Table 2, the organic light-emitting devices of Examples 1 to 4 were found to emit blue light and have a low-driving voltage, high current efficiency, and high durability, as compared with the organic light-emitting devices of Comparative Examples A to F.

As apparent from the foregoing description, the condensed cyclic compound according to embodiments has excellent electric characteristics and thermal stability. Accordingly, an organic light-emitting device including the condensed cyclic compound may have a low driving voltage, high efficiency, high power, high quantum yield, and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A condensed cyclic compound selected from Compounds 1 to 80 and 82 to 280

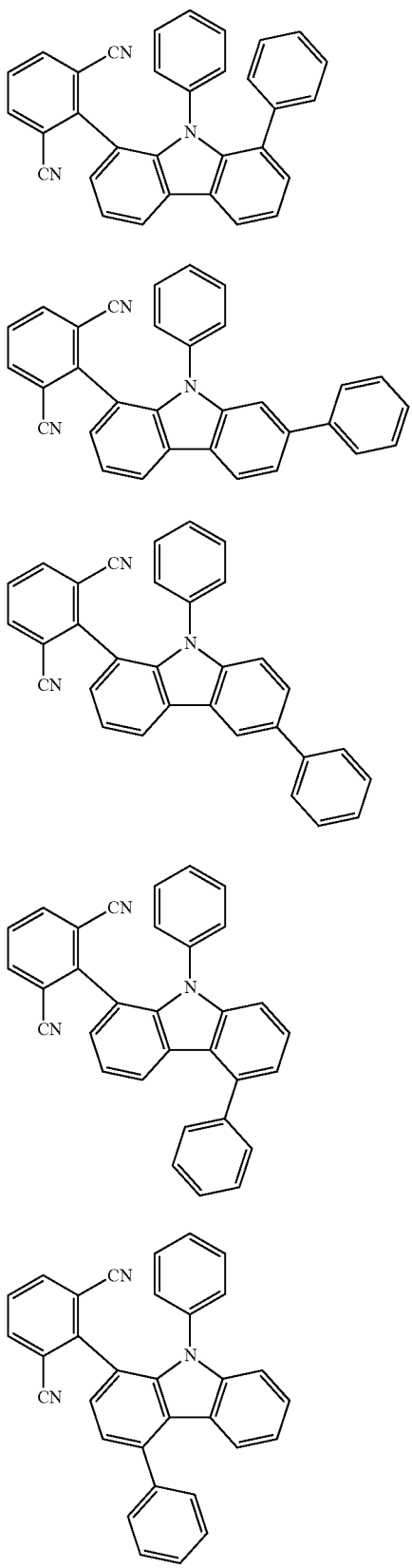
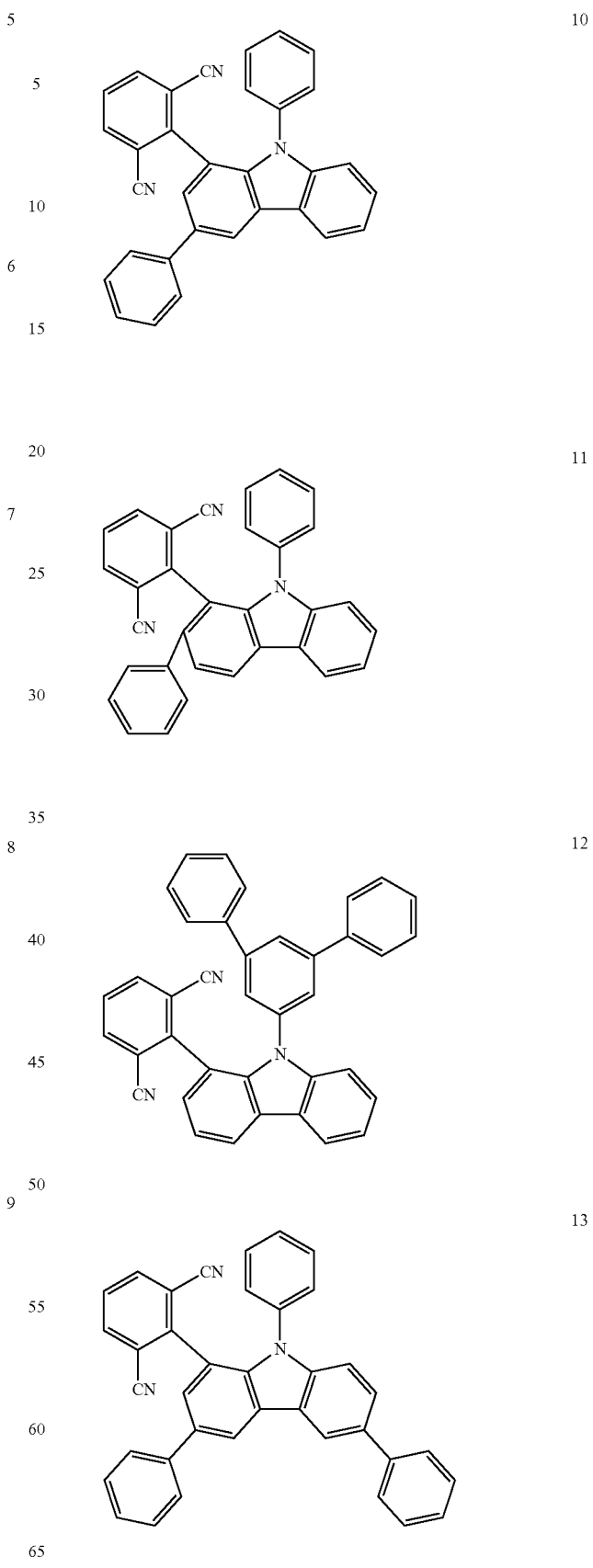

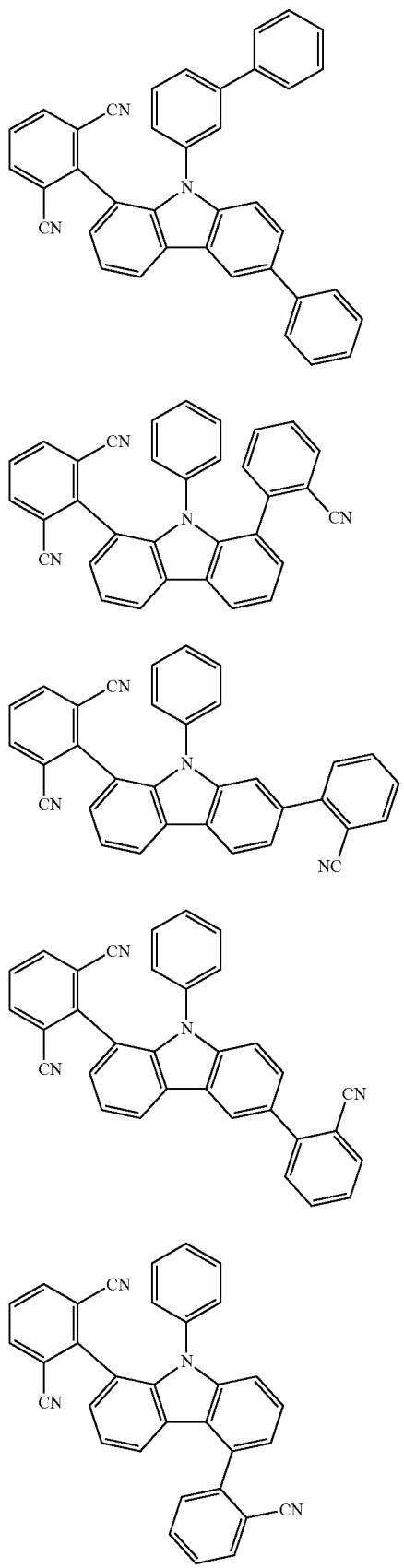
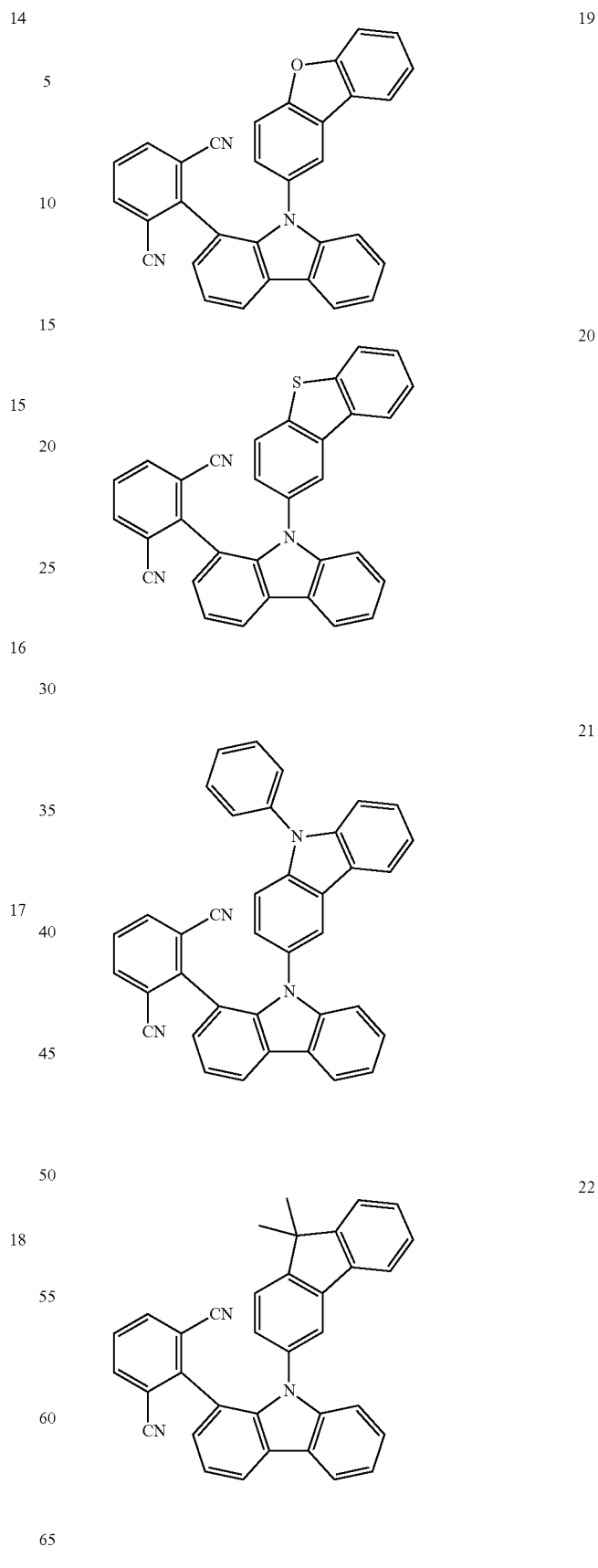

23
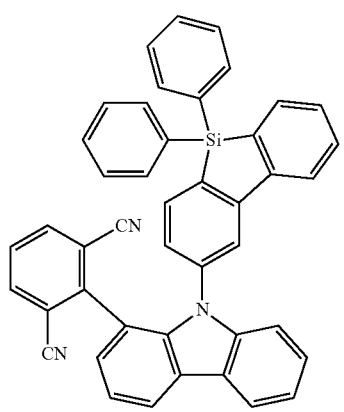
24
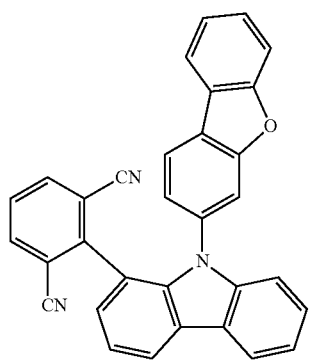
25
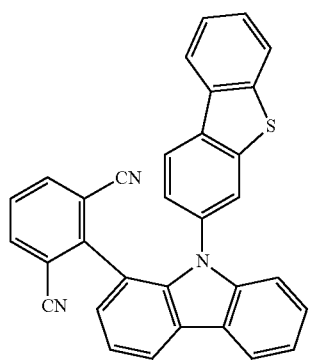
26
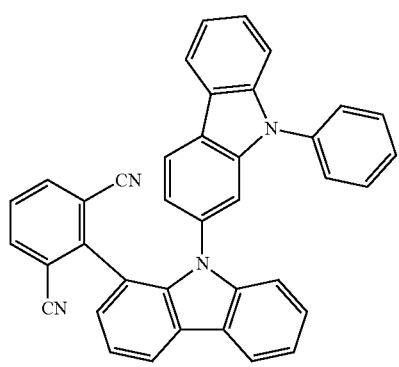
27
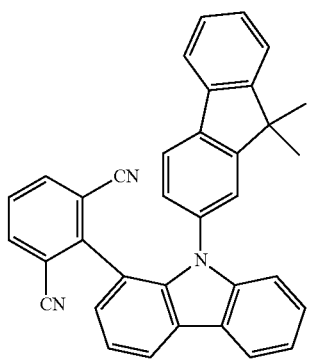
28
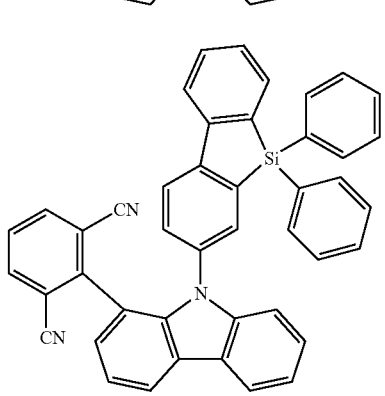
29
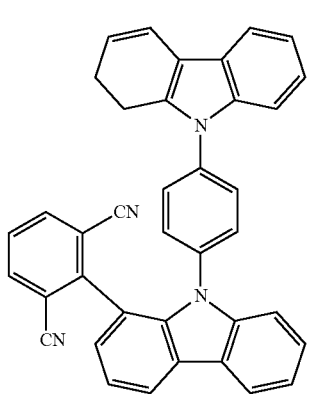
30
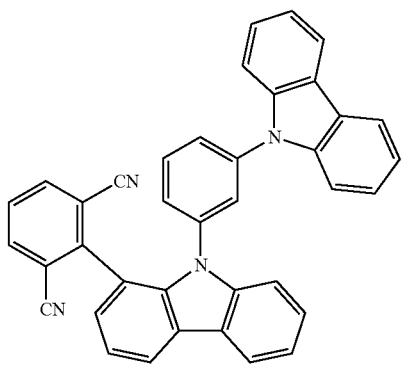

31
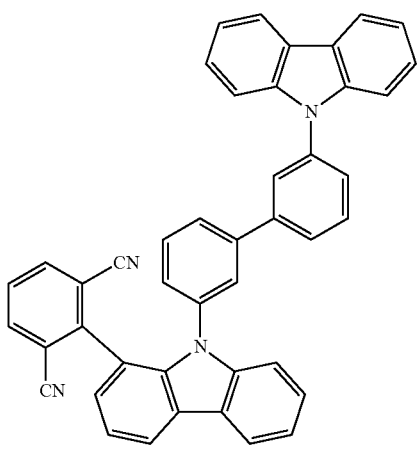
32
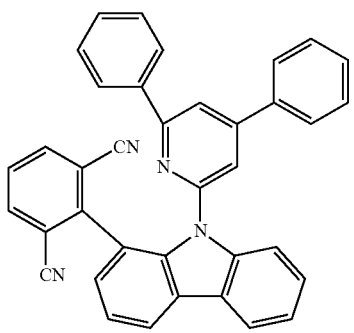
33
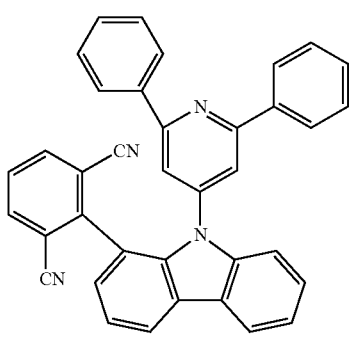
34
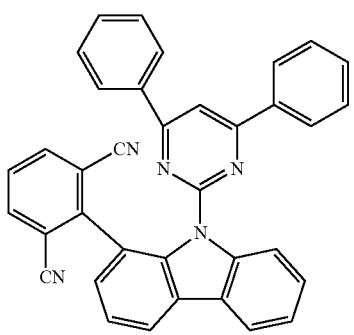
35
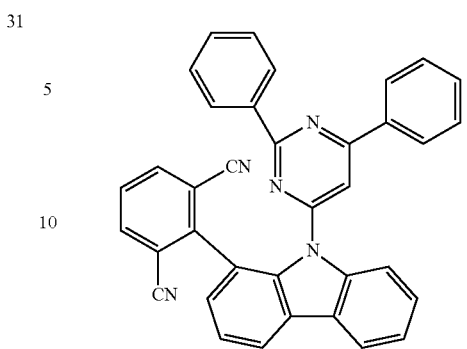
36
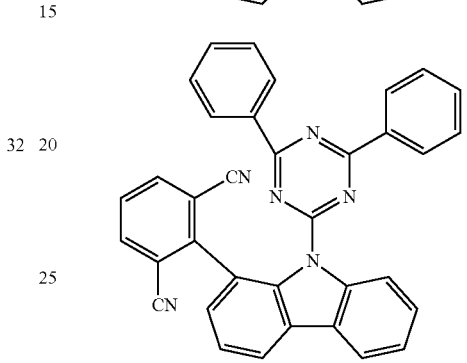
37
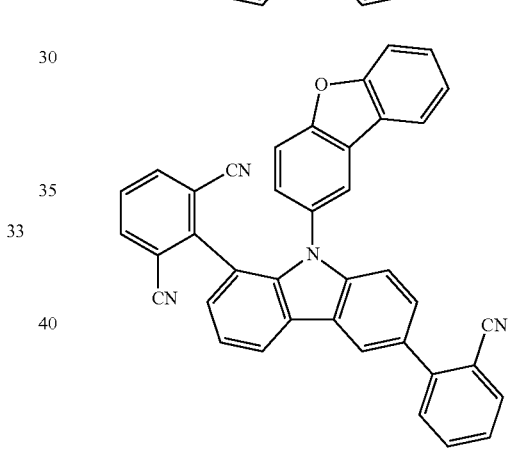
38
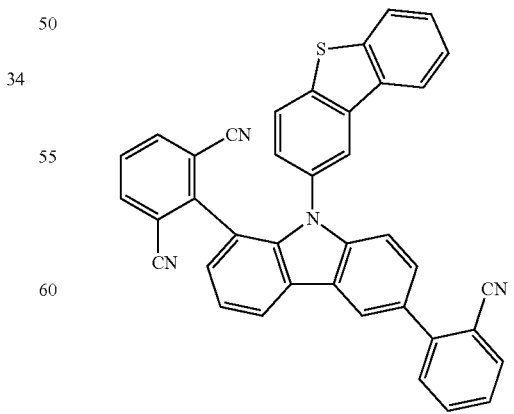

39
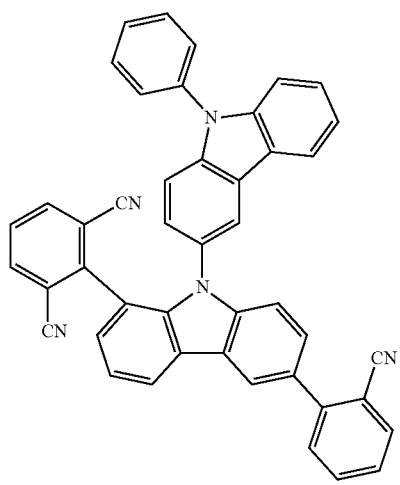
40
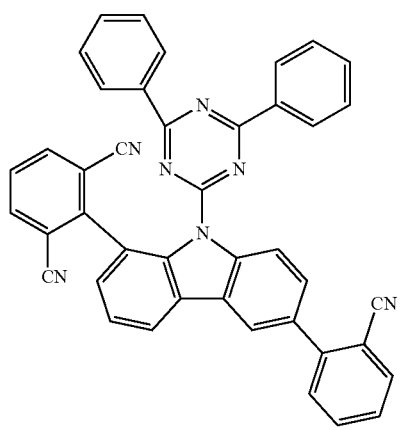
41
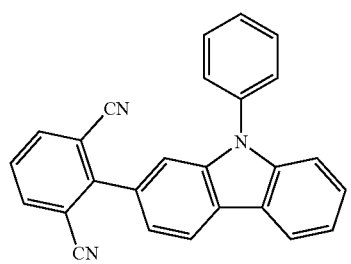
42
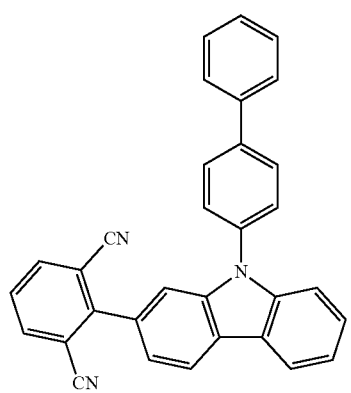
43
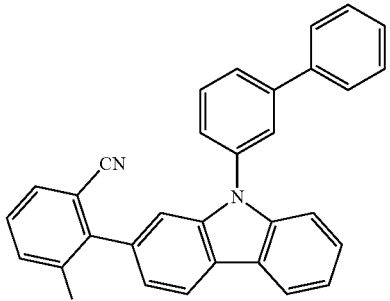
44
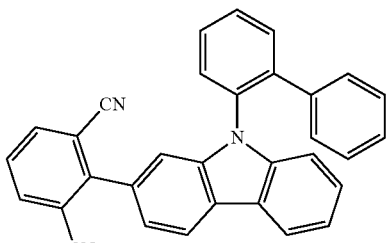
45
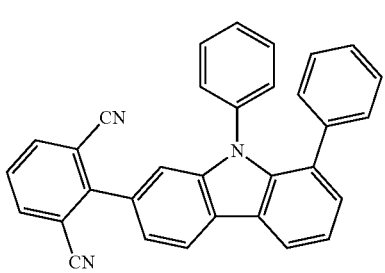
46
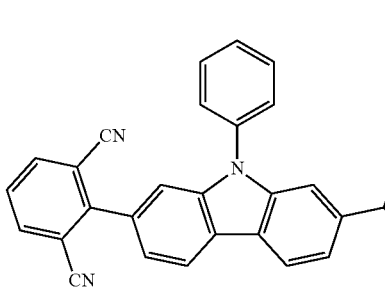
47
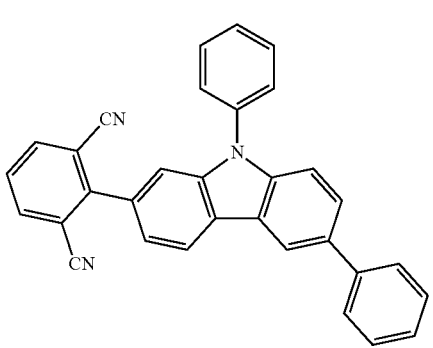

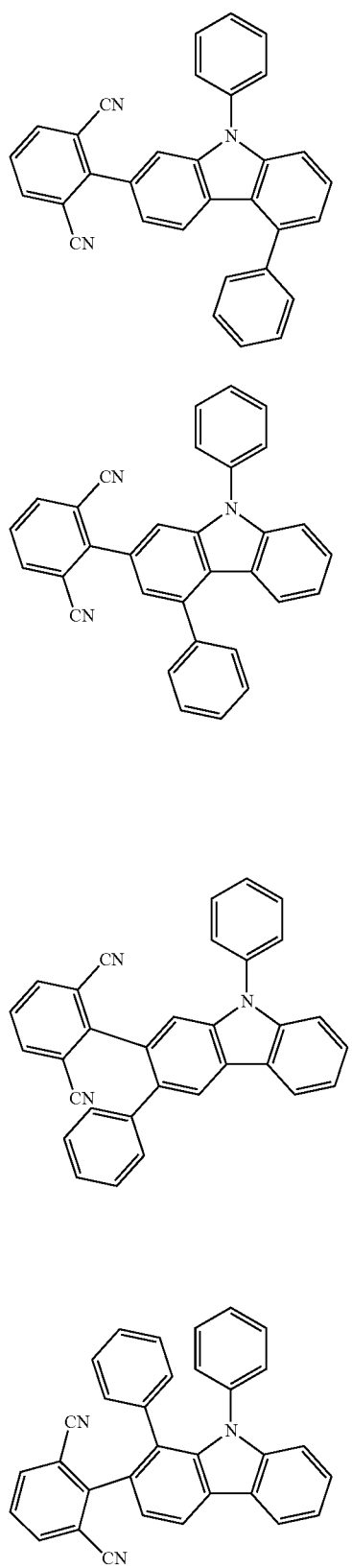
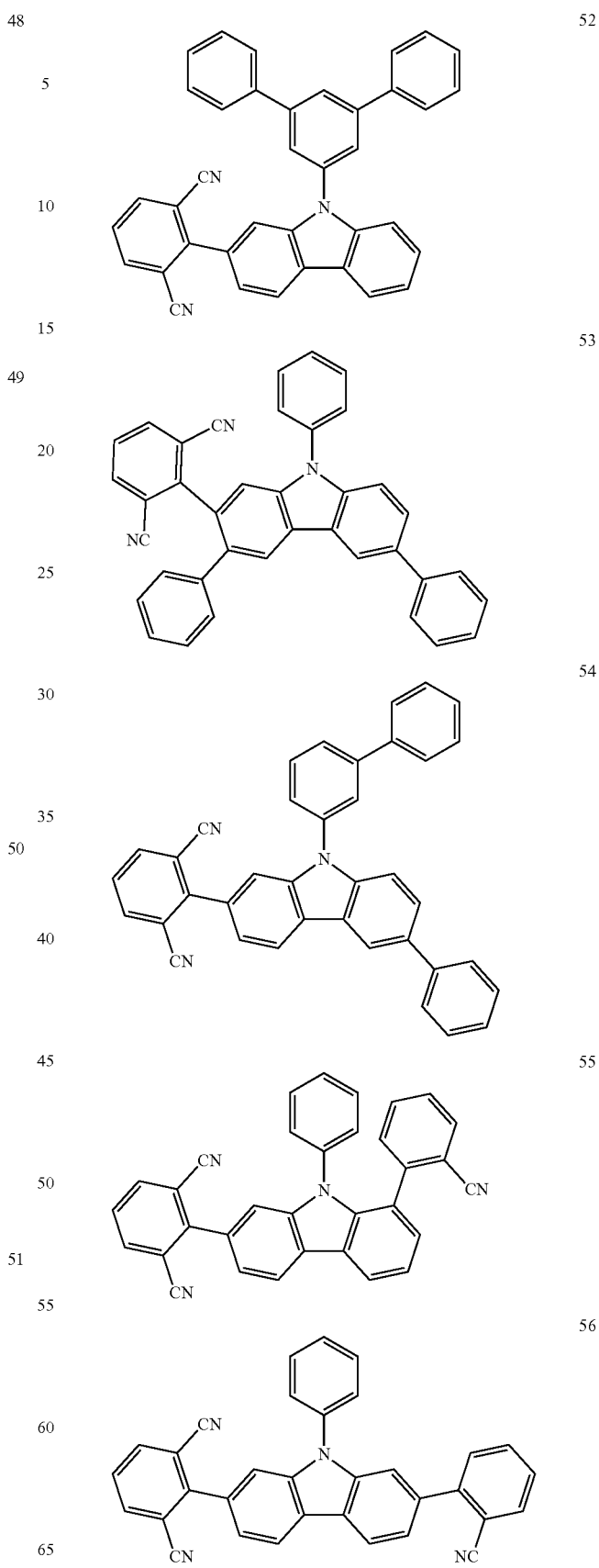

57
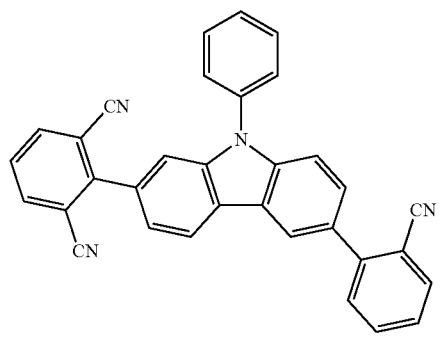
58
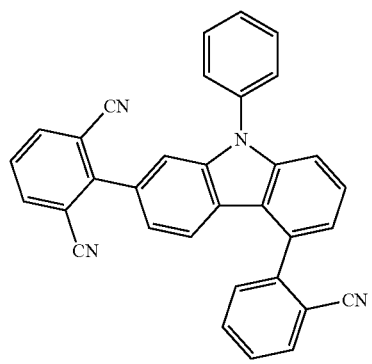
59
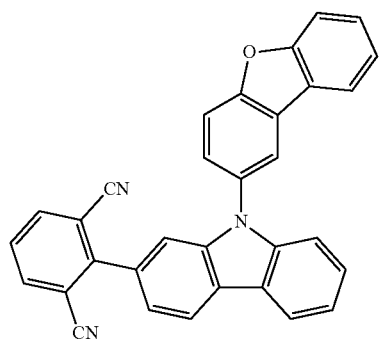
60
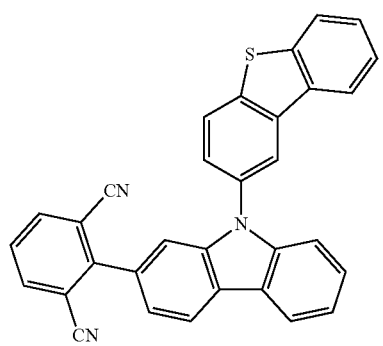
61
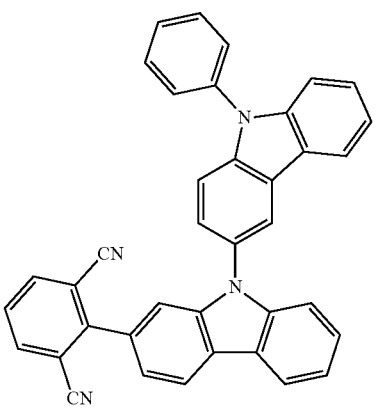
62
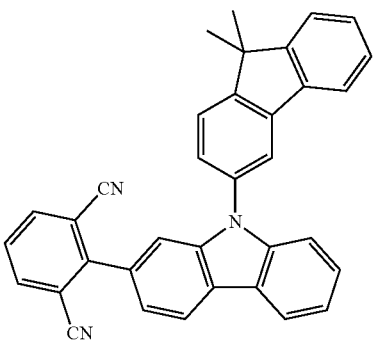
63
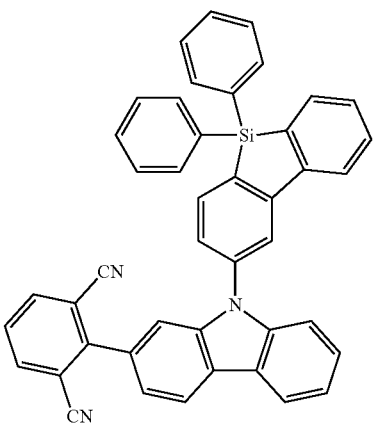
65
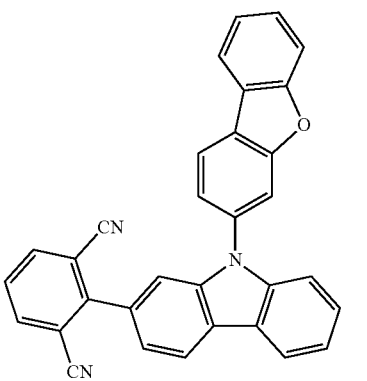

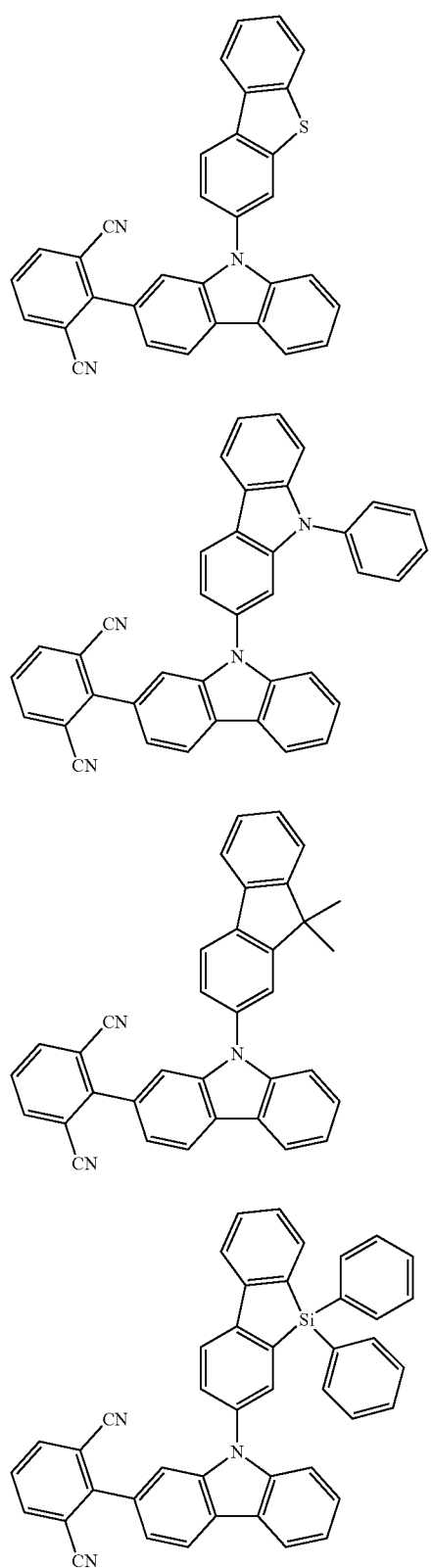
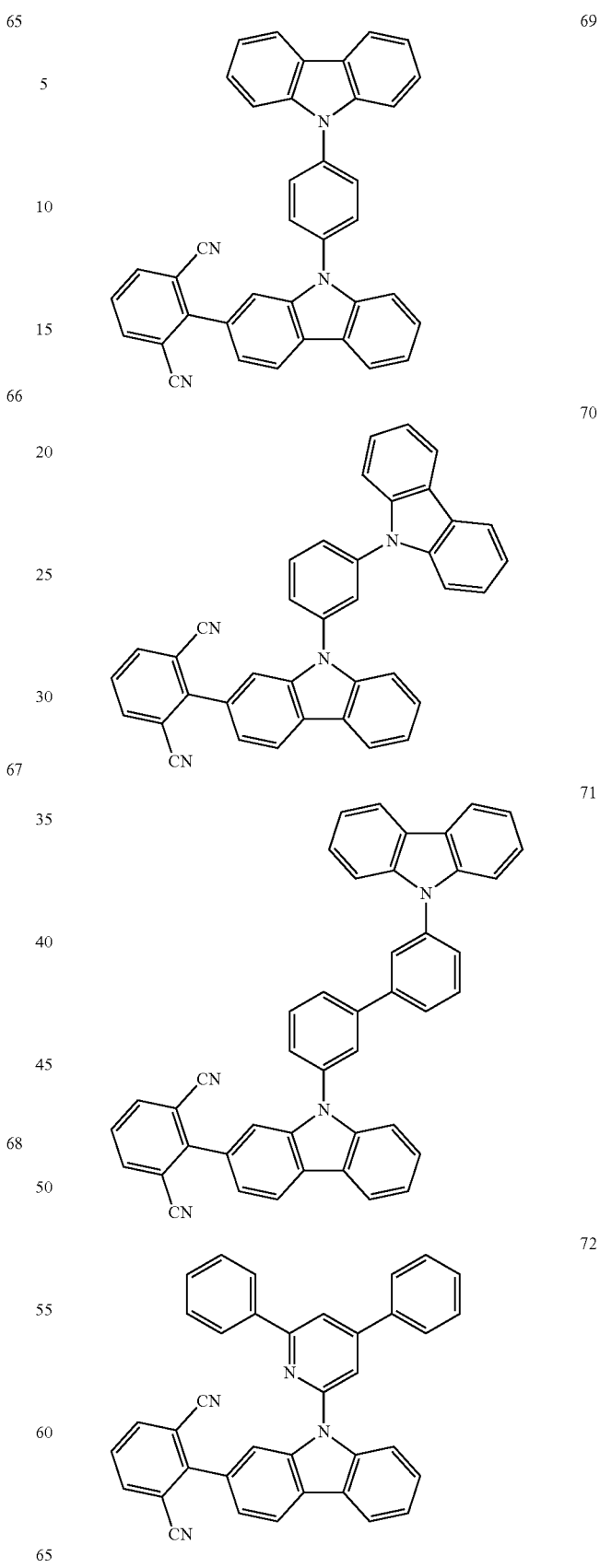

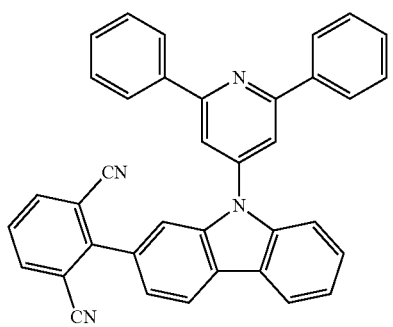
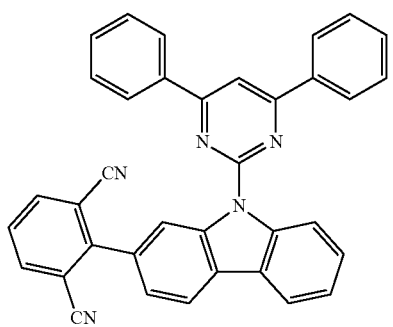
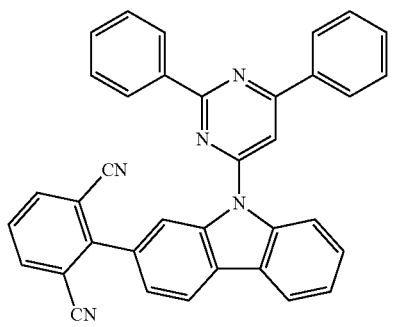
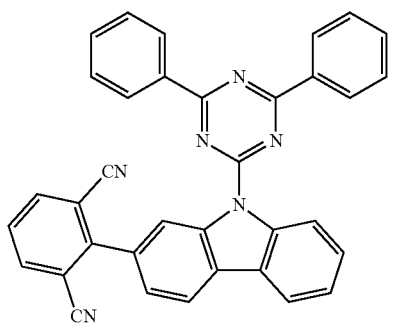
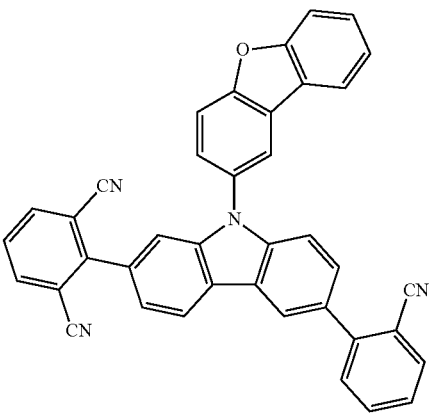
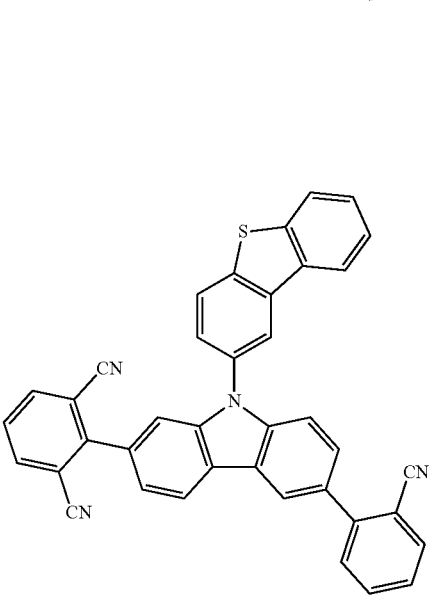
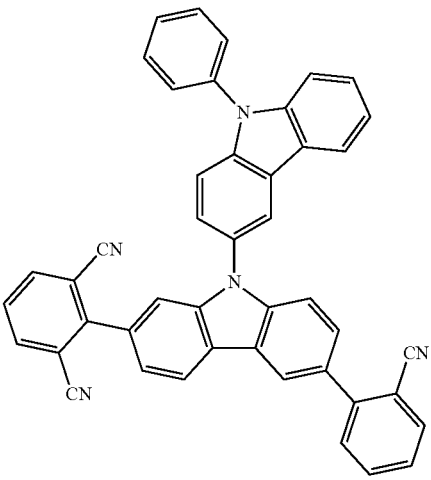

191
-continued
80
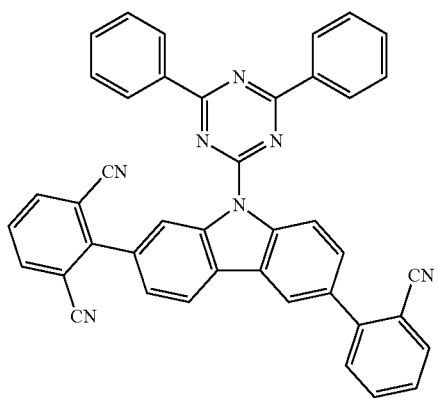
82
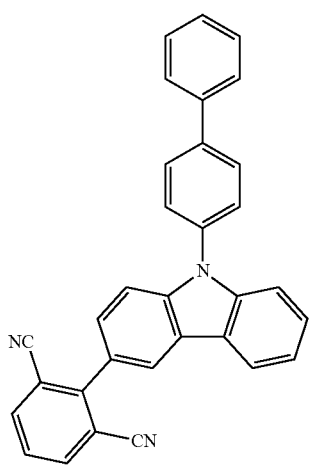
83
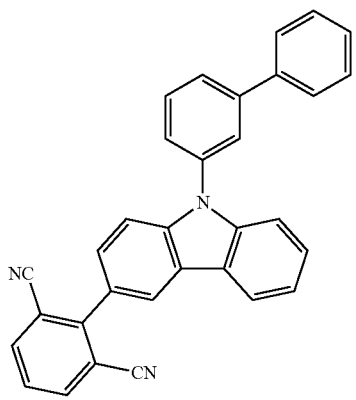
84
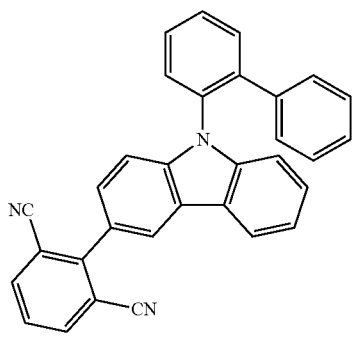
192
-continued
85
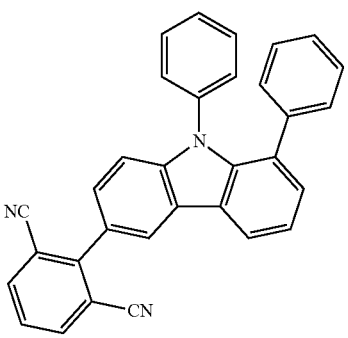
86
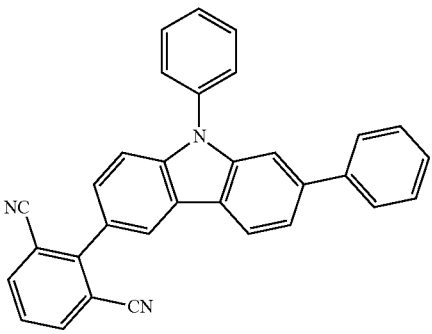
87
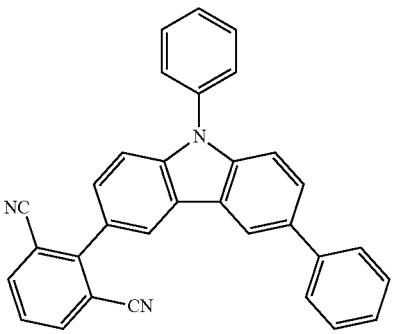
88
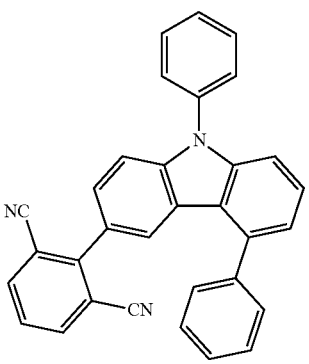

-continued
89
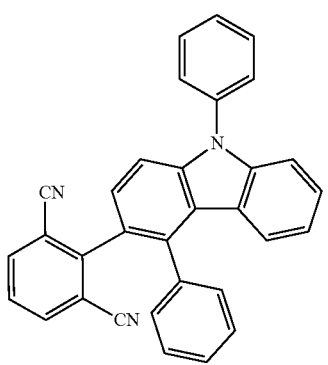
90
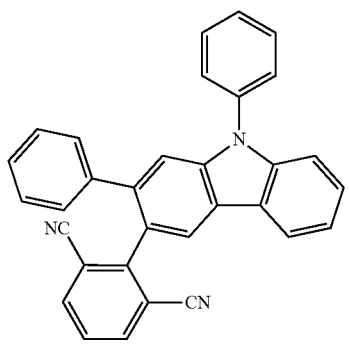
91
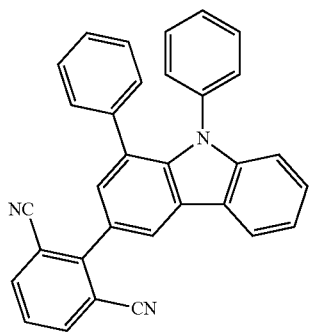
92
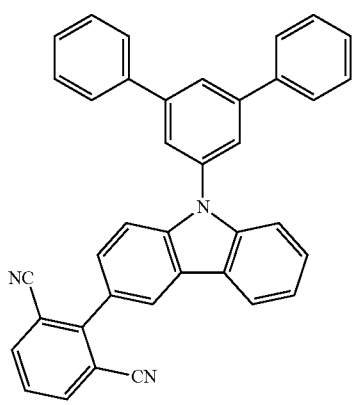
-continued
93
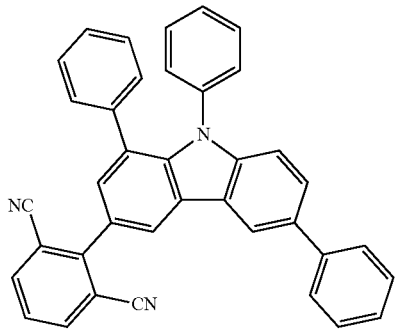
94
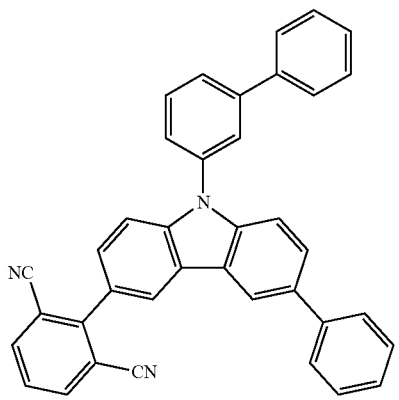
95
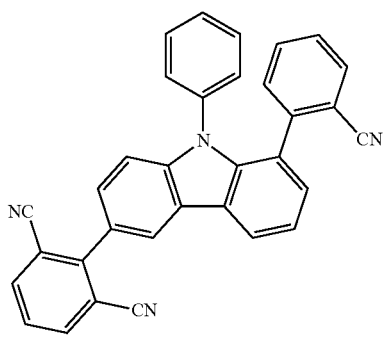
96
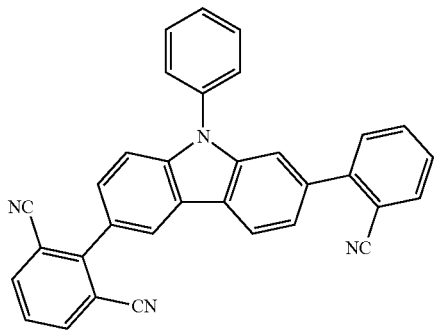

97
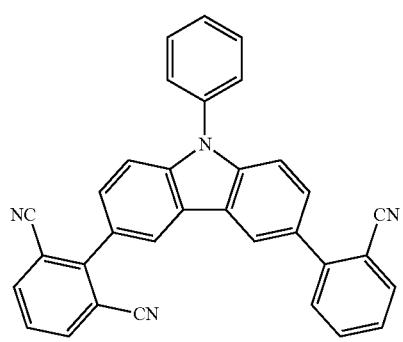
98
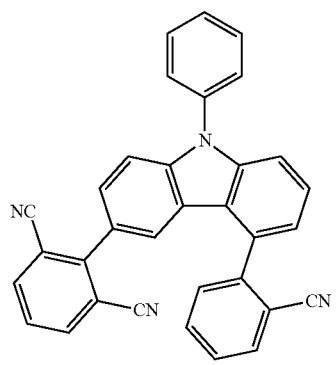
99
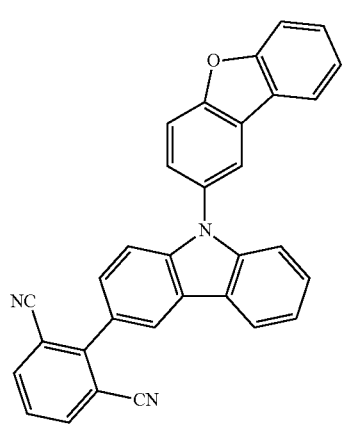
100
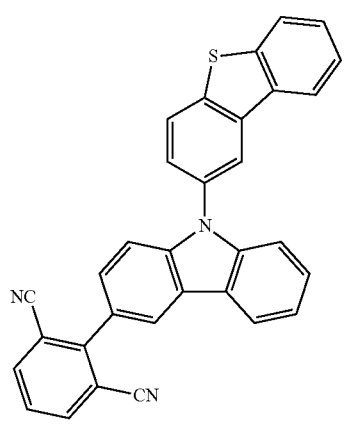
101
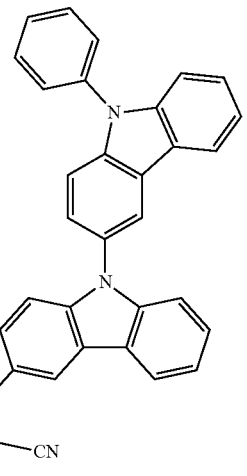
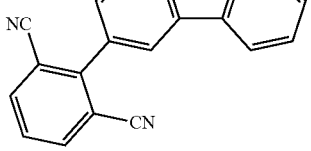
102
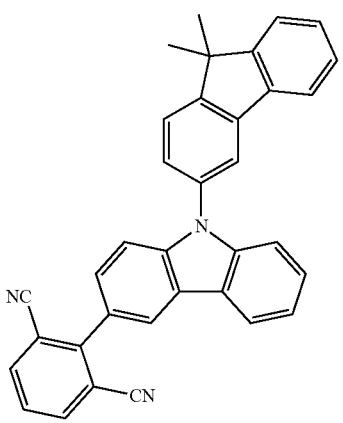
103
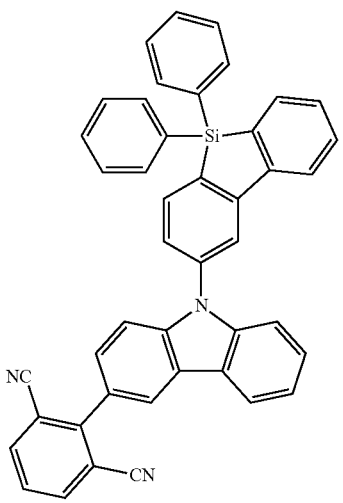

104
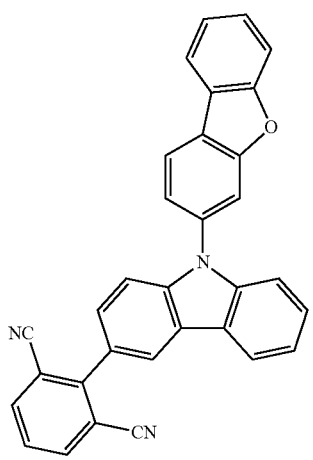
105
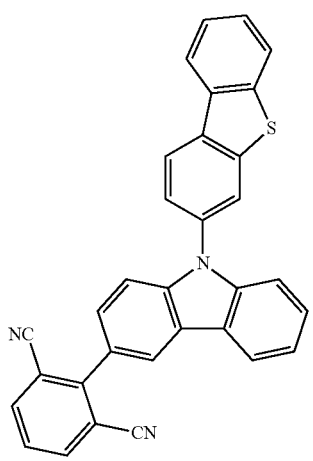
106
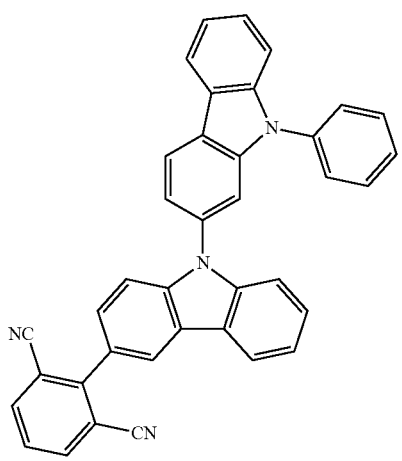
107
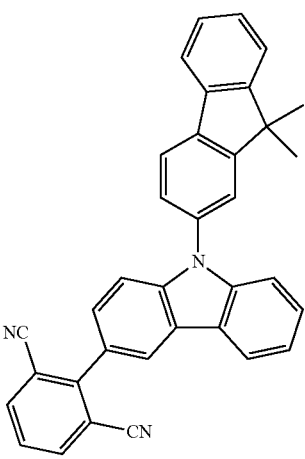
108
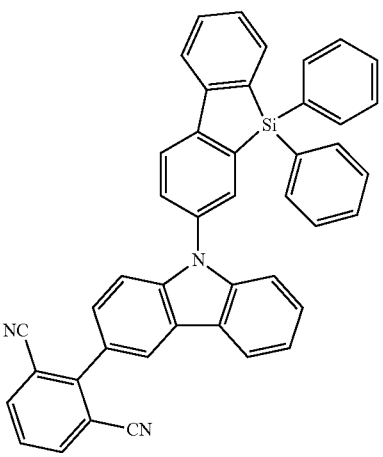
109
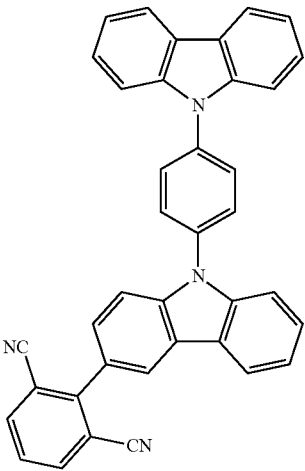

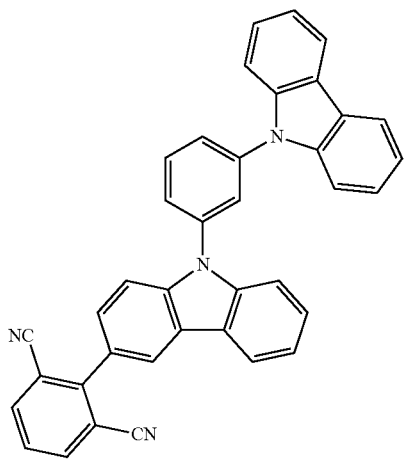
110
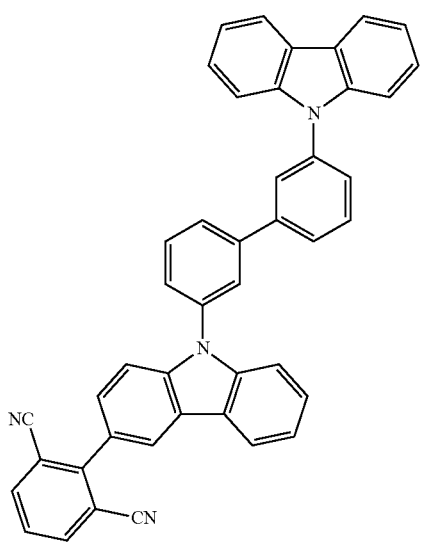
111
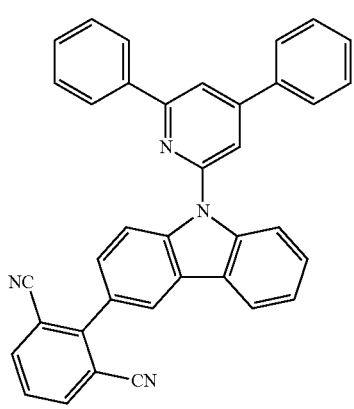
112
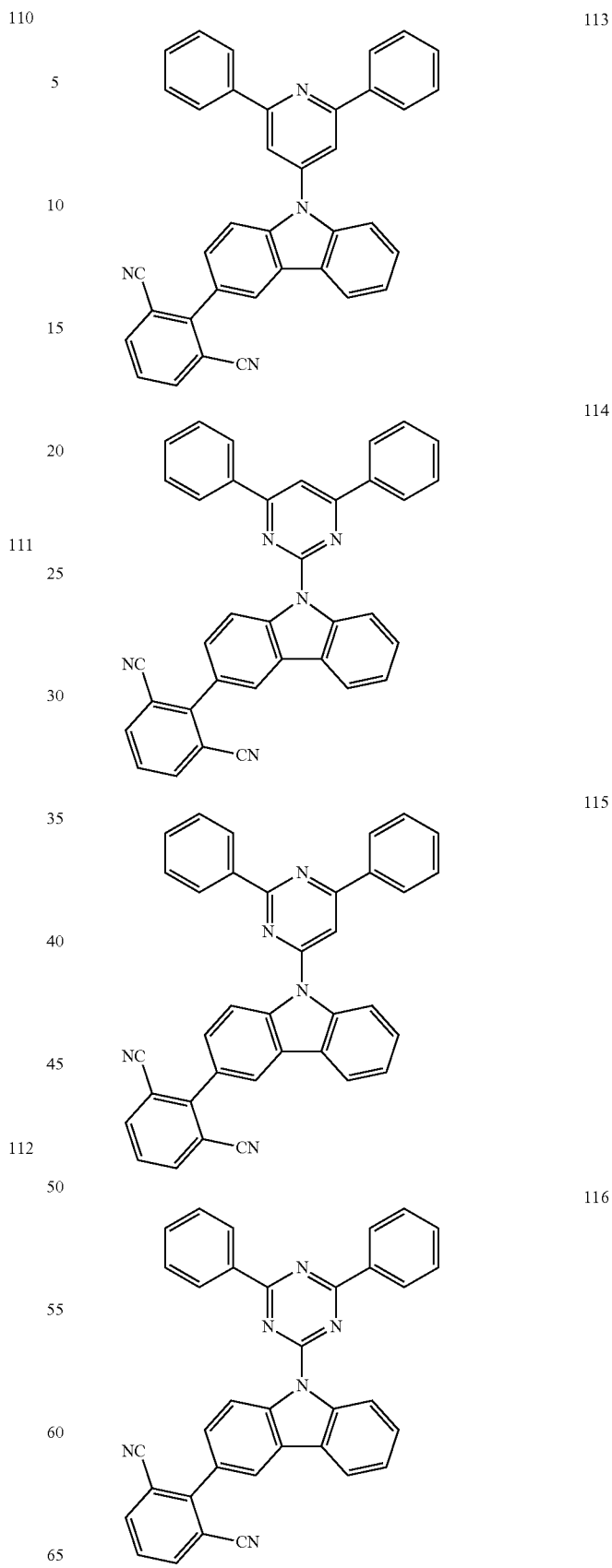
113
114
115
116

201
-continued
117
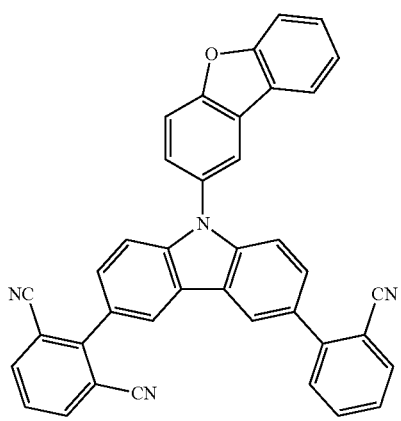
118
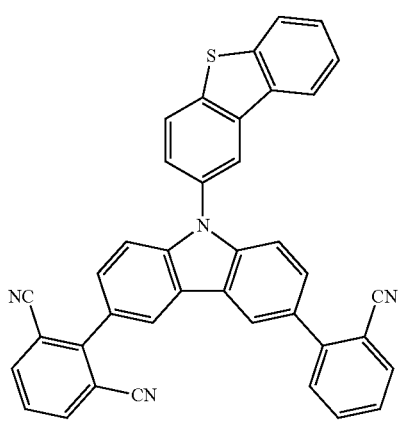
119
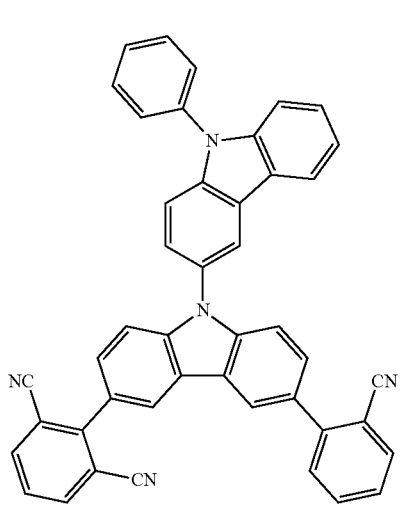
202
-continued
120
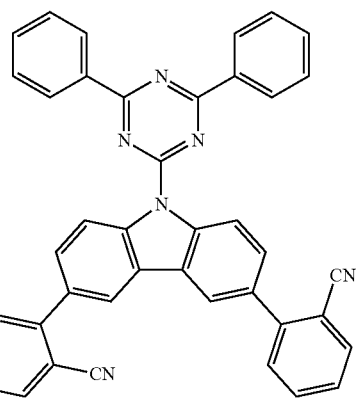
121
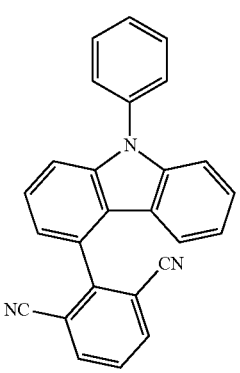
122
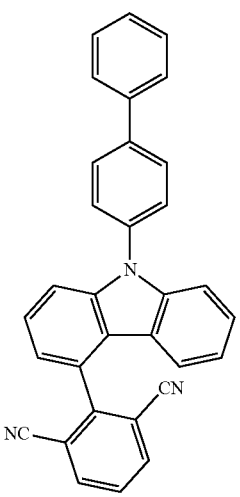

203
-continued
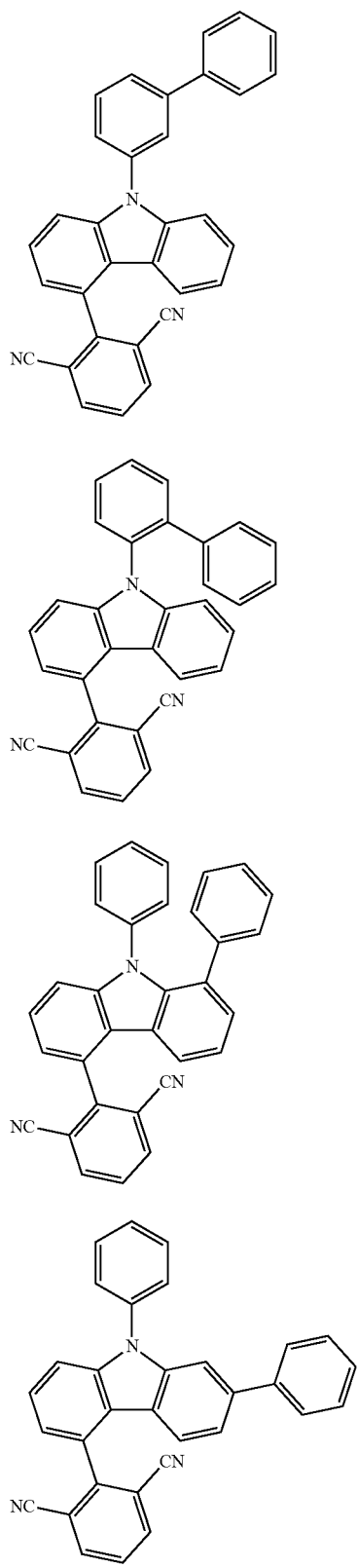
204
-continued
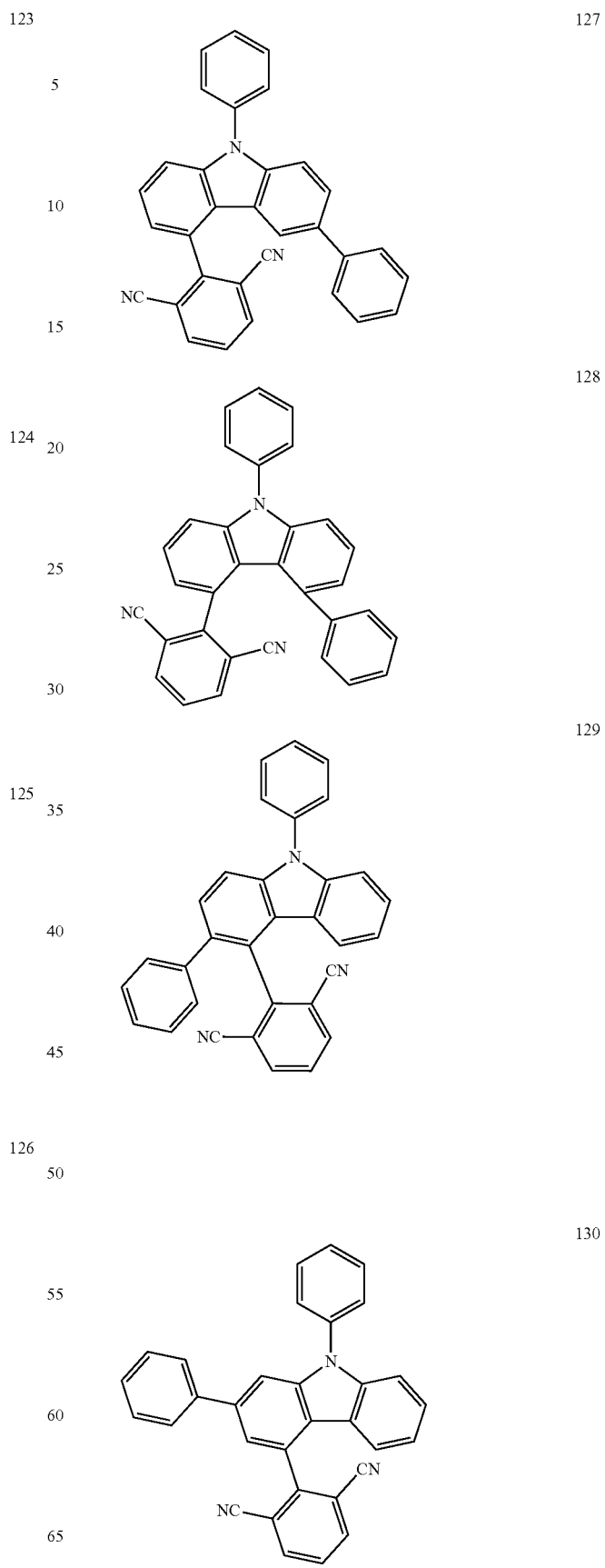

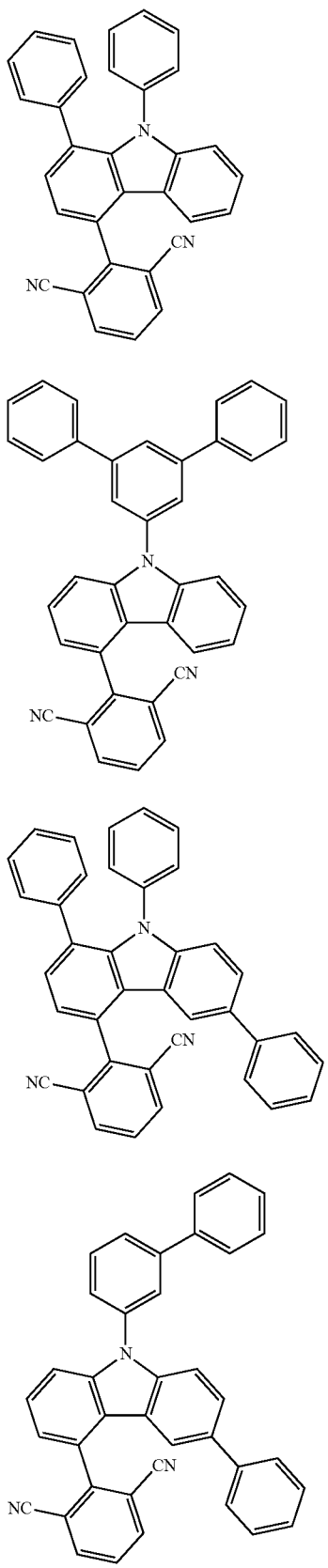
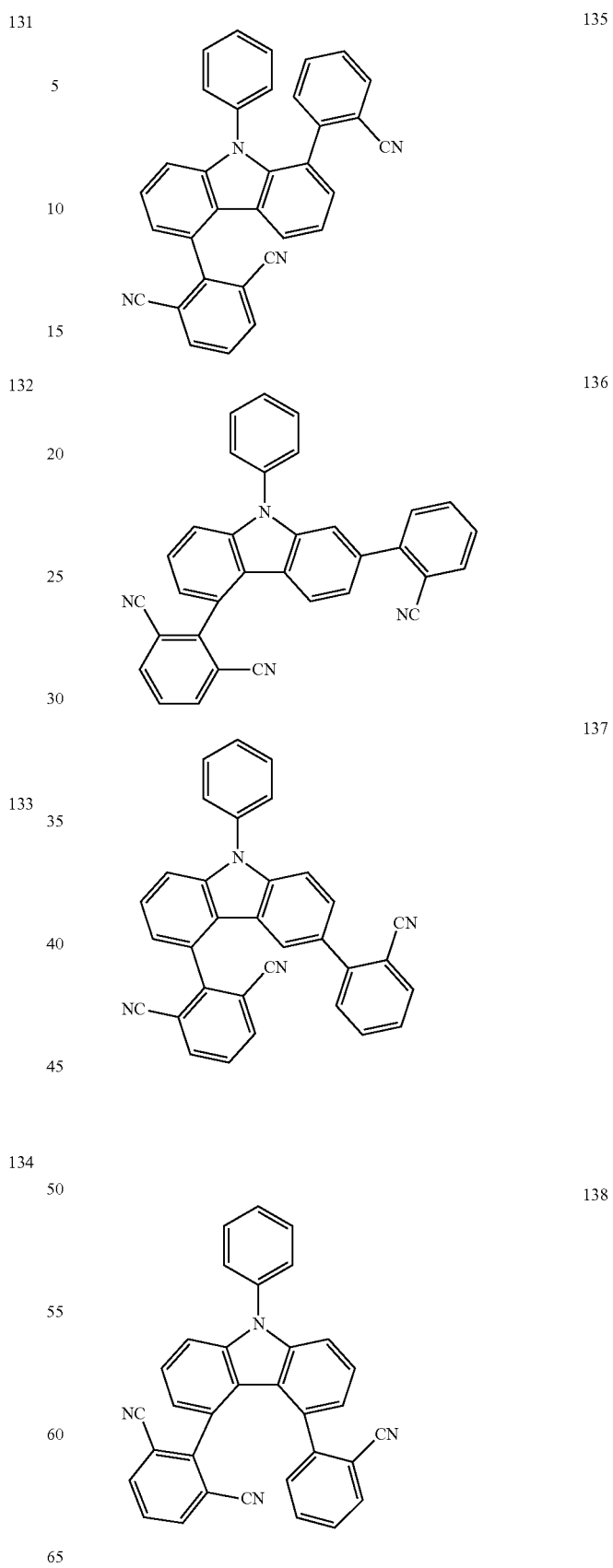

-continued
139
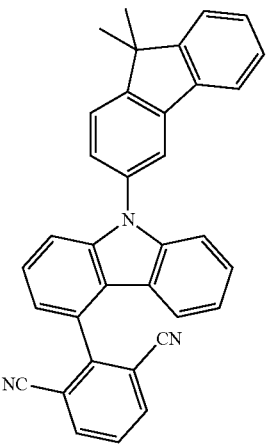
140
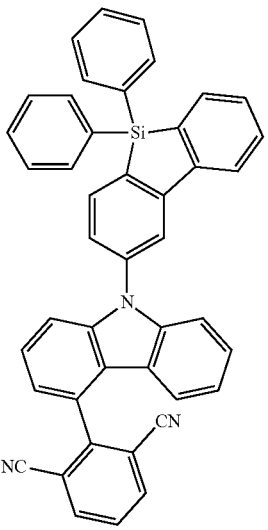
141
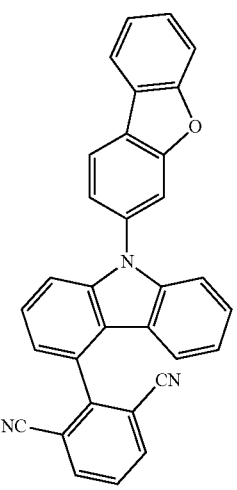
-continued
142
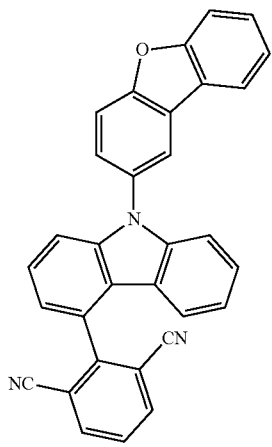
143
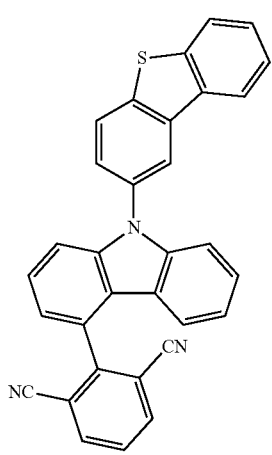
144
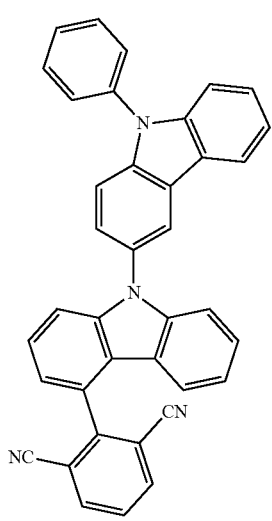

-continued
145
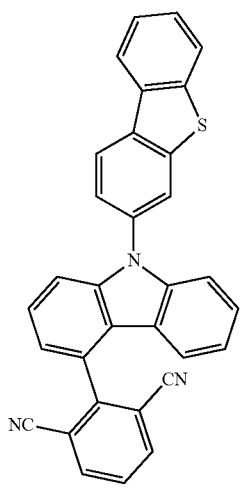
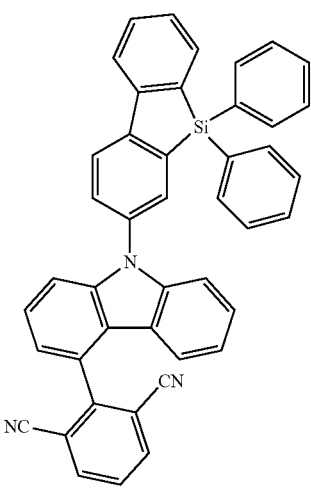
148
146
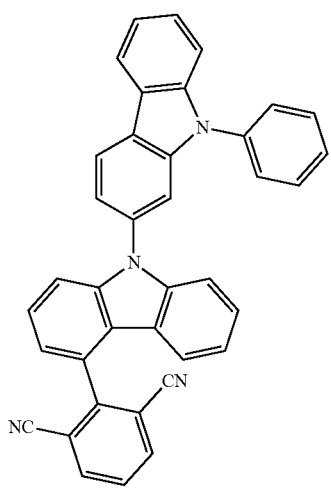
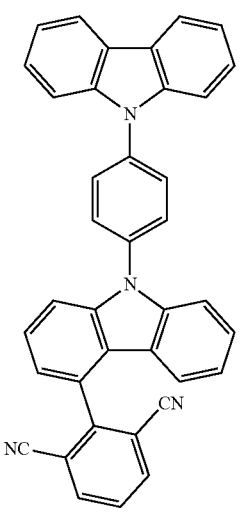
149
147
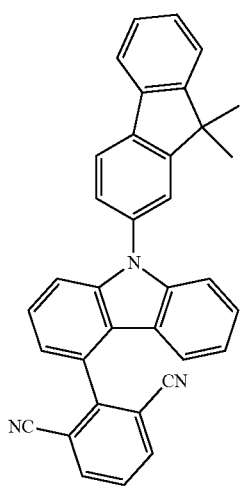
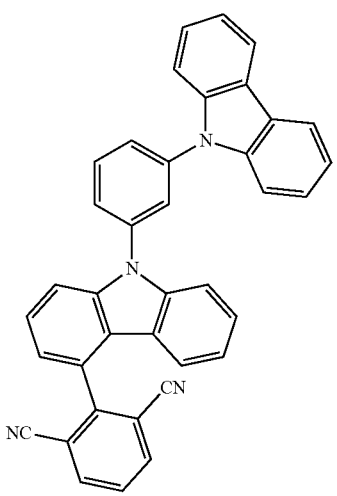
150

151
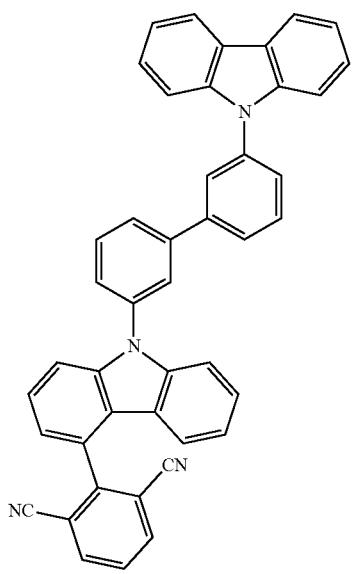
152
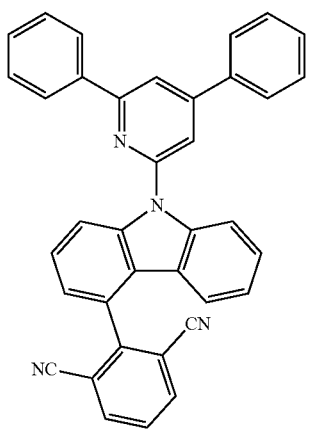
153
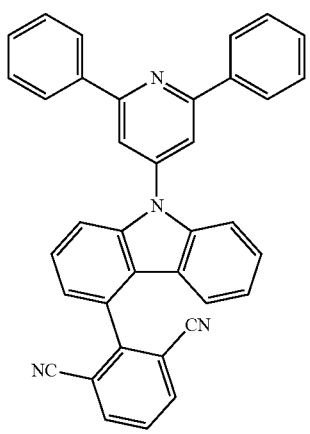
154
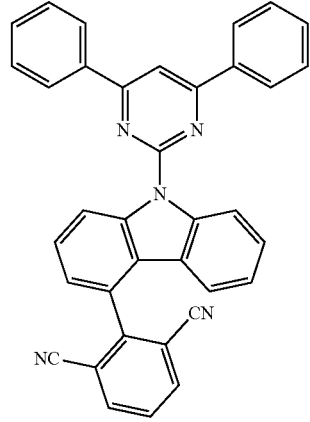
155
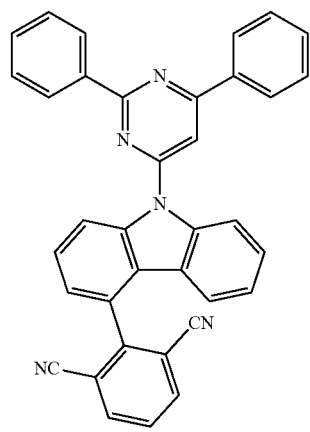
156
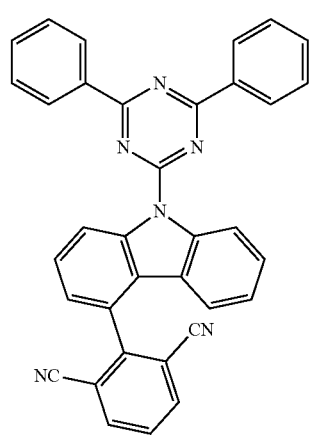

-continued
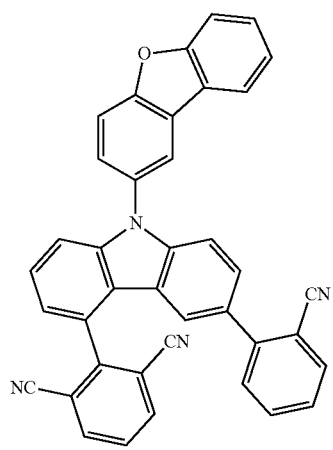
157
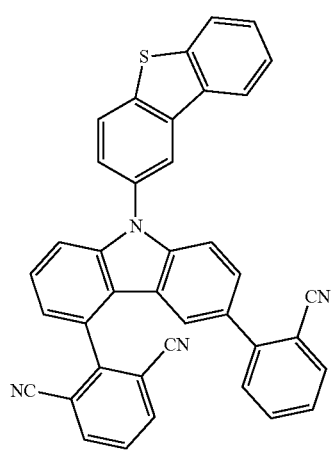
158
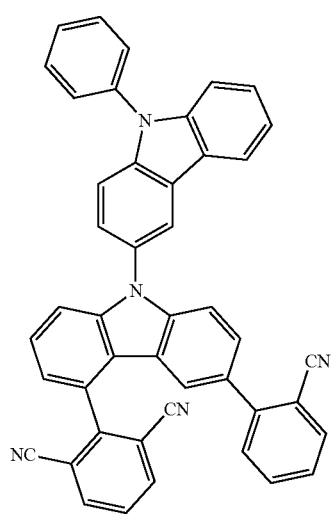
159
-continued
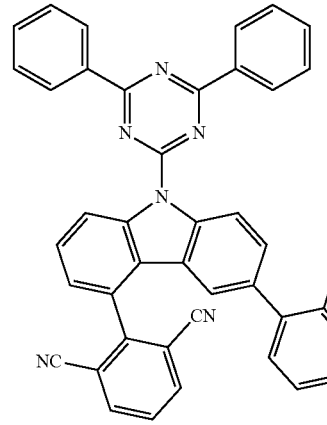
160
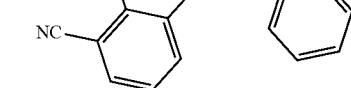
161
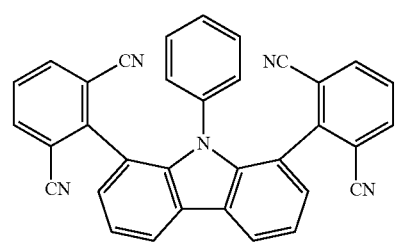
162
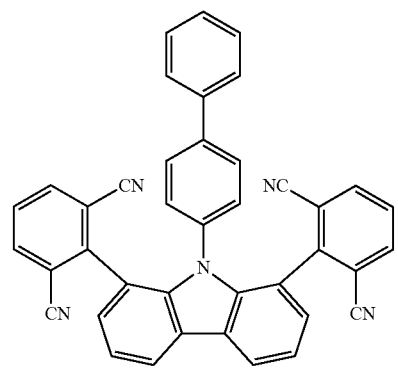
163

164
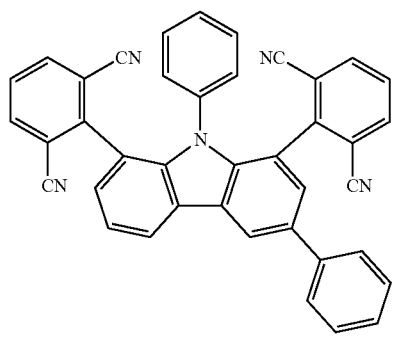
165
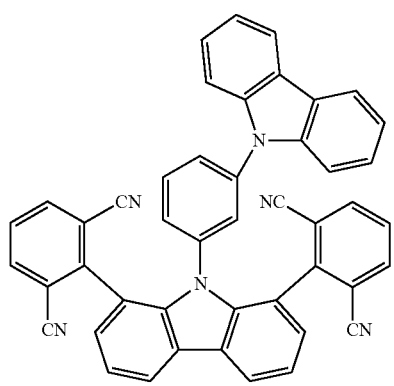
166
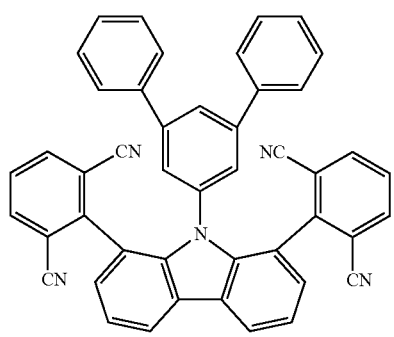
167
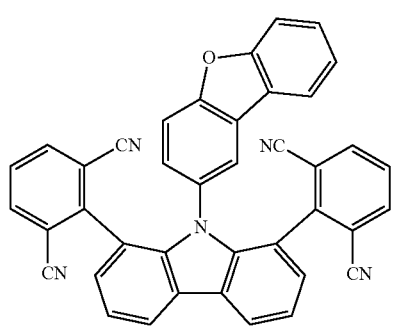
168
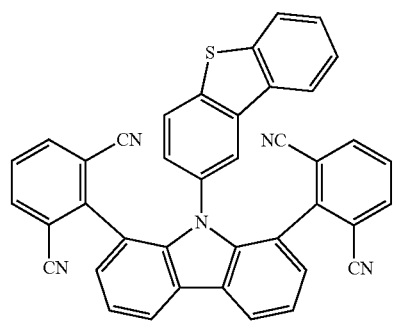
169
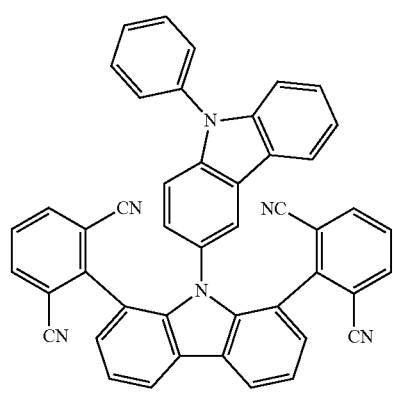
170
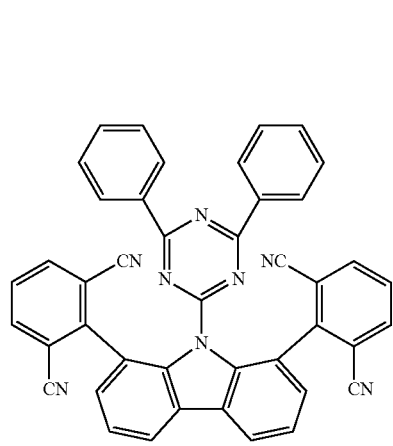
171
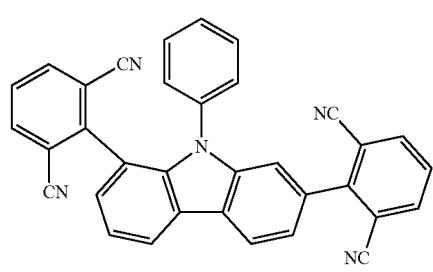

| 172 | 176 |
|---|---|
| 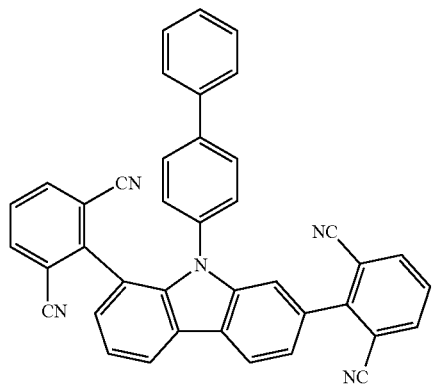 | 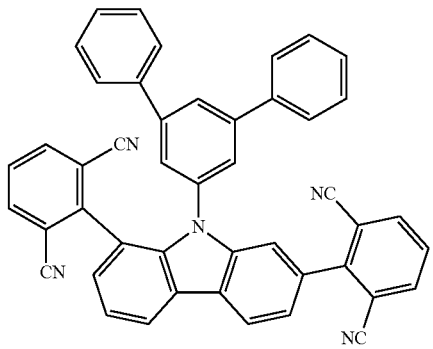 |
| 173 | 177 |
| 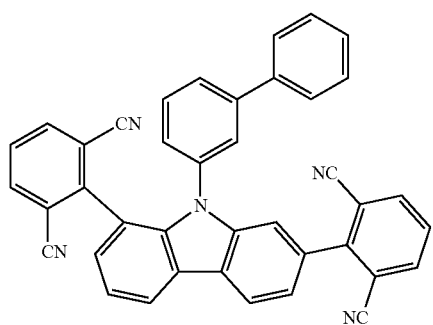 | 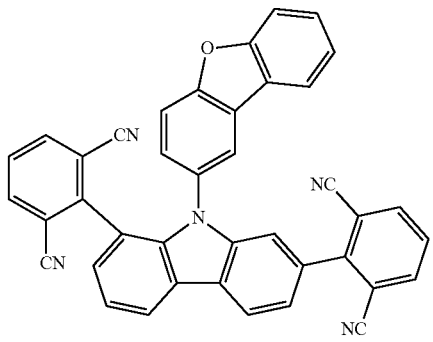 |
| 174 | 178 |
| 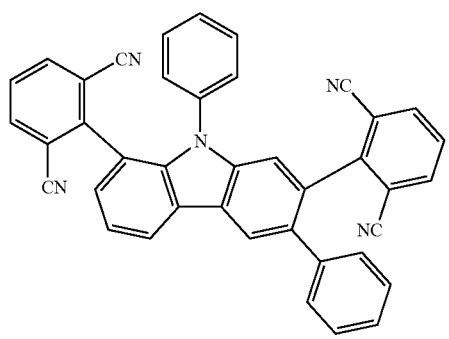 | 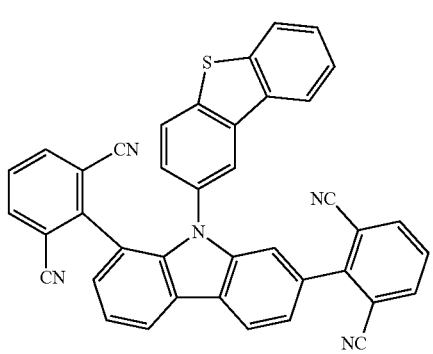 |
| 175 | 179 |
| 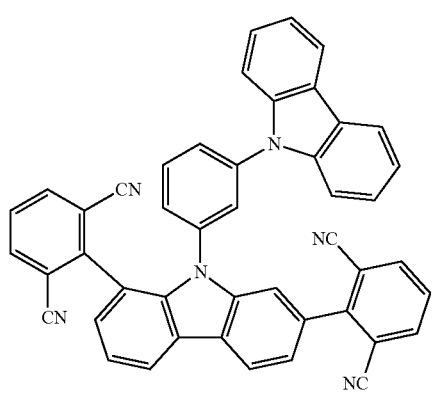 | 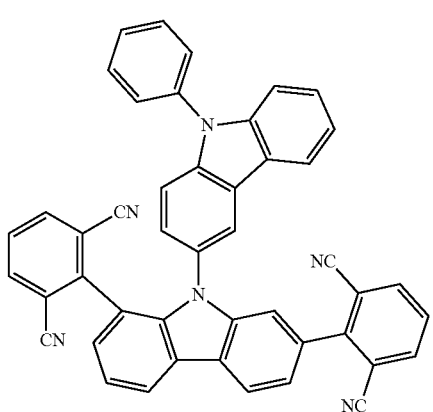 |

180
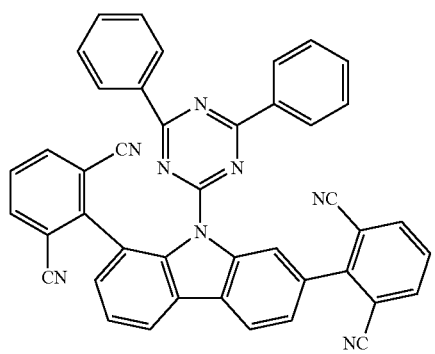
181
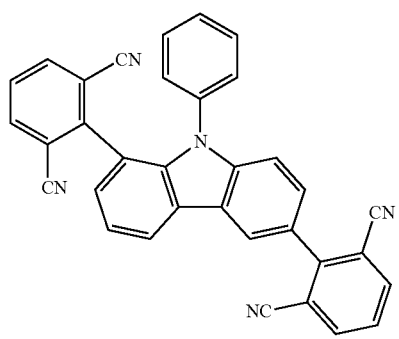
182
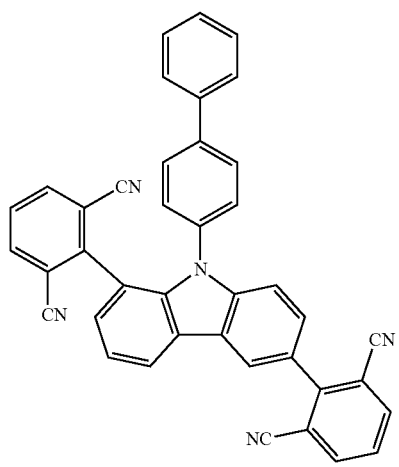
183
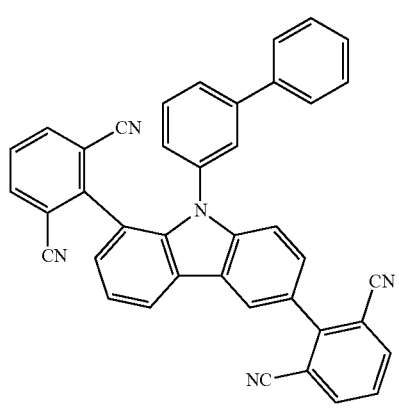
184
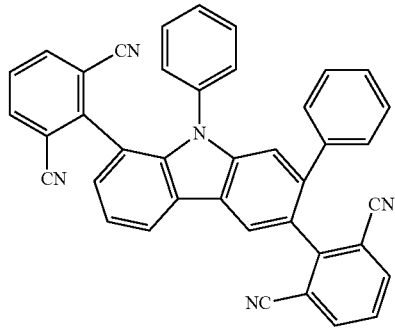
185
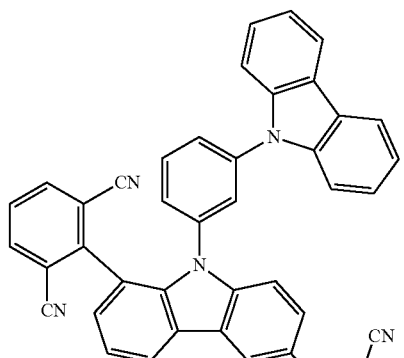
186
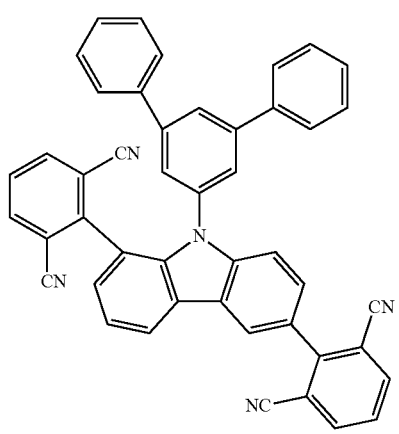
187
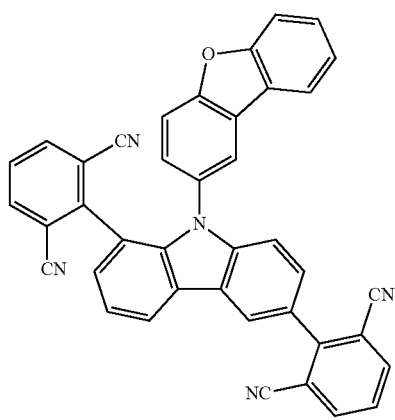

-continued
188
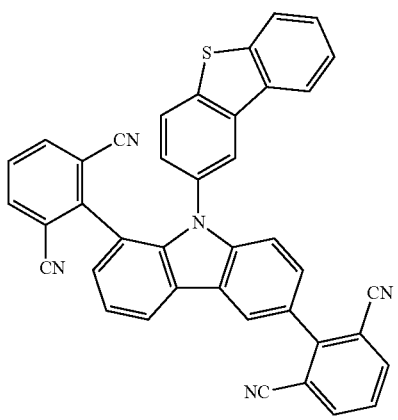
189
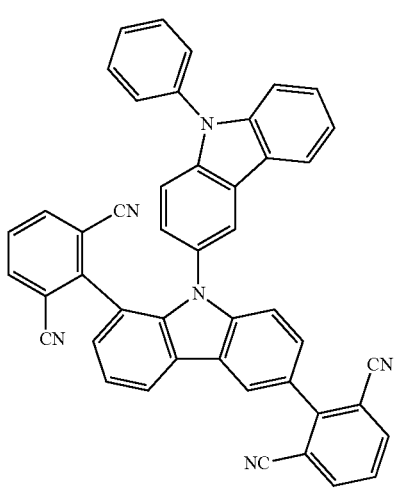
190
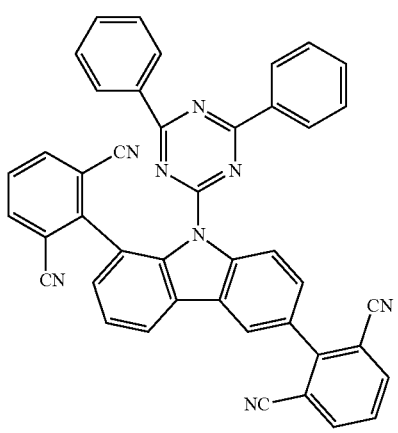
-continued
191
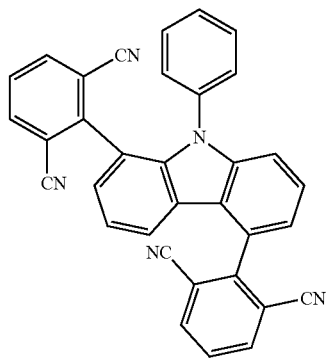
192
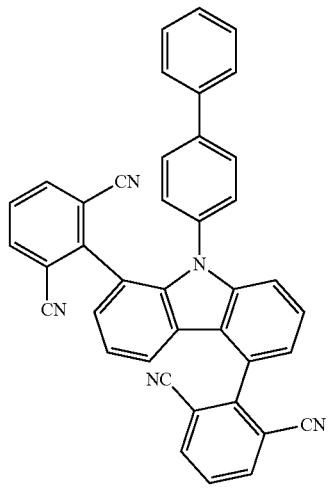
193
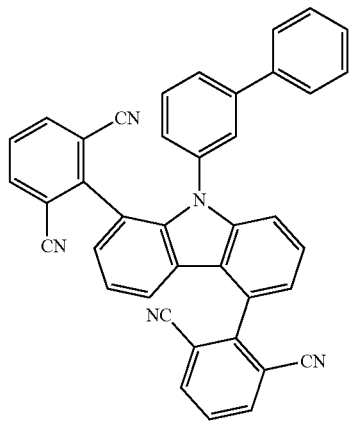
194
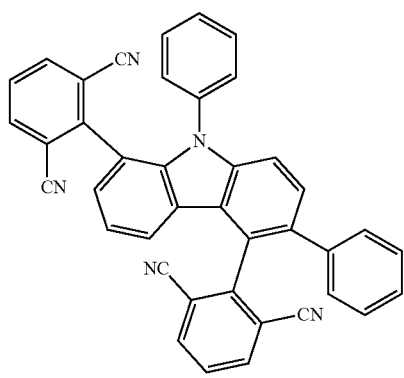

195
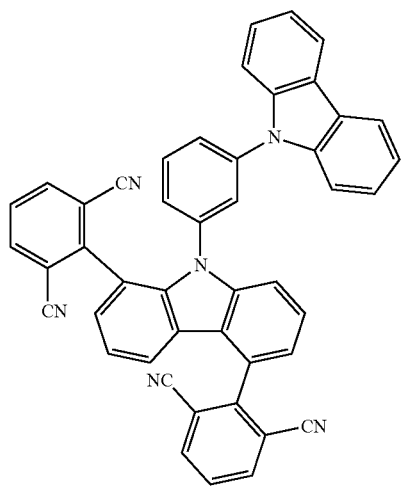
196
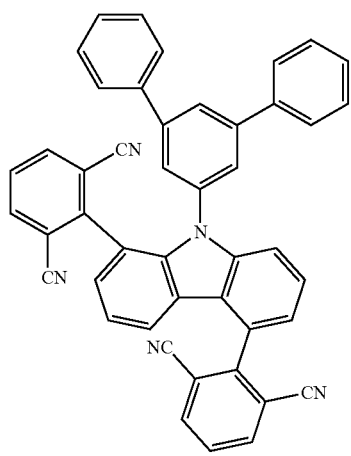
197
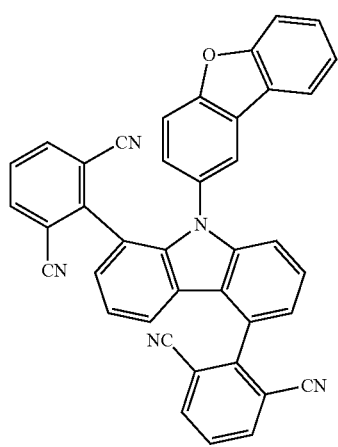
198
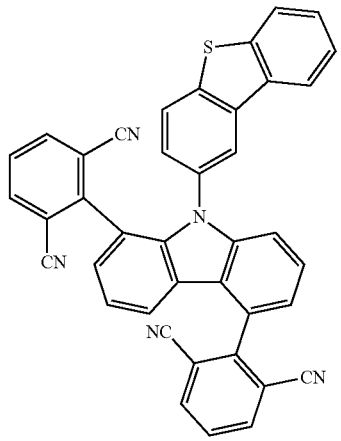
199
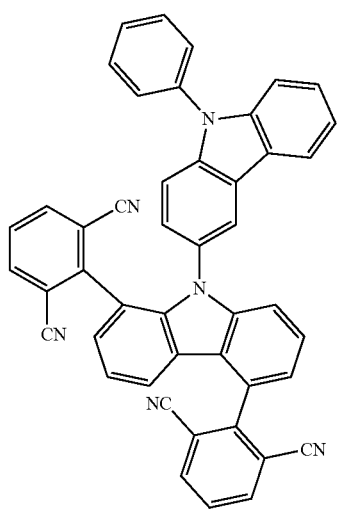
200
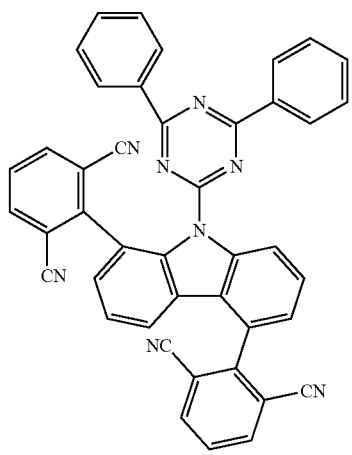
201
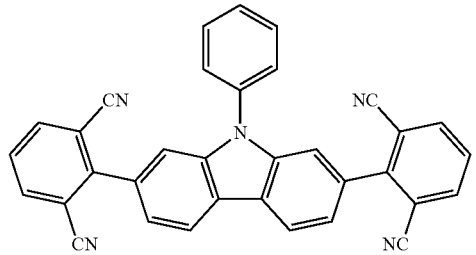

202
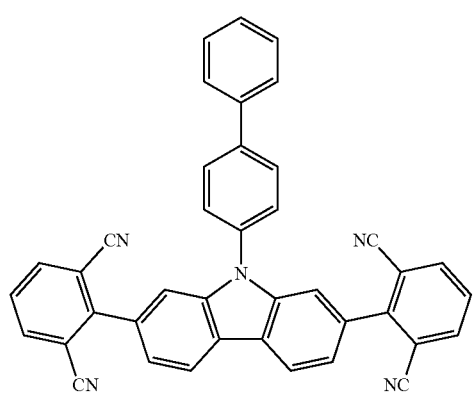
203
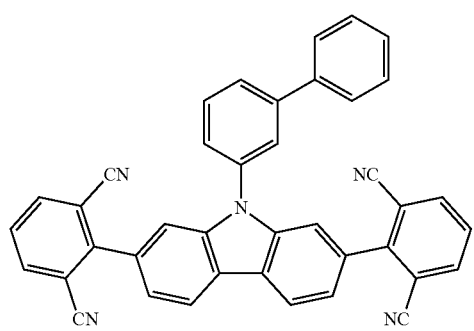
204
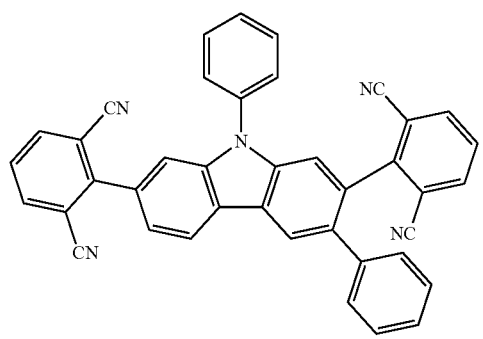
205
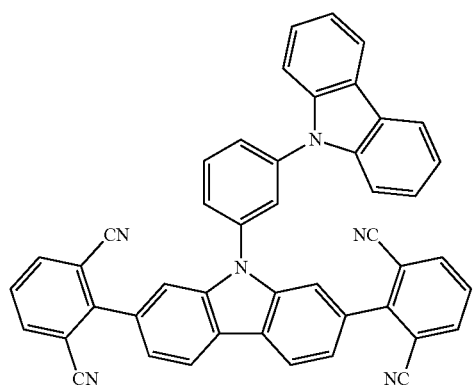
206
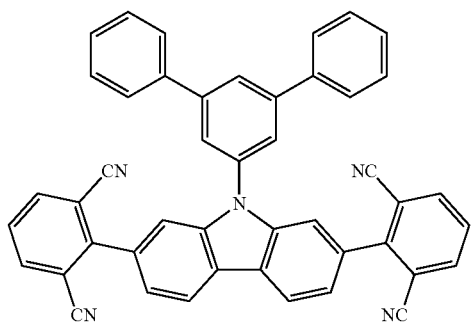
207
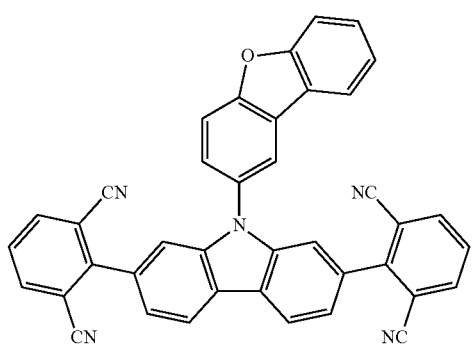
208
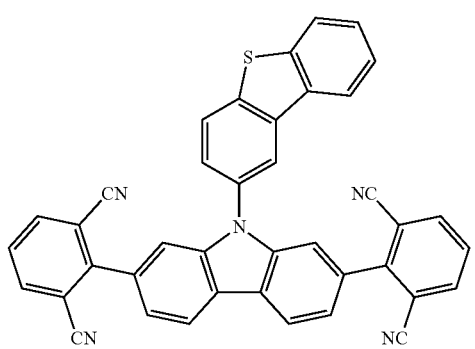
209
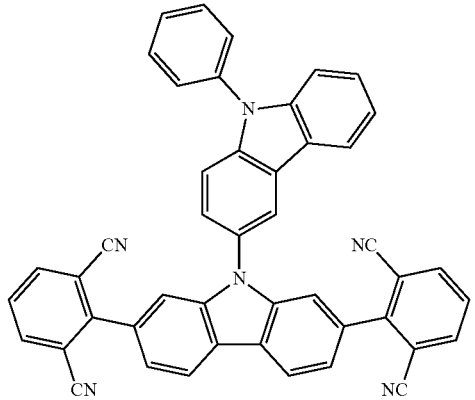

210
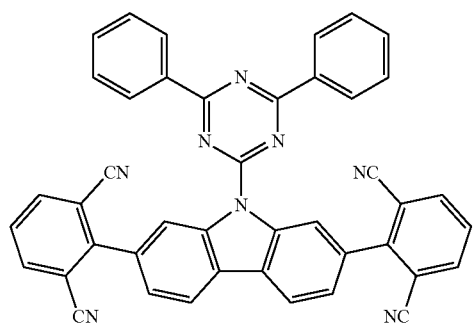
211
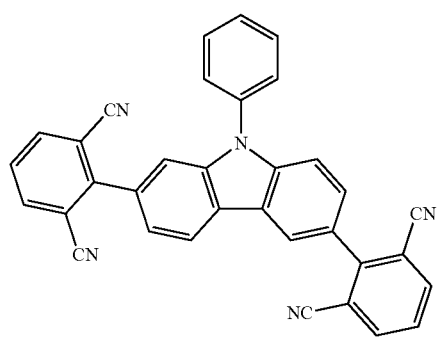
212
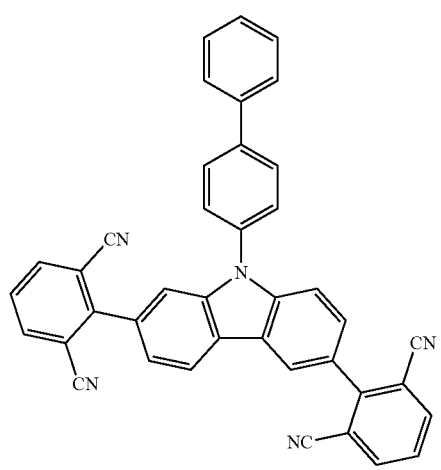
213
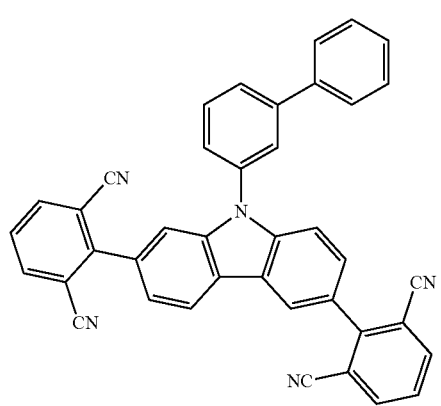
214
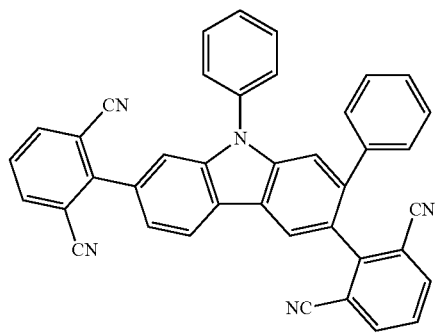
215
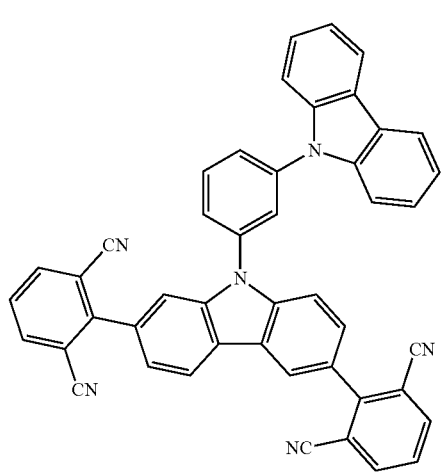
216
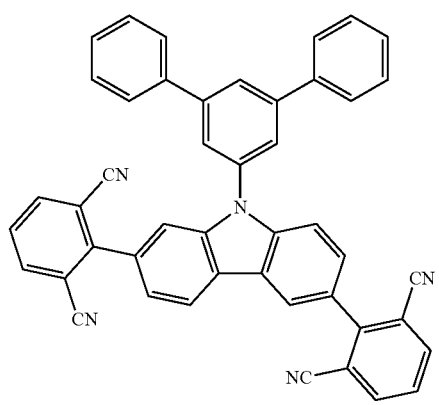
217
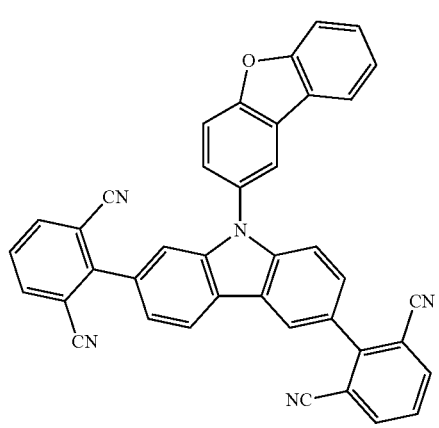

-continued
218
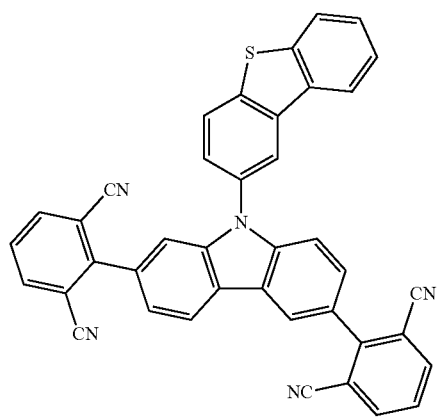
219
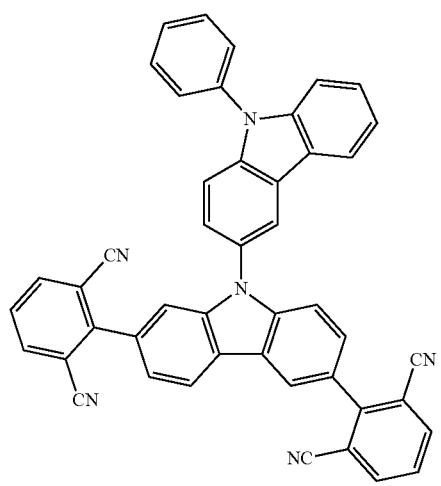
220
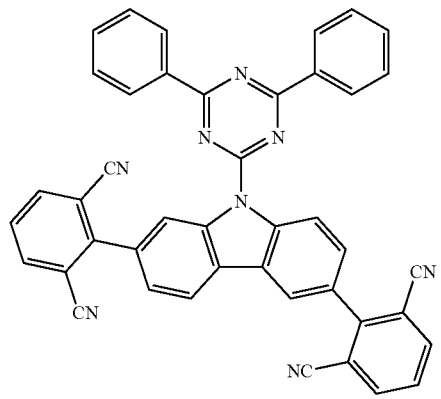
221
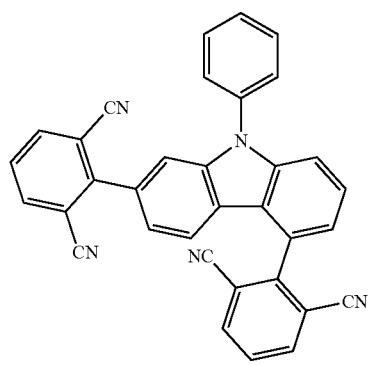
-continued
222
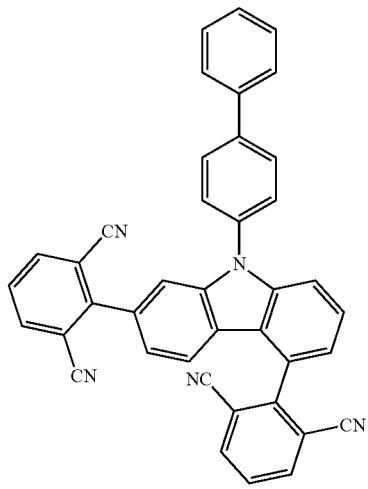
223
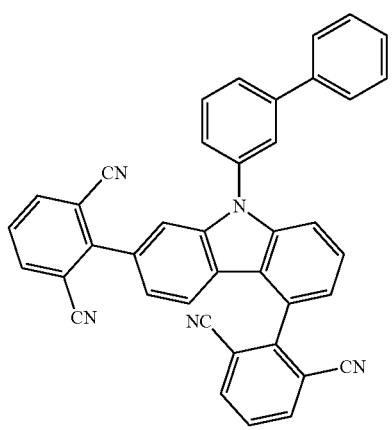
224
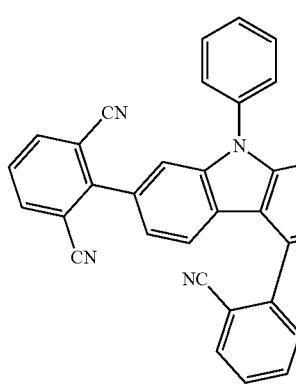

225
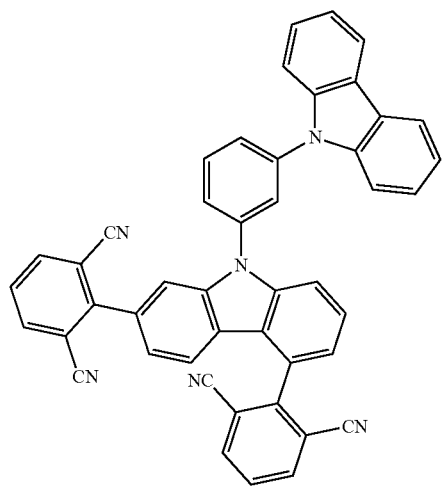
226
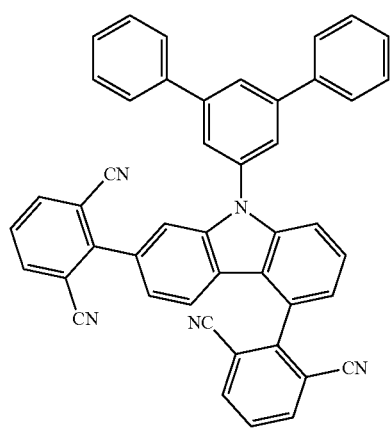
227
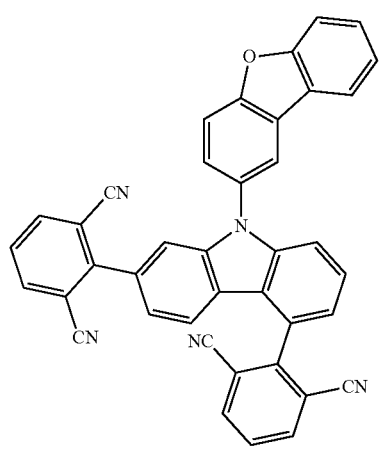
228
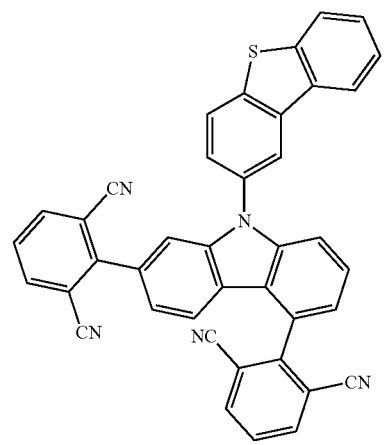
229
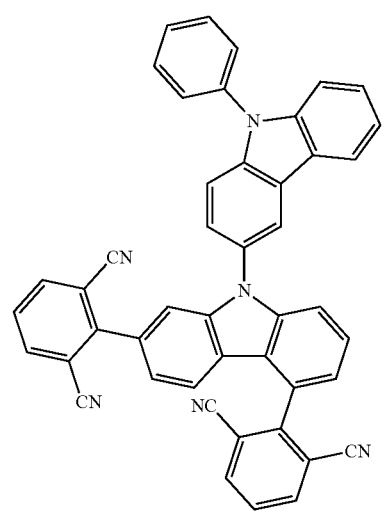
230
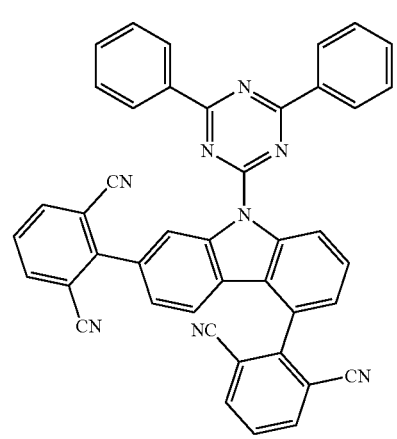

233
-continued
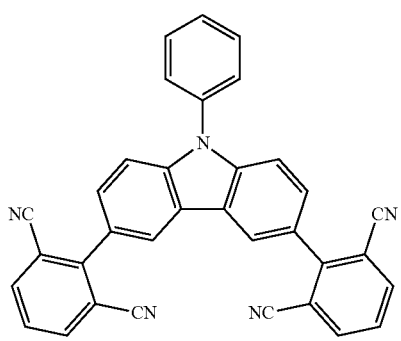
231
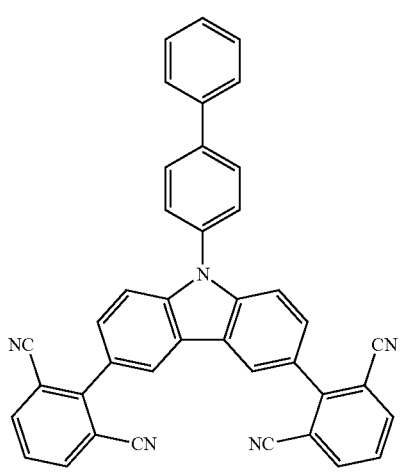
232
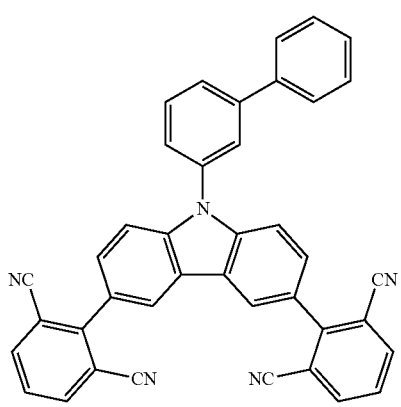
233
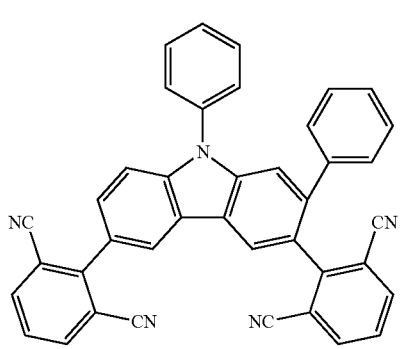
234
234
-continued
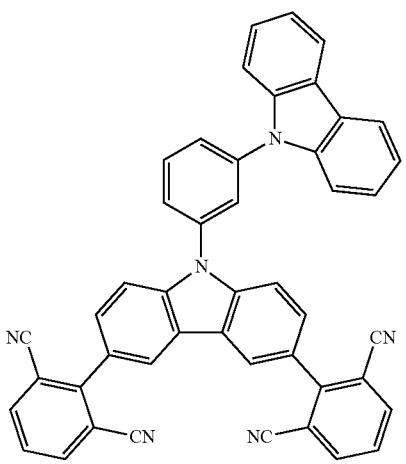
235
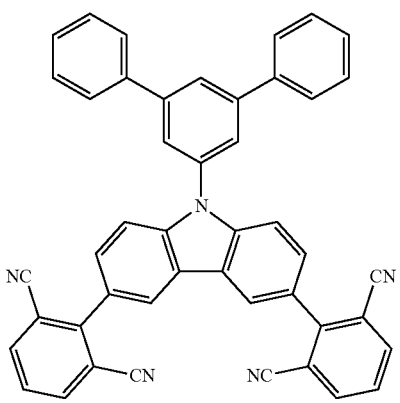
236
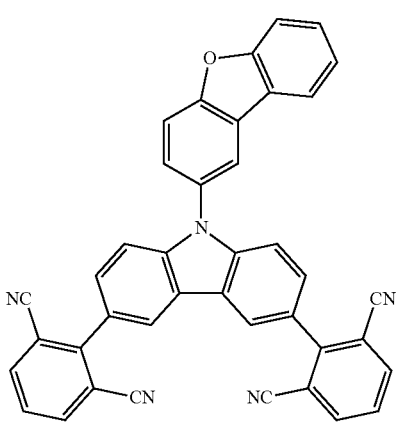
237

235
-continued
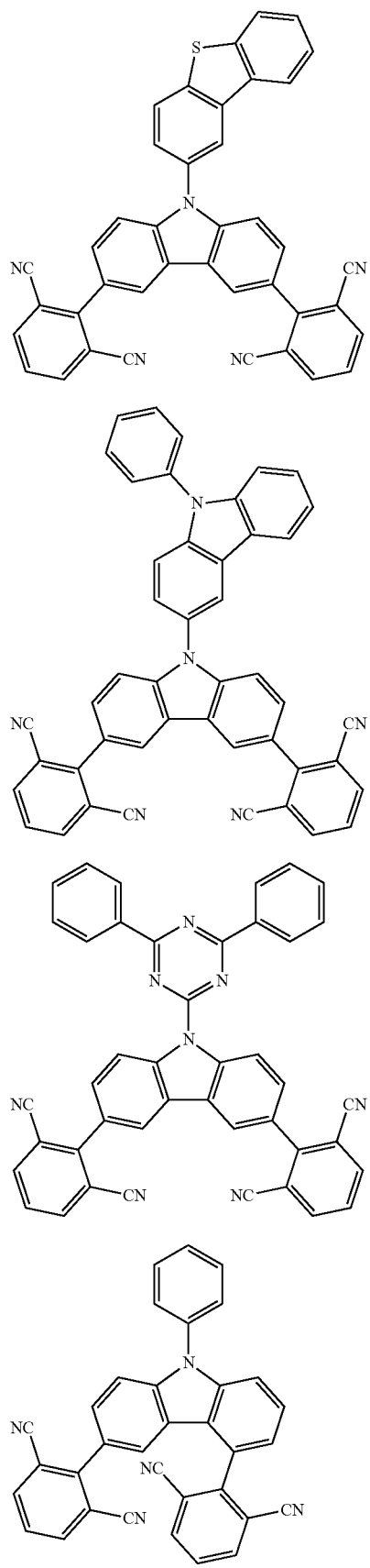
238
239
240
241
236
-continued
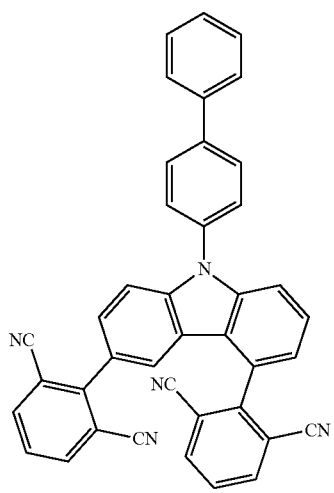
242
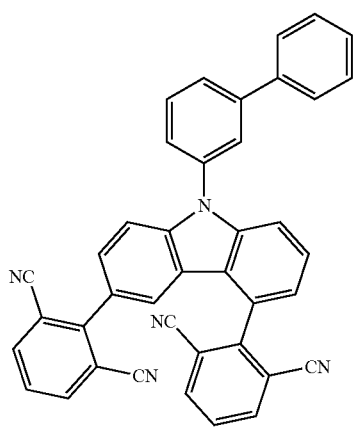
243
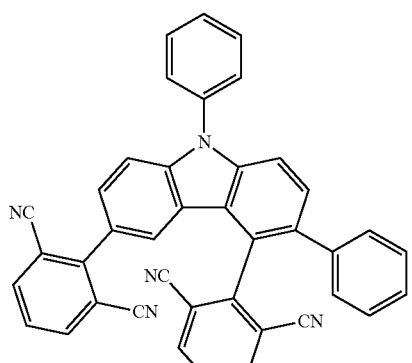
244

245
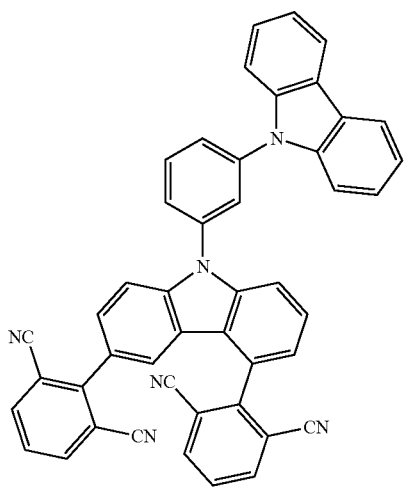
246
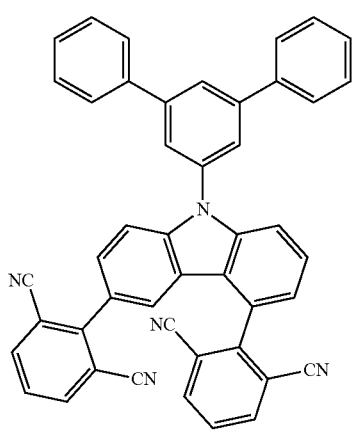
247
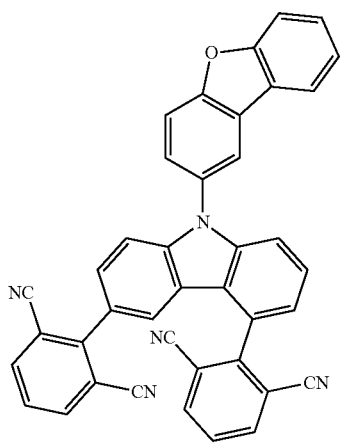
248
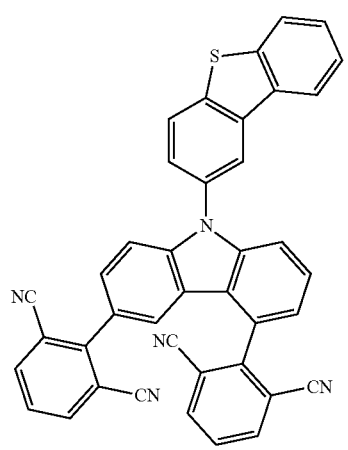
249
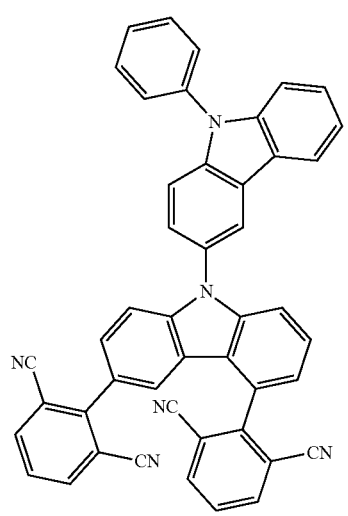
250
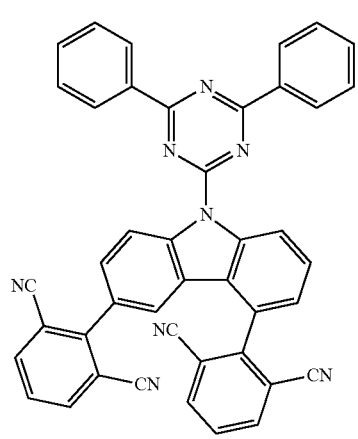

239
-continued
240
-continued
251
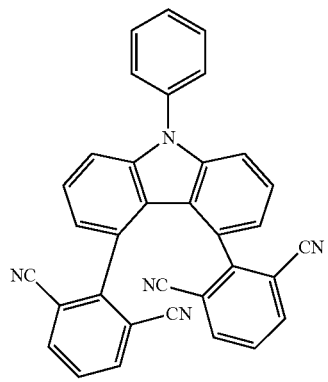
254
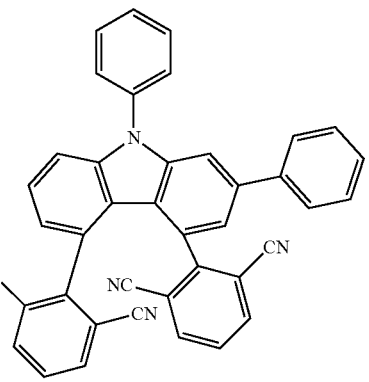
252
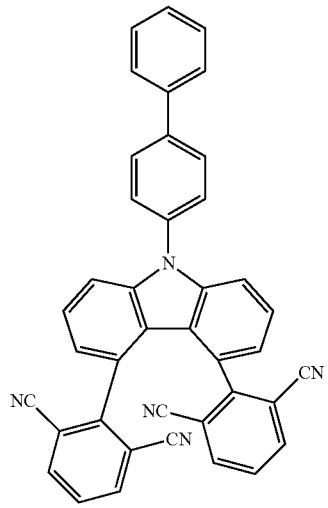
255
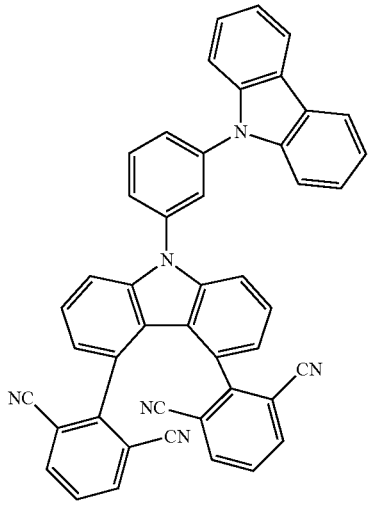
253
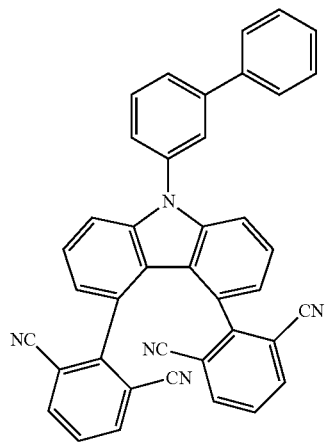
256
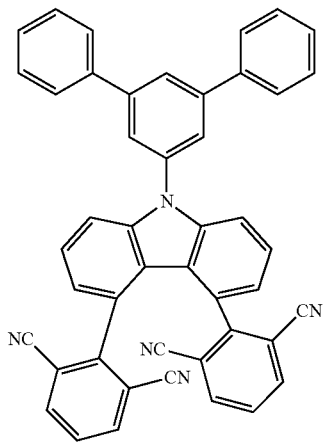

241
-continued
257
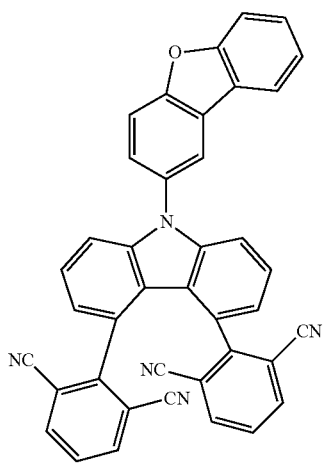
258
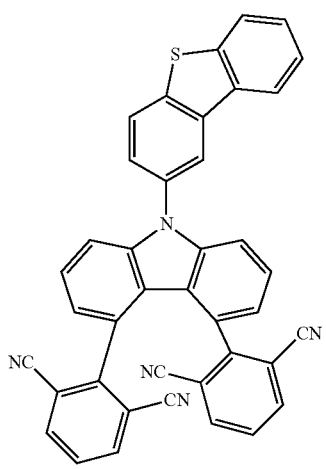
259
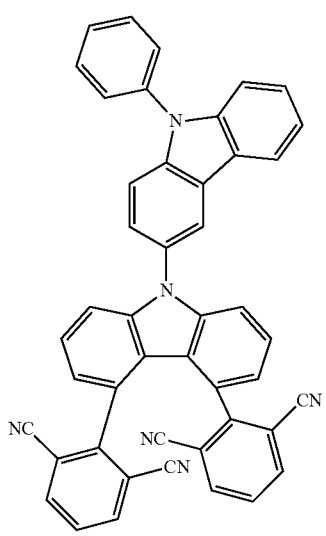
242
-continued
260
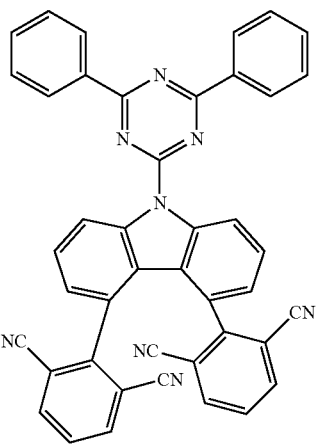
261
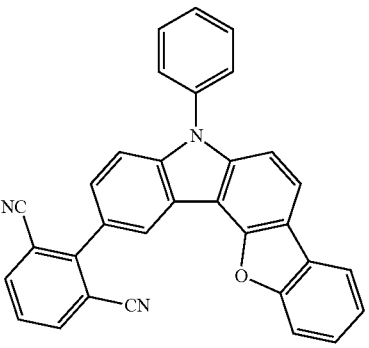
262
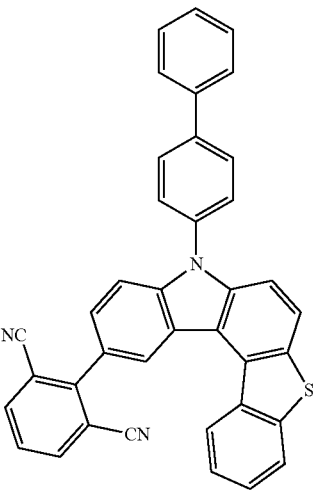

263
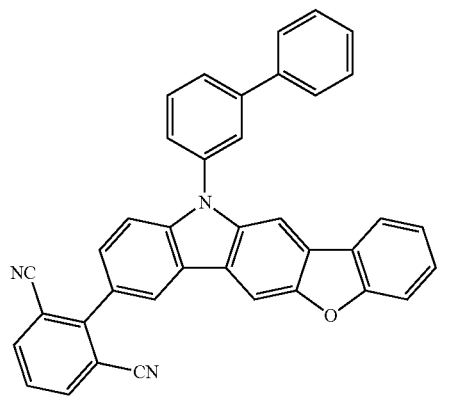
264
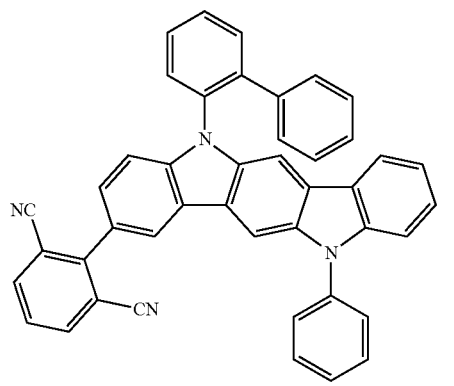
265
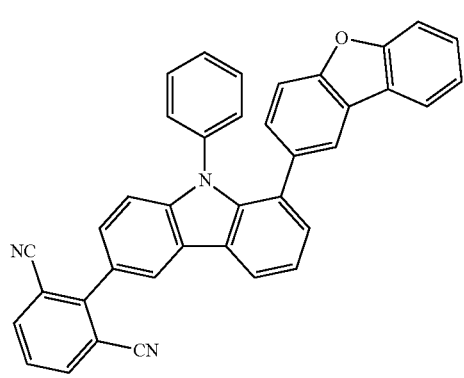
266
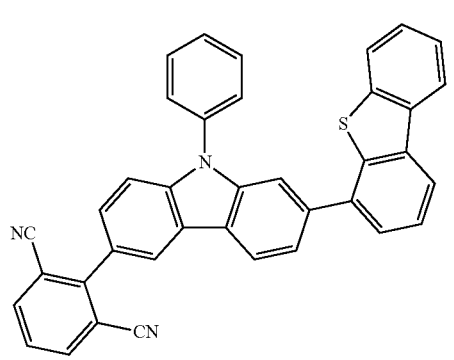
267
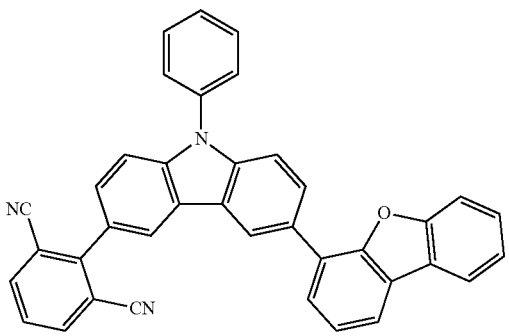
268
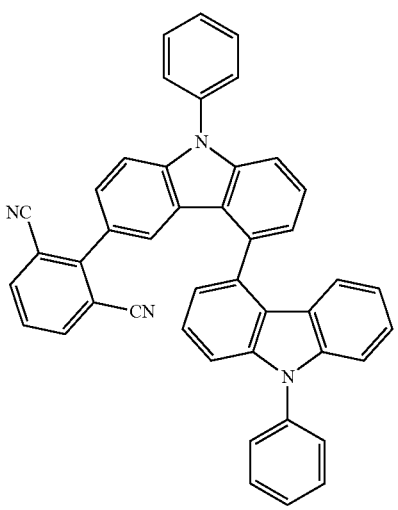
269
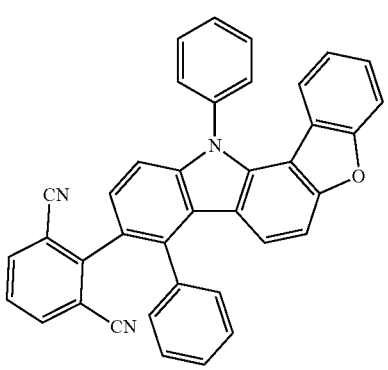
270
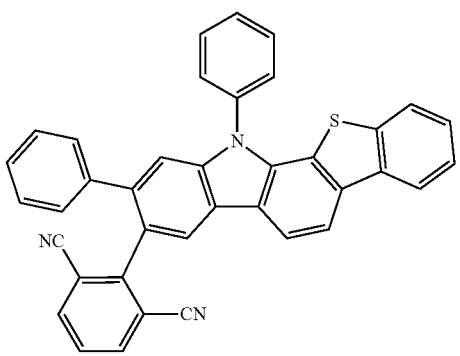

271 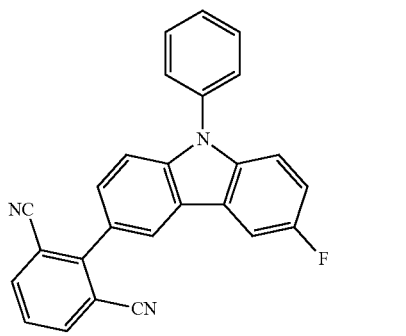
272 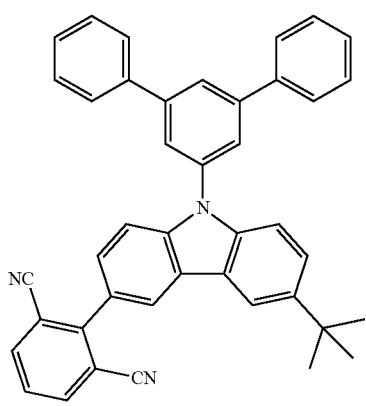
273 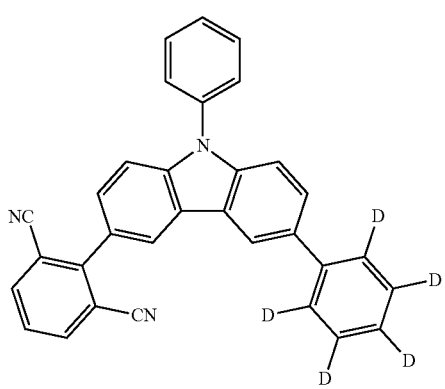
274 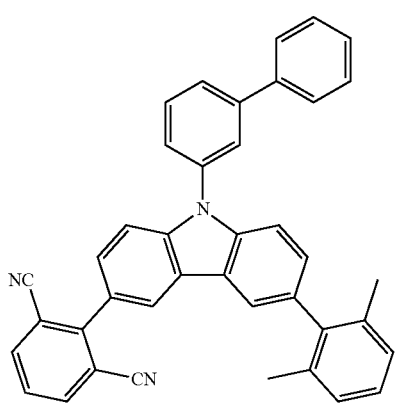
275 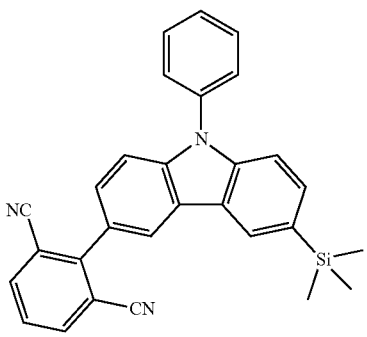
276 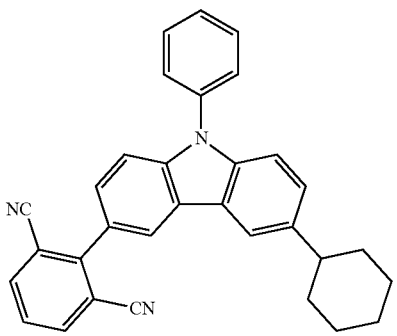
277 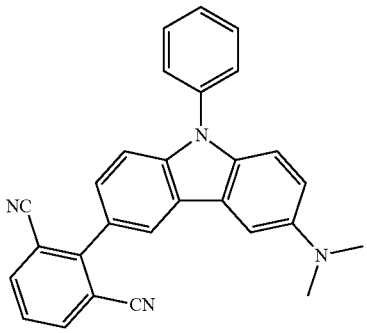

247
-continued

278

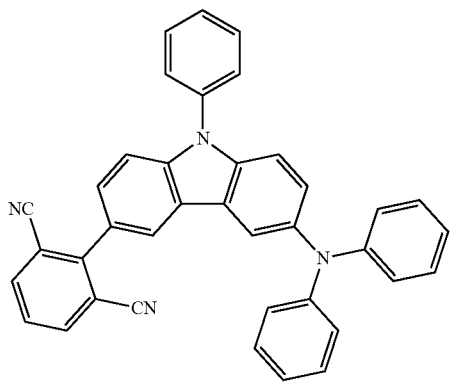

279

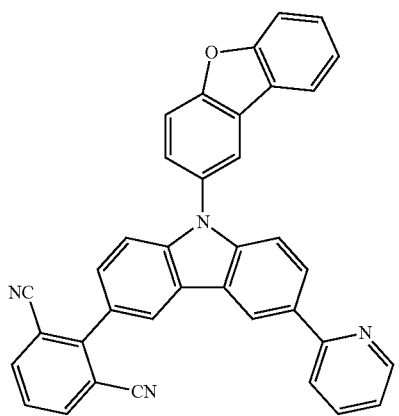

248
-continued

280

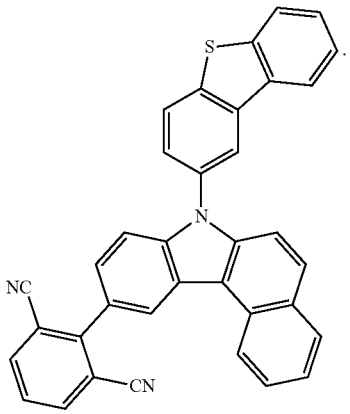

2. An organic light-emitting device comprising: a first electrode; a second electrode; and an organic layer between the first electrode and the second electrode and comprising an emission layer and at least one condensed cyclic compound of claim 1.

3. The organic light-emitting device of claim 2, wherein the emission layer comprises a host and a dopant, the host comprises the at least one condensed cyclic compound, and the dopant comprises a phosphorescent dopant.

4. The organic light-emitting device of claim 2, wherein the emission layer emits blue light.

5. An electronic device comprising the organic light-emitting device of claim 2.

6. The condensed cyclic compound of claim 1 selected from Compounds 82 to 120.

7. An organic light-emitting device comprising: a first electrode; a second electrode; and an organic layer between the first electrode and the second electrode and comprising an emission layer and at least one condensed cyclic compound of claim 6 and the emission layer emits blue light.

* * * * *